United States Patent
Blayo et al.

(10) Patent No.: US 12,194,051 B2
(45) Date of Patent: Jan. 14, 2025

(54) 5-AZAINDAZOLE DERIVATIVES AS ADENOSINE RECEPTOR ANTAGONISTS

(71) Applicant: MERCK PATENT GMBH, Darmstadt (DE)

(72) Inventors: Anne-Laure Blayo, Credin (FR); Baptiste Manteau, Ways (BE); Camille Amalric, Strassbourg (FR); Stanislas Mayer, Eschau (FR); Stephan Schann, Illkirch (FR); Mickaël Fer, Ostwald (FR)

(73) Assignee: MERCK PATENT GMBH, Darmstadt (DE)

( * ) Notice: Subject to any disclaimer, the term of this patent is extended or adjusted under 35 U.S.C. 154(b) by 716 days.

(21) Appl. No.: 17/288,164

(22) PCT Filed: Oct. 22, 2019

(86) PCT No.: PCT/EP2019/078625
§ 371 (c)(1),
(2) Date: Apr. 23, 2021

(87) PCT Pub. No.: WO2020/083856
PCT Pub. Date: Apr. 30, 2020

(65) Prior Publication Data
US 2021/0361669 A1    Nov. 25, 2021

(30) Foreign Application Priority Data

Oct. 25, 2018  (EP) ...................... 18306390

(51) Int. Cl.
| | | |
|---|---|---|
| *A61K 31/553* | (2006.01) | |
| *A61K 31/4545* | (2006.01) | |
| *A61K 31/46* | (2006.01) | |
| *A61K 31/497* | (2006.01) | |
| *A61K 31/506* | (2006.01) | |
| *A61K 31/5386* | (2006.01) | |
| *A61P 35/00* | (2006.01) | |
| *C07D 471/04* | (2006.01) | |
| *C07D 519/00* | (2006.01) | |
| *A61K 9/00* | (2006.01) | |
| *A61K 9/02* | (2006.01) | |
| *A61K 9/06* | (2006.01) | |

(Continued)

(52) U.S. Cl.
CPC ........ *A61K 31/553* (2013.01); *A61K 31/4545* (2013.01); *A61K 31/46* (2013.01); *A61K 31/497* (2013.01); *A61K 31/506* (2013.01); *A61K 31/5386* (2013.01); *A61P 35/00* (2018.01); *C07D 471/04* (2013.01); *C07D 519/00* (2013.01); *C07B 2200/05* (2013.01)

(58) Field of Classification Search
CPC .. A61K 31/553; A61K 31/4545; A61K 31/46; A61K 31/497; A61K 31/506; A61K 31/5386; A61K 9/0014; A61K 9/02; A61K 9/06; A61K 9/08; A61K 9/19; A61K 9/2018; A61K 9/286; A61K 45/06; A61K 47/06; A61P 35/00; A61P 31/00; C07D 471/04; C07D 519/00; C07B 2200/05; Y02A 50/30

See application file for complete search history.

(56) References Cited

U.S. PATENT DOCUMENTS

| | | |
|---|---|---|
| 5,756,028 A | 5/1998 | Liao |
| 5,760,028 A | 6/1998 | Jadhav et al. |

(Continued)

FOREIGN PATENT DOCUMENTS

| | | |
|---|---|---|
| RU | 2370496 C2 | 10/2009 |
| RU | 2467009 C2 | 11/2012 |

(Continued)

OTHER PUBLICATIONS

Bundgaard, Design of Prodrugs, 1985, CH 1 (Year: 1985) (Year: 1985).*

(Continued)

*Primary Examiner* — Bruck Kifle
*Assistant Examiner* — Kevin S Martin
(74) *Attorney, Agent, or Firm* — Millen White Zelano & Branigan; Csaba Henter

(57) ABSTRACT

The present invention relates to novel 5-azaindazole derivatives of formula (I), as described and defined herein, and pharmaceutically acceptable salts, solvates and prodrug thereof, as well as pharmaceutical compositions comprising such compounds. The 5-azaindazole derivatives according to the invention have been found to be highly effective dual $A_{2A}/A_{2B}$ adenosine receptor antagonists, and can thus be used as therapeutic agents, particularly in the treatment or prevention of hyperproliferative or infectious diseases or disorders.

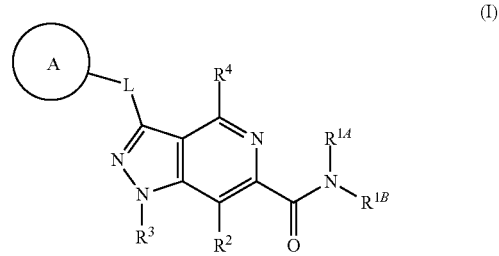

15 Claims, No Drawings

(51) Int. Cl.
  *A61K 9/08*    (2006.01)
  *A61K 9/19*    (2006.01)
  *A61K 9/20*    (2006.01)
  *A61K 9/28*    (2006.01)
  *A61K 45/06*   (2006.01)
  *A61K 47/06*   (2006.01)
  *A61P 31/00*   (2006.01)

(56) References Cited

U.S. PATENT DOCUMENTS

| | | |
|---|---|---|
| 7,985,754 B2 | 7/2011 | Beauglehole et al. |
| 8,796,290 B2 | 8/2014 | Ramdas et al. |
| 9,029,393 B2 | 5/2015 | Schann et al. |
| 9,284,316 B2 | 3/2016 | Palle et al. |
| 9,944,634 B2 | 4/2018 | Kawamura et al. |
| 10,696,687 B2 | 6/2020 | Zhang et al. |
| 2009/0023763 A1 | 1/2009 | Vidal Juan et al. |
| 2018/0237450 A1 | 8/2018 | Zhang et al. |

FOREIGN PATENT DOCUMENTS

| | | | |
|---|---|---|---|
| RU | 2015120625 A | 12/2016 | |
| WO | WO-9723480 A1 * | 7/1997 | ........... C07D 401/12 |
| WO | 2010084425 A1 | 7/2010 | |
| WO | 2010103547 A2 | 9/2010 | |
| WO | 2011055391 A1 | 5/2011 | |
| WO | 17028314 A1 | 2/2017 | |
| WO | 2017028314 A1 | 2/2017 | |

OTHER PUBLICATIONS

International Search Report for PCT/EP2019/078625 dated Nov. 18, 2019.

Thiel et al._"The critical role of adenosine A2A receptors in downregulation of inflammation and immunity in the pathogenesis of infectious diseases" Microbes and Infection._ 2003_ 5_ 515-526.

Sitkovsky et al._ "Adenosine A2A receptor antagonists: blockade of adenosinergic effects and T regulatory cells" British Journal of Pharmacology._ 2008_ 153_ S457-S464.

Harbeson et al._ "Deuterium in Drug Discovery . . . " Annual Reports in Medicinal Chemistry._ 2011_ 46_ 404-417.

Dyson G. et al., Chemistry of Synthetic Drugs, Moscow: Mir, 1964, pp. 12-19 (English translation).

Dyson G. et al., Chemistry of Synthetic Drugs, Moscow: Mir, 1964, pp. 12-19.

Burbello A. T. [ed.], "Drug compatibility and incompatibility. Problems of interaction. A guide for physicians. [in Russian]", Saint-Petersburg, 2009 (pp. 1-2).

Pokrovskij V. I. [ed.] "Popular medical encyclopedia [in Russian]", 4th edition, "Knogoej", 1997 (pp. 1-2).

Maškovskij M. D., "Medicaments [in Russian]", Moscow Medicina, 1993 (apges 1-2).

Harkevic, D. A., "Pharmacology [in Russian]", textbook, 8th edition, Moscow "GEOTAR-Media", 2005 (pp. 1-3).

\* cited by examiner

5-AZAINDAZOLE DERIVATIVES AS ADENOSINE RECEPTOR ANTAGONISTS

FIELD OF THE INVENTION

The present invention relates to novel 5-azaindazole derivatives of formula (I), as described and defined herein below, and pharmaceutically acceptable salts, solvates and prodrug thereof, as well as pharmaceutical compositions comprising such compounds. The 5-azaindazole derivatives according to the invention have been found to be highly effective dual $A_{2A}/A_{2B}$ adenosine receptor antagonists, and can thus be used as therapeutic agents, particularly in the treatment or prevention of hyperproliferative or infectious diseases or disorders.

BACKGROUND OF THE INVENTION

Adenosine is an ubiquitous modulator of numerous physiological activities, particularly within the cardiovascular, nervous and immune systems. Adenosine is related both structurally and metabolically to the bioactive nucleotides adenosine triphosphate (ATP), adenosine diphosphate (ADP), adenosine monophosphate (AMP) and cyclic adenosine monophosphate (cAMP), to the biochemical methylating agent S-adenosyl-L-methione (SAM) and structurally to the coenzymes NAD, FAD and coenzyme A and to RNA.

Via cell surface receptors, adenosine modulates diverse physiological functions including induction of sedation, vasodilatation, suppression of cardiac rate and contractility, inhibition of platelet aggregability, stimulation of gluconeogenesis and inhibition of lipolysis. Studies show that adenosine is able to activate adenylate cyclases, open potassium channels, reduce flux through calcium channels, and inhibit or stimulate phosphoinositide turnover through receptor-mediated mechanisms (Muller C. E. and Stein B., Current Pharmaceutical Design, 2: 501, 1996; Muller C. E., Exp. Opin. Ther. Patents, 7(5): 419, 1997).

Adenosine receptors belong to the superfamily of G-protein-coupled receptors (GPCRs). Four major subtypes of adenosine receptors have been pharmacologically, structurally and functionally characterized (Fredholm et al., Pharm. Rev., 46: 143-156, 1994) and referred to as $A_1$, $A_{2A}$, $A_{2B}$ and $A_3$. Though the same adenosine receptor can couple to different G-proteins, adenosine $A_1$ and $A_3$ receptors usually couple to inhibitory G-proteins referred to as $G_i$ and $G_o$ which inhibit adenylate cyclase and down-regulate cellular cAMP levels. In contrast, the adenosine $A_{2A}$ and $A_{2B}$ receptors couple to stimulatory G-proteins referred to as $G_s$ that activate adenylate cyclase and increase intracellular levels of cAMP (Linden J., Annu. Rev. Pharmacol. Toxicol., 41: 775-87 2001).

According to the invention, "adenosine-receptor-selective ligands" are substances which bind selectively to one or more subtypes of the adenosine receptors, thus either mimicking the action of adenosine (adenosine agonists) or blocking its action (adenosine antagonists). According to their receptor selectivity, adenosine-receptor-selective ligands can be divided into different categories, for example ligands which bind selectively to the $A_1$ or $A_2$ receptors and in the case of the latter also, for example, those which bind selectively to the $A_{2A}$ or the $A_{2B}$ receptors. Also possible are adenosine receptor ligands which bind selectively to a plurality of subtypes of the adenosine receptors, for example ligands which bind selectively to the $A_1$ and the $A_2$, but not to the $A_3$ receptors. The above-mentioned receptor selectivity can be determined by the effect of the substances on cell lines which, after stable transfection with the corresponding cDNA, express the receptor subtypes in question (Olah, M. E. et al., J. Biol. Chem., 267: 10764-10770, 1992). The effect of the substances on such cell lines can be monitored by biochemical measurement of the intracellular messenger cAMP (Klotz, K. N. et al., Naunyn Schmiedebergs Arch. Pharmacol. 357: 1-9, 1998).

It is known that the $A_1$ receptor system includes the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326-328 amino acids) was cloned from various species (canine, human, rat, dog, chick, bovine, guinea-pig) with 90-95% sequence identify among the mammalian species. The $A_{2A}$ receptor (409-412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317-320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$ and $A_3$) or increase the oxygen supply ($A_{2A}$) and so reinstate the balance of energy supply/demand within the tissue. The action of both subtypes is to increase the amount of available oxygen to tissue and to protect cells against damage caused by a short-term imbalance of oxygen. One of the important functions of endogenous adenosine is preventing damage during traumas such as hypoxia, ischaemia, hypotension and seizure activity. Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

These adenosine receptors are encoded by distinct genes and are classified according to their affinities for adenosine analogues and methylxanthine antagonists (Klinger et al., Cell Signal., 14 (2): 99-108, 2002).

Concerning the role of adenosine on the nervous system, the first observations were made on the effects of the most widely used of all psychoactive drugs being caffeine. Actually, caffeine is a well-known adenosine receptor antagonist that is able to enhance the awareness and learning abilities of mammals. The adenosine $A_{2A}$ receptor pathway is responsible for these effects (Fredholm et al., Pharmacol. Rev., 51 (1): 83-133, 1999; Huang et al., Nat Neurosci., 8 (7): 858-9, 2005), and the effects of caffeine on the adenosine $A_{2A}$ receptor signaling pathway encouraged the research of highly specific and potent adenosine $A_{2A}$ antagonists.

In mammals, adenosine $A_{2A}$ receptors have a limited distribution in the brain and are found in the striatum, olfactory tubercle and nucleus acumbens (Dixon et al., Br. J. Pharmacol., 118 (6): 1461-8, 1996). High and intermediate levels of expression can be observed in immune cells, heart, lung and blood vessels. In the peripheral system, $G_3$ seems to be the major G-protein associated with adenosine $A_{2A}$ receptor but in the striatum, it has been shown that striatal adenosine $A_{2A}$ receptors mediate their effects through activation of a G-protein referred to as $G_o$ (Kull et al., Mol.

Pharmacol., 58 (4): 772-7, 2000), which is similar to $G_3$ and also couples to adenylate cyclase.

To date, studies on genetically modified mice and pharmacological analysis suggest that $A_{2A}$ receptor is a promising therapeutic target for the treatment of central nervous system (CNS) disorders and diseases such as Parkinson's disease, Huntington's disease, attention deficit hyperactivity disorders (ADHD), stroke (ischemic brain injury), and Alzheimer's disease (Fredholm et al., Annu. Rev. Pharmacol. Toxicol., 45: 385-412, 2005; Higgins et al.; Behav. Brain Res. 185: 32-42, 2007; Dali'Igna et al., Exp. Neurol., 203 (1): 241-5, 2007; Arendash et al., Neuroscience, 142 (4): 941-52, 2006; Trends in Neurosci., 29 (11), 647-654, 2006; Expert Opinion Ther. Patents, 17, 979-991, 2007, Exp. Neurol., 184 (1), 285-284, 2003, Prog. Brain Res, 183, 183-208, 2010, J. Alzheimer Dis., Suppl 1, 1 17-126, 2010, J. Neurosci., 29 (47), 14741-14751, 2009, Neuroscience, 166 (2), 590-603, 2010, J. Pharmacol. Exp. Ther., 330 (1), 294-303, 2009; Frontiers Biosci., 13, 2614-2632, 2008) but also for various psychoses of organic origin (Weiss et al., Neurology, 61 (11 Suppl 6): 88-93, 2003).

The use of adenosine $A_{2A}$ receptor knockout mice has shown that adenosine $A_{2A}$ receptor inactivation protects against neuronal cell death induced by ischemia (Chen et al., J. Neurosci., 19 (21): 9192-200, 1999 and Monopoli et al., Neuroreport, 9 (17): 3955-9, 1998) and the mitochondrial toxin 3-NP (Blum et al., J. Neurosci., 23 (12): 5361-9, 2003). Those results provided a basis for treating ischaemia and Huntington's disease with adenosine $A_{2A}$ antagonists. The blockade of adenosine $A_{2A}$ receptors has also an antidepressant effect (El Yacoubi et al., Neuropharmacology, 40 (3): 424-32, 2001). Finally, this blockade prevents memory dysfunction (Cunha et al., Exp. Neurol., 210 (2): 776-81, 2008; Takahashi et al., Front. Biosci., 13: 2614-32, 2008) and this could be a promising therapeutic route for the treatment and/or prevention of Alzheimer's disease.

For reviews concerning $A_{2A}$ adenosine receptors see e.g. Moreau et al. (Brain Res. Reviews 31: 65-82, 1999) and Svenningsson et al. (Progress in Neurobiology 59: 355-396, 1999).

To date, several adenosine $A_{2A}$ receptor antagonists have shown promising potential for treatment of Parkinson's disease. As an example, KW-6002 (Istradefylline) completed a phase III clinical trial in the USA after studies demonstrated its efficacy in alleviation of symptoms of the disease (Bara-Himenez et al., Neurology, 61 (3): 293-6, 2003 and Hauser et al., Neurology, 61 (3): 297-303, 2003). SCH420814 (Preladenant), which is now in phase II clinical trial in the USA, produces an improvement in motor function in animal models of Parkinson's disease (Neustadt et al., Bioorg. Med. Chem. Lett., 17 (5): 1376-80, 2001) and also in human patients (Hunter J. C, poster Boston 2006—http://www.a2apd.org/Speaker abstracts/Hunter.pdf).

Besides the welcome utility of $A_{2A}$ receptor antagonists to treat neurodegenerative diseases, those compounds have been considered for complementary symptomatic indications. These are based on the evidence that $A_{2A}$ receptor activation may contribute to the pathophysiology of a range of neuropsychiatric disorders and dysfunctions such as depression, excessive daytime sleepiness, restless legs syndrome, attention deficit hyperactivity disorder, and cognitive fatigue (Neurology, 61 (Suppl 6), 82-87, 2003; Behav. Pharmacol., 20 (2), 134-145, 2009; CNS Drug Discov., 2 (1), 1-21, 2007).

Some authors suggest the application of $A_{2A}$ antagonists for the treatment of diabetes (WO1999035147; WO2001002400). Other studies suggest the involvement of $A_{2A}$ adenosine receptors in wound healing or atrial fibrillation (Am. J. Path., 6, 1774-1778, 2007; Arthritis & Rheumatism, 54 (8), 2632-2642, 2006).

Some of the potent adenosine $A_{2A}$ antagonists discovered in the past by the pharmaceutical companies, have advanced into clinical trials showing positive results and demonstrating the potential of this compound class for the treatment of neurodegenerative disorders like Parkinson's, Huntington's or Alzheimer's disease, but also in other CNS related diseases like depression, restless legs syndrome, sleep and anxiety disorders (Clin. Neuropharmacol., 33, 55-60, 2010; J. Neurosci., 30 (48), 2010), 16284-16292; Parkinson Relat. Disord., 16 (6), 423-426, 2010; Expert Opinion Ther. Patents, 20(8), 987-1005, 2010; Current Opinion in Drug Discovery & Development, 13 (4), 466-480, 2010 and references therein; Mov. Disorders, 25 (2), S305, 2010).

Known $A_{2A}$ inhibitors are Istradefylline (KW-6002), Preladenant (SCH420814), SCH58261, CGS15943, Tozadenant, Vipadenant (V-2006), V-81444 (CPI-444, HTL-1071, PBF-509, Medi-9447, PNQ-370, ZM-241385, ASO-5854, ST-1535, ST-4206, DT1133 and DT0926, which are in most cases developed for Parkinson's disease.

Adenosine $A_{2B}$ receptors were cloned from rat hypothalamus (Rivkees and Reppert, Mol Endocrinol. 1992 October; 6(10):1598-604), human hippocampus (Pierce et al., Biochem Biophys Res Commun. 1992 Aug. 31; 187(1):86-93), and mouse mast cells (Marquardt et al., J Immunol. 1994 May 1; 152(9):4508-15), employing standard polymerase chain reaction techniques with degenerate oligonucleotide primers designed to recognize conserved regions of most G protein-coupled receptors. The human $A_{2B}$ receptor shares 86 to 87% amino acid sequence homology with the rat and mouse $A_{2B}$ receptors (Rivkees and Reppert, 1992; Pierce et al., 1992; Marquardt et al., 1994) and 45% amino acid sequence homology with human $A_1$ and $A_{2A}$ receptors. As expected for closely related species, the rat and mouse $A_{2B}$ receptors share 96% amino acid sequence homology. By comparison, the overall amino acid identity between $A_1$ receptors from various species is 87% (Palmer and Stiles, Neuropharmacology, 1995 July; 34(7):683-94). $A_{2A}$ receptors share 90% of homology between species (Ongini and Fredholm, Trends Pharmacol Sci. 1996 October; 17(10): 364-72), with most differences occurring in the $2^{nd}$ extracellular loop and the long C-terminal domain (Palmer and Stiles, 1995). The lowest (72%) degree of identity between species is observed for $A_3$ receptor sequences (Palmer and Stiles, 1995).

The adenosine analog NECA remains the most potent $A_{2B}$ agonist (Bruns, Biochem Pharmacol. 1981 Feb. 15; 30(4): 325-33; Feoktistov and Biaggioni, Mol. Pharmacol. 1993 June; 43(6):909-14, Pharmacol. Rev. 1997 December; 49(4): 381-402; Brackett and Daly, Biochem Pharmacol, 1994 Mar. 2; 47(5):801-14), with a concentration producing a half-maximal effect ($EC_{50}$) for stimulation of adenyl cyclase of approximately 2 µM. It is, however, nonselective and activates other adenosine receptors with even greater affinity, with an $EC_{50}$ in the low nanomolar ($A_1$ and $A_{2A}$) or high nanomolar ($A_3$) range. The characterization of $A_{2B}$ receptors, therefore, often relies on the lack of effectiveness of compounds that are potent and selective agonists of other receptor types. $A_{2B}$ receptors have been characterized by a method of exclusion, i.e., by the lack of efficacy of agonists that are specific for other receptors. The $A_{2A}$ selective agonist CGS-21680 (Webb et al., J Biol Chem. 1992 Dec. 5; 267(34):24661-8), for example, has been useful in differentiating between $A_{2A}$ and $A_{2B}$ adenosine receptors (Hide et al., Mol Pharmacol. 1992 February; 41(2):352-9; Chern et al., Mol Pharmacol. 1993 November; 44(5):950-8; Feoktistov and Biaggioni, J Clin Invest. 1995 October; 96(4):1979-86; van der Ploeg et al., Naunyn Schmiedebergs Arch Pharmacol. 1996 February; 353(3): 250-60). Both receptors are positively coupled to adenyl cyclase and are activated by the nonselective agonist NECA. CGS-21680 is virtually ineffective on $A_{2B}$ receptors but is as potent as NECA in activating $A_{2A}$ receptors, with an $EC_{50}$ in the low nanomolar range for both agonists (Jarvis et al., Brain Res. 1989 Apr. 10; 484(1-2):111-8; Nakane and Chiba, Heart Vessels. 1990; 5(2):71-5; Webb et al., 1992; Hide et al., 1992; Feoktistov and Biaggioni, 1993; Alexander et al., Br J Pharmacol. 1996 November, 119(6):1286-90). $A_{2B}$ receptors have also a very low affinity for the $A_1$ selective agonist R-PIA (Feoktistov and Biaggioni, 1993; Brackett and Daly, Biochem Pharmacol. 1994 Mar. 2; 47(5):801-14) as well as for the $A_3$ selective agonist $N^6$-(3-iodobenzyl)-N-methyl-5'-carbamoyladenosine (IB-MECA) (Feoktistov and Biaggioni, 1997). The agonist profile NECA>R-PIA=IB-MECA>CGS-21680 was determined in human erythroleukemia (HEL) cells for $A_{2B}$-mediated cAMP accumulation. The difference between $EC_{50}$ for NECA and the rest of the agonists is approximately 2 orders of magnitude. Therefore, responses elicited by NECA at concentrations in the low micromolar range (1-10 μM), but not by R-PIA, IB-MECA or CGS-21680, are characteristic of $A_{2B}$ receptors.

Whereas $A_{2B}$ receptors have, in general, a lower affinity for agonists compared to other receptor subtypes, this is not true for antagonists. The structure activity relationship of adenosine antagonists on $A_{2B}$ receptors has not been fully characterized, but at least some xanthines are as or more potent antagonists of $A_{2B}$ receptor subtypes than of other subtypes. In particular, DPSPX (1,3-dipropyl-8-sulphophenylxanthine), DPCPX (1,3-dipropyl-8-cyclopentylxanthine), DPX (1,3-diethylphenylxanthine), the antiasthmatic drug enprofylline (3-n-propylxanthine) and the non-xanthine compound 2,4-dioxobenzopteridine (alloxazine) have affinities in the mid to high nM range.

Other known $A_{2B}$ inhibitors are ATL801, PSB-605, PSB-1115, ISAM-140, GS6201, MRS1706 and MRS1754.

It is disclosed herein that adenosine receptors play a non-redundant role in down-regulation of inflammation in vivo by acting as a physiological "STOP" (a termination mechanism) that can limit the immune response and thereby protect normal tissues form excessive immune damage during pathogenesis of different diseases.

$A_{2A}$ receptor antagonists provide long term enhancement of immune responses by reducing T-cell mediated tolerance to antigenic stimuli, enhancing the induction of memory T cells and enhancing the efficacy of passive antibody administration for the treatment of cancer and infectious diseases while $A_{2A}$ receptor agonists provide long term reduction of immune responses by enhancing T-cell mediated tolerance to antigenic stimuli, in particular to reduce use of immunosuppressive agents in certain conditions.

Immune modulation is a critical aspect of the treatment of a number of diseases and disorders. T cells in particular play a vital role in fighting infections and have the capability to recognize and destroy cancer cells. Enhancing T cell mediated responses is a key component to enhancing responses to therapeutic agents. However, it is critical in immune modulation that any enhancement of an immune response is balanced against the need to prevent autoimmunity as well as chronic inflammation. Chronic inflammation and self-recognition by T cells is a major cause for the pathogenesis of systemic disorders such as rheumatoid arthritis, multiple sclerosis and systemic lupus erythematosus. Furthermore, long term immune-suppression is required in preventing rejection of transplanted organs or grafts.

Tumor-induced immunosuppression is a major hurdle to the efficacy of current cancer therapies. Because of their remarkable clinical efficacy against a broader range of cancers, recent successes with immune checkpoint blockade inhibitors such as anti-CTLA-4 and anti-PD-1/PDL1 are revolutionizing cancer treatment.

Adenosine is one of the new promising immunosuppressive targets revealed in preclinical studies. This metabolite is produced by the ectoenzyme—CD73 expressed on host suppressor cells and tumor cells. Increased expression of CD73 correlates with poor prognosis in patients with a number of cancers, including colorectal cancer (Liu et al, J. Surgical Oncol, 2012), gastric cancer (Lu et al., World J. Gastroenterol., 2013), gallbladder cancer (Xiong et al., Cell and Tissue Res., 2014). Preclinical studies demonstrated that protumor effects of CD73 can be driven (at least in part) by adenosine-mediated immunosuppression. As disclosed above, adenosine binds to four known receptors $A_1$, $A_{2A}$, $A_{2B}$, and $A_3$, with the activation of $A_{2A}$ and $A_{2B}$ receptors known to suppress the effector functions of many immune cells, i.e. $A_{2A}$ and $A_{2B}$ receptors induce adenylate-cyclase-dependent accumulation of cAMP leading to immunosuppression. Since antagonizing $A_1$ and $A_3$ would counteract the desired effect and $A_1$ and $A_3$ agonists serve as potential cardioprotective agents, selectivity towards $A_1$ and $A_3$ needs to be achieved (Antonioli et al., Nat. rev. Cancer, 2013, Thiel et al., Microbes and Infection, 2003). In the microenvironment of the tumor, both $A_{2A}$ and $A_{2B}$ receptor activation has been demonstrated to suppress antitumor immunity and increase the spread of CD73 tumors. In addition, either $A_{2A}$ or $A_{2B}$ blockade with small molecule antagonists can reduce tumor metastasis. It has been found that blocking of $A_{2A}$ receptor can overcome tumor escape mechanisms including both anergy and regulatory T cell induction caused by tumor cells and cause long-term tumor susceptibility to treatment. Ohta et al. demonstrated rejection of approximately 60% of established CL8-1 melanoma tumors in $A_{2A}$ receptor-deficient mice compared to no rejection in normal mice (Ohta, et al.; PNAS 103 (35): 13132-7, 2006). In agreement, the investigators also showed improved inhibition of tumor growth, destruction of metastases and prevention of neovascularization by anti-tumor T cells after treatment with an $A_{2A}$ receptor antagonist.

Tumors have been shown to evade immune destruction by impeding T cell activation through inhibition of co-stimulatory factors in the B7-CD28 and TNF families, as well as by attracting regulatory T cells, which inhibit anti-tumor T cell responses (Wang, Cancer. Semin. Cancer. Biol. 16: 73-79, 2006; Greenwald, et al., Ann. Rev. Immunol. 23: 515-48, 2005; Watts, Ann. Rev. Immunol. 23: 23-68, 2005; Sadum et al., Clin. Canc. Res. 13 (13): 4016-4025, 2007). Because $A_{2A}$ receptor expression is increased in lymphocytes following activation, therapies that liberate lymphocyte effector responses, such as anti-CTLA-4 and anti-PD-1, may also increase the effects of $A_{2A}$-mediated immunosuppression. Immune checkpoint blockade in combination with $A_{2A}$ or dual $A_{2A/2B}$ antagonists increase the magnitude of immune responses to tumors and metastasis. Accordingly, combination of $A_{2A}$ inhibition with anti-PD-1 therapy enhances IFN-γ production by T-cells in a co-culture with MC38 tumor cells, improves mouse survival in 4T1 mammary tumor model and decreases tumor growth in AT-3ova$^{dim}$ CD73$^+$ tumors (Beavis et al., Cancer Immunol. Res., 2015; Mittal et al., Cancer Res., 2014).

Furthermore, preclinical studies demonstrated that $A_{2B}$ inhibition leads to decreased tumor growth and extended survival of mice in Lewis lung carcinoma, MB49 bladder carcinoma, ortho 4T1 mammary carcinoma models (Ryzhov et al., Purinergic Signal. 2009 September; 5(3):289-98, Cekic et al., J Immunol. 2012 Jan. 1; 188(1):198-205) and the combination of $A_{2B}$ inhibition with anti-PD-1 therapy reduces lung metastases of B16-F10 melanoma tumors and improves mouse survival in the 4T1 mammary tumor model.

WO 03/050241 describes the methods to increase an immune response to an antigen, increasing vaccine efficacy or increasing an immune response to a tumor antigen or immune cell-mediated tumor destruction by administering an agent that inhibits extracellular adenosine or inhibits adenosine receptors.

WO 2004/089942, WO 2005/000842 and WO 2006/008041 disclose benzothiazole derivatives and WO 2010/084425 discloses imidazopyridine-carbonyl-benzamide derivatives as $A_{2A}$ inhibitors for the treatment of Parkinson's disease. WO 2004/092171 and WO 2005/028484 disclose similar thiazolopyridine and pyrazolo-pyrimidine derivatives also as $A_{2A}$ inhibitors for the treatment of Parkinson's disease. However, these compounds do not show significant $A_{2B}$ inhibitory activity and do only show good pharmacokinetic properties in the rat, the Parkinson's disease animal model but not in the mouse, the cancer animal model. Furthermore, the compounds do not show that they are able to prevent immunosuppression and thus are able to support anti-tumor T cell induced inhibition of tumor growth, reduction or destruction of metastases and prevention of neovascularization.

Furthermore, WO 2017/028314, WO 2008/112695 and WO 2014/052563 disclose pyrazolo fused heterocyclic compounds as ERK or protein kinase inhibitors, respectively.

Thus, there remains a need for therapies that provide long term enhancement of immune responses to specific antigens, particularly for the treatment and prevention of hyperproliferative and infectious diseases and disorders. The object of the present invention is thus to provide methods of treatment that allow simplified treatment protocols and enhance immune responses against certain antigens. It is a specific object of the invention to provide improved methods of preventing or treating hyperproliferative and infectious diseases and disorders in a host, especially to provide effective dual $A_{2A/2B}$ antagonists for the treatment and prevention of such diseases.

SUMMARY OF THE INVENTION

Surprisingly, it has been found that the 5-azaindazole derivatives according to the present invention are highly effective inhibitors of both the $A_{2A}$ and $A_{2B}$ adenosine receptors and can thus be used as therapeutic agents, particularly for the treatment or prevention of hyperproliferative diseases and disorders (such as, e.g., cancer) as well as infectious diseases and disorders.

Particularly, in contrast to the known monospecific adenosine $A_{2A}$ receptor antagonists, e.g. the compounds disclosed in WO 2010/084425, the compounds of the present invention surprisingly show an $A_{2A}/A_{2B}$ dual activity which is preferred for the treatment and/or prevention of hyperproliferative and infectious diseases and disorders as it is disclosed above.

Furthermore, as discussed above, adenosine in tumor microenvironment can inhibit T cell activity by signaling through $A_{2A}$ receptors and suppress cytokine secretion by T cells. $A_{2A}$ specific agonists like NECA, similarly to adenosine, inhibit T cell cytokine secretion in vitro and in vivo. In contrast, potential $A_{2A}$ antagonists or $A_{2A}/A_{2B}$ dual antagonists can rescue T cells from this inhibition. The compounds of the present invention are able to prevent the suppression of cytokine secretion as induced by adenosine or $A_{2A}$ specific agonists like CGS-2168, which is preferred for the treatment and/or prevention of hyperproliferative and infectious diseases and disorders as it is disclosed above. Therefore, the compounds of the present invention surprisingly are able to prevent immunosuppression and thus are able to support anti-tumor T cell induced inhibition of tumor growth, reduction or destruction of metastases and prevention of neovascularization.

The present invention provides a 5-azaindazole derivative of the following formula (I) or a pharmaceutically acceptable salt, solvate or prodrug thereof:

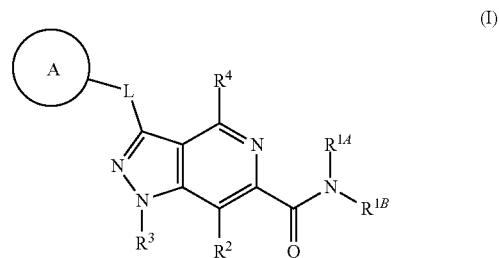

(I)

In formula (I), the groups $R^{1A}$ and $R^{1B}$ are mutually linked to form, together with the nitrogen atom that they are attached to, a heterocycloalkyl which is optionally substituted with one or more groups $R^{11}$; or, alternatively, $R^{1A}$ and $R^{1B}$ are each independently selected from hydrogen, $C_{1-5}$ alkyl, $C_{2-5}$ alkenyl, $C_{2-5}$ alkynyl, —CO($C_{1-5}$ alkyl), carbocyclyl, and heterocyclyl, wherein said alkyl, said alkenyl, said alkynyl, and the alkyl moiety of said —CO($C_{1-5}$ alkyl) are each optionally substituted with one or more groups $R^{12}$, and further wherein said carbocyclyl and said heterocyclyl are each optionally substituted with one or more groups $R^{13}$.

Each $R^{11}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-SO—($C_{1-5}$ alkyl), —($C_{0-3}$ alkylene)-SO$_2$—($C_{1-5}$ alkyl), —($C_{0-3}$ alkylene)-carbocyclyl, and —($C_{0-3}$ alkylene)-heterocyclyl, wherein the carbocyclyl moiety of said —($C_{0-3}$ alkylene)-carbocyclyl and the heterocyclyl moiety of said —($C_{0-3}$ alkylene)-heterocyclyl are each optionally substituted with one or more groups independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl.

Each $R^{12}$ is independently selected from —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl.

Each $R^{13}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-SO—($C_{1-5}$ alkyl), —($C_{0-3}$ alkylene)-SO$_2$—($C_{1-5}$ alkyl), —($C_{0-3}$ alkylene)-carbocyclyl, and —($C_{0-3}$ alkylene)-heterocyclyl, wherein the carbocyclyl moiety of said —($C_{0-3}$ alkylene)-carbocyclyl and the heterocyclyl moiety of said —($C_{0-3}$ alkylene)-heterocyclyl are each optionally substituted with one or more groups independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl.

$R^3$ is selected from hydrogen, $C_{1-5}$ alkyl, $C_{2-5}$ alkenyl, $C_{2-5}$ alkynyl, —($C_{1-5}$ alkylene)-OH, —($C_{1-5}$ alkylene)-O($C_{1-5}$ alkyl), —($C_{1-5}$ alkylene)-O($C_{1-5}$ alkylene)-OH, —($C_{1-5}$ alkylene)-O($C_{1-5}$ alkylene)-O($C_{1-5}$ alkyl), —($C_{1-5}$ alkylene)-SH, —($C_{1-5}$ alkylene)-S($C_{1-5}$ alkyl), —($C_{1-5}$ alkylene)-NH$_2$, —($C_{1-5}$ alkylene)-NH($C_{1-5}$ alkyl), —($C_{1-5}$ alkylene)-N($C_{1-5}$ alkyl)($C_{1-5}$ alkyl), —($C_{1-5}$ alkylene)-halogen, $C_{1-5}$ haloalkyl, —($C_{1-5}$ alkylene)-O—($C_{1-5}$ haloalkyl), —($C_{1-5}$ alkylene)-CF$_3$, —($C_{1-5}$ alkylene)-CN, —($C_{1-5}$ alkylene)-NO$_2$, —($C_{1-5}$ alkylene)-Si($C_{1-5}$ alkyl)$_3$, —($C_{1-5}$ alkylene)-O($C_{1-5}$ alkylene)-Si($C_{1-5}$ alkyl)$_3$, —($C_{1-5}$ alkylene)-CHO, —($C_{1-5}$ alkylene)-CO—($C_{1-5}$ alkyl), —($C_{1-5}$ alkylene)-COOH, —($C_{1-5}$ alkylene)-CO—O—($C_{1-5}$ alkyl), —($C_{1-5}$ alkylene)-O—CO—($C_{1-5}$ alkyl), —($C_{1-5}$ alkylene)-CO—NH$_2$, —($C_{1-5}$ alkylene)-CO—NH($C_{1-5}$ alkyl), —($C_{1-5}$ alkylene)-CO—N($C_{1-5}$ alkyl)($C_{1-5}$ alkyl), —($C_{1-5}$ alkylene)-NH—CO—($C_{1-5}$ alkyl), —($C_{1-5}$ alkylene)-N($C_{1-5}$ alkyl)-CO—($C_{1-5}$ alkyl), —($C_{1-5}$ alkylene)-NH—CO—O—($C_{1-5}$ alkyl), —($C_{1-5}$ alkylene)-N($C_{1-5}$ alkyl)-CO—O—($C_{1-5}$ alkyl), —($C_{1-5}$ alkylene)-O—CO—NH—($C_{1-5}$ alkyl), —($C_{1-5}$ alkylene)-O—CO—N($C_{1-5}$ alkyl)-($C_{1-5}$ alkyl), —($C_{1-5}$ alkylene)-SO$_2$—NH$_2$, —($C_{1-5}$ alkylene)-SO$_2$—NH($C_{1-5}$ alkyl), —($C_{1-5}$ alkylene)-SO$_2$—N($C_{1-5}$ alkyl)($C_{1-5}$ alkyl), —($C_{1-5}$ alkylene)-NH—SO$_2$—($C_{1-5}$ alkyl), —($C_{1-5}$ alkylene)-N($C_{1-5}$ alkyl)-SO$_2$—($C_{1-5}$ alkyl), —($C_{1-5}$ alkylene)-SO—($C_{1-5}$ alkyl), —($C_{1-5}$ alkylene)-SO$_2$—($C_{1-5}$ alkyl), —($C_{0-5}$ alkylene)-carbocyclyl, and —($C_{0-5}$ alkylene)-heterocyclyl, wherein the carbocyclyl moiety of said —($C_{0-5}$ alkylene)-carbocyclyl and the heterocyclyl moiety of said —($C_{0-5}$ alkylene)-heterocyclyl are each optionally substituted with one or more groups independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —NH—CO—O—($C_{1-5}$ alkyl), —N($C_{1-5}$ alkyl)-CO—O—($C_{1-5}$ alkyl), —O—CO—NH—($C_{1-5}$ alkyl), —O—CO—N($C_{1-5}$ alkyl)-($C_{1-5}$ alkyl), —SO$_2$—NH$_2$, —SO$_2$—NH(C$_{1-5}$ alkyl), —SO$_2$—N(C$_{1-5}$ alkyl)(C$_{1-5}$ alkyl), —NH—SO$_2$—(C$_{1-5}$ alkyl), —N(C$_{1-5}$ alkyl)-SO$_2$—(C$_{1-5}$ alkyl), —SO—(C$_{1-5}$ alkyl), —SO$_2$—(C$_{1-5}$ alkyl), cycloalkyl, and heterocycloalkyl.

L is C$_{1-5}$ alkylene, wherein one or more —CH$_2$— units comprised in said alkylene are each optionally replaced by a group independently selected from —N(R$^L$)—, —N(R$^L$)—CO—, —CO—N(R$^L$)—, —CO—, —O—, —CO—O—, —O—CO—, —S—, —SO—, —SO$_2$—, —SO$_2$—N(R$^L$)—, and —N(R$^L$)—SO$_2$—.

Each R$^L$ is independently selected from hydrogen and C$_{1-5}$ alkyl.

The ring group A is aryl or monocyclic heteroaryl, wherein said aryl or said monocyclic heteroaryl is optionally substituted with one or more groups R$^A$.

Each R$^A$ is independently selected from C$_{1-5}$ alkyl, C$_{2-5}$ alkenyl, C$_{2-5}$ alkynyl, —(C$_{0-3}$ alkylene)-OH, —(C$_{0-3}$ alkylene)-O(C$_{1-5}$ alkyl), —(C$_{0-3}$ alkylene)-O(C$_{1-5}$ alkylene)-OH, —(C$_{0-3}$ alkylene)-O(C$_{1-5}$ alkylene)-O(C$_{1-5}$ alkyl), —(C$_{0-3}$ alkylene)-SH, —(C$_{0-3}$ alkylene)-S(C$_{1-5}$ alkyl), —(C$_{0-3}$ alkylene)-NH$_2$, —(C$_{0-3}$ alkylene)-NH(C$_{1-5}$ alkyl), —(C$_{0-3}$ alkylene)-N(C$_{1-5}$ alkyl)(C$_{1-5}$ alkyl), —(C$_{0-3}$ alkylene)-halogen, —(C$_{0-3}$ alkylene)-(C$_{1-5}$ haloalkyl), —(C$_{0-3}$ alkylene)-O—(C$_{1-5}$ haloalkyl), —(C$_{0-3}$ alkylene)-CF$_3$, —(C$_{0-3}$ alkylene)-CN, —(C$_{0-3}$ alkylene)-NO$_2$, —(C$_{0-3}$ alkylene)-CHO, —(C$_{0-3}$ alkylene)-CO—(C$_{1-5}$ alkyl), —(C$_{0-3}$ alkylene)-COOH, —(C$_{0-3}$ alkylene)-CO—O—(C$_{1-5}$ alkyl), —(C$_{0-3}$ alkylene)-O—CO—(C$_{1-5}$ alkyl), —(C$_{0-3}$ alkylene)-CO—NH$_2$, —(C$_{0-3}$ alkylene)-CO—NH(C$_{1-5}$ alkyl), —(C$_{0-3}$ alkylene)-CO—N(C$_{1-5}$ alkyl)(C$_{1-5}$ alkyl), —(C$_{0-3}$ alkylene)-NH—CO—(C$_{1-5}$ alkyl), —(C$_{0-3}$ alkylene)-N(C$_{1-5}$ alkyl)-CO—(C$_{1-5}$ alkyl), —(C$_{0-3}$ alkylene)-SO$_2$—NH$_2$, —(C$_{0-3}$ alkylene)-SO$_2$—NH(C$_{1-5}$ alkyl), —(C$_{0-3}$ alkylene)-SO$_2$—N(C$_{1-5}$ alkyl)(C$_{1-5}$ alkyl), —(C$_{0-3}$ alkylene)-NH—SO$_2$—(C$_{1-5}$ alkyl), —(C$_{0-3}$ alkylene)-N(C$_{1-5}$ alkyl)-SO$_2$—(C$_{1-5}$ alkyl), —(C$_{0-3}$ alkylene)-SO—(C$_{1-5}$ alkyl), —(C$_{0-3}$ alkylene)-SO$_2$—(C$_{1-5}$ alkyl), —(C$_{0-3}$ alkylene)-carbocyclyl, and —(C$_{0-3}$ alkylene)-heterocyclyl, wherein the carbocyclyl moiety of said —(C$_{0-3}$ alkylene)-carbocyclyl and the heterocyclyl moiety of said —(C$_{0-3}$ alkylene)-heterocyclyl are each optionally substituted with one or more groups independently selected from C$_{1-5}$ alkyl, C$_{2-5}$ alkenyl, C$_{2-5}$ alkynyl, —OH, —O(C$_{1-5}$ alkyl), —O(C$_{1-5}$ alkylene)-OH, —O(C$_{1-5}$ alkylene)-O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —O—(C$_{1-5}$ haloalkyl), —CF$_3$, —CN, —NO$_2$, —CHO, —CO—(C$_{1-5}$ alkyl), —COOH, —CO—O—(C$_{1-5}$ alkyl), —O—CO—(C$_{1-5}$ alkyl), —CO—NH$_2$, —CO—NH(C$_{1-5}$ alkyl), —CO—N(C$_{1-5}$ alkyl)(C$_{1-5}$ alkyl), —NH—CO—(C$_{1-5}$ alkyl), —N(C$_{1-5}$ alkyl)-CO—(C$_{1-5}$ alkyl), —SO$_2$—NH$_2$, —SO$_2$—NH(C$_{1-5}$ alkyl), —SO$_2$—N(C$_{1-5}$ alkyl)(C$_{1-5}$ alkyl), —NH—SO$_2$—(C$_{1-5}$ alkyl), —N(C$_{1-5}$ alkyl)-SO$_2$—(C$_{1-5}$ alkyl), —SO—(C$_{1-5}$ alkyl), —SO$_2$—(C$_{1-5}$ alkyl), cycloalkyl, and heterocycloalkyl.

The present invention also relates to a pharmaceutical composition comprising a compound of formula (I) or a pharmaceutically acceptable salt, solvate or prodrug thereof, in combination with a pharmaceutically acceptable excipient. Accordingly, the invention relates to a compound of formula (I) or a pharmaceutically acceptable salt, solvate or prodrug thereof, or a pharmaceutical composition comprising any of the afore-mentioned entities and a pharmaceutically acceptable excipient, for use as a medicament. Moreover, the pharmaceutical composition may also comprise one or more further therapeutic agents (or active compounds).

The invention likewise relates to a pharmaceutical preparation comprising a compound of formula (I) or a pharmaceutically acceptable salt, solvate or prodrug thereof. The pharmaceutical preparation optionally further comprises one or more excipients and/or adjuvants. Moreover, the pharmaceutical preparation may also comprise one or more further therapeutic agents (or active compounds).

The invention further relates to a compound of formula (I) or a pharmaceutically acceptable salt, solvate or prodrug thereof, or a pharmaceutical composition comprising any of the afore-mentioned entities and a pharmaceutically acceptable excipient, for use in the treatment or prevention of a hyperproliferative disease or disorder or an infectious disease or disorder.

Moreover, the present invention relates to the use of a compound of formula (I) or a pharmaceutically acceptable salt, solvate or prodrug thereof in the preparation of a medicament for the treatment or prevention of a hyperproliferative disease or disorder or an infectious disease or disorder.

The invention likewise relates to a method of treating or preventing a hyperproliferative disease or disorder or an infectious disease or disorder, the method comprising administering a compound of formula (I) or a pharmaceutically acceptable salt, solvate or prodrug thereof, or a pharmaceutical composition comprising any of the afore-mentioned entities in combination with a pharmaceutically acceptable excipient, to a subject (preferably a human) in need thereof. It will be understood that a therapeutically effective amount of the compound of formula (I) or the pharmaceutically acceptable salt, solvate or prodrug thereof, or of the pharmaceutical composition, is to be administered in accordance with this method.

DETAILED DESCRIPTION OF THE INVENTION

As explained above, it has surprisingly been found that the 5-azaindazole derivatives of formula (I) according to the present invention are highly effective dual inhibitors of the A$_{2A}$ and A$_{2B}$ adenosine receptors, as also demonstrated in the appended examples, which renders them particularly suitable as therapeutic agents, including for the treatment or prevention of a disease or disorder which is caused, promoted and/or propagated by adenosine or other A$_{2A}$ and/or A$_{2B}$ receptor agonists, or a disease or disorder which is connected to (or associated with) adenosine A$_{2A}$ and/or A$_{2B}$ receptors; in particular, the compounds of formula (I) can advantageously be used for the treatment or prevention of a hyperproliferative disease or disorder (such as, e.g., cancer) or an infectious disease or disorder.

The hyperproliferative disease or disorder to be treated or prevented in accordance with the present invention is preferably cancer. The cancer is preferably selected from the group consisting of acute granulocytic leukemia, acute lymphocytic leukemia, acute myeloid leukemia, adrenal cortex cancer, bladder cancer, brain cancer, breast cancer, cervical cancer, cervical hyperplasia, cervical cancer, chorio cancer, chronic granulocytic leukemia, chronic lymphocytic leukemia, chronic myeloid leukemia, colon cancer, endometrial cancer, esophageal cancer, essential thrombocytosis, genitourinary carcinoma, glioma, glioblastoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, neuroblastoma, non-Hodgkin's lymphoma, non-small cell lung cancer, osteogenic sarcoma, ovarian carcinoma, pancreatic carcinoma, polycythemia vera, primary brain carcinoma, primary macroglobulinemia, prostatic cancer, renal cell cancer, rhabdomyosarcoma, skin cancer, small-cell lung cancer, soft-tissue sarcoma, squamous cell cancer, stomach cancer, testicular cancer, thyroid cancer, and Wilms' tumor.

The hyperproliferative disease or disorder to be treated or prevented in accordance with the invention may also be selected from age-related macular degeneration, Crohn's disease, cirrhosis, a chronic inflammatory-related disorder, proliferative diabetic retinopathy, proliferative vitreo-retinopathy, retinopathy of prematurity, granulomatosis, immune hyperproliferation associated with organ or tissue transplantation, and an immunoproliferative disease or disorder. The immune-proliferative disease/disorder is preferably selected from inflammatory bowel disease, psoriasis, rheumatoid arthritis, systemic lupus erythematosus (SLE), vascular hyperproliferation secondary to retinal hypoxia, and vasculitis.

Moreover, the infectious disease or disorder to be treated or prevented in accordance with the present invention is preferably selected from the group consisting of:

(a) virally induced infectious diseases, preferably those which are caused by retroviruses, hepadnaviruses, herpesviruses, flaviviridae and/or adenoviruses, wherein the retroviruses are preferably selected from lentiviruses or oncoretroviruses, wherein the lentivirus is preferably selected from the group consisting of HIV-1, HIV-2, FIV, BIV, SIVs, SHIV, CAEV, VMV and EIAV, wherein the oncoretrovirus is preferably selected from the group consisting of HTLV-I, HTLV-II and BLV, wherein the hepadnavirus is preferably selected from the group consisting of HBV, GSHV and WHV, wherein the herpesvirus is preferably selected from the group consisting of HSV I, HSV II, EBV, VZV, HCMV and HHV 8, and wherein the flaviviridae are preferably selected from the group consisting of HCV, West nile and Yellow Fever;

(b) bacterial infectious diseases which are caused by Gram-positive bacteria, wherein the Gram-positive bacteria are preferably selected from the group consisting of methicillin-susceptible and methicillin-resistant staphylococci (including, e.g., *Staphylococcus aureus, Staphylococcus epidermidis, Staphylococcus haemolyticus, Staphylococcus hominis, Staphylococcus saprophyticus*, and coagulase-negative staphylococci), glycopeptides-intermediate susceptible *Staphylococcus aureus* (GISA), penicillin-susceptible and penicillin-resistant streptococci (including, e.g., *Streptococcus pneumoniae, Streptococcus pyogenes, Streptococcus agalactiae, Streptococcus avium, Streptococcus bovis, Streptococcus lactis, Streptococcus sanguis* and Streptococci Group C (GCS), Streptococci Group G (GGS) and *viridans* streptococci), enterococci (including, e.g., vancomycin-susceptible and vancomycin-resistant strains such as *Enterococcus faecalis* and *Enterococcus faecium*), *Clostridium difficile, Listeria monocytogenes, Corynebacterium jeikeium, Chlamydia* spp (including, e.g., *C. pneumoniae*) and *Mycobacterium tuberculosis;*

(c) bacterial infectious diseases which are caused by Gram-negative bacteria, wherein the Gram-negative bacteria are preferably selected from the group consisting of the genus Enterobacteriaceae, including e.g. *Escherichia* spp. (including, e.g., *Escherichia coli*), *Klebsiella* spp., *Enterobacter* spp., *Citrobacter* spp., *Serratia* spp., *Proteus* spp., *Providencia* spp., *Salmonella* spp., *Shigella* spp., the genus *Pseudomonas* (including, e.g., *P. aeruginosa*), *Moraxella* spp. (including, e.g., *M. catarrhalis*), *Haemophilus* spp. and *Neisseria* spp.; and (d) infectious diseases induced by intracellular active parasites which are preferably selected from the group consisting of the phylum Apicomplexa, Sarcomastigophora (including, e.g., *Trypanosoma, Plasmodia, Leishmania, Babesia* or *Theileria*), Cryptosporidia, Sacrocystida, Amoebia, Coccidia and Trichomonadia.

Since the compounds of formula (I) according to the present invention are highly efficient $A_{2A}$ receptor antagonists, they can also be used in the treatment or prevention of movement disorders, acute and chronic pain, affective disorders, central and peripheral nervous system degeneration disorders, schizophrenia and related psychosis, cognitive disorders, attention disorders, central nervous system injury, cerebral ischemia, myocardial ischemia, muscle ischemia, sleep disorders, eye disorders, cardiovascular disorders, hepatic fibrosis, cirrhosis, fatty liver, substance abuse, Parkinson's disease, Alzheimer's disease or attention-deficit hyperactivity disorder.

The compound of formula (I) or the pharmaceutically acceptable salt, solvate or prodrug thereof, as provided in accordance with the present invention, will be described in more detail in the following:

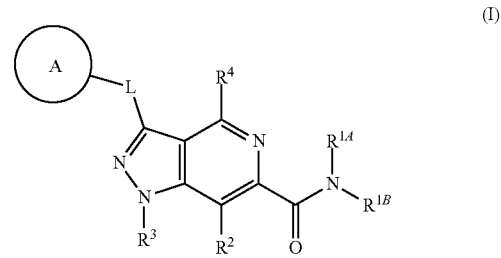

(I)

In formula (I), the groups $R^{1A}$ and $R^{1B}$ are mutually linked to form, together with the nitrogen atom that they are attached to, a heterocycloalkyl which is optionally substituted with one or more (e.g., one, two or three) groups $R^{11}$; or, alternatively, $R^{1A}$ and $R^{1B}$ are each independently selected from hydrogen, $C_{1-5}$ alkyl, $C_{2-5}$ alkenyl, $C_{2-5}$ alkynyl, —CO($C_{1-5}$ alkyl), carbocyclyl, and heterocyclyl, wherein said alkyl, said alkenyl, said alkynyl, and the alkyl moiety of said —CO($C_{1-5}$ alkyl) are each optionally substituted with one or more (e.g., one, two or three) groups $R^{12}$, and further wherein said carbocyclyl and said heterocyclyl are each optionally substituted with one or more (e.g., one, two or three) groups $R^{13}$.

Preferably, the groups $R^{1A}$ and $R^{1B}$ are mutually linked to form, together with the nitrogen atom that they are attached to, a heterocycloalkyl which is optionally substituted with one or more groups $R^{11}$.

The heterocycloalkyl which is formed from $R^{1A}$, $R^{1B}$ and the nitrogen atom linking $R^{1A}$ and $R^{1B}$ (and which is optionally substituted with one or more groups $R^{11}$) is preferably a monocyclic, bicyclic or tricyclic heterocycloalkyl; more preferably, it is a monocyclic heterocycloalkyl having 5, 6, 7 or 8 ring atoms, or a bicyclic heterocycloalkyl (e.g., a bicyclic fused, bridged or spirocyclic heterocycloalkyl; particularly a bicyclic bridged heterocycloalkyl) wherein each ring of said bicyclic heterocycloalkyl independently has 5, 6, 7 or 8 ring atoms. It is furthermore preferred that the heterocycloalkyl (including any one of the aforementioned preferred examples of the heterocycloalkyl) contains one nitrogen ring atom (i.e., the nitrogen atom linking $R^{1A}$ and $R^{1B}$) and optionally one further ring heteroatom selected from nitrogen, oxygen and sulfur (wherein said optional further ring heteroatom, if present, is preferably an oxygen ring atom), wherein the remaining ring atoms are all carbon atoms. Examples of the heterocycloalkyl, which is formed from $R^{1A}$, $R^{1B}$ and the nitrogen atom linking $R^{1A}$ and $R^{1B}$, include any of the respective heterocycloalkyl groups comprised in any of the specific compounds of the invention disclosed herein below in the examples section. Particularly preferred examples of the heterocycloalkyl, which is formed from $R^{1A}$, $R^{1B}$ and the nitrogen atom which $R^{1A}$ and $R^{1B}$ are attached to (and which is optionally substituted with one or more groups $R^{11}$), include 1,4-oxazepan-4-yl, piperidin-1-yl, 8-oxa-3-azabicyclo[3.2.1]octan-3-yl, or 8-azabicyclo[3.2.1]octan-8-yl, wherein said 1,4-oxazepan-4-yl, said piperidin-1-yl, said 8-oxa-3-azabicyclo[3.2.1]octan-3-yl, and said 8-azabicyclo[3.2.1]octan-8-yl are each optionally substituted with one or more groups $R^{11}$; said piperidin-1-yl is preferably substituted with —OH in position 4, and is optionally further substituted with one or more groups $R^{11}$; said 8-azabicyclo[3.2.1]-octan-8-yl is preferably substituted with —OH in position 3 (particularly in endo-configuration; i.e., 3-endo-hydroxy-8-azabicyclo[3.2.1]octan-8-yl), and is optionally further substituted with one or more groups $R^{11}$.

Accordingly, it is particularly preferred that $R^{1A}$ and $R^{1B}$ are mutually linked to form, together with the nitrogen atom that they are attached to, a group which is selected from

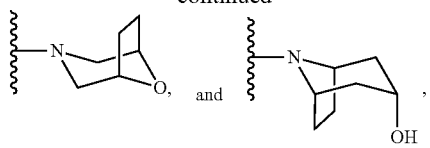

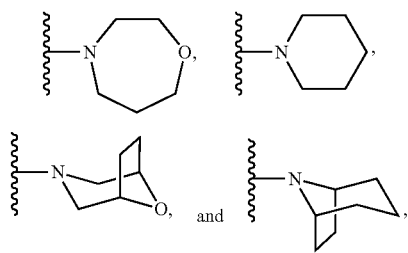

wherein each one of the above-depicted groups is optionally substituted with one or more $R^{11}$.

Even more preferably, $R^{1A}$ and $R^{1B}$ are mutually linked to form, together with the nitrogen atom that they are attached to, a group which is selected from

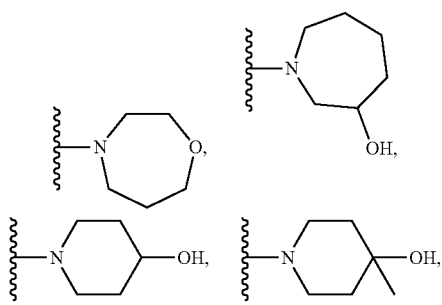

wherein each one of the above-depicted groups is optionally substituted with one or more $R^{11}$.

Yet even more preferably, $R^{1A}$ and $R^{1B}$ are mutually linked to form, together with the nitrogen atom that they are attached to, a group which is selected from

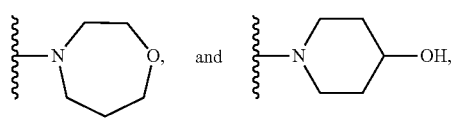

wherein each one of the above-depicted groups is optionally substituted with one or more $R^{11}$.

Each $R^{11}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-SO—($C_{1-5}$ alkyl), —($C_{0-3}$ alkylene)-SO$_2$—($C_{1-5}$ alkyl), —($C_{0-3}$ alkylene)-carbocyclyl, and —($C_{0-3}$ alkylene)-heterocyclyl, wherein the carbocyclyl moiety of said —($C_{0-3}$ alkylene)-carbocyclyl and the heterocyclyl moiety of said —($C_{0-3}$ alkylene)-heterocyclyl are each optionally substituted with one or more (e.g., one, two or three) groups independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl) ($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N ($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl.

Preferably, each $R^{11}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —$CF_3$, —CN, —$NO_2$, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), cycloalkyl, and heterocycloalkyl. More preferably, each $R^{11}$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —$CF_3$, and —CN. Even more preferably, each $R^{11}$ is independently selected from $C_{1-4}$ alkyl (e.g., methyl or ethyl), —OH, —O($C_{1-4}$ alkyl) (e.g., —$OCH_3$ or —$OCH_2CH_3$), —$NH_2$, —NH($C_{1-4}$ alkyl) (e.g., —$NHCH_3$), —N($C_{1-4}$ alkyl)($C_{1-4}$ alkyl) (e.g., —N($CH_3$)$_2$), halogen (e.g., —F, —Cl, —Br, or —I), —$CF_3$, and —CN.

Each $R^{12}$ is independently selected from —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —$CF_3$, —CN, —$NO_2$, —CHO, —CO—($C_{1-5}$ alkyl), —COOH, —CO—O—($C_{1-5}$ alkyl), —O—CO—($C_{1-5}$ alkyl), —CO—$NH_2$, —CO—NH—($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), cycloalkyl, and heterocycloalkyl. Preferably, each $R^{12}$ is independently selected from —OH, —O($C_{1-4}$ alkyl), —$NH_2$, —NH($C_{1-4}$ alkyl), —N($C_{1-4}$ alkyl)($C_{1-4}$ alkyl), halogen, —$CF_3$, and —CN.

Each $R^{13}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, and —($C_{0-3}$ alkylene)-heterocycloalkyl. Preferably, each $R^{13}$ is independently selected from $C_{1-4}$ alkyl, —OH, —O($C_{1-4}$ alkyl), —$NH_2$, —NH($C_{1-4}$ alkyl), —N($C_{1-4}$ alkyl)($C_{1-4}$ alkyl), halogen, —$CF_3$, and —CN.

$R^2$ and $R^4$ are each independently selected from hydrogen, $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-carbocyclyl, and —($C_{0-3}$ alkylene)-heterocyclyl, wherein the carbocyclyl moiety of said —($C_{0-3}$ alkylene)-carbocyclyl and the heterocyclyl moiety of said —($C_{0-3}$ alkylene)-heterocyclyl are each optionally substituted with one or more (e.g., one, two or three) groups independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —$CF_3$, —CN, —$NO_2$, —CHO, —CO—($C_{1-5}$ alkyl), —COOH, —CO—O—($C_{1-5}$ alkyl), —O—CO—($C_{1-5}$ alkyl), —CO—$NH_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —$SO_2$—$NH_2$, —$SO_2$—NH($C_{1-5}$ alkyl), —$SO_2$—N($C_{1-5}$ alkyl)($C_{1-5}$ alkyl), —NH—$SO_2$—($C_{1-5}$ alkyl), —N($C_{1-5}$ alkyl)-$SO_2$—($C_{1-5}$ alkyl), —SO—($C_{1-5}$ alkyl), —$SO_2$—($C_{1-5}$ alkyl), cycloalkyl, and heterocycloalkyl.

Preferably, $R^2$ and $R^4$ are each independently selected from hydrogen, $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-$NH_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-$CF_3$, —($C_{0-3}$ alkylene)-CN, —($C_{0-3}$ alkylene)-$NO_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—$NH_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-$SO_2$—$NH_2$, —($C_{0-3}$ alkylene)-$SO_2$—NH($C_{1-5}$ alkyl), —($C_{0-3}$ alkylene)-$SO_2$—N($C_{1-5}$ alkyl)($C_{1-5}$ alkyl), —($C_{0-3}$ alkylene)-NH—$SO_2$—($C_{1-5}$ alkyl), —($C_{0-3}$ alkylene)-N($C_{1-5}$ alkyl)-$SO_2$—($C_{1-5}$ alkyl), —($C_{0-3}$ alkylene)-SO—($C_{1-5}$ alkyl), —($C_{0-3}$ alkylene)-$SO_2$—($C_{1-5}$ alkyl), —($C_{0-3}$ alkylene)-cycloalkyl, and —($C_{0-3}$ alkylene)-heterocycloalkyl. More preferably, $R^2$ and $R^4$ are each independently selected from hydrogen, $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —$NH_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—(C$_{1-5}$ alkyl), —COOH, —CO—O—(C$_{1-5}$ alkyl), —O—CO—(C$_{1-5}$ alkyl), —CO—NH$_2$, —CO—NH(C$_{1-5}$ alkyl), —CO—N(C$_{1-5}$ alkyl)(C$_{1-5}$ alkyl), —NH—CO—(C$_{1-5}$ alkyl), —N(C$_{1-5}$ alkyl)-CO—(C$_{1-5}$ alkyl), —SO$_2$—NH$_2$, —SO$_2$—NH(C$_{1-5}$ alkyl), —SO$_2$—N(C$_{1-5}$ alkyl)(C$_{1-5}$ alkyl), —NH—SO$_2$—(C$_{1-5}$ alkyl), —N(C$_{1-5}$ alkyl)-SO$_2$—(C$_{1-5}$ alkyl), —SO—(C$_{1-5}$ alkyl), —SO$_2$—(C$_{1-5}$ alkyl), cycloalkyl, and heterocycloalkyl. Even more preferably, R$^2$ and R$^4$ are each independently selected from hydrogen, C$_{1-5}$ alkyl, —OH, —O(C$_{1-5}$ alkyl), —O(C$_{1-5}$ alkylene)-OH, —O(C$_{1-5}$ alkylene)-O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —CF$_3$, and —CN. Yet even more preferably, R$^2$ and R$^4$ are each independently selected from hydrogen, C$_{1-4}$ alkyl (e.g., methyl or ethyl), —OH, —O(C$_{1-4}$ alkyl) (e.g., —OCH$_3$ or —OCH$_2$CH$_3$), —NH$_2$, —NH(C$_{1-4}$ alkyl) (e.g., —NHCH$_3$), —N(C$_{1-4}$ alkyl)(C$_{1-4}$ alkyl) (e.g., —N(CH$_3$)$_2$), halogen (e.g., —F, —Cl, —Br, or —I), —CF$_3$, and —CN. Still more preferably, R$^2$ and R$^4$ are each hydrogen.

R$^3$ is selected from hydrogen, C$_{1-5}$ alkyl, C$_{2-5}$ alkenyl, C$_{2-5}$ alkynyl, —(C$_{1-5}$ alkylene)-OH, —(C$_{1-5}$ alkylene)-O(C$_{1-5}$ alkyl), —(C$_{1-5}$ alkylene)-O(C$_{1-5}$ alkylene)-OH, —(C$_{1-5}$ alkylene)-O(C$_{1-5}$ alkylene)-O(C$_{1-5}$ alkyl), —(C$_{1-5}$ alkylene)-SH, —(C$_{1-5}$ alkylene)-S(C$_{1-5}$ alkyl), —(C$_{1-5}$ alkylene)-NH$_2$, —(C$_{1-5}$ alkylene)-NH(C$_{1-5}$ alkyl), —(C$_{1-5}$ alkylene)-N(C$_{1-5}$ alkyl)(C$_{1-5}$ alkyl), —(C$_{1-5}$ alkylene)-halogen, C$_{1-5}$ haloalkyl, —(C$_{1-5}$ alkylene)-O—(C$_{1-5}$ haloalkyl), —(C$_{1-5}$ alkylene)-CF$_3$, —(C$_{1-5}$ alkylene)-CN, —(C$_{1-5}$ alkylene)-NO$_2$, —(C$_{1-5}$ alkylene)-Si(C$_{1-5}$ alkyl)$_3$, —(C$_{1-5}$ alkylene)-O(C$_{1-5}$ alkylene)-Si(C$_{1-5}$ alkyl)$_3$, —(C$_{1-5}$ alkylene)-CHO, —(C$_{1-5}$ alkylene)-CO—(C$_{1-5}$ alkyl), —(C$_{1-5}$ alkylene)-COOH, —(C$_{1-5}$ alkylene)-CO—O—(C$_{1-5}$ alkyl), —(C$_{1-5}$ alkylene)-O—CO—(C$_{1-5}$ alkyl), —(C$_{1-5}$ alkylene)CO—NH$_2$, —(C$_{1-5}$ alkylene)-CO—NH(C$_{1-5}$ alkyl), —(C$_{1-5}$ alkylene)-CO—N(C$_{1-5}$ alkyl)(C$_{1-5}$ alkyl), —(C$_{1-5}$ alkylene)-NH—CO—(C$_{1-5}$ alkyl), —(C$_{1-5}$ alkylene)-N(C$_{1-5}$ alkyl)-CO—(C$_{1-5}$ alkyl), —(C$_{1-5}$ alkylene)-NH—CO—O—(C$_{1-5}$ alkyl), —(C$_{1-5}$ alkylene)-N(C$_{1-5}$ alkyl)-CO—O—(C$_{1-5}$ alkyl), —(C$_{1-5}$ alkylene)-O—CO—NH—(C$_{1-5}$ alkyl), —(C$_{1-5}$ alkylene)-O—CO—N(C$_{1-5}$ alkyl)-(C$_{1-5}$ alkyl), —(C$_{1-5}$ alkylene)-SO$_2$—NH$_2$, —(C$_{1-5}$ alkylene)-SO$_2$—NH(C$_{1-5}$ alkyl), —(C$_{1-5}$ alkylene)-SO$_2$—N(C$_{1-5}$ alkyl)(C$_{1-5}$ alkyl), —(C$_{1-5}$ alkylene)-NH—SO$_2$—(C$_{1-5}$ alkyl), —(C$_{1-5}$ alkylene)-N(C$_{1-5}$ alkyl)-SO$_2$—(C$_{1-5}$ alkyl), —(C$_{1-5}$ alkylene)-SO—(C$_{1-5}$ alkyl), —(C$_{1-5}$ alkylene)-SO$_2$—(C$_{1-5}$ alkyl), —(C$_{0-5}$ alkylene)-carbocyclyl, and —(C$_{0-5}$ alkylene)-heterocyclyl, wherein the carbocyclyl moiety of said —(C$_{0-5}$ alkylene)-carbocyclyl and the heterocyclyl moiety of said —(C$_{0-5}$ alkylene)-heterocyclyl are each optionally substituted with one or more groups independently selected from C$_{1-5}$ alkyl, C$_{2-5}$ alkenyl, C$_{2-5}$ alkynyl, —OH, —O(C$_{1-5}$ alkyl), —O(C$_{1-5}$ alkylene)-OH, —O(C$_{1-5}$ alkylene)-O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —O—(C$_{1-5}$ haloalkyl), —CF$_3$, —CN, —NO$_2$, —CHO, —CO—(C$_{1-5}$ alkyl), —COOH, —CO—O—(C$_{1-5}$ alkyl), —O—CO—(C$_{1-5}$ alkyl), —CO—NH$_2$, —CO—NH(C$_{1-5}$ alkyl), —CO—N(C$_{1-5}$ alkyl)(C$_{1-5}$ alkyl), —NH—CO—(C$_{1-5}$ alkyl), —N(C$_{1-5}$ alkyl)-CO—(C$_{1-5}$ alkyl), —NH—CO—O—(C$_{1-5}$ alkyl), —N(C$_{1-5}$ alkyl)-CO—O—(C$_{1-5}$ alkyl), —O—CO—NH—(C$_{1-5}$ alkyl), —O—CO—N(C$_{1-5}$ alkyl)-(C$_{1-5}$ alkyl), —SO$_2$—NH$_2$, —SO$_2$—NH(C$_{1-5}$ alkyl), —SO$_2$—N(C$_{1-5}$ alkyl)(C$_{1-5}$ alkyl), —NH—SO$_2$—(C$_{1-5}$ alkyl), —N(C$_{1-5}$ alkyl)-SO$_2$—(C$_{1-5}$ alkyl), —SO—(C$_{1-5}$ alkyl), —SO$_2$—(C$_{1-5}$ alkyl), cycloalkyl, and heterocycloalkyl.

Preferably, R$^3$ is selected from C$_{1-3}$ haloalkyl (e.g., —CH$_2$—CF$_3$, —CH$_2$—CHF$_2$, or —CH$_2$—CH$_2$F), —(C$_{1-3}$ alkylene)-SO—(C$_{1-3}$ alkyl) (e.g., —CH$_2$—SO—CH$_3$) and —(C$_{1-3}$ alkylene)-SO$_2$—(C$_{1-3}$ alkyl) (e.g., —CH$_2$—SO$_2$—CH$_3$). More preferably, R$^3$ is —CH$_2$—CF$_3$ or —CH$_2$—SO$_2$—CH$_3$.

L is C$_{1-5}$ alkylene, wherein one or more (e.g., one or two) —CH$_2$— units comprised in said alkylene are each optionally replaced by a group independently selected from —N(R$^L$)—, —N(R$^L$)—CO—, —CO—N(R$^L$)—, —CO—, —O—, —CO—O—, —O—CO—, —S—, —SO—, —SO$_2$—, —SO$_2$—N(R$^L$)—, and —N(R$^L$)—SO$_2$—.

Preferably, L is C$_{1-3}$ alkylene, wherein one or two —CH$_2$— units (preferably one —CH$_2$— unit) comprised in said alkylene is/are each optionally replaced by a group independently selected from —N(R$^L$)—, —N(R$^L$)—CO—, —CO—N(R$^L$)—, —CO—, —O—, —CO—O—, —O—CO—, —S—, —SO—, —SO$_2$—, —SO$_2$—N(R$^1$)—, and —N(R$^L$)—SO$_2$—. More preferably, L is C$_{1-3}$ alkylene, wherein one —CH$_2$— unit comprised in said alkylene is optionally replaced by a group selected from —N(R$^L$)—, —N(R$^L$)—CO—, —CO—N(R$^L$)—, and —CO—. Accordingly, L be may, for example, —N(R$^L$)—, —N(R$^L$)—CH$_2$—, —CH$_2$—N(R$^L$)—, —CH$_2$—, —CH$_2$—CH$_2$—, —N(R$^L$)—CO—, —CO—N(R$^L$)—, —CO—, —CH$_2$—CO—, or —CO—CH$_2$—. It is particularly preferred that L is —N(R$^L$)—. Even more preferably, L is —NH—.

Each R$^L$ is independently selected from hydrogen and C$_{1-5}$ alkyl. Preferably, each R$^L$ is independently selected from hydrogen, methyl and ethyl. More preferably, each R$^L$ is hydrogen.

The ring group A is aryl or monocyclic heteroaryl, wherein said aryl or said monocyclic heteroaryl is optionally substituted with one or more (e.g., one, two or three) groups R$^A$.

Preferably, ring A is phenyl or monocyclic heteroaryl, wherein said phenyl or said monocyclic heteroaryl is optionally substituted with one or more (e.g., one, two or three; particularly one) groups R$^A$. It is preferred that said monocyclic heteroaryl is a 5- or 6-membered monocyclic heteroaryl (particularly a 6-membered monocyclic heteroaryl), which preferably comprises 1, 2 or 3 ring heteroatoms selected independently from nitrogen, oxygen and sulfur (wherein it is preferred that said 1, 2 or 3 ring heteroatoms are all nitrogen ring atoms), wherein the other ring atoms are all carbon ring atoms. Accordingly, said monocyclic heteroaryl may be, for example, pyridinyl, a diazinyl (e.g., pyrimidinyl, pyrazinyl, or pyridazinyl), or a triazinyl (e.g., 1,2,3-triazinyl, 1,2,4-triazinyl, or 1,3,5-triazinyl), wherein said pyridinyl, said diazinyl and said triazinyl are each optionally substituted with one or more groups R$^A$.

More preferably, ring A is selected from phenyl, pyridinyl (e.g., pyridin-2-yl, pyridin-3-yl, or pyridin-4-yl; particularly pyridin-2-yl), pyrimidinyl (e.g., pyrimidin-2-yl, pyrimidin-4-yl, or pyrimidin-5-yl), and pyrazinyl (e.g., pyrazin-2-yl), wherein said phenyl, said pyridinyl, said pyrimidinyl and said pyrazinyl are each optionally substituted with one or more groups R$^A$. Even more preferably, ring A is phenyl or pyridinyl (preferably pyridin-2-yl), wherein said phenyl or said pyridinyl is optionally substituted with one or more groups R$^A$. Still more preferably, ring A is pyridin-2-yl which is optionally substituted with one or more groups R$^A$.

It is preferred that ring A (including any one of the above-described preferred or exemplary ring groups A) is unsubstituted or is substituted with one group R$^A$.

Furthermore, if ring A is phenyl which is substituted with one group R$^A$ (e.g., halogen or —OCH$_3$; preferably —F), it is preferred that the group $R^A$ is attached to said phenyl in meta or para position (with respect to the point of attachment of the group L), more preferably in meta position (with respect to the group L). Alternatively, if ring A is pyridin-2-yl which is substituted with one group $R^A$ (e.g., halogen, such as —F or —Cl; preferably —F), it is preferred that the group $R^A$ is attached to said pyridin-2-yl in position 4 or 5, more preferably in position 4.

Each $R^A$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-SO—($C_{1-5}$ alkyl), —($C_{0-3}$ alkylene)-SO$_2$—($C_{1-5}$ alkyl), —($C_{0-3}$ alkylene)-carbocyclyl, and —($C_{0-3}$ alkylene)-heterocyclyl, wherein the carbocyclyl moiety of said —($C_{0-3}$ alkylene)-carbocyclyl and the heterocyclyl moiety of said —($C_{0-3}$ alkylene)-heterocyclyl are each optionally substituted with one or more (e.g., one, two or three) groups independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl.

Preferably, each $R^A$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl. More preferably, each $R^A$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —CF$_3$, and —CN. Even more preferably, each $R^A$ is independently selected from $C_{1-4}$ alkyl (e.g., methyl or ethyl), —OH, —O($C_{1-4}$ alkyl) (e.g., —OCH$_3$ or —OCH$_2$CH$_3$), —NH$_2$, —NH($C_{1-4}$ alkyl) (e.g., —NHCH$_3$), —N($C_{1-4}$ alkyl)($C_{1-4}$ alkyl) (e.g., —N(CH$_3$)$_2$), halogen (e.g., —F, —Cl, —Br, or —I), —CF$_3$, and —CN. It is particularly preferred that each $R^A$ is independently halogen, and still more preferably each $R^A$ is —F.

It is particularly preferred that the compound of formula (I) according to the present invention is one of the specific compounds of formula (I) described further below in the examples section of this specification, either in non-salt form (e.g., free base/acid form) or as a pharmaceutically acceptable salt, solvate or prodrug of the respective compound.

Accordingly, it is particularly preferred that the compound of formula (I) is selected from:

| No. | IUPAC name |
| --- | --- |
| 1 | [3-(2-fluoroanilino)-1-(2,2,2-trifluoroethyl)pyrazolo[4,3-c]pyridin-6-yl]-(1,4-oxazepan-4-yl)methanone |
| 2 | [3-anilino-1-(2,2,2-trifluoroethyl)pyrazolo[4,3-c]pyridin-6-yl]-(1,4-oxazepan-4-yl)methanone |
| 3 | [3-(2-methoxyanilino)-1-(2,2,2-trifluoroethyl)pyrazolo[4,3-c]pyridin-6-yl]-(1,4-oxazepan-4-yl)methanone |
| 4 | [3-(2-methylanilino)-1-(2,2,2-trifluoroethyl)pyrazolo[4,3-c]pyridin-6-yl]-(1,4-oxazepan-4-yl)methanone |
| 5 | [3-(N-methylanilino)-1-(2,2,2-trifluoroethyl)pyrazolo[4,3-c]pyridin-6-yl]-(1,4-oxazepan-4-yl)methanone |
| 6 | [3-(3-fluoroanilino)-1-(2,2,2-trifluoroethyl)pyrazolo[4,3-c]pyridin-6-yl]-(1,4-oxazepan-4-yl)methanone |
| 7 | [3-(3-methoxyanilino)-1-(2,2,2-trifluoroethyl)pyrazolo[4,3-c]pyridin-6-yl]-(1,4-oxazepan-4-yl)methanone |
| 8 | 3-[[6-(1,4-oxazepane-4-carbonyl)-1-(2,2,2-trifluoroethyl)pyrazolo[4,3-c]pyridin-3-yl]amino]benzonitrile |
| 9 | 3-[[6-(1,4-oxazepane-4-carbonyl)-1-(2,2,2-trifluoroethyl)pyrazolo[4,3-c]pyridin-3-yl]amino]benzamide |
| 10 | [3-(4-fluoroanilino)-1-(2,2,2-trifluoroethyl)pyrazolo[4,3-c]pyridin-6-yl]-(1,4-oxazepan-4-yl)methanone |
| 11 | [3-(4-methoxyanilino)-1-(2,2,2-trifluoroethyl)pyrazolo[4,3-c]pyridin-6-yl]-(1,4-oxazepan-4-yl)methanone |
| 12 | 1,4-oxazepan-4-yl-[3-(3-pyridylamino)-1-(2,2,2-trifluoroethyl)pyrazolo[4,3-c]pyridin-6-yl]methanone |
| 13 | 4-[[6-(1,4-oxazepane-4-carbonyl)-1-(2,2,2-trifluoroethyl)pyrazolo[4,3-c]pyridin-3-yl]amino]benzonitrile |

| No. | IUPAC name |
|---|---|
| 14 | 4-[[6-(1,4-oxazepane-4-carbonyl)-1-(2,2,2-trifluoroethyl)pyrazolo[4,3-c]pyridin-3-yl]amino]benzamide |
| 15 | [3-(3,5-difluoroanilino)-1-(2,2,2-trifluoroethyl)pyrazolo[4,3-c]pyridin-6-yl]-(1,4-oxazepan-4-yl)methanone |
| 16 | [3-(3-fluoro-4-methylanilino)-1-(2,2,2-trifluoroethyl)pyrazolo[4,3-c]pyridin-6-yl]-(1,4-oxazepan-4-yl)methanone |
| 17 | [3-(3,4-difluoroanilino)-1-(2,2,2-trifluoroethyl)pyrazolo[4,3-c]pyridin-6-yl]-(1,4-oxazepan-4-yl)methanone |
| 18 | [3-(3-chloro-4-fluoroanilino)-1-(2,2,2-trifluoroethyl)pyrazolo[4,3-c]pyridin-6-yl]-(1,4-oxazepan-4-yl)methanone |
| 19 | [3-(4-chloro-3-fluoroanilino)-1-(2,2,2-trifluoroethyl)pyrazolo[4,3-c]pyridin-6-yl]-(1,4-oxazepan-4-yl)methanone |
| 20 | [3-(3-fluoroanilino)-1-(2,2,2-trifluoroethyl)pyrazolo[4,3-c]pyridin-6-yl]-(8-oxa-3-azabicyclo[3.2.1]octan-3-yl)methanone |
| 21 | [3-(4-fluoroanilino)-1-(2,2,2-trifluoroethyl)pyrazolo[4,3-c]pyridin-6-yl]-(8-oxa-3-azabicyclo[3.2.1]octan-3-yl)methanone |
| 22 | [3-(4-fluoroanilino)-1-(2,2,2-trifluoroethyl)pyrazolo[4,3-c]pyridin-6-yl]-(4-hydroxy-1-piperidyl)methanone |
| 23 | [3-(3-fluoroanilino)-1-(2,2,2-trifluoroethyl)pyrazolo[4,3-c]pyridin-6-yl]-(4-hydroxy-1-piperidyl)methanone |
| 24 | (4-hydroxy-1-piperidyl)-[3-(2-pyridylamino)-1-(2,2,2-trifluoroethyl)pyrazolo[4,3-c]pyridin-6-yl]methanone |
| 25 | [3-(3-fluoroanilino)-1-(2,2,2-trifluoroethyl)pyrazolo[4,3-c]pyridin-6-yl]-(3-endo-hydroxy-8-azabicyclo[3.2.1]octan-8-yl)methanone |
| 26 | [3-(4-fluoroanilino)-1-(2,2,2-trifluoroethyl)pyrazolo[4,3-c]pyridin-6-yl]-(3-endo-hydroxy-8-azabicyclo[3.2.1]octan-8-yl)methanone |
| 27 | [3-(4-fluoroanilino)-1-(methylsulfonylmethyl)pyrazolo[4,3-c]pyridin-6-yl]-(1,4-oxazepan-4-yl)methanone |
| 28 | [3-(3-fluoroanilino)-1-(methylsulfonylmethyl)pyrazolo[4,3-c]pyridin-6-yl]-(1,4-oxazepan-4-yl)methanone |
| 29 | [3-anilino-1-(methylsulfonylmethyl)pyrazolo[4,3-c]pyridin-6-yl]-(3-endo-hydroxy-8-azabicyclo[3.2.1]octan-8-yl)methanone |
| 30 | [3-(4-fluoroanilino)-1-(methylsulfonylmethyl)pyrazolo[4,3-c]pyridin-6-yl]-(3-endo-hydroxy-8-azabicyclo[3.2.1]octan-8-yl)methanone |
| 31 | [3-(3-fluoroanilino)-1-(methylsulfonylmethyl)pyrazolo[4,3-c]pyridin-6-yl]-(3-endo-hydroxy-8-azabicyclo[3.2.1]octan-8-yl)methanone |
| 32 | [3-(3-fluoroanilino)-1-(2,2,2-trifluoroethyl)pyrazolo[4,3-c]pyridin-6-yl]-(6-hydroxy-1,4-oxazepan-4-yl)methanone |
| 33 | [3-(4-fluoroanilino)-1-(2,2,2-trifluoroethyl)pyrazolo[4,3-c]pyridin-6-yl]-(6-hydroxy-1,4-oxazepan-4-yl)methanone |
| 34 | [3-(4-fluoroanilino)-1-(2,2,2-trifluoroethyl)pyrazolo[4,3-c]pyridin-6-yl]-(4-hydroxy-4-methyl-1-piperidyl)methanone |
| 35 | [3-(3-fluoroanilino)-1-(2,2,2-trifluoroethyl)pyrazolo[4,3-c]pyridin-6-yl]-(4-hydroxy-4-methyl-1-piperidyl)methanone |
| 36 | 1,4-oxazepan-4-yl-[3-(pyrimidin-2-ylamino)-1-(2,2,2-trifluoroethyl)pyrazolo[4,3-c]pyridin-6-yl]methanone |
| 37 | [3-(3-chloroanilino)-1-(2,2,2-trifluoroethyl)pyrazolo[4,3-c]pyridin-6-yl]-(1,4-oxazepan-4-yl)methanone |
| 38 | [3-(4-chloroanilino)-1-(2,2,2-trifluoroethyl)pyrazolo[4,3-c]pyridin-6-yl]-(1,4-oxazepan-4-yl)methanone |
| 39 | [3-(2-chloroanilino)-1-(2,2,2-trifluoroethyl)pyrazolo[4,3-c]pyridin-6-yl]-(1,4-oxazepan-4-yl)methanone |
| 40 | (6,6-dideuterio-1,4-oxazepan-4-yl)-[3-(3-fluoroanilino)-1-(2,2,2-trifluoroethyl)pyrazolo[4,3-c]pyridin-6-yl]methanone |
| 41 | (6,6-dideuterio-1,4-oxazepan-4-yl)-[3-(4-fluoroanilino)-1-(2,2,2-trifluoroethyl)pyrazolo[4,3-c]pyridin-6-yl]methanone |
| 42 | 1,4-oxazepan-4-yl-[3-(2-pyridylamino)-1-(2,2,2-trifluoroethyl)pyrazolo[4,3-c]pyridin-6-yl]methanone |
| 43 | 1,4-oxazepan-4-yl-[3-(4-pyridylamino)-1-(2,2,2-trifluoroethyl)pyrazolo[4,3-c]pyridin-6-yl]methanone |
| 44 | [3-[(5-fluoro-2-pyridyl)amino]-1-(2,2,2-trifluoroethyl)pyrazolo[4,3-c]pyridin-6-yl]-(1,4-oxazepan-4-yl)methanone |
| 45 | [3-[(6-methoxy-2-pyridyl)amino]-1-(2,2,2-trifluoroethyl)pyrazolo[4,3-c]pyridin-6-yl]-(1,4-oxazepan-4-yl)methanone |
| 46 | [3-[(4-fluoro-2-pyridyl)amino]-1-(2,2,2-trifluoroethyl)pyrazolo[4,3-c]pyridin-6-yl]-(1,4-oxazepan-4-yl)methanone |
| 47 | 8-oxa-3-azabicyclo[3.2.1]octan-3-yl-[3-(2-pyridylamino)-1-(2,2,2-trifluoroethyl)pyrazolo[4,3-c]pyridin-6-yl]methanone |
| 48 | [3-[(5-chloro-2-pyridyl)amino]-1-(2,2,2-trifluoroethyl)pyrazolo[4,3-c]pyridin-6-yl]-(1,4-oxazepan-4-yl)methanone |
| 49 | [3-[(6-fluoro-2-pyridyl)amino]-1-(2,2,2-trifluoroethyl)pyrazolo[4,3-c]pyridin-6-yl]-(1,4-oxazepan-4-yl)methanone |
| 50 | [3-[(5-methoxy-3-methyl-2-pyridyl)amino]-1-(2,2,2-trifluoroethyl)pyrazolo[4,3-c]pyridin-6-yl]-(1,4-oxazepan-4-yl)methanone |

| No. | IUPAC name |
|---|---|
| 51 | [3-[(6-chloro-2-pyridyl)amino]-1-(2,2,2-trifluoroethyl)pyrazolo[4,3-c]pyridin-6-yl]-(1,4-oxazepan-4-yl)methanone |
| 52 | (6-hydroxy-1,4-oxazepan-4-yl)-[3-(2-pyridylamino)-1-(2,2,2-trifluoroethyl)pyrazolo[4,3-c]pyridin-6-yl]methanone |
| 53 | (4-hydroxy-4-methyl-1-piperidyl)-[3-(2-pyridylamino)-1-(2,2,2-trifluoroethyl)pyrazolo[4,3-c]pyridin-6-yl]methanone |
| 54 | [3-[(3-fluoro-2-pyridyl)amino]-1-(2,2,2-trifluoroethyl)pyrazolo[4,3-c]pyridin-6-yl]-(1,4-oxazepan-4-yl)methanone |
| 55 | [3-[(3-chloro-2-pyridyl)amino]-1-(2,2,2-trifluoroethyl)pyrazolo[4,3-c]pyridin-6-yl]-(1,4-oxazepan-4-yl)methanone |
| 56 | [3-[(5-fluoro-3-methyl-2-pyridyl)amino]-1-(2,2,2-trifluoroethyl)pyrazolo[4,3-c]pyridin-6-yl]-(1,4-oxazepan-4-yl)methanone |
| 57 | [3-[(5-fluoro-4-methyl-2-pyridyl)amino]-1-(2,2,2-trifluoroethyl)pyrazolo[4,3-c]pyridin-6-yl]-(1,4-oxazepan-4-yl)methanone |
| 58 | [3-[(5-fluoro-6-methyl-2-pyridyl)amino]-1-(2,2,2-trifluoroethyl)pyrazolo[4,3-c]pyridin-6-yl]-(1,4-oxazepan-4-yl)methanone |
| 59 | (6,6-dideuterio-1,4-oxazepan-4-yl)-[3-(2-pyridylamino)-1-(2,2,2-trifluoroethyl)pyrazolo[4,3-c]pyridin-6-yl]methanone |
| 60 | (6,6-dideuterio-1,4-oxazepan-4-yl)-[3-[(4-fluoro-2-pyridyl)amino]-1-(2,2,2-trifluoroethyl)pyrazolo[4,3-c]pyridin-6-yl]methanone |
| 61 | 1,4-oxazepan-4-yl-[3-(pyrazin-2-ylamino)-1-(2,2,2-trifluoroethyl)pyrazolo[4,3-c]pyridin-6-yl]methanone |
| 62 | 1,4-oxazepan-4-yl-[1-(2,2,2-trifluoroethyl)-3-[[4-(trifluoromethyl)-2-pyridyl]amino]pyrazolo[4,3-c]pyridin-6-yl]methanone |
| 63 | [3-[(4-methoxy-2-pyridyl)amino]-1-(2,2,2-trifluoroethyl)pyrazolo[4,3-c]pyridin-6-yl]-(1,4-oxazepan-4-yl)methanone |
| 64 | [3-[(4-chloro-2-pyridyl)amino]-1-(2,2,2-trifluoroethyl)pyrazolo[4,3-c]pyridin-6-yl]-(1,4-oxazepan-4-yl)methanone |
| 65 | [3-[(6-chloro-5-fluoro-2-pyridyl)amino]-1-(2,2,2-trifluoroethyl)pyrazolo[4,3-c]pyridin-6-yl]-(1,4-oxazepan-4-yl)methanone |
| 66 | [3-[(4-chloro-5-fluoro-2-pyridyl)amino]-1-(2,2,2-trifluoroethyl)pyrazolo[4,3-c]pyridin-6-yl]-(1,4-oxazepan-4-yl)methanone |
| 67 | [3-[(3-chloro-5-fluoro-2-pyridyl)amino]-1-(2,2,2-trifluoroethyl)pyrazolo[4,3-c]pyridin-6-yl]-(1,4-oxazepan-4-yl)methanone |
| 68 | [3-[(4-methyl-2-pyridyl)amino]-1-(2,2,2-trifluoroethyl)pyrazolo[4,3-c]pyridin-6-yl]-(1,4-oxazepan-4-yl)methanone |
| 69 | 1,4-oxazepan-4-yl-[3-(pyridazin-3-ylamino)-1-(2,2,2-trifluoroethyl)pyrazolo[4,3-c]pyridin-6-yl]methanone |
| 70 | [3-[(4-fluoro-3-methyl-2-pyridyl)amino]-1-(2,2,2-trifluoroethyl)pyrazolo[4,3-c]pyridin-6-yl]-(1,4-oxazepan-4-yl)methanone |
| 71 | [3-[(5-chloro-4-fluoro-2-pyridyl)amino]-1-(2,2,2-trifluoroethyl)pyrazolo[4,3-c]pyridin-6-yl]-(1,4-oxazepan-4-yl)methanone |
| 72 | [3-[(3,5-difluoro-2-pyridyl)amino]-1-(2,2,2-trifluoroethyl)pyrazolo[4,3-c]pyridin-6-yl]-(1,4-oxazepan-4-yl)methanone |
| 73 | [1,4]Oxazepan-4-yl-[3-(pyrimidin-4-ylamino)-1-(2,2,2-trifluoro-ethyl)-1H-pyrazolo[4,3-c]pyridin-6-yl]-methanone |
| 74 | (4-Hydroxy-piperidin-1-yl)-[3-(pyrazin-2-ylamino)-1-(2,2,2-trifluoro-ethyl)-1H-pyrazolo[4,3-c]pyridin-6-yl]-methanone |
| 75 | [3-(5-Chloro-pyrazin-2-ylamino)-1-(2,2,2-trifluoro-ethyl)-1H-pyrazolo[4,3-c]pyridin-6-yl]-(4-hydroxy-piperidin-1-yl)-methanone |
| 76 | (4-Hydroxy-piperidin-1-yl)-[3-(pyrimidin-4-ylamino)-1-(2,2,2-trifluoro-ethyl)-1H-pyrazolo[4,3-c]pyridin-6-yl]-methanone |
| 77 | [3-(5-Fluoro-pyridin-2-ylamino)-1-methanesulfonylmethyl-1H-pyrazolo[4,3-c]pyridin-6-yl]-[1,4]oxazepan-4-yl-methanone |
| 78 | [3-(5-Chloro-pyridin-2-ylamino)-1-methanesulfonylmethyl-1H-pyrazolo[4,3-c]pyridin-6-yl]-[1,4]oxazepan-4-yl-methanone |
| 79 | [3-(4-Chloro-pyridin-2-ylamino)-1-methanesulfonylmethyl-1H-pyrazolo[4,3-c]pyridin-6-yl]-[1,4]oxazepan-4-yl-methanone |
| 80 | [3-[(5,6-difluoro-2-pyridyl)amino]-1-(2,2,2-trifluoroethyl)pyrazolo[4,3-c]pyridin-6-yl]-(1,4-oxazepan-4-yl)methanone |
| 81 | [3-[(5-fluoro-4-methoxy-2-pyridyl)amino]-1-(2,2,2-trifluoroethyl)pyrazolo[4,3-c]pyridin-6-yl]-(1,4-oxazepan-4-yl)methanone |
| 82 | [3-[(5-fluoro-6-methoxy-2-pyridyl)amino]-1-(2,2,2-trifluoroethyl)pyrazolo[4,3-c]pyridin-6-yl]-(1,4-oxazepan-4-yl)methanone |
| 83 | [3-(5-Methoxy-pyridin-2-ylamino)-1-(2,2,2-trifluoro-ethyl)-1H-pyrazolo[4,3-c]pyridin-6-yl]-[1,4]oxazepan-4-yl-methanone |
| 84 | [1,4]Oxazepan-4-yl-[3-(thiazol-5-ylamino)-1-(2,2,2-trifluoro-ethyl)-1H-pyrazolo[4,3-c]pyridin-6-yl]methanone |
| 85 | [1,4]Oxazepan-4-yl-[3-(thiazol-2-ylamino)-1-(2,2,2-trifluoro-ethyl)-1H-pyrazolo[4,3-c]pyridin-6-yl]methanone |
| 86 | 6-[6-([1,4]Oxazepane-4-carbonyl)-1-(2,2,2-trifluoro-ethyl)-1H-pyrazolo[4,3-c]pyridin-3-ylamino]-1H-pyridin-2-one |
| 87 | 3-[[6-(1,4-oxazepane-4-carbonyl)-1-(2,2,2-trifluoroethyl)pyrazolo[4,3-c]pyridin-3-yl]amino]-1H-pyridin-2-one |
| 88 | [3-[(5-fluoro-4-hydroxy-2-pyridyl)amino]-1-(2,2,2-trifluoroethyl)pyrazolo[4,3-c]pyridin-6-yl]-(1,4-oxazepan-4-yl)methanone |

| No. | IUPAC name |
|---|---|
| 89 | [3-[(5-fluoro-3-hydroxy-2-pyridyl)amino]-1-(2,2,2-trifluoroethyl)pyrazolo[4,3-c]pyridin-6-yl]-(1,4-oxazepan-4-yl)methanone |
| 90 | [3-[(4-fluoro-3-hydroxy-2-pyridyl)amino]-1-(2,2,2-trifluoroethyl)pyrazolo[4,3-c]pyridin-6-yl]-(1,4-oxazepan-4-yl)methanone |
| 91 | (6,6-dideuterio-1,4-oxazepan-4-yl)-[3-[(5-fluoro-2-pyridyl)amino]-1-(2,2,2-trifluoroethyl)pyrazolo[4,3-c]pyridin-6-yl]methanone |
| 92 | [3-[(5-fluoro-2-pyridyl)amino]-1-(2,2,2-trifluoroethyl)pyrazolo[4,3-c]pyridin-6-yl]-(6-hydroxy-1,4-oxazepan-4-yl)methanone |
| 93 | [(6S)-6-fluoro-1,4-oxazepan-4-yl]-[3-[(5-fluoro-2-pyridyl)amino]-1-(2,2,2-trifluoroethyl)pyrazolo[4,3-c]pyridin-6-yl]methanone |
| 94 | [3-[(5-fluoro-2-pyridyl)amino]-1-(2,2,2-trifluoroethyl)pyrazolo[4,3-c]pyridin-6-yl]-(4-hydroxypiperidin-1-yl)methanone |
| 95 | [3-(5-Fluoro-pyridin-2-ylamino)-1-(2,2,2-trifluoro-ethyl)-1H-pyrazolo[4,3-c]pyridin-6-yl]-(4-hydroxy-4-methyl-piperidin-1-yl)-methanone |
| 96 | (4-Fluoro-piperidin-1-yl)-[3-(5-fluoro-pyridin-2-ylamino)-1-(2,2,2-trifluoro-ethyl)-1H-pyrazolo[4,3-c]pyridin-6-yl]-methanone |
| 97 | [(3R)-3-hydroxy-piperidin-1-yl]-[3-(5-Fluoro-pyridin-2-ylamino)-1-(2,2,2-trifluoro-ethyl)-1H-pyrazolo[4,3-c]pyridin-6-yl]-methanone |
| 98 | [(3S)-3-hydroxy-piperidin-1-yl]-[3-(5-Fluoro-pyridin-2-ylamino)-1-(2,2,2-trifluoro-ethyl)-1H-pyrazolo[4,3-c]pyridin-6-yl]methanone |
| 99 | [(3R)-3-fluoro-piperidin-1-yl]-[3-(5-Fluoro-pyridin-2-ylamino)-1-(2,2,2-trifluoro-ethyl)-1H-pyrazolo[4,3-c]pyridin-6-yl]methanone |
| 100 | [(3S)-3-fluoro-piperidin-1-yl]-[3-(5-Fluoro-pyridin-2-ylamino)-1-(2,2,2-trifluoro-ethyl)-1H-pyrazolo[4,3-c]pyridin-6-yl]methanone |
| 101 | [3-[(5-fluoro-2-pyridyl)amino]-1-(2,2,2-trifluoroethyl)pyrazolo[4,3-c]pyridin-6-yl]-[(3R)-3-(hydroxymethyl)-1-piperidyl]methanone |
| 102 | [3-[(5-fluoro-2-pyridyl)amino]-1-(2,2,2-trifluoroethyl)pyrazolo[4,3-c]pyridin-6-yl]-[(3S)-3-(hydroxymethyl)-1-piperidyl]methanone |
| 103 | (3,3-Difluoro-4-hydroxy-piperidin-1-yl)-[3-(5-fluoro-pyridin-2-ylamino)-1-(2,2,2-trifluoro-ethyl)-1H-pyrazolo[4,3-c]pyridin-6-yl]-methanone |
| 104 | [3-[(5-fluoro-2-pyridyl)amino]-1-(2,2,2-trifluoroethyl)pyrazolo[4,3-c]pyridin-6-yl]-(3-hydroxy-3-methyl-piperidin-1-yl)methanone |
| 105 | Cis-[3-(5-Fluoro-pyridin-2-ylamino)-1-(2,2,2-trifluoro-ethyl)-1H-pyrazolo[4,3-c]pyridin-6-yl]-(3-hydroxy-4-methyl-piperidin-1-yl)-methanone |
| 106 | Cis-(3-Fluoro-4-hydroxy-piperidin-1-yl)-[3-(5-fluoro-pyridin-2-ylamino)-1-(2,2,2-trifluoro-ethyl)-1H-pyrazolo[4,3-c]pyridin-6-yl]-methanone |
| 107 | [3-[(5-fluoro-2-pyridyl)amino]-1-(2,2,2-trifluoroethyl)pyrazolo[4,3-c]pyridin-6-yl]-(3-endo-hydroxy-8-azabicyclo[3.2.1]octan-8-yl)methanone |
| 108 | 1-[3-[(5-fluoro-2-pyridyl)amino]-1-(2,2,2-trifluoroethyl)pyrazolo[4,3-c]pyridine-6-carbonyl]pyridine-4-carboxylic acid |
| 109 | [3-[(4-fluoro-2-pyridyl)amino]-1-(2,2,2-trifluoroethyl)pyrazolo[4,3-c]pyridin-6-yl]-(6-hydroxy-1,4-oxazepan-4-yl)methanone |
| 110 | [(6S)-6-fluoro-1,4-oxazepan-4-yl]-[3-(4-fluoro-pyridin-2-ylamino)-1-(2,2,2-trifluoro-ethyl)-1H-pyrazolo[4,3-c]pyridin-6-yl]-methanone |
| 111 | [3-[(4-fluoro-2-pyridyl)amino]-1-(2,2,2-trifluoroethyl)pyrazolo[4,3-c]pyridin-6-yl]-(4-hydroxypiperidin-1-yl)methanone |
| 112 | [3-(4-Fluoro-pyridin-2-ylamino)-1-(2,2,2-trifluoro-ethyl)-1H-pyrazolo[4,3-c]pyridin-6-yl]-(4-hydroxy-4-methyl-piperidin-1-yl)-methanone |
| 113 | [3-(4-Fluoro-pyridin-2-ylamino)-1-(2,2,2-trifluoro-ethyl)-1H-pyrazolo[4,3-c]pyridin-6-yl]-(4-ethyl-4-hydroxypiperidin-1-yl)-methanone |
| 114 | [3-(4-Fluoro-pyridin-2-ylamino)-1-(2,2,2-trifluoro-ethyl)-1H-pyrazolo[4,3-c]pyridin-6-yl]-(4-isopropyl-4-hydroxypiperidin-1-yl)-methanone |
| 115 | [3-(4-Fluoro-pyridin-2-ylamino)-1-(2,2,2-trifluoro-ethyl)-1H-pyrazolo[4,3-c]pyridin-6-yl]-(4-cyclopropyl-4-hydroxypiperidin-1-yl)-methanone |
| 116 | (4-Fluoro-piperidin-1-yl)-[3-(4-fluoro-pyridin-2-ylamino)-1-(2,2,2-trifluoro-ethyl)-1H-pyrazolo[4,3-c]pyridin-6-yl]-methanone |
| 117 | [(3S)-3-hydroxy-piperidin-1-yl]-[3-(4-fluoro-pyridin-2-ylamino)-1-(2,2,2-trifluoro-ethyl)-1H-pyrazolo[4,3-c]pyridin-6-yl]methanone |
| 118 | [3-(4-Fluoro-pyridin-2-ylamino)-1-(2,2,2-trifluoro-ethyl)-1H-pyrazolo[4,3-c]pyridin-6-yl]-(4-hydroxy-2,2-dimethyl-piperidin-1-yl)-methanone |
| 119 | (3,3-Difluoro-4-hydroxy-piperidin-1-yl)-[3-(4-fluoro-pyridin-2-ylamino)-1-(2,2,2-trifluoro-ethyl)-1H-pyrazolo[4,3-c]pyridin-6-yl]-methanone |
| 120 | [3-[(4-fluoro-2-pyridyl)amino]-1-(2,2,2-trifluoroethyl)pyrazolo[4,3-c]pyridin-6-yl]-(3-endo-hydroxy-8-azabicyclo[3.2.1]octan-8-yl)methanone |
| 121 | 6,6-dideuterio-1,4-oxazepan-4-yl)-[3-(pyrazin-2ylamino)-1-(2,2,2-trifluoroethyl)pyrazolo[4,3-c]pyridin-6-yl]methanone |
| 122 | [(6S)-6-fluoro-1,4-oxazepan-4-yl]-[3-(pyrazin-2ylamino)-1-(2,2,2-trifluoro-ethyl)-1H-pyrazolo[4,3-c]pyridin-6-yl]-methanone |
| 123 | [3-(pyrazin-2ylamino)-1-(2,2,2-trifluoro-ethyl)-1H-pyrazolo[4,3-c]pyridin-6-yl]-(4-hydroxy-4-methyl-piperidin-1-yl)-methanone |
| 124 | [3-(pyrazin-2ylamino)-1-(2,2,2-trifluoro-ethyl)-1H-pyrazolo[4,3-c]pyridin-6-yl]-(4-fluoro-piperidin-1-yl)-methanone |
| 125 | [3-[(5-fluoro-2-pyridyl)amino]-1-(2,2,2-trifluoroethyl)pyrazolo[4,3-c]pyridin-6-yl]-[(2R)-2-(2-hydroxy-2-methyl-propyl)pyrrolidin-1-yl]methanone |

| No. | IUPAC name |
|---|---|
| 126 | [3-[(5-fluoro-2-pyridyl)amino]-1-(2,2,2-trifluoroethyl)pyrazolo[4,3-c]pyridin-6-yl]-[(2S)-2-(2-hydroxy-2-methyl-propyl)pyrrolidin-1-yl]methanone |
| 127 | (3-endo-hydroxy-8-azabicyclo[3.2.1]octan-8-yl)-[3-(2-pyridylamino)-1-(2,2,2-trifluoroethyl)pyrazolo[4,3-c]pyridin-6-yl]methanone | and pharmaceutically acceptable salts, solvates and prodrugs of any one of these compounds.

The present invention also relates to each of the intermediates described further below in the examples section of this specification, including any one of these intermediates in non-salt form or in the form of a salt (e.g., a pharmaceutically acceptable salt) of the respective compound. Such intermediates can be used, in particular, in the synthesis of the compounds of formula (I).

In a first specific embodiment, the present invention relates to a compound of formula (I) or a pharmaceutically acceptable salt, solvate or prodrug thereof, wherein the groups/variables in formula (I) have the following meanings:

The groups $R^{1A}$ and $R^{1B}$ are mutually linked to form, together with the nitrogen atom that they are attached to, a heterocycloalkyl group which is selected from

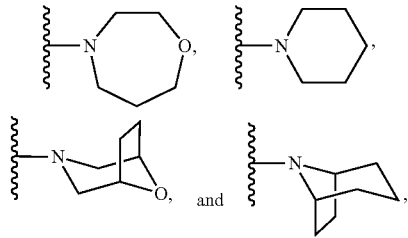

wherein each one of the above-depicted heterocycloalkyl groups is optionally substituted with one or more groups $R^{11}$.

Preferably, $R^{1A}$ and $R^{1B}$ are mutually linked to form, together with the nitrogen atom that they are attached to, a group which is selected from

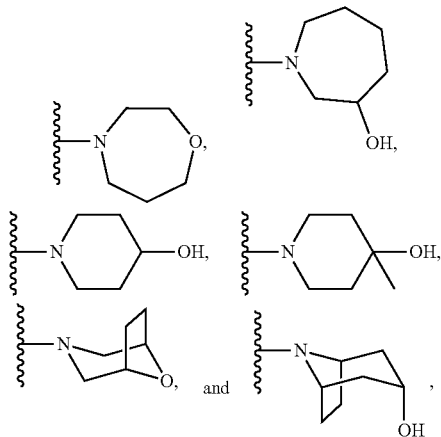

wherein each one of the above-depicted groups is optionally substituted with one or more $R^{11}$.

More preferably, $R^{1A}$ and $R^{1B}$ are mutually linked to form, together with the nitrogen atom that they are attached to, a group which is selected from

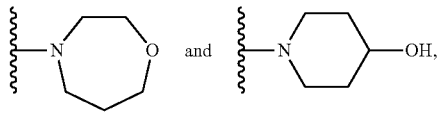 [SMILES: *N1CCCOCC1 ; "and" ; *N1CCC(O)CC1]

wherein each one of the above-depicted groups is optionally substituted with one or more $R^{11}$.

In this first embodiment, each $R^{11}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl. Preferably, each $R^{11}$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —CF$_3$, and —CN. More preferably, each $R^{11}$ is independently selected from $C_{1-4}$ alkyl (e.g., methyl or ethyl), —OH, —O($C_{1-4}$ alkyl) (e.g., —OCH$_3$ or —OCH$_2$CH$_3$), —NH$_2$, —NH($C_{1-4}$ alkyl) (e.g., —NHCH$_3$), —N($C_{1-4}$ alkyl)($C_{1-4}$ alkyl) (e.g., —N(CH$_3$)$_2$), halogen (e.g., —F, —Cl, —Br, or —I), —CF$_3$, and —CN.

In this first embodiment, $R^2$ and $R^4$ are each independently selected from hydrogen, $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —(C$_{0-3}$ alkylene)-SO—(C$_{1-5}$ alkyl), —(C$_{0-3}$ alkylene)-SO$_2$—(C$_{1-5}$ alkyl), —(C$_{0-3}$ alkylene)-cycloalkyl, and —(C$_{0-3}$ alkylene)-heterocycloalkyl. Preferably, R$^2$ and R$^4$ are each independently selected from hydrogen, C$_{1-5}$ alkyl, C$_{2-5}$ alkenyl, C$_{2-5}$ alkynyl, —OH, —O(C$_{1-5}$ alkyl), —O(C$_{1-5}$ alkylene)-OH, —O(C$_{1-5}$ alkylene)-O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —O—(C$_{1-5}$ haloalkyl), —CF$_3$, —CN, —NO$_2$, —CHO, —CO—(C$_{1-5}$ alkyl), —COOH, —CO—O—(C$_{1-5}$ alkyl), —O—CO—(C$_{1-5}$ alkyl), —CO—NH$_2$, —CO—NH(C$_{1-5}$ alkyl), —CO—N(C$_{1-5}$ alkyl)(C$_{1-5}$ alkyl), —NH—CO—(C$_{1-5}$ alkyl), —N(C$_{1-5}$ alkyl)-CO—(C$_{1-5}$ alkyl), —SO$_2$—NH$_2$, —SO$_2$—NH(C$_{1-5}$ alkyl), —SO$_2$—N(C$_{1-5}$ alkyl)(C$_{1-5}$ alkyl), —NH—SO$_2$—(C$_{1-5}$ alkyl), —N(C$_{1-5}$ alkyl)-SO$_2$—(C$_{1-5}$ alkyl), —SO—(C$_{1-5}$ alkyl), —SO$_2$—(C$_{1-5}$ alkyl), cycloalkyl, and heterocycloalkyl. More preferably, R$^2$ and R$^4$ are each independently selected from hydrogen, C$_{1-5}$ alkyl, —OH, —O(C$_{1-5}$ alkyl), —O(C$_{1-5}$ alkylene)-OH, —O(C$_{1-5}$ alkylene)-O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —CF$_3$, and —CN. Even more preferably, R$^2$ and R$^4$ are each independently selected from hydrogen, C$_{1-4}$ alkyl (e.g., methyl or ethyl), —OH, —O(C$_{1-4}$ alkyl) (e.g., —OCH$_3$ or —OCH$_2$CH$_3$), —NH$_2$, —NH(C$_{1-4}$ alkyl) (e.g., —NHCH$_3$), —N(C$_{1-4}$ alkyl)(C$_{1-4}$ alkyl) (e.g., —N(CH$_3$)$_2$), halogen (e.g., —F, —Cl, —Br, or —I), —CF$_3$, and —CN. Still more preferably, R$^2$ and R$^4$ are each hydrogen.

In this first embodiment, R$^3$ is selected from C$_{1-5}$ haloalkyl, —(C$_{1-5}$ alkylene)-SO—(C$_{1-5}$ alkyl) and —(C$_{1-5}$ alkylene)-SO$_2$—(C$_{1-5}$ alkyl). Preferably, R$^3$ is selected from C$_{1-3}$ haloalkyl (e.g., —CH$_2$—CF$_3$, —CH$_2$—CHF$_2$, or —CH$_2$—CH$_2$F), —(C$_{1-3}$ alkylene)-SO—(C$_{1-3}$ alkyl) (e.g., —CH$_2$—SO—CH$_3$) and —(C$_{1-3}$ alkylene)-SO$_2$—(C$_{1-3}$ alkyl) (e.g., —CH$_2$—SO$_2$—CH$_3$). More preferably, R$^3$ is —CH$_2$—CF$_3$ or —CH$_2$—SO$_2$—CH$_3$.

In this first embodiment, L is —N(R$^L$)—, wherein R$^L$ is selected from hydrogen and C$_{1-5}$ alkyl. Preferably, L is —NH—.

In this first embodiment, the ring group A is aryl or monocyclic heteroaryl, wherein said aryl or said monocyclic heteroaryl is optionally substituted with one or more (e.g., one, two or three) groups R$^A$. Preferably, ring A is phenyl or monocyclic heteroaryl, wherein said phenyl or said monocyclic heteroaryl is optionally substituted with one or more (e.g., one, two or three; particularly one) groups R$^A$. It is preferred that said monocyclic heteroaryl is a 5- or 6-membered monocyclic heteroaryl (particularly a 6-membered monocyclic heteroaryl), which preferably comprises 1, 2 or 3 ring heteroatoms selected independently from nitrogen, oxygen and sulfur (wherein it is preferred that said 1, 2 or 3 ring heteroatoms are all nitrogen ring atoms), wherein the other ring atoms are all carbon ring atoms. Accordingly, said monocyclic heteroaryl may be, for example, pyridinyl, a diazinyl (e.g., pyrimidinyl, pyrazinyl, or pyridazinyl), or a triazinyl (e.g., 1,2,3-triazinyl, 1,2,4-triazinyl, or 1,3,5-triazinyl), wherein said pyridinyl, said diazinyl and said triazinyl are each optionally substituted with one or more groups R$^A$. More preferably, ring A is selected from phenyl, pyridinyl (e.g., pyridin-2-yl, pyridin-3-yl, or pyridin-4-yl; particularly pyridin-2-yl), pyrimidinyl (e.g., pyrimidin-2-yl, pyrimidin-4-yl, or pyrimidin-5-yl), and pyrazinyl (e.g., pyrazin-2-yl), wherein said phenyl, said pyridinyl, said pyrimidinyl and said pyrazinyl are each optionally substituted with one or more groups R$^A$. Even more preferably, ring A is phenyl or pyridinyl (preferably pyridin-2-yl), wherein said phenyl or said pyridinyl is optionally substituted with one or more groups R$^A$. Still more preferably, ring A is pyridin-2-yl which is optionally substituted with one or more groups R$^A$.

It is preferred that ring A (including any one of the above-described preferred or exemplary ring groups A) is unsubstituted or is substituted with one group R$^A$. Furthermore, if ring A is phenyl which is substituted with one group R$^A$ (e.g., halogen or —OCH$_3$; preferably —F), it is preferred that the group R$^A$ is attached to said phenyl in meta or para position (with respect to the point of attachment of the group L), more preferably in meta position (with respect to the group L). Alternatively, if ring A is pyridin-2-yl which is substituted with one group R$^A$ (e.g., halogen, such as —F or —Cl; preferably —F), it is preferred that the group R$^A$ is attached to said pyridin-2-yl in position 4 or 5, more preferably in position 4.

In this first embodiment, each R$^A$ is independently selected from C$_{1-5}$ alkyl, C$_{2-5}$ alkenyl, C$_{2-5}$ alkynyl, —OH, —O(C$_{1-5}$ alkyl), —O(C$_{1-5}$ alkylene)-OH, —O(C$_{1-5}$ alkylene)-O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —O—(C$_{1-5}$ haloalkyl), —CF$_3$, —CN, —NO$_2$, —CHO, —CO—(C$_{1-5}$ alkyl), —COOH, —CO—O—(C$_{1-5}$ alkyl), —O—CO—(C$_{1-5}$ alkyl), —CO—NH$_2$, —CO—NH(C$_{1-5}$ alkyl), —CO—N(C$_{1-5}$ alkyl)(C$_{1-5}$ alkyl), —NH—CO—(C$_{1-5}$ alkyl), —N(C$_{1-5}$ alkyl)-CO—(C$_{1-5}$ alkyl), —SO$_2$—NH$_2$, —SO$_2$—NH(C$_{1-5}$ alkyl), —SO$_2$—N(C$_{1-5}$ alkyl)(C$_{1-5}$ alkyl), —NH—SO$_2$—(C$_{1-5}$ alkyl), —N(C$_{1-5}$ alkyl)-SO$_2$—(C$_{1-5}$ alkyl), —SO—(C$_{1-5}$ alkyl), —SO$_2$—(C$_{1-5}$ alkyl), cycloalkyl, and heterocycloalkyl. Preferably, each R$^A$ is independently selected from C$_{1-5}$ alkyl, —OH, —O(C$_{1-5}$ alkyl), —O(C$_{1-5}$ alkylene)-OH, —O(C$_{1-5}$ alkylene)-O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —CF$_3$, and —CN. More preferably, each R$^A$ is independently selected from C$_{1-4}$ alkyl (e.g., methyl or ethyl), —OH, —O(C$_{1-4}$ alkyl) (e.g., —OCH$_3$ or —OCH$_2$CH$_3$), —NH$_2$, —NH(C$_{1-4}$ alkyl) (e.g., —NHCH$_3$), —N(C$_{1-4}$ alkyl)(C$_{1-4}$ alkyl) (e.g., —N(CH$_3$)$_2$), halogen (e.g., —F, —Cl, —Br, or —I), —CF$_3$, and —CN. It is particularly preferred that each R$^A$ is independently halogen, and still more preferably each R$^A$ is —F.

In a second specific embodiment, the present invention relates to a compound of formula (I) or a pharmaceutically acceptable salt, solvate or prodrug thereof, wherein the groups/variables in formula (I) have the following meanings:

The groups R$^{1A}$ and R$^{1B}$ are mutually linked to form, together with the nitrogen atom that they are attached to, a heterocycloalkyl group which is selected from

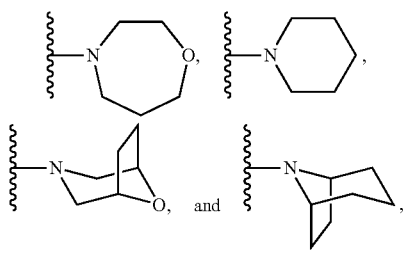

wherein each one of the above-depicted heterocycloalkyl groups is optionally substituted with one or more groups R$^{11}$.

Preferably, $R^{1A}$ and $R^{1B}$ are mutually linked to form, together with the nitrogen atom that they are attached to, a group which is selected from

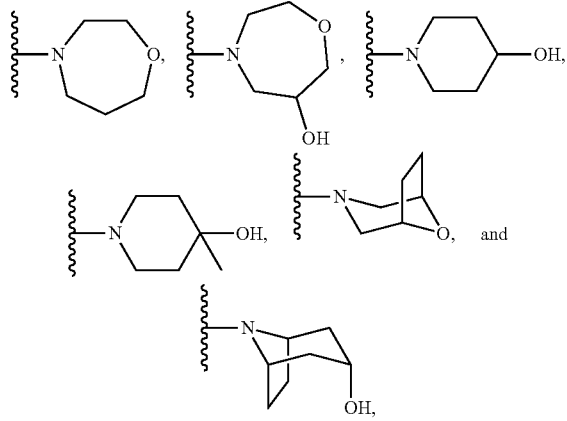

wherein each one of the above-depicted groups is optionally substituted with one or more $R^{11}$.

More preferably, $R^{1A}$ and $R^{1B}$ are mutually linked to form, together with the nitrogen atom that they are attached to, a group which is selected from

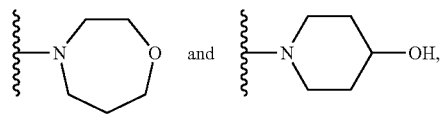 [SMILES: *N1CCCOCC1 ; "and" ; *N1CCC(O)CC1]

wherein each one of the above-depicted groups is optionally substituted with one or more $R^{11}$.

In this second embodiment, each $R^{11}$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl. Preferably, each $R^{11}$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —CF$_3$, and —CN. More preferably, each $R^{11}$ is independently selected from $C_{1-4}$ alkyl (e.g., methyl or ethyl), —OH, —O($C_{1-4}$ alkyl) (e.g., —OCH$_3$ or —OCH$_2$CH$_3$), —NH$_2$, —NH($C_{1-4}$ alkyl) (e.g., —NHCH$_3$), —N($C_{1-4}$ alkyl)($C_{1-4}$ alkyl) (e.g., —N(CH$_3$)$_2$), halogen (e.g., —F, —Cl, —Br, or —I), —CF$_3$, and —CN.

In this second embodiment, $R^2$ and $R^4$ are each independently selected from hydrogen, $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-SO—($C_{1-5}$ alkyl), —($C_{0-3}$ alkylene)-SO$_2$—($C_{1-5}$ alkyl), —($C_{0-3}$ alkylene)-cycloalkyl, and —($C_{0-3}$ alkylene)-heterocycloalkyl. Preferably, $R^2$ and $R^4$ are each independently selected from hydrogen, $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl. More preferably, $R^2$ and $R^4$ are each independently selected from hydrogen, $C_{1-5}$ alkyl, —OH, —O($C_{1-5}$ alkyl), —O($C_{1-5}$ alkylene)-OH, —O($C_{1-5}$ alkylene)O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —CF$_3$, and —CN. Even more preferably, $R^2$ and $R^4$ are each independently selected from hydrogen, $C_{1-4}$ alkyl (e.g., methyl or ethyl), —OH, —O($C_{1-4}$ alkyl) (e.g., —OCH$_3$ or —OCH$_2$CH$_3$), —NH$_2$, —NH($C_{1-4}$ alkyl) (e.g., —NHCH$_3$), —N($C_{1-4}$ alkyl)($C_{1-4}$ alkyl) (e.g., —N(CH$_3$)$_2$), halogen (e.g., —F, —Cl, —Br, or —I), —CF$_3$, and —CN. Still more preferably, $R^2$ and $R^4$ are each hydrogen.

In this second embodiment, $R^3$ is —CH$_2$—CF$_3$ or —CH$_2$—SO$_2$—CH$_3$.

In this second embodiment, L is —NH—.

In this second embodiment, the ring group A is aryl or monocyclic heteroaryl, wherein said aryl or said monocyclic heteroaryl is optionally substituted with one or more (e.g., one, two or three) groups $R^4$. Preferably, ring A is phenyl or monocyclic heteroaryl, wherein said phenyl or said monocyclic heteroaryl is optionally substituted with one or more (e.g., one, two or three; particularly one) groups $R^4$. It is preferred that said monocyclic heteroaryl is a 5- or 6-membered monocyclic heteroaryl (particularly a 6-membered monocyclic heteroaryl), which preferably comprises 1, 2 or 3 ring heteroatoms selected independently from nitrogen, oxygen and sulfur (wherein it is preferred that said 1, 2 or 3 ring heteroatoms are all nitrogen ring atoms), wherein the other ring atoms are all carbon ring atoms. Accordingly, said monocyclic heteroaryl may be, for example, pyridinyl, a diazinyl (e.g., pyrimidinyl, pyrazinyl, or pyridazinyl), or a triazinyl (e.g., 1,2,3-triazinyl, 1,2,4-triazinyl, or 1,3,5-triazinyl), wherein said pyridinyl, said diazinyl and said triazinyl are each optionally substituted with one or more groups $R^4$. More preferably, ring A is selected from phenyl, pyridinyl (e.g., pyridin-2-yl, pyridin-3-yl, or pyridin-4-yl; particularly pyridin-2-yl), pyrimidinyl (e.g., pyrimidin-2-yl, pyrimidin-4-yl, or pyrimidin-5-yl), and pyrazinyl (e.g., pyrazin-2-yl), wherein said phenyl, said pyridinyl, said pyrimidinyl and said pyrazinyl are each optionally substituted with one or more groups $R^4$. Even more preferably, ring A is phenyl or pyridinyl (preferably pyridin-2-yl), wherein said phenyl or said pyridinyl is optionally substituted with one or more groups $R^4$. Still more preferably, ring A is pyridin-2-yl which is optionally substituted with one or more groups $R^4$.

It is preferred that ring A (including any one of the above-described preferred or exemplary ring groups A) is unsubstituted or is substituted with one group $R^4$. Furthermore, if ring A is phenyl which is substituted with one group $R^4$ (e.g., halogen or —OCH$_3$; preferably —F), it is preferred that the group $R^4$ is attached to said phenyl in meta or para position (with respect to the point of attachment of the group L), more preferably in meta position (with respect to the group L). Alternatively, if ring A is pyridin-2-yl which is substituted with one group $R^4$ (e.g., halogen, such as —F or —Cl; preferably —F), it is preferred that the group $R^4$ is attached to said pyridin-2-yl in position 4 or 5, more preferably in position 4.

In this second embodiment, each $R^4$ is independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl. Preferably, each $R^4$ is independently selected from $C_{1-5}$ alkyl, —OH, —O($C_{1-5}$ alkyl), —O($C_{1-5}$ alkylene)-OH, —O($C_{1-5}$ alkylene)-O($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —CF$_3$, and —CN. More preferably, each $R^4$ is independently selected from $C_{1-4}$ alkyl (e.g., methyl or ethyl), —OH, —O($C_{1-4}$ alkyl) (e.g., —OCH$_3$ or —OCH$_2$CH$_3$), —NH$_2$, —NH($C_{1-4}$ alkyl) (e.g., —NHCH$_3$), —N($C_{1-4}$ alkyl)($C_{1-4}$ alkyl) (e.g., —N(CH$_3$)$_2$), halogen (e.g., —F, —Cl, —Br, or —I), —CF$_3$, and —CN. It is particularly preferred that each $R^4$ is independently halogen, and still more preferably each $R^4$ is —F.

In a third specific embodiment, the present invention relates to a compound of formula (I) or a pharmaceutically acceptable salt, solvate or prodrug thereof, wherein the groups/variables in formula (I) have the following meanings:

The groups $R^{1A}$ and $R^{1B}$ are mutually linked to form, together with the nitrogen atom that they are attached to, a group having the following formula:

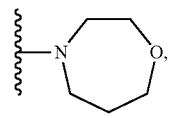 [SMILES: *N1CCCOCC1]

wherein the above-depicted group is optionally substituted with one or more $R^{11}$.

In this third embodiment, the groups $R^{11}$, $R^2$, $R^4$ and $R^A$ are each as defined in the above-described second specific embodiment.

In this third embodiment, $R^3$ is —CH$_2$—CF$_3$.
In this third embodiment, L is —NH—.
In this third embodiment, the ring group A is phenyl which is optionally substituted with one or more groups $R^4$.

It is preferred that ring A, which is phenyl, is unsubstituted or is substituted with one group $R^4$. If ring A is phenyl which is substituted with one group $R^4$ (e.g., halogen or —OCH$_3$; preferably —F), it is preferred that the group $R^4$ is attached to said phenyl in meta or para position (with respect to the point of attachment of the group L), more preferably in meta position (with respect to the group L).

In a fourth specific embodiment, the present invention relates to a compound of formula (I) or a pharmaceutically acceptable salt, solvate or prodrug thereof, wherein the groups/variables in formula (I) have the following meanings:

The groups $R^{1A}$ and $R^{1B}$ are mutually linked to form, together with the nitrogen atom that they are attached to, a group having the following formula:

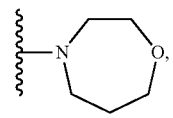

wherein the above-depicted group is optionally substituted with one or more $R^{11}$.

In this fourth embodiment, the groups $R^{11}$, $R^2$, $R^4$ and $R^A$ are each as defined in the above-described second specific embodiment.

In this fourth embodiment, $R^3$ is —CH$_2$—CF$_3$.
In this fourth embodiment, L is —NH—.
In this fourth embodiment, the ring group A is pyridin-2-yl which is optionally substituted with one or more groups $R^4$.

It is preferred that ring A, which is pyridin-2-yl, is unsubstituted or is substituted with one group $R^4$. If ring A is pyridin-2-yl which is substituted with one group $R^4$ (e.g., halogen, such as —F or —Cl; preferably —F), it is preferred that the group $R^4$ is attached to said pyridin-2-yl in position 4 or 5, more preferably in position 4.

In a fifth specific embodiment, the present invention relates to a compound of formula (I) or a pharmaceutically acceptable salt, solvate or prodrug thereof, wherein the groups/variables in formula (I) have the following meanings:

The groups $R^{1A}$ and $R^{1B}$ are mutually linked to form, together with the nitrogen atom that they are attached to, a group having the following formula:

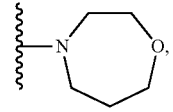

wherein the above-depicted group is optionally substituted with one or more $R^{11}$.

In this fifth embodiment, the groups $R^{11}$, $R^2$, $R^4$ and $R^A$ are each as defined in the above-described second specific embodiment.

In this fifth embodiment, R³ is —CH₂—SO₂—CH₃.
In this fifth embodiment, L is —NH—.
In this fifth embodiment, the ring group A is phenyl which is optionally substituted with one or more groups $R^A$.

It is preferred that ring A, which is phenyl, is unsubstituted or is substituted with one group $R^A$. If ring A is phenyl which is substituted with one group $R^A$ (e.g., halogen or —OCH₃; preferably —F), it is preferred that the group $R^A$ is attached to said phenyl in meta or para position (with respect to the point of attachment of the group L), more preferably in meta position (with respect to the group L).

In a sixth specific embodiment, the present invention relates to a compound of formula (I) or a pharmaceutically acceptable salt, solvate or prodrug thereof, wherein the groups/variables in formula (I) have the following meanings:

The groups $R^{1A}$ and $R^{1B}$ are mutually linked to form, together with the nitrogen atom that they are attached to, a group having the following formula:

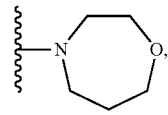 [SMILES: *N1CCCOCC1]

wherein the above-depicted group is optionally substituted with one or more $R^{11}$.

In this sixth embodiment, the groups $R^{11}$, $R^2$, $R^4$ and $R^A$ are each as defined in the above-described second specific embodiment.

In this sixth embodiment, R³ is —CH₂—SO₂—CH₃.
In this sixth embodiment, L is —NH—.
In this sixth embodiment, the ring group A is pyridin-2-yl which is optionally substituted with one or more groups $R^A$.

It is preferred that ring A, which is pyridin-2-yl, is unsubstituted or is substituted with one group $R^A$. If ring A is pyridin-2-yl which is substituted with one group $R^A$ (e.g., halogen, such as —F or —Cl; preferably —F), it is preferred that the group $R^A$ is attached to said pyridin-2-yl in position 4 or 5, more preferably in position 4.

In a seventh specific embodiment, the present invention relates to a compound of formula (I) or a pharmaceutically acceptable salt, solvate or prodrug thereof, wherein the groups/variables in formula (I) have the following meanings:

The groups $R^{1A}$ and $R^{1B}$ are mutually linked to form, together with the nitrogen atom that they are attached to, a group having the following formula:

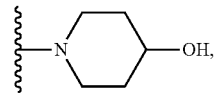

wherein the above-depicted group is optionally substituted with one or more $R^{11}$.

In this seventh embodiment, the groups $R^{11}$, $R^2$, $R^4$ and $R^A$ are each as defined in the above-described second specific embodiment.

In this seventh embodiment, R³ is —CH₂—CF₃.
In this seventh embodiment, L is —NH—.
In this seventh embodiment, the ring group A is phenyl which is optionally substituted with one or more groups $R^A$.

It is preferred that ring A, which is phenyl, is unsubstituted or is substituted with one group $R^A$. If ring A is phenyl which is substituted with one group $R^A$ (e.g., halogen or —OCH₃; preferably —F), it is preferred that the group $R^A$ is attached to said phenyl in meta or para position (with respect to the point of attachment of the group L), more preferably in meta position (with respect to the group L).

In an eighth specific embodiment, the present invention relates to a compound of formula (I) or a pharmaceutically acceptable salt, solvate or prodrug thereof, wherein the groups/variables in formula (I) have the following meanings:

The groups $R^{1A}$ and $R^{1B}$ are mutually linked to form, together with the nitrogen atom that they are attached to, a group having the following formula:

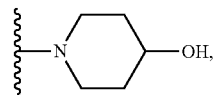

wherein the above-depicted group is optionally substituted with one or more $R^{11}$.

In this eighth embodiment, the groups $R^{11}$, $R^2$, $R^4$ and $R^A$ are each as defined in the above-described second specific embodiment.

In this eighth embodiment, R³ is —CH₂—CF₃.
In this eighth embodiment, L is —NH—.
In this eighth embodiment, the ring group A is pyridin-2-yl which is optionally substituted with one or more groups $R^A$.

It is preferred that ring A, which is pyridin-2-yl, is unsubstituted or is substituted with one group $R^A$. If ring A is pyridin-2-yl which is substituted with one group $R^A$ (e.g., halogen, such as —F or —Cl; preferably —F), it is preferred that the group $R^A$ is attached to said pyridin-2-yl in position 4 or 5, more preferably in position 4.

In a ninth specific embodiment, the present invention relates to a compound of formula (I) or a pharmaceutically acceptable salt, solvate or prodrug thereof, wherein the groups/variables in formula (I) have the following meanings:

The groups $R^{1A}$ and $R^{1B}$ are mutually linked to form, together with the nitrogen atom that they are attached to, a group having the following formula:

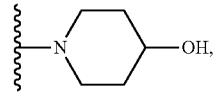 [SMILES: *N1CCC(O)CC1]

wherein the above-depicted group is optionally substituted with one or more $R^{11}$.

In this ninth embodiment, the groups $R^{11}$, $R^2$, $R^4$ and $R^A$ are each as defined in the above-described second specific embodiment.

In this ninth embodiment, R³ is —CH₂—SO₂—CH₃.
In this ninth embodiment, L is —NH—.
In this ninth embodiment, the ring group A is phenyl which is optionally substituted with one or more groups $R^A$.

It is preferred that ring A, which is phenyl, is unsubstituted or is substituted with one group $R^A$. If ring A is phenyl which is substituted with one group $R^A$ (e.g., halogen or —OCH₃; preferably —F), it is preferred that the group $R^A$ is attached to said phenyl in meta or para position (with respect to the point of attachment of the group L), more preferably in meta position (with respect to the group L).

In a tenth specific embodiment, the present invention relates to a compound of formula (I) or a pharmaceutically acceptable salt, solvate or prodrug thereof, wherein the subgroups/variables in formula (I) have the following meanings:

The groups $R^{1A}$ and $R^{1B}$ are mutually linked to form, together with the nitrogen atom that they are attached to, a group having the following formula:

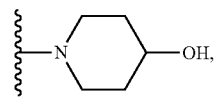

wherein the above-depicted group is optionally substituted with one or more $R^{11}$.

In this tenth embodiment, the groups $R^{11}$, $R^2$, $R^4$ and $R^A$ are each as defined in the above-described second specific embodiment.

In this tenth embodiment, $R^3$ is —$CH_2$—$SO_2$—$CH_3$.

In this tenth embodiment, L is —NH—.

In this tenth embodiment, the ring group A is pyridin-2-yl which is optionally substituted with one or more groups $R^A$.

It is preferred that ring A, which is pyridin-2-yl, is unsubstituted or is substituted with one group $R^A$. If ring A is pyridin-2-yl which is substituted with one group $R^A$ (e.g., halogen, such as —F or —Cl; preferably —F), it is preferred that the group $R^A$ is attached to said pyridin-2-yl in position 4 or 5, more preferably in position 4.

The compounds of formula (I) according to the present invention can be prepared, e.g., in accordance with or in analogy to the synthetic routes described in the examples section, particularly in Example 2.

It is also possible to carry out the reactions stepwise in each case and to modify the sequence of the linking reactions of the building blocks with adaptation of the protecting-group concept.

The starting materials or starting compounds are generally known. If they are novel, they can be prepared by methods known per se.

If desired, the starting materials can also be formed in situ by not isolating them from the reaction mixture, but instead immediately converting them further into the compounds of the formula I.

The compounds of the formula I are preferably obtained by liberating them from their functional derivatives by solvolysis, in particular by hydrolysis, or by hydrogenolysis. Preferred starting materials for the solvolysis or hydrogenolysis are those which contain correspondingly protected amino, carboxyl and/or hydroxyl groups instead of one or more free amino, carboxyl and/or hydroxyl groups, preferably those which carry an amino-protecting group instead of an H atom which is connected to an N atom. Preference is furthermore given to starting materials which carry a hydroxyl-protecting group instead of the H atom of a hydroxyl group. Preference is also given to starting materials which carry a protected carboxyl group instead of a free carboxyl group. It is also possible for a plurality of identical or different protected amino, carboxyl and/or hydroxyl groups to be present in the molecule of the starting material. If the protecting groups present are different from one another, they can in many cases be cleaved off selectively.

The term "amino-protecting group" is generally known and relates to groups which are suitable for protecting (blocking) an amino group against chemical reactions, but which can easily be removed after the desired chemical reaction has been carried out elsewhere in the molecule. Typical of such groups are, in particular, unsubstituted or substituted acyl groups, furthermore unsubstituted or substituted aryl (for example 2,4-dinitrophenyl) or aralkyl groups (for example benzyl, 4-nitrobenzyl, triphenylmethyl). Since the amino-protecting groups are removed after the desired reaction or reaction sequence, their type and size is, in addition, not crucial, but preference is given to those having 1-20, in particular 1-8, C atoms. The term "acyl group" is to be understood in the broadest sense in connection with the present process. It encompasses acyl groups derived from aliphatic, araliphatic, aromatic or heterocyclic carboxylic acids or sulfonic acids and, in particular, alkoxycarbonyl, aryloxycarbonyl and especially aralkoxycarbonyl groups. Examples of such acyl groups are alkanoyl, such as acetyl, propionyl, buturyl, aralkanoyl, such as phenyl-acetyl, aroyl, such as benzoyl or toluyl, aryoxyaklkanoyl, such as phenoxyacetyl, alkyoxycarbonyyl, such as methoxycarbonyl, ethoxycarbonyl, 2,2,2-trichloroethoxy-carbonyl, BOC (tert-butoxycarbonyl), 2-iodoethoxycaronyl, aralkoxycarbonyl, such as CBZ (benzyloxycarbonyl), 4-methoxybenzyloxycarbonyl or FMOC (9-fluorenyl-methoxycarbonyl). Preferred acyl groups are CBZ, FMOC, benzyl and acetyl.

The term "acid-protecting group" or "carboxyl-protecting group" is likewise generally known and relates to groups which are suitable for protecting a —COOH group against chemical reactions, but which can easily be removed after the desired chemical reaction has been carried out elsewhere in the molecule. The use of esters instead of the free acids, for example of substituted and unsubstituted alkyl esters (such as methyl, ethyl, tert-butyl and substituted derivatives thereof), of substituted and unsubstituted benzyl esters or silyl esters, is typical. The type and size of the acid-protecting groups is not crucial, but preference is given to those having 1-20, in particular 1-10, C atoms.

The term "hydroxyl-protecting group" is likewise generally known and relates to groups which are suitable for protecting a hydroxyl group against chemical reactions, but which can easily be removed after the desired chemical reaction has been carried out elsewhere in the molecule. Typical of such groups are the above-mentioned unsubstituted or substituted aryl, aralkyl or acyl groups, furthermore also alkyl groups. Their type and size of the hydroxyl-protecting groups is not crucial, but preference is given to those having 1-20, in particular 1-10, C atoms. Examples of hyrdoxyl-protecting groups are, inter alia, benzyl, p-nitrobenzoyl, p-toluenesulfonyl and acetyl, where benzyl and acetyl are preferred.

Further typical examples of amino-, acid- and hydroxyl-protecting groups are found, for example, in "Greene's Protective Groups in Organic Synthesis", fourth edition, Wiley-Interscience, 2007.

The compounds of the formula I are liberated from their functional derivatives, depending on the protecting group used, for example, with the aid of strong acids, advantageously using trifluoroacetic acid or perchloric acid, but also using other strong inorganic acids, such as hydrochloric acid or sulfuric acid, strong organic acids, such as trichloroacetic acid, or sulfonic acids, such as benzoyl- or p-toluenesulfonic acid. The presence of an additional inert solvent and/or a catalyst is possible but is not always necessary.

Depending on the respective synthetic route, the starting materials can optionally be reacted in the presence of an inert solvent.

Suitable inert solvents are, for example, heptane, hexane, petroleum ether, DMSO, benzene, toluene, xylene, trichloroethylene-, 1,2-dichloroethanecarbon tetrachloride, chloroform or dichloromethane; alcohols, such as methanol, ethanol, isopropanol, n-propanol, n-butanol or tert-butanol; ethers, such as diethyl ether, diisopropyl ether (preferably for substitution on the indole nitrogen), tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; esters, such as ethyl acetate, carboxylic acids or acid anhydrides, such as, for example, such as acetic acid or acetic anhydride, nitro compounds, such as nitromethane or nitrobenzene, optionally also mixtures of the said solvents with one another or mixtures with water.

The amount of solvent is not crucial; 10 g to 500 g of solvent can preferably be added per g of the compound of the formula I to be reacted.

It may be advantageous to add an acid-binding agent, for example an alkali metal or alkaline-earth metal hydroxide, carbonate or bicarbonate or other alkali or alkaline-earth metal salts of weak acids, preferably a potassium, sodium or calcium salt, or to add an organic base, such as, for example, on triethylamine, dimethylamine, pyridine or quinoline, or an excess of the amine component.

The resultant compounds according to the invention can be separated from the corresponding solution in which they are prepared (for example by centrifugation and washing) and can be stored in another composition after separation, or they can remain directly in the preparation solution. The resultant compounds according to the invention can also be taken up in desired solvents for the particular use.

The reaction duration depends on the reaction conditions selected. In general, the reaction duration is 0.5 hour to 10 days, preferably 1 to 24 hours. On use of a microwave, the reaction time can be reduced to values of 1 to 60 minutes.

The compounds of the formula I and also the starting materials for their preparation are, in addition, prepared by known methods, as described in the literature (for example in standard works, such as Houben-Weyl, Methoden der organischen Chemie [Methods of Organic Chemistry], Georg-Thieme-Verlag, Stuttgart), for example under reaction conditions which are known and suitable for the said reactions. Use can also be made here of variants known per se, which are not described here in greater detail.

Conventional work-up steps, such as, for example, addition of water to the reaction mixture and extraction, enable the compounds to be obtained after removal of the solvent. It may be advantageous, for further purification of the product, to follow this with a distillation or crystallisation or to carry out a chromatographic purification.

An acid of the formula I can be converted into the associated addition salt using a base, for example by reaction of equivalent amounts of the acid and base in an inert solvent, such as ethanol, and inclusive evaporation. Suitable bases for this reaction are, in particular, those which give physiologically acceptable salts. Thus, the acid of the formula I can be converted into the corresponding metal salt, in particular alkali or alkaline-earth metal salt, using a base (for example sodium hydroxide, potassium hydroxide, sodium carbonate or potassium carbonate) or into the corresponding ammonium salt. Organic bases which give physiologically acceptable salts, such as, for example, ethanolamine, are also suitable for this reaction.

On the other hand, a base of the formula I can be converted into the associated acid-addition salt using an acid, for example by reaction of equivalent amounts of the base and acid in an inert solvent, such as ethanol, with subsequent evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic, mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxysulfonic acid, benzenesulfonic acid, p-toluenesulfonic acid, naphthalenemom- and disulfonic acids or laurylsulfuric acid. Salts with physiologically unacceptable acids, for example picrates, can be used for the isolation and/or purification of the compounds of the formula I.

The following definitions apply throughout the present specification and the claims, unless specifically indicated otherwise.

The term "hydrocarbon group" refers to a group consisting of carbon atoms and hydrogen atoms.

As used herein, the term "alkyl" refers to a monovalent saturated acyclic (i.e., non-cyclic) hydrocarbon group which may be linear or branched. Accordingly, an "alkyl" group does not comprise any carbon-to-carbon double bond or any carbon-to-carbon triple bond. A "$C_{1-5}$ alkyl" denotes an alkyl group having 1 to 5 carbon atoms. Preferred exemplary alkyl groups are methyl, ethyl, propyl (e.g., n-propyl or isopropyl), or butyl (e.g., n-butyl, isobutyl, sec-butyl, or tert-butyl). Unless defined otherwise, the term "alkyl" preferably refers to $C_{1-4}$ alkyl, more preferably to methyl or ethyl, and even more preferably to methyl.

As used herein, the term "alkenyl" refers to a monovalent unsaturated acyclic hydrocarbon group which may be linear or branched and comprises one or more (e.g., one or two) carbon-to-carbon double bonds while it does not comprise any carbon-to-carbon triple bond. The term "$C_{2-5}$ alkenyl" denotes an alkenyl group having 2 to 5 carbon atoms. Preferred exemplary alkenyl groups are ethenyl, propenyl (e.g., prop-1-en-1-yl, prop-1-en-2-yl, or prop-2-en-1-yl), butenyl, butadienyl (e.g., buta-1,3-dien-1-yl or buta-1,3-dien-2-yl), pentenyl, or pentadienyl (e.g., isoprenyl). Unless defined otherwise, the term "alkenyl" preferably refers to $C_{2-4}$ alkenyl.

As used herein, the term "alkynyl" refers to a monovalent unsaturated acyclic hydrocarbon group which may be linear or branched and comprises one or more (e.g., one or two) carbon-to-carbon triple bonds and optionally one or more (e.g., one or two) carbon-to-carbon double bonds. The term "$C_{2-5}$ alkynyl" denotes an alkynyl group having 2 to 5 carbon atoms. Preferred exemplary alkynyl groups are ethynyl, propynyl (e.g., propargyl), or butynyl. Unless defined otherwise, the term "alkynyl" preferably refers to $C_{2-4}$ alkynyl.

As used herein, the term "alkylene" refers to an alkanediyl group, i.e. a divalent saturated acyclic hydrocarbon group which may be linear or branched. A "$C_{1-5}$ alkylene" denotes an alkylene group having 1 to 5 carbon atoms, and the term "$C_{0-3}$ alkylene" indicates that a covalent bond (corresponding to the option "$C_0$ alkylene") or a $C_{1-3}$ alkylene is present.

Preferred exemplary alkylene groups are methylene (—CH$_2$—), ethylene (e.g., —CH$_2$—CH$_2$— or —CH(—CH$_3$)—), propylene (e.g., —CH$_2$—CH$_2$—CH$_2$—, —CH(—CH$_2$—CH$_3$)—, —CH$_2$—CH(—CH$_3$)—, or —CH(—CH$_3$)—CH$_2$—), or butylene (e.g., —CH$_2$—CH$_2$—CH$_2$—CH$_2$—). Unless defined otherwise, the term "alkylene" preferably refers to C$_{1-4}$ alkylene (including, in particular, linear C$_{1-4}$ alkylene), more preferably to methylene or ethylene.

As used herein, the term "carbocyclyl" refers to a hydrocarbon ring group, including monocyclic rings as well as bridged ring, spiro ring and/or fused ring systems (which may be composed, e.g., of two or three rings), wherein said ring group may be saturated, partially unsaturated (i.e., unsaturated but not aromatic) or aromatic. Unless defined otherwise, "carbocyclyl" preferably refers to aryl, cycloalkyl or cycloalkenyl.

As used herein, the term "heterocyclyl" refers to a ring group, including monocyclic rings as well as bridged ring, spiro ring and/or fused ring systems (which may be composed, e.g., of two or three rings), wherein said ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group may be saturated, partially unsaturated (i.e., unsaturated but not aromatic) or aromatic. For example, each heteroatom-containing ring comprised in said ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. Unless defined otherwise, "heterocyclyl" preferably refers to heteroaryl, heterocycloalkyl or heterocycloalkenyl.

As used herein, the term "aryl" refers to an aromatic hydrocarbon ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic). "Aryl" may, e.g., refer to phenyl, naphthyl, dialinyl (i.e., 1,2-dihydro-naphthyl), tetralinyl (i.e., 1,2,3,4-tetrahydronaphthyl), indanyl, indenyl (e.g., 1H-indenyl), anthracenyl, phenanthrenyl, 9H-fluorenyl, or azulenyl. Unless defined otherwise, an "aryl" preferably has 6 to 14 ring atoms, more preferably 6 to 10 ring atoms, even more preferably refers to phenyl or naphthyl, and most preferably refers to phenyl.

As used herein, the term "heteroaryl" refers to an aromatic ring group, including monocyclic aromatic rings as well as bridged ring and/or fused ring systems containing at least one aromatic ring (e.g., ring systems composed of two or three fused rings, wherein at least one of these fused rings is aromatic; or bridged ring systems composed of two or three rings, wherein at least one of these bridged rings is aromatic), wherein said aromatic ring group comprises one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said aromatic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heteroaryl" may, e.g., refer to thienyl (i.e., thiophenyl), benzo[b]thienyl, naphtho[2,3-b]thienyl, thianthrenyl, furyl (i.e., furanyl), benzofuranyl, isobenzofuranyl, chromanyl, chromenyl (e.g., 2H-1-benzopyranyl or 4H-1-benzopyranyl), isochromenyl (e.g., 1H-2-benzopyranyl), chromonyl, xanthenyl, phenoxathiinyl, pyrrolyl (e.g., 1H-pyrrolyl), imidazolyl, pyrazolyl, pyridyl (i.e., pyridinyl; e.g., 2-pyridyl, 3-pyridyl, or 4-pyridyl), pyrazinyl, pyrimidinyl, pyridazinyl, indolyl (e.g., 3H-indolyl), isoindolyl, indazolyl, indolizinyl, purinyl, quinolyl, isoquinolyl, phthalazinyl, naphthyridinyl, quinoxalinyl, cinnolinyl, pteridinyl, carbazolyl, β-carbolinyl, phenanthridinyl, acridinyl, perimidinyl, phenanthrolinyl (e.g., [1,10]phenanthrolinyl, [1,7]phenanthrolinyl, or [4,7] phenanthrolinyl), phenazinyl, thiazolyl, isothiazolyl, phenothiazinyl, oxazolyl, isoxazolyl, oxadiazolyl (e.g., 1,2,4-oxadiazolyl, 1,2,5-oxadiazolyl (i.e., furazanyl), or 1,3,4-oxadiazolyl), thiadiazolyl (e.g., 1,2,4-thiadiazolyl, 1,2,5-thiadiazolyl, or 1,3,4-thiadiazolyl), phenoxazinyl, pyrazolo[1,5-a]pyrimidinyl (e.g., pyrazolo[1,5-a]pyrimidin-3-yl), 1,2-benzoisoxazol-3-yl, benzothiazolyl, benzothiadiazolyl, benzoxazolyl, benzisoxazolyl, benzimidazolyl, benzo[b] thiophenyl (i.e., benzothienyl), triazolyl (e.g., 1H-1,2,3-triazolyl, 2H-1,2,3-triazolyl, 1H-1,2,4-triazolyl, or 4H-1,2,4-triazolyl), benzotriazolyl, 1H-tetrazolyl, 2H-tetrazolyl, triazinyl (e.g., 1,2,3-triazinyl, 1,2,4-triazinyl, or 1,3,5-triazinyl), furo[2,3-c]pyridinyl, dihydrofuropyridinyl (e.g., 2,3-dihydrofuro[2,3-c]pyridinyl or 1,3-dihydrofuro[3,4-c]pyridinyl), imidazo-pyridinyl (e.g., imidazo[1,2-a]pyridinyl or imidazo[3,2-a]pyridinyl), quinazolinyl, thienopyridinyl, tetrahydrothienopyridinyl (e.g., 4,5,6,7-tetrahydrothieno[3,2-c]pyridinyl), dibenzofuranyl, 1,3-benzodioxolyl, benzodioxanyl (e.g., 1,3-benzodioxanyl or 1,4-benzodioxanyl), or coumarinyl. Unless defined otherwise, the term "heteroaryl" preferably refers to a 5 to 14 membered (more preferably 5 to 10 membered) monocyclic ring or fused ring system comprising one or more (e.g., one, two, three or four) ring heteroatoms independently selected from O, S and N, wherein one or more S ring atoms (if present) and/or one or more N ring atoms (if present) are optionally oxidized, and wherein one or more carbon ring atoms are optionally oxidized; even more preferably, a "heteroaryl" refers to a 5 or 6 membered monocyclic ring comprising one or more (e.g., one, two or three) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "cycloalkyl" refers to a saturated hydrocarbon ring group, including monocyclic rings as well as bridged ring, spiro ring and/or fused ring systems (which may be composed, e.g., of two or three rings; such as, e.g., a fused ring system composed of two or three fused rings). "Cycloalkyl" may, e.g., refer to cyclopropyl, cyclobutyl, cyclopentyl, cyclohexyl, cycloheptyl, decalinyl (i.e., decahydronaphthyl), or adamantyl. Unless defined otherwise, "cycloalkyl" preferably refers to a C$_{3-11}$ cycloalkyl, and more preferably refers to a $C_{3-7}$ cycloalkyl. A particularly preferred "cycloalkyl" is a monocyclic saturated hydrocarbon ring having 3 to 7 ring members.

As used herein, the term "heterocycloalkyl" refers to a saturated ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, and further wherein one or more carbon ring atoms may optionally be oxidized (i.e., to form an oxo group). For example, each heteroatom-containing ring comprised in said saturated ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkyl" may, e.g., refer to aziridinyl, azetidinyl, pyrrolidinyl, imidazolidinyl, pyrazolidinyl, piperidinyl, piperazinyl, azepanyl, diazepanyl (e.g., 1,4-diazepanyl), oxazolidinyl, isoxazolidinyl, thiazolidinyl, isothiazolidinyl, morpholinyl (e.g., morpholin-4-yl), thiomorpholinyl (e.g., thio-morpholin-4-yl), oxazepanyl, oxiranyl, oxetanyl, tetrahydrofuranyl, 1,3-dioxolanyl, tetrahydropyranyl, 1,4-dioxanyl, oxepanyl, thiiranyl, thietanyl, tetrahydrothiophenyl (i.e., thiolanyl), 1,3-dithiolanyl, thianyl, thiepanyl, decahydroquinolinyl, decahydroisoquinolinyl, or 2-oxa-5-aza-bicyclo[2.2.1]hept-5-yl. Unless defined otherwise, "heterocycloalkyl" preferably refers to a 3 to 11 membered saturated ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, and wherein one or more carbon ring atoms are optionally oxidized.

As used herein, the term "cycloalkenyl" refers to an unsaturated alicyclic (i.e., non-aromatic) hydrocarbon ring group, including monocyclic rings as well as bridged ring, spiro ring and/or fused ring systems (which may be composed, e.g., of two or three rings; such as, e.g., a fused ring system composed of two or three fused rings), wherein said hydrocarbon ring group comprises one or more (e.g., one or two) carbon-to-carbon double bonds and does not comprise any carbon-to-carbon triple bond. "Cycloalkenyl" may, e.g., refer to cyclopropenyl, cyclobutenyl, cyclopentenyl, cyclohexenyl, cyclohexadienyl, cycloheptenyl, or cycloheptadienyl. Unless defined otherwise, "cycloalkenyl" preferably refers to a $C_{3-11}$ cycloalkenyl, and more preferably refers to a $C_{3-7}$ cycloalkenyl. A particularly preferred "cycloalkenyl" is a monocyclic unsaturated alicyclic hydrocarbon ring having 3 to 7 ring members and containing one or more (e.g., one or two; preferably one) carbon-to-carbon double bonds.

As used herein, the term "heterocycloalkenyl" refers to an unsaturated alicyclic (i.e., non-aromatic) ring group, including monocyclic rings as well as bridged ring, spiro ring and/or fused ring systems (which may be composed, e.g., of two or three rings; such as, e.g., a fused ring system composed of two or three fused rings), wherein said ring group contains one or more (such as, e.g., one, two, three, or four) ring heteroatoms independently selected from O, S and N, and the remaining ring atoms are carbon atoms, wherein one or more S ring atoms (if present) and/or one or more N ring atoms (if present) may optionally be oxidized, wherein one or more carbon ring atoms may optionally be oxidized (i.e., to form an oxo group), and further wherein said ring group comprises at least one double bond between adjacent ring atoms and does not comprise any triple bond between adjacent ring atoms. For example, each heteroatom-containing ring comprised in said unsaturated alicyclic ring group may contain one or two O atoms and/or one or two S atoms (which may optionally be oxidized) and/or one, two, three or four N atoms (which may optionally be oxidized), provided that the total number of heteroatoms in the corresponding heteroatom-containing ring is 1 to 4 and that there is at least one carbon ring atom (which may optionally be oxidized) in the corresponding heteroatom-containing ring. "Heterocycloalkenyl" may, e.g., refer to imidazolinyl (e.g., 2-imidazolinyl (i.e., 4,5-dihydro-1H-imidazolyl), 3-imidazolinyl, or 4-imidazolinyl), tetrahydropyridinyl (e.g., 1,2,3,6-tetrahydropyridinyl), dihydropyridinyl (e.g., 1,2-dihydropyridinyl or 2,3-dihydropyridinyl), pyranyl (e.g., 2H-pyranyl or 4H-pyranyl), thiopyranyl (e.g., 2H-thiopyranyl or 4H-thiopyranyl), dihydropyranyl, dihydrofuranyl, dihydropyrazolyl, dihydropyrazinyl, dihydroisoindolyl, octahydroquinolinyl (e.g., 1,2,3,4,4a,5,6,7-octahydroquinolinyl), or octahydroisoquinolinyl (e.g., 1,2,3,4,5,6,7,8-octahydroisoquinolinyl). Unless defined otherwise, "heterocycloalkenyl" preferably refers to a 3 to 11 membered unsaturated alicyclic ring group, which is a monocyclic ring or a fused ring system (e.g., a fused ring system composed of two fused rings), wherein said ring group contains one or more (e.g., one, two, three, or four) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms; more preferably, "heterocycloalkenyl" refers to a 5 to 7 membered monocyclic unsaturated non-aromatic ring group containing one or more (e.g., one, two, or three) ring heteroatoms independently selected from O, S and N, wherein one or more S ring atoms (if present) and/or one or more N ring atoms (if present) are optionally oxidized, wherein one or more carbon ring atoms are optionally oxidized, and wherein said ring group comprises at least one double bond between adjacent ring atoms and does not comprise any triple bond between adjacent ring atoms.

As used herein, the term "halogen" refers to fluoro (—F), chloro (—Cl), bromo (—Br), or iodo (—I).

As used herein, the term "haloalkyl" refers to an alkyl group substituted with one or more (preferably 1 to 6, more preferably 1 to 3) halogen atoms which are selected independently from fluoro, chloro, bromo and iodo, and are preferably all fluoro atoms. It will be understood that the maximum number of halogen atoms is limited by the number of available attachment sites and, thus, depends on the number of carbon atoms comprised in the alkyl moiety of the haloalkyl group. "Haloalkyl" may, e.g., refer to —$CF_3$, —$CHF_2$, —$CH_2F$, —$CF_2$—$CH_3$, —$CH_2$—$CF_3$, —$CH_2$—$CHF_2$, —$CH_2$—$CF_2$—$CH_3$, —$CH_2$—$CF_2$—$CF_3$, or —$CH(CF_3)_2$. A particularly preferred "haloalkyl" group is —$CF_3$.

As used herein, the terms "optional", "optionally" and "may" denote that the indicated feature may be present but can also be absent. Whenever the term "optional", "optionally" or "may" is used, the present invention specifically relates to both possibilities, i.e., that the corresponding feature is present or, alternatively, that the corresponding feature is absent. For example, the expression "X is optionally substituted with Y" (or "X may be substituted with Y") means that X is either substituted with Y or is unsubstituted. Likewise, if a component of a composition is indicated to be "optional", the invention specifically relates to both possibilities, i.e., that the corresponding component is present (contained in the composition) or that the corresponding component is absent from the composition.

Various groups are referred to as being "optionally substituted" in this specification. Generally, these groups may carry one or more substituents, such as, e.g., one, two, three or four substituents. It will be understood that the maximum number of substituents is limited by the number of attachment sites available on the substituted moiety. Unless defined otherwise, the "optionally substituted" groups referred to in this specification carry preferably not more than two substituents and may, in particular, carry only one substituent. Moreover, unless defined otherwise, it is preferred that the optional substituents are absent, i.e. that the corresponding groups are unsubstituted.

A skilled person will appreciate that the substituent groups comprised in the compounds of the present invention may be attached to the remainder of the respective compound via a number of different positions of the corresponding specific substituent group. Unless defined otherwise, the preferred attachment positions for the various specific substituent groups are as illustrated in the examples.

As used herein, unless explicitly indicated otherwise or contradicted by context, the terms "a", "an" and "the" are used interchangeably with "one or more" and "at least one". Thus, for example, a composition comprising "a" compound of formula (I) can be interpreted as referring to a composition comprising "one or more" compounds of formula (I).

As used herein, the term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

The scope of the present invention embraces all pharmaceutically acceptable salt forms of the compounds of formula (I) which may be formed, e.g., by protonation of an atom carrying an electron lone pair which is susceptible to protonation, such as an amino group, with an inorganic or organic acid, or as a salt of an acid group (such as a carboxylic acid group) with a physiologically acceptable cation. Exemplary base addition salts comprise, for example: alkali metal salts such as sodium or potassium salts; alkaline earth metal salts such as calcium or magnesium salts; zinc salts; ammonium salts; aliphatic amine salts such as trimethylamine, triethylamine, dicyclohexylamine, ethanolamine, diethanolamine, triethanolamine, procaine salts, meglumine salts, ethylenediamine salts, or choline salts; aralkyl amine salts such as N,N-dibenzylethylenediamine salts, benzathine salts, benethamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts, lysine salts, or histidine salts. Exemplary acid addition salts comprise, for example: mineral acid salts such as hydrochloride, hydrobromide, hydroiodide, sulfate salts (such as, e.g., sulfate or hydrogensulfate salts), nitrate salts, phosphate salts (such as, e.g., phosphate, hydrogenphosphate, or dihydrogenphosphate salts), carbonate salts, hydrogencarbonate salts, perchlorate salts, borate salts, or thiocyanate salts; organic acid salts such as acetate, propionate, butyrate, pentanoate, hexanoate, heptanoate, octanoate, cyclopentanepropionate, decanoate, undecanoate, oleate, stearate, lactate, maleate, oxalate, fumarate, tartrate, malate, citrate, succinate, adipate, gluconate, glycolate, nicotinate, benzoate, salicylate, ascorbate, pamoate (embonate), camphorate, glucoheptanoate, or pivalate salts; sulfonate salts such as methanesulfonate (mesylate), ethanesulfonate (esylate), 2-hydroxyethanesulfonate (isethionate), benzenesulfonate (besylate), p-toluenesulfonate (tosylate), 2-naphthalenesulfonate (napsylate), 3-phenylsulfonate, or camphorsulfonate salts; glycerophosphate salts; and acidic amino acid salts such as aspartate or glutamate salts. It will be understood that the present invention also relates to the compounds of formula (I), including any one of the specific compounds described herein, in non-salt form.

Moreover, the scope of the invention embraces the compounds of formula (I) in any solvated form, including, e.g., solvates with water (i.e., as a hydrate) or solvates with organic solvents such as, e.g., methanol, ethanol or acetonitrile (i.e., as a methanolate, ethanolate or acetonitrilate). All physical forms, including any amorphous or crystalline forms (i.e., polymorphs), of the compounds of formula (I) are also encompassed within the scope of the invention. It is to be understood that such solvates and physical forms of pharmaceutically acceptable salts of the compounds of the formula (I) are likewise embraced by the invention.

Furthermore, the compounds of formula (I) may exist in the form of different isomers, in particular stereoisomers (including, e.g., geometric isomers (or cis/trans isomers), enantiomers, and diastereomers) or tautomers (including, in particular, prototropic tautomers). All such isomers of the compounds of formula (I) are contemplated as being part of the present invention, either in admixture or in pure or substantially pure form. As for stereoisomers, the invention embraces the isolated optical isomers of the compounds according to the invention as well as any mixtures thereof (including, in particular, racemic mixtures/racemates). The racemates can be resolved by physical methods, such as, e.g., fractional crystallization, separation or crystallization of diastereomeric derivatives, or separation by chiral column chromatography. The individual optical isomers can also be obtained from the racemates via salt formation with an optically active acid followed by crystallization. The present invention further encompasses any tautomers of the compounds provided herein (e.g., keto/enol tautomers).

The present invention also relates to mixtures of the compounds of formula (I) according to the invention, for example mixtures of two diastereomers, for example in the ratio 1:1, 1:2, 1:3, 1:4, 1:5, 1:10, 1:100 or 1:1000. These are particularly preferably mixtures of two stereoisomeric compounds. However, preference is also given to mixtures of two or more compounds of formula (I).

The scope of the invention also embraces compounds of formula (I), in which one or more atoms are replaced by a specific isotope of the corresponding atom. For example, the invention encompasses compounds of formula (I), in which one or more hydrogen atoms (or, e.g., all hydrogen atoms) are replaced by deuterium atoms (i.e., $^2H$; also referred to as "D"). Accordingly, the invention also embraces compounds of formula (I) which are enriched in deuterium. Naturally occurring hydrogen is an isotopic mixture comprising about 99.98 mol-% hydrogen-1 ($^1H$) and about 0.0156 mol-% deuterium ($^2H$ or D). The content of deuterium in one or more hydrogen positions in the compounds of formula (I) can be increased using deuteration techniques known in the art. For example, a compound of formula (I) or a reactant or precursor to be used in the synthesis of the compound of formula (I) can be subjected to an H/D exchange reaction using, e.g., heavy water ($D_2O$). Further suitable deuteration techniques are described in: Atzrodt J et al., Bioorg Med Chem, 20(18), 5658-5667, 2012; William J S et al., Journal of Labelled Compounds and Radiopharmaceuticals, 53(11-12), 635-644, 2010; Modvig A et al., J Org Chem, 79, 5861-5868, 2014. The content of deuterium can be determined, e.g., using mass spectrometry or NMR spectroscopy. Unless specifically indicated otherwise, it is preferred that the compound of formula (I) is not enriched in deuterium. Accordingly, the presence of naturally occurring hydrogen atoms or $^1H$ hydrogen atoms in the compounds of formula (I) is preferred.

As explained above, it is intended that a compound of formula (I) includes isotope-labelled forms thereof. An isotope-labelled form of a compound of formula (I) is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula (I) by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of formula (I) or a pharmaceutically acceptable salt, solvate or prodrug thereof, any of which contains one or more of the above-mentioned isotopes and/or other isotopes of other atoms, is intended to be part of the present invention. An isotope-labelled compound of formula (I) can be used in a number of beneficial ways. For example, an isotope-labelled compound of formula (I) into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to their simple preparation and excellent detectability. Incorporation of heavier isotopes, for example deuterium ($^2H$), into a compound of formula (I) may have therapeutic advantages owing to the higher metabolic stability of this isotope-labelled compound. Higher metabolic stability translates directly into an increased in-vivo half-life or lower dosages, which under most circumstances would represent a preferred embodiment of the present invention. An isotope-labelled compound of the formula (I) can usually be prepared by carrying out the procedures disclosed in the synthesis schemes and the related description, in the example section and in the preparation part in the present specification, replacing a non-isotope-labelled reactant with a readily available isotope-labelled reactant.

In order to manipulate the oxidative metabolism of the compound by way of the primary kinetic isotope effect, deuterium ($^2H$) can also be incorporated into a compound of formula (I). The primary kinetic isotope effect is a change in the rate of a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom in a non-exchangeable position, rate differences of $k_M/k_D=2-7$ are typical. If this rate difference is successfully applied to a compound of formula (I) that is susceptible to oxidation, the profile of this compound in vivo can thereby be drastically modified and result in improved pharmacokinetic properties.

When discovering and developing therapeutic agents, the person skilled in the art attempts to optimise pharmacokinetic parameters while retaining desirable in-vitro properties. It is reasonable to assume that many compounds with poor pharmacokinetic profiles are susceptible to oxidative metabolism. In-vitro liver microsomal assays currently available provide valuable information on the course of oxidative metabolism of this type, which in turn permits the rational design of deuterated compounds of formula (I) with improved stability through resistance to such oxidative metabolism. Significant improvements in the pharmacokinetic profiles of the compounds of the formula I are thereby obtained and can be expressed quantitatively in terms of increases in the in-vivo half-life (T/2), concentration at maximum therapeutic effect ($C_{max}$), area under the dose response curve (AUC), and F; and in terms of reduced clearance, dose and costs of materials.

The following is intended to illustrate the above: a compound of formula (I) which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent to which the improvement in resistance to oxidative metabolism has improved. In this way, it is determined that the half-life of the parent compound can be extended by up to 100% as the result of deuterium-hydrogen exchange of this type.

The replacement of hydrogen by deuterium in a compound of formula (I) can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the undesired metabolite, even if the particular oxidation is not a rate-determining step. Further information on the state of the art with respect to deuterium-hydrogen exchange is given, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al., Biochemistry 33(10), 2927-2937, 1994, and Jarman et al., Carcinogenesis 16(4), 683-688, 1993.

The present invention also embraces compounds of formula (I), in which one or more atoms are replaced by a positron-emitting isotope of the corresponding atom, such as, e.g., $^{18}F$, $^{11}C$, $^{13}N$, $^{15}O$, $^{76}Br$, $^{77}Br$, $^{120}I$ and/or $^{124}I$. Such compounds can be used as tracers, trackers or imaging probes in positron emission tomography (PET). The invention thus includes (i) compounds of formula (I), in which one or more fluorine atoms (or, e.g., all fluorine atoms) are replaced by $^{18}F$ atoms, (ii) compounds of formula (I), in which one or more carbon atoms (or, e.g., all carbon atoms) are replaced by $^{11}C$ atoms, (iii) compounds of formula (I), in which one or more nitrogen atoms (or, e.g., all nitrogen atoms) are replaced by $^{13}N$ atoms, (iv) compounds of formula (I), in which one or more oxygen atoms (or, e.g., all oxygen atoms) are replaced by $^{15}O$ atoms, (v) compounds of formula (I), in which one or more bromine atoms (or, e.g., all bromine atoms) are replaced by $^{76}Br$ atoms, (vi) compounds of formula (I), in which one or more bromine atoms (or, e.g., all bromine atoms) are replaced by $^{77}Br$ atoms, (vii) compounds of formula (I), in which one or more iodine atoms (or, e.g., all iodine atoms) are replaced by $^{120}I$ atoms, and (viii) compounds of formula (I), in which one or more iodine atoms (or, e.g., all iodine atoms) are replaced by $^{124}I$ atoms. In general, it is preferred that none of the atoms in the compounds of formula (I) are replaced by specific isotopes.

The compounds of formula (I) can also be employed in the form of a pharmaceutically acceptable prodrug, i.e., as derivatives of the compounds of formula (I) which have chemically or metabolically cleavable groups and become, by solvolysis or under physiological conditions, the compounds of formula (I) which are pharmaceutically active in vivo. Prodrugs of the compounds according to the present invention may be formed in a conventional manner with a functional group of the compounds such as, e.g., with an amino, hydroxy or carboxy group. The prodrug form often offers advantages in terms of solubility, tissue compatibility or delayed release in a mammalian organism (see, Bundgaard, H., Design of Prodrugs, pp. 7-9, 21-24, Elsevier, Amsterdam 1985). Prodrugs include acid derivatives, such as, e.g., esters prepared by reaction of the parent acidic compound with a suitable alcohol, or amides prepared by reaction of the parent acid compound with a suitable amine. If a compound of the present invention has a carboxyl group, an ester derivative prepared by reacting the carboxyl group with a suitable alcohol or an amide derivative prepared by reacting the carboxyl group with a suitable amine is exemplified as a prodrug. An especially preferred ester derivative as a prodrug is methylester, ethylester, n-propylester, isopropylester, n-butylester, isobutylester, tert-butylester, morpholino-ethylester, N,N-diethylglycolamidoester or α-acetoxyethylester. If a compound of the present invention has a hydroxy group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH$_3$, —OC(=O)—C$_2$H$_5$, —OC(=O)-(tert-Bu), —OC(=O)—C$_{1-5}$H$_{31}$, —OC(=O)-(m-COONa-Ph), —OC(=O)—CH$_2$CH$_2$COONa, —O(C=O)—CH(NH$_2$)CH$_3$ or —OC(=O)—CH$_2$—N(CH$_3$)$_2$. If a compound of the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH$_2$)$_2$OCH$_3$ or —NHC(=O)—CH(NH$_2$)CH$_3$.

It has been found that the compounds of the formula (I) are well tolerated and have valuable pharmacological properties.

Since adenosine receptors, such as $A_{2A}$ and $A_{2B}$, are shown to down-regulate the immune response during inflammation and protect tissues from immune damage, inhibition of signaling through adenosine receptors can be used to intensify and prolong the immune response.

Methods are provided herein to increase an immune response. In one example, the method increases desirable and targeted tissue damage, such as damage of a tumor, for example cancer. Provided herein are methods of inhibiting one or more processes conducive to the production of extracellular adenosine and adenosine-triggered signaling through adenosine receptors. For example, enhancement of an immune response, local tissue inflammation, and targeted tissue destruction is accomplished by: inhibiting or reducing the adenosine-producing local tissue hypoxia; by degrading (or rendering inactive) accumulated extracellular adenosine; by preventing or decreasing expression of adenosine receptors on immune cells; and/or by inhibiting/antagonizing signaling by adenosine ligands through adenosine receptors. The results disclosed herein demonstrate that by in vivo administration of agents that disrupt the "hypoxia→adenosine accumulation→immunosuppressive adenosine receptor signaling to immune cells" pathway in subjects suffering from various diseases (e.g. cancer and sepsis) can result in in vivo treatment of tumors or improved immunization.

In one example, the method includes administering one or more inhibitors of extracellular adenosine and/or adenosine receptor inhibitors, such as an adenosine receptor antagonist. To increase the efficacy of a vaccine, one or more adenosine receptor inhibitors and/or inhibitors of extracellular adenosine can be administered in conjunction with the vaccine. In one example, one or more adenosine receptor inhibitors or inhibitors of extracellular adenosine are administered to increase an immune response/inflammation. In another example, a method is provided to achieve targeted tissue damage, such as for tumor destruction.

The invention therefore furthermore relates to the use of compounds according to the invention for the preparation of a medicament for the treatment and/or prophylaxis of diseases which are caused, promoted and/or propagated by adenosine or other $A_{2A}$ and/or $A_{2B}$ receptor agonists.

The invention thus also relates, in particular, to a medicament comprising at least one compound according to the invention and/or one of its pharmaceutically acceptable salts, solvates, prodrugs and stereoisomers, including mixtures thereof in all ratios, for use in the treatment and/or prophylaxis of physiological and/or pathophysiological states.

Particular preference is given, in particular, to physiological and/or pathophysiological states which are connected to adenosine $A_{2A}$ and/or $A_{2B}$ receptors.

Physiological and/or pathophysiological states are taken to mean physiological and/or pathophysiological states which are medically relevant, such as, for example, diseases or illnesses and medical disorders, complaints, symptoms or complications and the like, in particular diseases.

The invention furthermore relates to a medicament comprising at least one compound according to the invention and/or one of its pharmaceutically acceptable salts, solvates, prodrugs and stereoisomers, including mixtures thereof in all ratios, for use in the treatment and/or prophylaxis of physiological and/or pathophysiological states selected from the group consisting of hyperproliferative and infectious diseases or disorders.

The invention further relates to a medicament comprising at least one compound according to the invention and/or one of its pharmaceutically acceptable salts, solvates, prodrugs and stereoisomers, including mixtures thereof in all ratios, for use in the treatment and/or prophylaxis of physiological and/or pathophysiological states selected from the group consisting of hyperproliferative and infectious diseases or disorders, wherein the hyperproliferative disease or disorder is cancer.

The invention thus particularly preferably relates to a medicament comprising at least one compound according to the invention and/or one of its pharmaceutically acceptable salts, solvates, prodrugs and stereoisomers, including mixtures thereof in all ratios, wherein the cancer is selected from the group consisting of acute and chronic lymphocytic leukemia, acute granulocytic leukemia, adrenal cortex cancer, bladder cancer, brain cancer, breast cancer, cervical cancer, cervical hyperplasia, cervical cancer, chorio cancer, chronic granulocytic leukemia, chronic lymphocytic leukemia, colon cancer, endometrial cancer, esophageal cancer, essential thrombocytosis, genitourinary carcinoma, glioma, glioblastoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, non-small cell lung cancer, osteogenic sarcoma, ovarian carcinoma, pancreatic carcinoma, polycythemia vera, primary brain carcinoma, primary macroglobulinemia, prostatic cancer, renal cell cancer, rhabdomyosarcoma, skin cancer, small-cell lung cancer, soft-tissue sarcoma, squamous cell cancer, stomach cancer, testicular cancer, thyroid cancer and Wilms' tumor.

The invention further preferably relates to a medicament comprising at least one compound according to the invention and/or one of its pharmaceutically acceptable salts, solvates, prodrugs and stereoisomers, including mixtures thereof in all ratios, for use in the treatment and/or prophylaxis of physiological and/or pathophysiological states selected from the group consisting of hyperproliferative and infectious diseases or disorders, wherein the hyperproliferative disease or disorder is selected from the group consisting of age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ or tissue transplantation and an immune-proliferative disease or disorder selected from the group consisting of inflammatory bowel disease, psoriasis, rheumatoid arthritis, systemic lupus erythematosus (SLE), vascular hyperproliferation secondary to retinal hypoxia and vasculitis.

The invention further preferably relates to a medicament comprising at least one compound according to the invention and/or one of its pharmaceutically acceptable salts, solvates, prodrugs and stereoisomers, including mixtures thereof in all ratios, for use in the treatment and/or prophylaxis of physiological and/or pathophysiological states selected from the group consisting of hyperproliferative and infectious diseases or disorders, wherein the infectious disease or disorder is selected from the group consisting of
 (a) virally induced infectious diseases which are caused by retroviruses, hepadnaviruses, herpesviruses, flaviviridae and/or adenoviruses wherein the retroviruses are selected from lentiviruses or oncoretroviruses, wherein the lentivirus is selected from the group consisting of HIV-1, HIV-2, FIV, BIV, SIVs, SHIV, CAEV, VMV and EIAV and the oncoretrovirus is selected from the group consisting of HTLV-I, HTLV-II and BLV, the hepadnavirus is selected from the group consisting of HBV, GSHV and WHV, the herpesivirus is selected from the group from the group consisting of HSV I, HSV II, EBV, VZV, HCMV or HHV 8 and the flaviviridae is selected from the group consisting of HCV, West nile and Yellow Fever,
 (b) bacterial infectious diseases which are caused by Gram-positive bacteria wherein the Gram-positive bacteria are selected from the group consisting of methicillin-susceptible and methicillin-resistant staphylococci (including *Staphylococcus aureus, Staphylococcus epidermidis, Staphylococcus haemolyticus, Staphylococcus hominis, Staphylococcus saprophyticus*, and coagulase-negative staphylococci), glycopeptides-intermediate susceptible *Staphylococcus aureus* (GISA), penicillin-susceptible and penicillin-resistant streptococci (including *Streptococcus pneumoniae, Streptococcus pyogenes, Streptococcus agalactiae, Streptococcus avium, Streptococcus bovis, Streptococcus lactis, Streptococcus sanguis* and Streptococci Group C (GCS), Streptococci Group G (GGS) and *viridans* streptococci), enterococci (including vancomycinsusceptible and vancomycin-resistant strains such as *Enterococcus faecalis* and *Enterococcus faecium*), *Clostridium difficile, Listeria monocytogenes, Corynebacterium jeikeium, Chlamydia* spp (including *C. pneumoniae*) and *Mycobacterium tuberculosis*,
 (c) bacterial infectious diseases which are caused by Gram-negative bacteria wherein the Gram-negative bacteria are selected from the group consisting of the Genus Enterobacteriacae, including *Escherichia* spp. (including *Escherichia coli*), *Klebsiella* spp., *Enterobacter* spp., *Citrobacter* spp., *Serratia* spp., *Proteus* spp., *Providencia* spp., *Salmonella* spp., *Shigella* spp., the genus *Pseudomonas* (including *P. aeruginosa*), *Moraxella* spp. (including *M. catarrhalis*), *Haemophilus* spp. and *Neisseria* spp.,
 (d) infectious diseases induced by intracellular active parasites selected from the group consisting of phylum Apicomplexa, or Sarcomastigophora (including *Trypanosoma, Plasmodia, Leishmania, Babesia* or *Theileria*), Cryptosporidia, Sacrocystida, Amoebia, Coccidia and Trichomonadia.

Since the compounds of the present invention are highly efficient $A_{2A}$ receptor antagonists, the invention further preferably relates to a medicament comprising at least one compound according to the invention and/or one of its pharmaceutically acceptable salts, solvates, prodrugs and stereoisomers, including mixtures thereof in all ratios, for use in the treatment and/or prophylaxis of physiological and/or pathophysiological states selected from the group consisting of movement disorders, acute and chronic pain, affective disorders, central and peripheric nervous system degeneration disorders, schizophrenia and related psychosis, cognitive disorders, attention disorders, central nervous system injury, cerebral ischemia, myocardial ischemia, muscle ischemia, sleep disorders, eye disorders, cardiovascular disorders, hepatic fibrosis, cirrhosis, fatty liver, substance abuse, Parkinson's disease, Alzheimer's disease and attention-deficit hyperactivity disorder.

It is intended that the medicaments disclosed above include a corresponding use of the compounds according to the invention for the preparation of a medicament for the treatment and/or prophylaxis of the above physiological and/or pathophysiological states.

It is additionally intended that the medicaments disclosed above include a compound of the present invention for use in the treatment and/or prophylaxis of the above physiological and/or pathophysiological states.

It is additionally intended that the medicaments disclosed above include a corresponding method for the treatment and/or prophylaxis of the above physiological and/or pathophysiological states in which at least one compound according to the invention is administered to a patient in need of such a treatment.

The compounds according to the invention preferably exhibit an advantageous biological activity which can easily be demonstrated in enzyme assays and animal experiments, as described in the examples. In such enzyme-based assays, the compounds according to the invention preferably exhibit and cause an inhibiting effect, which is usually documented by $IC_{50}$ values in a suitable range, preferably in the micromolar range and more preferably in the nanomolar range.

The compounds according to the invention can be administered to humans or animals, in particular mammals, such as apes, dogs, cats, rats or mice, and can be used in the therapeutic treatment of the human or animal body and in the combating of the above-mentioned diseases. They can furthermore be used as diagnostic agents or as reagents.

Furthermore, compounds according to the invention can be used for the isolation and investigation of the activity or expression of adenosine $A_{2A}$ and/or $A_{2B}$ receptors. In addition, they are particularly suitable for use in diagnostic methods for diseases in connection with disturbed adenosine $A_{2A}$ and/or $A_{2B}$ receptor activity. The invention therefore furthermore relates to the use of the compounds according to the invention for the isolation and investigation of the activity or expression of adenosine $A_{2A}$ and/or $A_{2B}$ receptors or as binders and inhibitors of adenosine $A_{2A}$ and/or $A_{2B}$ receptors.

For diagnostic purposes, the compounds according to the invention can, for example, be radioactively labelled. Examples of radioactive labels are $^3H$, $^{14}C$, $^{231}I$ and $^{125}I$. A preferred labelling method is the iodogen method (Fraker et al., 1978). In addition, the compounds according to the invention can be labelled by enzymes, fluorophores and chemophores. Examples of enzymes are alkaline phosphatase, β-galactosidase and glucose oxidase, an example of a fluorophore is fluorescein, an example of a chemophore is luminol, and automated detection systems, for example for fluorescent colorations, are described, for example, in U.S. Pat. Nos. 4,125,828 and 4,207,554.

The present invention further relates to pharmaceutical compositions containing the compounds of the present invention and their use for the treatment and/or prophylaxis of diseases and disorders where the partial or total inactivation of adenosine $A_{2A}$ and/or $A_{2B}$ receptors could be beneficial.

The compounds of the formula (I) can be used for the preparation of pharmaceutical preparations, in particular by non-chemical methods. In this case, they are brought into a suitable dosage form together with at least one solid, liquid and/or semi-liquid excipient or adjuvant and optionally in combination with one or more further active compound(s).

The invention therefore furthermore relates to pharmaceutical preparations comprising at least one compound of the formula (I) and/or pharmaceutically acceptable salts, solvates, prodrugs and stereoisomers thereof, including mixtures thereof in all ratios. In particular, the invention also relates to pharmaceutical preparations which comprise further excipients and/or adjuvants, and also to pharmaceutical preparations which comprise at least one further medicament active compound (or therapeutic agent).

In particular, the invention also relates to a process for the preparation of a pharmaceutical preparation, characterised in that a compound of the formula (I) and/or one of its pharmaceutically acceptable salts, solvates, prodrugs and stereoisomers, including mixtures thereof in all ratios, is brought into a suitable dosage form together with a solid, liquid or semi-liquid excipient or adjuvant and optionally with a further medicament active compound.

The pharmaceutical preparations according to the invention can be used as medicaments in human or veterinary medicine. The patient or host can belong to any mammal species, for example a primate species, particularly humans; rodents, including mice, rats and hamsters; rabbits; horses, cattle, dogs, cats, etc. Animal models are of interest for experimental investigations, where they provide a model for the treatment of a human disease.

Suitable carrier substances are organic or inorganic substances which are suitable for enteral (for example oral), parenteral or topical administration and do not react with the novel compounds, for example water, vegetable oils (such as sunflower oil or cod-liver oil), benzyl alcohols, polyethylene glycols, gelatine, carbohydrates, such as lactose or starch, magnesium stearate, talc, lanolin or Vaseline. Owing to his expert knowledge, the person skilled in the art is familiar with which adjuvants are suitable for the desired medicament formulation. Besides solvents, for example water, physiological saline solution or alcohols, such as, for example, ethanol, propanol or glycerol, sugar solutions, such as glucose or mannitol solutions, or a mixture of the said solvents, gel formers, tablet assistants and other active-ingredient carriers, it is also possible to use, for example, lubricants, stabilisers and/or wetting agents, emulsifiers, salts for influencing the osmotic pressure, antioxidants, dispersants, antifoams, buffer substances, flavours and/or aromas or flavour correctants, preservatives, solubilisers or dyes. If desired, preparations or medicaments according to the invention may comprise one or more further active compounds, for example one or more vitamins.

If desired, preparations or medicaments according to the invention may comprise one or more further active compounds and/or one or more action enhancers (adjuvants).

The terms "pharmaceutical formulation" and "pharmaceutical preparation" are used as synonyms for the purposes of the present invention.

As used here, "pharmaceutically acceptable relates to medicaments, precipitation reagents, excipients, adjuvants, stabilisers, solvents and other agents which facilitate the administration of the pharmaceutical preparations obtained therefrom to a mammal without undesired physiological side effects, such as, for example, nausea, dizziness, digestion problems or the like.

In pharmaceutical preparations for parenteral administration, there is a requirement for isotonicity, euhydration and tolerability and safety of the formulation (low toxicity), of the adjuvants employed and of the primary packaging. Surprisingly, the compounds according to the invention preferably have the advantage that direct use is possible and further purification steps for the removal of toxicologically unacceptable agents, such as, for example, high concentrations of organic solvents or other toxicologically unacceptable adjuvants, are thus unnecessary before use of the compounds according to the invention in pharmaceutical formulations.

The invention particularly preferably also relates to pharmaceutical preparations comprising at least one compound according to the invention in precipitated non-crystalline, precipitated crystalline or in dissolved or suspended form, and optionally excipients and/or adjuvants and/or further pharmaceutical active compounds.

The compounds according to the invention preferably enable the preparation of highly concentrated formulations without unfavourable, undesired aggregation of the compounds according to the invention occurring. Thus, ready-to-use solutions having a high active-ingredient content can be prepared with the aid of compounds according to the invention with aqueous solvents or in aqueous media.

The compounds and/or physiologically acceptable salts and solvates thereof can also be lyophilised and the resultant lyophilisates used, for example, for the preparation of injection preparations.

Aqueous preparations can be prepared by dissolving or suspending compounds according to the invention in an aqueous solution and optionally adding adjuvants. To this end, defined volumes of stock solutions comprising the said further adjuvants in defined concentration are advantageously added to a solution or suspension having a defined concentration of compounds according to the invention, and the mixture is optionally diluted with water to the pre-calculated concentration. Alternatively, the adjuvants can be added in solid form. The amounts of stock solutions and/or water which are necessary in each case can subsequently be added to the aqueous solution or suspension obtained. Compounds according to the invention can also advantageously be dissolved or suspended directly in a solution comprising all further adjuvants.

The solutions or suspensions comprising compounds according to the invention and having a pH of 4 to 10, preferably having a pH of 5 to 9, and an osmolality of 250 to 350 mOsmol/kg can advantageously be prepared. The pharmaceutical preparation can thus be administered directly substantially without pain intravenously, intra-arterially, intra-articularly, subcutaneously or percutaneously. In addition, the preparation may also be added to infusion solutions, such as, for example, glucose solution, isotonic saline solution or Ringer's solution, which may also contain further active compounds, thus also enabling relatively large amounts of active compound to be administered.

Pharmaceutical preparations according to the invention may also comprise mixtures of a plurality of compounds according to the invention.

The preparations according to the invention are physiologically well tolerated, easy to prepare, can be dispensed precisely and are preferably stable with respect to assay, decomposition products and aggregates throughout storage and transport and during multiple freezing and thawing processes. They can preferably be stored in a stable manner over a period of at least three months to two years at refrigerator temperature (2-8° C.) and at room temperature (23-27° C.) and 60% relative atmospheric humidity (R.H.).

For example, the compounds according to the invention can be stored in a stable manner by drying and when necessary converted into a ready-to-use pharmaceutical preparation by dissolution or suspension. Possible drying methods are, for example, without being restricted to these examples, nitrogen-gas drying, vacuum-oven drying, lyophilisation, washing with organic solvents and subsequent air drying, liquid-bed drying, fluidised-bed drying, spray drying, roller drying, layer drying, air drying at room temperature and further methods.

The term "effective amount" denotes the amount of a medicament or of a pharmaceutical active compound which causes in a tissue, system, animal or human a biological or medical response which is sought or desired, for example, by a researcher or physician.

In addition, the term "therapeutically effective amount" denotes an amount which, compared with a corresponding subject who has not received this amount, has the following consequence: improved treatment, healing, prevention or elimination of a disease, syndrome, disease state, complaint, disorder or prevention of side effects or also a reduction in the progress of a disease, complaint or disorder. The term "therapeutically effective amount" also encompasses the amounts which are effective for increasing normal physiological function.

On use of preparations or medicaments according to the invention, the compounds according to the invention and/or physiologically acceptable salts and solvates thereof are generally used analogously to known, commercially available preparations or preparations, preferably in dosages of between 0.1 and 500 mg, in particular 5 and 300 mg, per use unit. The daily dose is preferably between 0.001 and 250 mg/kg, in particular 0.01 and 100 mg/kg, of body weight. The preparation can be administered one or more times per day, for example two, three or four times per day. However, the individual dose for a patient depends on a large number of individual factors, such as, for example, on the efficacy of the particular compound used, on the age, body weight, general state of health, sex, nutrition, on the time and method of administration, on the excretion rate, on the combination with other medicaments and on the severity and duration of the particular disease.

A measure of the uptake of a medicament active compound in an organism is its bioavailability. If the medicament active compound is delivered to the organism intravenously in the form of an injection solution, its absolute bioavailability, i.e. the proportion of the pharmaceutical which reaches the systemic blood, i.e. the major circulation, in unchanged form, is 100%. In the case of oral administration of a therapeutic active compound, the active compound is generally in the form of a solid in the formulation and must therefore first be dissolved in order that it is able to overcome the entry barriers, for example the gastrointestinal tract, the oral mucous membrane, nasal membranes or the skin, in particular the stratum corneum, or can be absorbed by the body. Data on the pharmacokinetics, i.e. on the bioavailability, can be obtained analogously to the method of J. Shaffer et al., J. Pharm. Sciences, 88 (1999), 313-318.

Furthermore, medicaments of this type can be prepared by means of one of the processes generally known in the pharmaceutical art.

Medicaments can be adapted for administration via any desired suitable route, for example by the oral (including buccal or sublingual), rectal, pulmonary, nasal, topical (including buccal, sublingual or transdermal), vaginal or parenteral (including subcutaneous, intramuscular, intravenous, intradermal and intra-articular routes. Medicaments of this type can be prepared by means of all processes known in the pharmaceutical art by, for example, combining the active compound with the excipient(s) or adjuvant(s).

The compounds according to the invention are also suitable for the preparation of medicaments to be administered parenterally having slow, sustained and/or controlled release of active compound. They are thus also suitable for the preparation of delayed-release formulations, which are advantageous for the patient since administration is only necessary at relatively large time intervals.

The medicaments include aqueous and non-aqueous sterile injection solutions comprising antioxidants, buffers, bacteriostatics and solutes, by means of which the formulation is rendered isotonic with the blood or synovial fluid of the recipient to be treated; as well as aqueous and non-aqueous sterile suspensions, which can comprise suspension media and thickeners. The formulations can be delivered in single-dose or multi-dose containers, for example sealed ampoules and vials, and stored in the freeze-dried (lyophilised) state, so that only the addition of the sterile carrier liquid, for example water for injection purposes, immediately before use is necessary. Injection solutions and suspensions prepared in accordance with the formulation can be prepared from sterile powders, granules and tablets.

The compounds according to the invention can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention can also be coupled to soluble polymers as targeted medicament excipients. Such polymers can encompass polyvinyl-pyrrolidone, pyran copolymer, polyhydroxypropylmethacrylamidophenol, polyhydroxy-ethylaspartamidophenol or polyethylene oxide polylysine, substituted by palmitoyl radicals. The compounds according to the invention can furthermore be coupled to a class of biodegradable polymers which are suitable for achieving slow release of a medicament, for example polylactic acid, poly-epsilon-caprolactone, polyhydroxybutyric acid, polyorthoesters, polyacetals, polydihydroxypyrans, poly-cyanoacrylates, polylactic-co-glycolic acid, polymers, such as conjugates between dextran and methacrylates, polyphosphoesters, various polysaccharides and poly-amines and poly-ε-caprolactone, albumin, chitosan, collagen or modified gelatine and crosslinked or amphipathic block copolymers of hydrogels.

Suitable for enteral administration (oral or rectal) are, in particular, tablets, dragees, capsules, syrups, juices, drops or suppositories, and suitable for topical use are ointments, creams, pastes, lotions, gels, sprays, foams, aerosols, solutions (for example solutions in alcohols, such as ethanol or isopropanol, acetonitrile, DMF, dimethylacetamide, 1,2-propanediol or mixtures thereof with one another and/or with water) or powders. Also particularly suitable for topical uses are liposomal preparations.

In the case of formulation to give an ointment, the active compound can be employed either with a paraffinic or a water-miscible cream base. Alternatively, the active compound can be formulated to a cream with an oil-in-water cream base or a water-in-oil base.

Medicaments adapted to transdermal administration can be delivered as independent plasters for extended, close contact with the epidermis of the recipient. Thus, for example, the active compound can be supplied from the plaster by means of iontophoresis, as described in general terms in Pharmaceutical Research, 3 (6), 318 (1986).

It goes without saying that, besides the constituents particularly mentioned above, the medicaments according to the invention may also comprise other agents usual in the art with respect to the particular type of pharmaceutical formulation.

The invention also relates to a set (or kit) comprising (or consisting of) separate packs of:
(a) a compound of formula (I) or a pharmaceutically acceptable salt, solvate or prodrug thereof; and (b) a further therapeutic agent.

In particular, the present invention relates to a set (or kit) comprising (or consisting of) separate packs of:
(a) an effective amount of a compound of the formula (I) and/or pharmaceutically acceptable salts, solvates, prodrugs and stereoisomers thereof, including mixtures thereof in all ratios; and
(b) an effective amount of a further medicament active compound (or further therapeutic agent).

The set comprises suitable containers, such as boxes or cartons, individual bottles, bags or ampoules. The set may, for example, comprise separate ampoules each containing an effective amount of a compound of the formula I and/or pharmaceutically acceptable salts, derivatives, solvates, prodrugs and stereoisomers thereof, including mixtures thereof in all ratios, and an effective amount of a further medicament active compound in dissolved or lyophilised form.

Furthermore, the medicaments according to the invention can be used in order to provide additive or synergistic effects in certain known therapies and/or can be used in order to restore the efficacy of certain existing therapies.

Besides the compounds according to the invention, the pharmaceutical preparations according to the invention may also comprise further medicament active compounds, for example for use in the treatment of cancer, other anti-tumor medicaments. For the treatment of the other diseases mentioned, the pharmaceutical preparations according to the invention may also, besides the compounds according to the invention, comprise further medicament active compounds which are known to the person skilled in the art in the treatment thereof.

In one principal embodiment, methods are provided for enhancing an immune response in a host in need thereof. The immune response can be enhanced by reducing T cell tolerance, including by increasing IFN-γ release, by decreasing regulatory T cell production or activation, or by increasing antigen-specific memory T cell production in a host. In one embodiment, the method comprises administering a compound of the present invention to a host in combination or alternation with an antibody. In particular subembodiments, the antibody is a therapeutic antibody. In one particular embodiment, a method of enhancing efficacy of passive antibody therapy is provided comprising administering a compound of the present invention in combination or alternation with one or more passive antibodies. This method can enhance the efficacy of antibody therapy for treatment of abnormal cell proliferative disorders such as cancer or can enhance the efficacy of therapy in the treatment or prevention of infectious diseases. The compound of the present invention can be administered in combination or alternation with antibodies such as rituximab, herceptin or erbitux, for example.

In another principal embodiment, a method of treating or preventing abnormal cell proliferation is provided comprising administering a compound of the present invention to a host in need thereof substantially in the absence of another anti-cancer agent.

In another principal embodiment, a method of treating or preventing abnormal cell proliferation in a host in need thereof is provided, comprising administering a first a compound of the present invention substantially in combination with a first anti-cancer agent to the host and subsequently administering a second $A_{2A}$ and/or $A_{2B}$ receptor antagonist. In one subembodiment, the second antagonist is administered substantially in the absence of another anti-cancer agent. In another principal embodiment, a method of treating or preventing abnormal cell proliferation in a host in need thereof is provided, comprising administering a compound of the present invention substantially in combination with a first anti-cancer agent to the host and subsequently administering a second anti-cancer agent in the absence of the antagonist.

Thus, the cancer treatment disclosed here can be carried out as therapy with a compound of the present invention or in combination with an operation, irradiation or chemotherapy. Chemotherapy of this type can include the use of one or more active compounds of the following categories of antitumour active compounds:

(i) antiproliferative/antineoplastic/DNA-damaging active compounds and combinations thereof, as used in medical oncology, such as alkylating active compounds (for example cis-platin, parboplatin, cyclophosphamide, nitrogen mustard, melphalan, chlorambucil, busulphan and nitrosoureas); antimetabolites (for example antifolates such as fluoropyrimidines such as 5-fluorouracil and tegafur, raltitrexed, methotrexate, cytosine arabinoside, hydroxyurea and gemcitabine); antitumour antibiotics (for example anthracyclines, such as adriamycin, bleomycin, doxorubicin, daunomycin, epirubicin, idarubicin, mitomycin-C, dactinomycin and mithramycin); antimitotic active compounds (for example *vinca* alkaloids, such as vincristine, vinblastine, vindesine and vinorelbine, and taxoids, such as taxol and taxotere); topoisomerase inhibitors (for example epipodophyllotoxins, such as etoposide and teniposide, amsacrine, topotecan, irinotecan and camptothecin) and cell-differentiating active compounds (for example all-trans-retinoic acid, 13-cis-retinoic acid and fenretinide);

(ii) cytostatic active compounds, such as anti-oestrogens (for example tamoxifen, toremifene, raloxifene, droloxifene and iodoxyfene), oestrogen receptor regulators (for example fulvestrant), anti-androgens (for example bicalutamide, flutamide, nilutamide and cyproterone acetate), LHRH antagonists or LHRH agonists (for example goserelin, leuprorelin and buserelin), progesterones (for example megestrol acetate), aromatase inhibitors (for example anastrozole, letrozole, vorazole and exemestane) and inhibitors of 5α-reductase, such as finasteride;

(iii) active compounds which inhibit cancer invasion including for example metallo-proteinase inhibitors, like marimastat, and inhibitors of urokinase plasminogen activator receptor function;

(iv) inhibitors of growth factor function, for example growth factor antibodies, growth factor receptor antibodies, for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033), for example inhibitors of the platelet-derived growth factor family and, for example, inhibitors of the hepatocyte growth factor family;

(v) anti-angiogenic active compounds, such as bevacizumab, angiostatin, endostatin, linomide, batimastat, captopril, cartilage derived inhibitor, genistein, interleukin 12, lavendustin, medroxypregesterone acetate, recombinant human platelet factor 4, tecogalan, thrombospondin, TNP-470, anti-VEGF monoclonal antibody, soluble VEGF-receptor chimaeric protein, anti-VEGF receptor antibodies, anti-PDGF receptors, inhibitors of integrins, tyrosine kinase inhibitors, serine/threonine kinase inhibitors, antisense oligonucleotides, antisense oligodexoynucleotides, siRNAs, anti-VEGF aptamers, pigment epithelium derived factor and compounds which have been published in the international patent applications WO 97/22596, WO 97/30035, WO 97/32856 and WO 98/13354);

(vi) vessel-destroying agents, such as combretastatin A4 and compounds which have been published in the international patent applications WO 99/02166, WO 00/40529, WO 00/41669, WO 01/92224, WO 02/04434 and WO 02/08213;

(vii) antisense therapies, for example those directed to the targets mentioned above, such as ISIS 2503, an anti-Ras antisense;

(viii) gene therapy approaches, including, for example, approaches for replacement of abnormal, modified genes, such as abnormal p53 or abnormal BRCA1 or BRCA2, GDEPT approaches (gene-directed enzyme pro-drug therapy), such as those which use cytosine deaminase, thymidine kinase or a bacterial nitroreductase enzyme, and approaches which increase the tolerance of a patient to chemotherapy or radiotherapy, such as multi-drug resistance therapy;

(ix) immunotherapy approaches, including, for example, ex-vivo and in-vivo approaches for increasing the immunogenicity of tumour cells of a patient, such as transfection with cytokines, such as interleukin 2, interleukin 4 or granulocyte macrophage colony stimulating factor, approaches for decreasing T-cell anergy, approaches using transfected immune cells, such as cytokine-transfected dendritic cells, approaches for use of cytokine-transfected tumour cells and approaches for use of anti-idiotypic antibodies; and (x) chemotherapeutic agents including for example abarelix, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, epirubicin, epoetin alfa, estramustine, etoposide, exemestane, filgrastim, floxuridine, fludarabine, fluorouracil, fulvestrant and gemcitabine.

Furthermore, the compound of formula (I) or the pharmaceutically acceptable salt, solvate or prodrug thereof, or the pharmaceutical composition comprising the compound of formula (I) or a pharmaceutically acceptable salt, solvate or prodrug thereof, can be administered in monotherapy (e.g., without concomitantly administering any further therapeutic agents, or without concomitantly administering any further therapeutic agents against the same disease/disorder that is to be treated or prevented with the compound of formula (I)).

However, as has been explained above, the compound of formula (I) or the pharmaceutically acceptable salt, solvate or prodrug thereof, or the pharmaceutical composition comprising the compound of formula (I) or a pharmaceutically acceptable salt, solvate or prodrug thereof, can also be administered in combination with one or more further therapeutic agents. If the compound of formula (I) or the pharmaceutically acceptable salt, solvate or prodrug thereof is used in combination with a second therapeutic agent active against the same disease/disorder, the dose of each compound may differ from that when the corresponding compound is used alone, in particular, a lower dose of each compound may be used. The combination of the compound of formula (I) or the pharmaceutically acceptable salt, solvate or prodrug thereof with one or more further therapeutic agents may comprise the simultaneous/concomitant administration of the compound of formula (I) or the pharmaceutically acceptable salt, solvate or prodrug thereof and the further therapeutic agent(s) (either in a single pharmaceutical formulation or in separate pharmaceutical formulations), or the sequential/separate administration of the compound of formula (I) or the pharmaceutically acceptable salt, solvate or prodrug thereof and the further therapeutic agent(s). If administration is sequential, either the compound of formula (I) or the pharmaceutically acceptable salt, solvate or prodrug thereof according to the present invention, or the one or more further therapeutic agents may be administered first. If administration is simultaneous, the one or more further therapeutic agents may be included in the same pharmaceutical formulation as the compound of formula (I) or the pharmaceutically acceptable salt, solvate or prodrug thereof, or they may be administered in two or more different (separate) pharmaceutical formulations. The further therapeutic agent(s) may be, for example, selected from any one of the corresponding exemplary compounds described herein above, including any of the compounds listed in table 1.

The subject or patient to be treated in accordance with the present invention may be an animal (e.g., a non-human animal). Preferably, the subject/patient is a mammal. More preferably, the subject/patient is a human (e.g., a male human or a female human) or a non-human mammal (such as, e.g., a guinea pig, a hamster, a rat, a mouse, a rabbit, a dog, a cat, a horse, a monkey, an ape, a marmoset, a baboon, a gorilla, a chimpanzee, an orangutan, a gibbon, a sheep, cattle, or a pig). Most preferably, the subject/patient to be treated in accordance with the invention is a human.

The term "treatment" of a condition, disorder or disease, as used herein, is well known in the art. "Treatment" of a condition, disorder or disease implies that a condition, disorder or disease is suspected or has been diagnosed in a patient/subject. A patient/subject suspected of suffering from a condition, disorder or disease typically shows specific clinical and/or pathological symptoms which a skilled person can easily attribute to a specific pathological condition (i.e., diagnose a condition, disorder or disease).

The "treatment" of a condition, disorder or disease may, for example, lead to a halt in the progression of the condition, disorder or disease (e.g., no deterioration of symptoms) or a delay in the progression of the condition, disorder or disease (in case the halt in progression is of a transient nature only). The "treatment" of a condition, disorder or disease may also lead to a partial response (e.g., amelioration of symptoms) or complete response (e.g., disappearance of symptoms) of the subject/patient suffering from the condition, disorder or disease. Accordingly, the "treatment" of a condition, disorder or disease may also refer to an amelioration of the condition, disorder or disease, which may, e.g., lead to a halt in the progression of the condition, disorder or disease or a delay in the progression of the condition, disorder or disease. Such a partial or complete response may be followed by a relapse. It is to be understood that a subject/patient may experience a broad range of responses to a treatment (such as the exemplary responses as described herein above). The treatment of a condition, disorder or disease may, inter alia, comprise curative treatment (preferably leading to a complete response and eventually to healing of the condition, disorder or disease) and palliative treatment (including symptomatic relief).

The term "prevention" of a condition, disorder or disease, as used herein, is also well known in the art. For example, a patient/subject suspected of being prone to suffer from a condition, disorder or disease may particularly benefit from a prevention of the condition, disorder or disease. The subject/patient may have a susceptibility or predisposition for a condition, disorder or disease, including but not limited to hereditary predisposition. Such a predisposition can be determined by standard methods or assays, using, e.g., genetic markers or phenotypic indicators. It is to be understood that a condition, disorder or disease to be prevented in accordance with the present invention has not been diagnosed or cannot be diagnosed in the patient/subject (for example, the patient/subject does not show any clinical or pathological symptoms). Thus, the term "prevention" comprises the use of a compound of the present invention before any clinical and/or pathological symptoms are diagnosed or determined or can be diagnosed or determined by the attending physician.

The present invention furthermore relates to the use of a compound of formula (I) or a pharmaceutically acceptable salt, solvate or prodrug thereof as an adenosine $A_{2A}$ and/or $A_{2B}$ receptor antagonist (particularly as a dual adenosine $A_{2A}$ and $A_{2B}$ receptor antagonist) in research, particularly as a research tool compound for inhibiting/antagonizing the adenosine $A_{2A}$ and/or $A_{2B}$ receptor. Accordingly, the invention refers to the in vitro use of a compound of formula (I) or a pharmaceutically acceptable salt, solvate or prodrug thereof as an adenosine $A_{2A}$ and/or $A_{2B}$ receptor antagonist (particularly as a dual adenosine $A_{2A}$ and $A_{2B}$ receptor antagonist) and, in particular, to the in vitro use of a compound of formula (I) or a pharmaceutically acceptable salt, solvate or prodrug thereof as a research tool compound acting as an adenosine $A_{2A}$ and/or $A_{2B}$ receptor antagonist (particularly as a dual adenosine $A_{2A}$ and $A_{2B}$ receptor antagonist). The invention likewise relates to a method, particularly an in vitro method, of inhibiting the adenosine $A_{2A}$ and/or $A_{2B}$ receptor, the method comprising the application of a compound of formula (I) or a pharmaceutically acceptable salt, solvate or prodrug thereof. The invention further relates to a method of inhibiting the adenosine $A_{2A}$ and/or $A_{2B}$ receptor, the method comprising applying a compound of formula (I) or a pharmaceutically acceptable salt, solvate or prodrug thereof to a test sample (e.g., a biological sample) or a test animal (i.e., a non-human test animal). The invention also refers to a method, particularly an in vitro method, of inhibiting the adenosine $A_{2A}$ and/or $A_{2B}$ receptor in a sample (e.g., a biological sample), the method comprising applying a compound of formula (I) or a pharmaceutically acceptable salt, solvate or prodrug thereof to said sample. The present invention further provides a method of inhibiting the adenosine $A_{2A}$ and/or $A_{2B}$ receptor, the method comprising contacting a test sample (e.g., a biological sample) or a test animal (i.e., a non-human test animal) with a compound of formula (I) or a pharmaceutically acceptable salt, solvate or prodrug thereof. The terms "sample", "test sample" and "biological sample" include, without being limited thereto: a cell, a cell culture or a cellular or subcellular extract; biopsied material obtained from an animal (e.g., a human), or an extract thereof; or blood, serum, plasma, saliva, urine, feces, or any other body fluid, or an extract thereof. It is to be understood that the term "in vitro" is used in this specific context in the sense of "outside a living human or animal body", which includes, in particular, experiments performed with cells, cellular or subcellular extracts, and/or biological molecules in an artificial environment such as an aqueous solution or a culture medium which may be provided, e.g., in a flask, a test tube, a Petri dish, a microtiter plate, etc.

It is to be understood that the present invention specifically relates to each and every combination of features and embodiments described herein, including any combination of general and/or preferred features/embodiments. In particular, the invention specifically relates to each combination of meanings (including general and/or preferred meanings) for the various groups and variables comprised in formula (I).

In this specification, a number of documents including patents, patent applications and scientific literature are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The reference in this specification to any prior publication (or information derived therefrom) is not and should not be taken as an acknowledgment or admission or any form of suggestion that the corresponding prior publication (or the information derived therefrom) forms part of the common general knowledge in the technical field to which the present specification relates.

The invention will now be described by reference to the following examples which are merely illustrative and are not to be construed as a limitation of the scope of the present invention.

EXAMPLES

The compounds described in this section are defined by their chemical formulae and their corresponding chemical names. In case of conflict between any chemical formula and the corresponding chemical name indicated herein, the present invention relates to both the compound defined by the chemical formula and the compound defined by the chemical name, and particularly relates to the compound defined by the chemical formula.

Unless indicated otherwise, percent data denote percent by weight. All temperatures are indicated in degrees Celsius. "Conventional work-up": water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate, filtered and evaporated, and the product is purified by chromatography on silica gel and/or by crystallisation.

Rf values on silica gel; mass spectrometry: EI (electron impact ionisation): $M^+$, FAB (fast atom bombardment): $(M+H)^+$, THF (tetrahydrofuran), NMP (N-methlpyrrolidone), DMSO (dimethyl sulfoxide), EA (ethyl acetate), MeOH (methanol), TLC (thin-layer chromatography)

LIST OF ABBREVIATIONS

AcOEt Ethyl Acetate
DCM Dichloromethane
DMA Dimethylacetamide
DMF Dimethylformamide
DMSO Dimethyl sulfoxide
iv Intravenous
LC-MS Liquid Chromatography coupled to Mass Spectrometry
MeOH Methanol
NC Not calculated
ND Not determined
NMR Nuclear Magnetic Resonance
PEG Polyethylene glycol
po Per os (oral)
UPLC Ultra performance liquid chromatography
v/v Volume to volume

Example 1: Examples of Compounds of the Present Invention

The present invention especially relates to the compounds of table 2 and pharmaceutically/physiologically acceptable salts, solvates and prodrugs thereof (including also stereoisomers thereof, as well as mixtures thereof in all ratios).

TABLE 2 examples of compounds of the present invention

| No. | Structure | IUPAC-Name | MW |
|---|---|---|---|
| 1 | 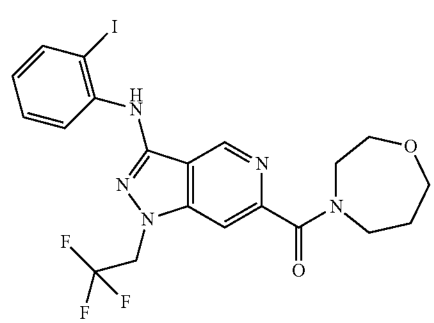 [SMILES: O=C(c1cc2c(cn1)c(Nc1ccccc1I)nn2CC(F)(F)F)N1CCCOCC1] | [3-(2-fluoroanilino)-1-(2,2,2-trifluoroethyl)pyrazolo[4,3-c]pyridin-6-yl]-(1,4-oxazepan-4-yl)methanone | 437.39 |

TABLE 2-continued examples of compounds of the present invention

| No. | Structure | IUPAC-Name | MW |
|---|---|---|---|
| 2 | 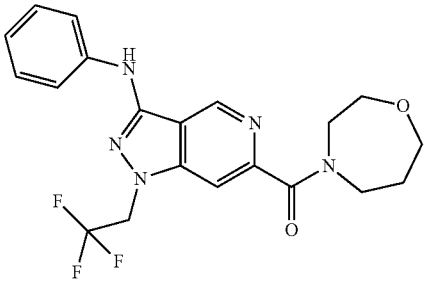 [SMILES: O=C(c1cc2c(cn1)c(Nc1ccccc1)nn2CC(F)(F)F)N1CCCOCC1] | [3-anilino-1-(2,2,2-trifluoroethyl)pyrazolo[4,3-c]pyridin-6-yl]-(1,4-oxazepan-4-yl)methanone | 419.40 |
| 3 | 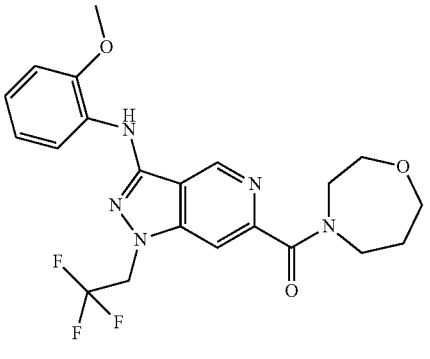 [SMILES: COc1ccccc1Nc1nn(CC(F)(F)F)c2cc(C(=O)N3CCCOCC3)ncc12] | [3-(2-methoxyanilino)-1-(2,2,2-trifluoroethyl)pyrazolo[4,3-c]pyridin-6-yl]-(1,4-oxazepan-4-yl)methanone | 449.43 |
| 4 | 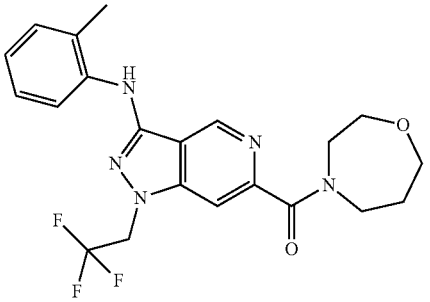 [SMILES: Cc1ccccc1Nc1nn(CC(F)(F)F)c2cc(C(=O)N3CCCOCC3)ncc12] | [3-(2-methylanilino)-1-(2,2,2-trifluoroethyl)pyrazolo[4,3-c]pyridin-6-yl]-(1,4-oxazepan-4-yl)methanone | 433.43 |
| 5 | 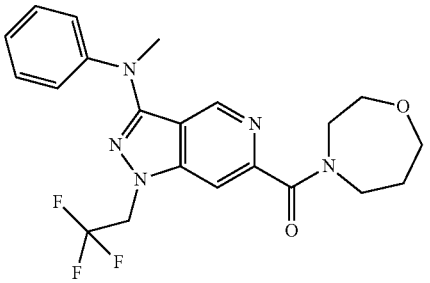 [SMILES: CN(c1ccccc1)c1nn(CC(F)(F)F)c2cc(C(=O)N3CCCOCC3)ncc12] | [3-(N-methylanilino)-1-(2,2,2-trifluoroethyl)pyrazolo[4,3-c]pyridin-6-yl]-(1,4-oxazepan-4-yl)methanone | 433.43 |
| 6 | 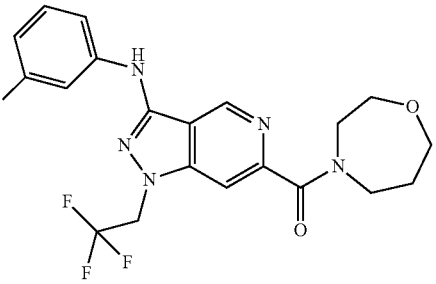 | [3-(3-fluoroanilino)-1-(2,2,2-trifluoroethyl)pyrazolo[4,3-c]pyridin-6-yl]-(1,4-oxazepan-4-yl)methanone | 437.39 |

TABLE 2-continued examples of compounds of the present invention

| No. | Structure | IUPAC-Name | MW |
|-----|-----------|------------|-----|
| 7 | 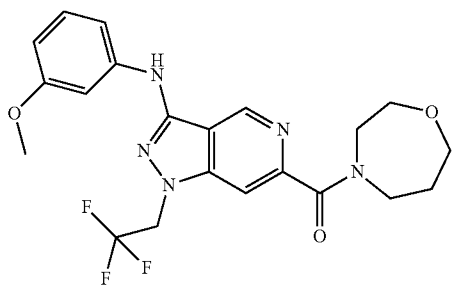 [SMILES: COc1cccc(Nc2nn(CC(F)(F)F)c3cc(C(=O)N4CCCOCC4)ncc23)c1] | [3-(3-methoxyanilino)-1-(2,2,2-trifluoroethyl)pyrazolo[4,3-c]pyridin-6-yl]-(1,4-oxazepan-4-yl)methanone | 449.43 |
| 8 | 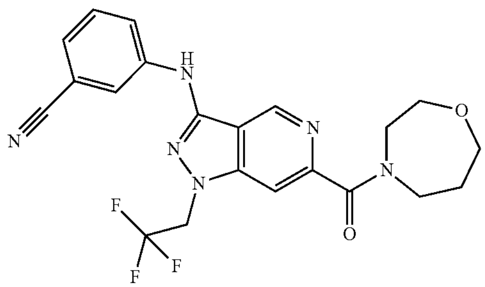 [SMILES: N#Cc1cccc(Nc2nn(CC(F)(F)F)c3cc(C(=O)N4CCCOCC4)ncc23)c1] | 3-[[6-(1,4-oxazepane-4-carbonyl)-1-(2,2,2-trifluoroethyl)pyrazolo[4,3-c]pyridin-3-yl]amino]benzonitrile | 444.41 |
| 9 | 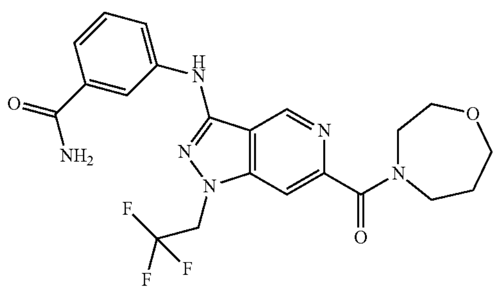 [SMILES: NC(=O)c1cccc(Nc2nn(CC(F)(F)F)c3cc(C(=O)N4CCCOCC4)ncc23)c1] | 3-[[6-(1,4-oxazepane-4-carbonyl)-1-(2,2,2-trifluoroethyl)pyrazolo[4,3-c]pyridin-3-yl]amino]benzamide | 462.43 |
| 10 | 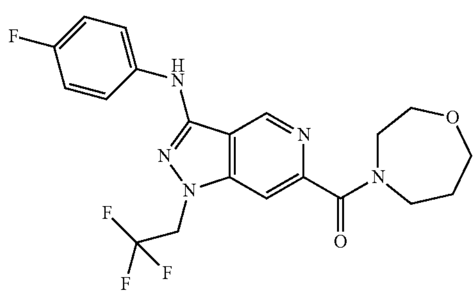 [SMILES: O=C(c1cc2c(cn1)c(Nc1ccc(F)cc1)nn2CC(F)(F)F)N1CCCOCC1] | [3-(4-fluoroanilino)-1-(2,2,2-trifluoroethyl)pyrazolo[4,3-c]pyridin-6-yl]-(1,4-oxazepan-4-yl)methanone | 437.39 |
| 11 | 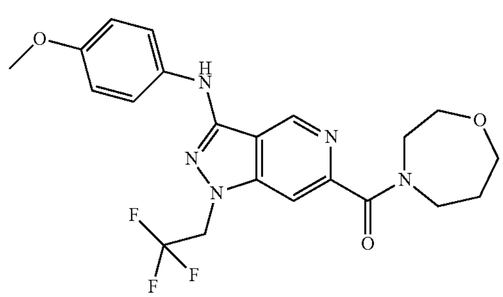 [SMILES: COc1ccc(Nc2nn(CC(F)(F)F)c3cc(C(=O)N4CCCOCC4)ncc23)cc1] | [3-(4-methoxyanilino)-1-(2,2,2-trifluoroethyl)pyrazolo[4,3-c]pyridin-6-yl]-(1,4-oxazepan-4-yl)methanone | 449.43 |

TABLE 2-continued examples of compounds of the present invention

| No. | Structure | IUPAC-Name | MW |
|---|---|---|---|
| 12 | 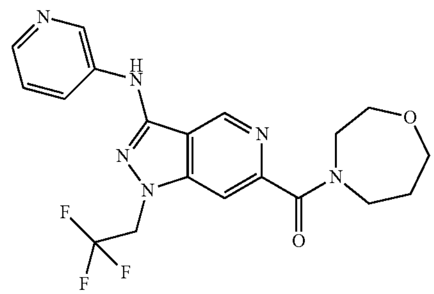 [SMILES: O=C(c1cc2c(cn1)c(Nc1cccnc1)nn2CC(F)(F)F)N1CCCOCC1] | 1,4-oxazepan-4-yl-[3-(3-pyridylamino)-1-(2,2,2-trifluoroethyl)pyrazolo[4,3-c]pyridin-6-yl]methanone | 420.39 |
| 13 | 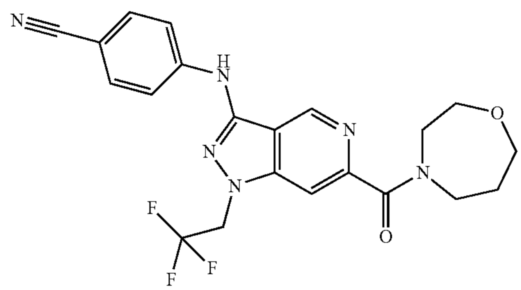 [SMILES: N#Cc1ccc(Nc2nn(CC(F)(F)F)c3cc(C(=O)N4CCCOCC4)ncc23)cc1] | 4-[[6-(1,4-oxazepane-4-carbonyl)-1-(2,2,2-trifluoroethyl)pyrazolo[4,3-c]pyridin-3-yl]amino]benzonitrile | 444.41 |
| 14 | 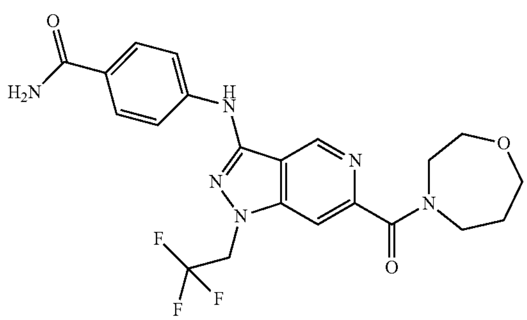 [SMILES: NC(=O)c1ccc(Nc2nn(CC(F)(F)F)c3cc(C(=O)N4CCCOCC4)ncc23)cc1] | 4-[[6-(1,4-oxazepane-4-carbonyl)-1-(2,2,2-trifluoroethyl)pyrazolo[4,3-c]pyridin-3-yl]amino]benzamide | 462.43 |
| 15 | 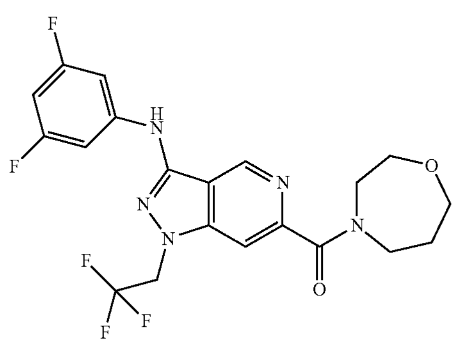 [SMILES: O=C(c1cc2c(cn1)c(Nc1cc(F)cc(F)c1)nn2CC(F)(F)F)N1CCCOCC1] | [3-(3,5-difluoroanilino)-1-(2,2,2-trifluoroethyl)pyrazolo[4,3-c]pyridin-6-yl]-(1,4-oxazepan-4-yl)methanone | 455.38 |
| 16 | 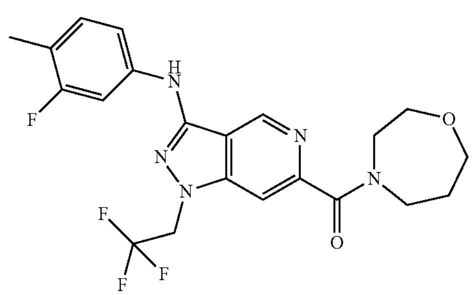 [SMILES: Cc1ccc(Nc2nn(CC(F)(F)F)c3cc(C(=O)N4CCCOCC4)ncc23)cc1F] | [3-(3-fluoro-4-methylanilino)-1-(2,2,2-trifluoroethyl)pyrazolo[4,3-c]pyridin-6-yl]-(1,4-oxazepan-4-yl)methanone | 451.42 |

TABLE 2-continued examples of compounds of the present invention

| No. | Structure | IUPAC-Name | MW |
|---|---|---|---|
| 17 | 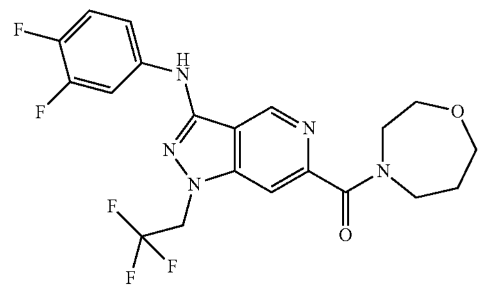 | [3-(3,4-difluoroanilino)-1-(2,2,2-trifluoroethyl)pyrazolo[4,3-c]pyridin-6-yl]-(1,4-oxazepan-4-yl)methanone | 455.38 |
| 18 | 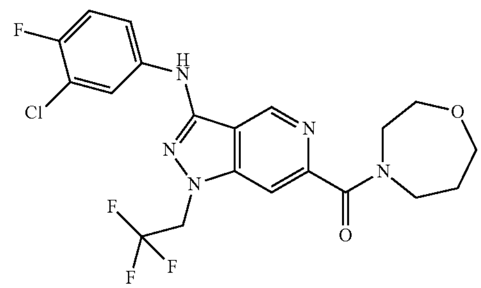 | [3-(3-chloro-4-fluoroanilino)-1-(2,2,2-trifluoroethyl)pyrazolo[4,3-c]pyridin-6-yl]-(1,4-oxazepan-4-yl)methanone | 471.84 |
| 19 | 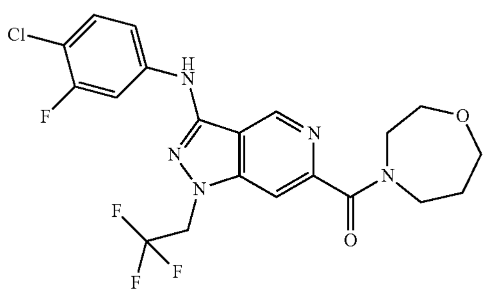 [SMILES: O=C(c1cc2c(cn1)c(Nc1ccc(Cl)c(F)c1)nn2CC(F)(F)F)N1CCCOCC1] | [3-(4-chloro-3-fluoroanilino)-1-(2,2,2-trifluoroethyl)pyrazolo[4,3-c]pyridin-6-yl]-(1,4-oxazepan-4-yl)methanone | 471.84 |
| 20 | 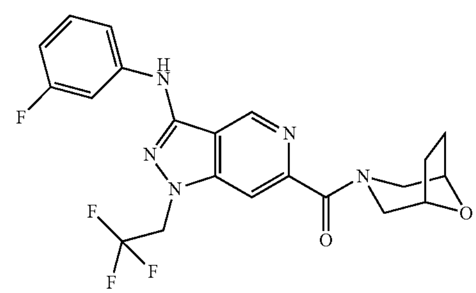 [SMILES: O=C(c1cc2c(cn1)c(Nc1cccc(F)c1)nn2CC(F)(F)F)N1CC2CCC(C1)O2] | [3-(3-fluoroanilino)-1-(2,2,2-trifluoroethyl)pyrazolo[4,3-c]pyridin-6-yl]-(8-oxa-3-azabicyclo[3.2.1]octan-3-yl)methanone | 449.40 |
| 21 | 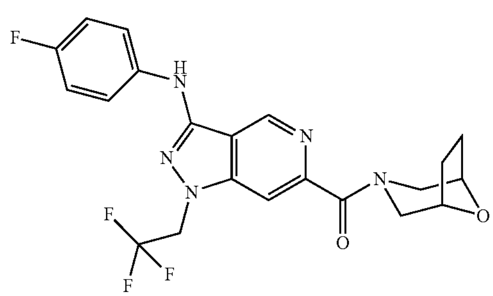 [SMILES: O=C(c1cc2c(cn1)c(Nc1ccc(F)cc1)nn2CC(F)(F)F)N1CC2CCC(C1)O2] | [3-(4-fluoroanilino)-1-(2,2,2-trifluoroethyl)pyrazolo[4,3-c]pyridin-6-yl]-(8-oxa-3-azabicyclo[3.2.1]octan-3-yl)methanone | 449.40 |

TABLE 2-continued examples of compounds of the present invention

| No. | Structure | IUPAC-Name | MW |
|---|---|---|---|
| 22 | 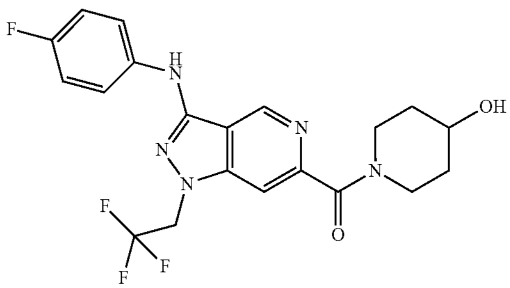 [SMILES: O=C(c1cc2c(cn1)c(Nc1ccc(F)cc1)nn2CC(F)(F)F)N1CCC(O)CC1] | [3-(4-fluoroanilino)-1-(2,2,2-trifluoroethyl)pyrazolo[4,3-c]pyridin-6-yl]-(4-hydroxy-1-piperidyl)methanone | 437.39 |
| 23 | 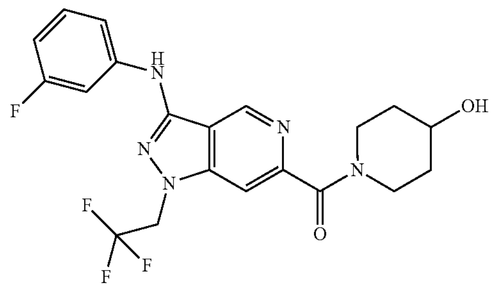 [SMILES: O=C(c1cc2c(cn1)c(Nc1cccc(F)c1)nn2CC(F)(F)F)N1CCC(O)CC1] | [3-(3-fluoroanilino)-1-(2,2,2-trifluoroethyl)pyrazolo[4,3-c]pyridin-6-yl]-(4-hydroxy-1-piperidyl)methanone | 437.39 |
| 24 | 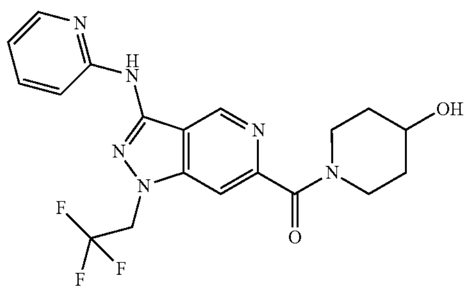 [SMILES: O=C(c1cc2c(cn1)c(Nc1ccccn1)nn2CC(F)(F)F)N1CCC(O)CC1] | (4-hydroxy-1-piperidyl)-[3-(2-pyridylamino)-1-(2,2,2-trifluoroethyl)pyrazolo[4,3-c]pyridin-6-yl]methanone | 420.39 |
| 25 | 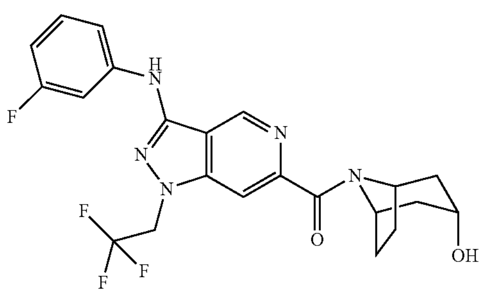 [SMILES: O=C(c1cc2c(cn1)c(Nc1cccc(F)c1)nn2CC(F)(F)F)N1C2CCC1CC(O)C2] | [3-(3-fluoroanilino)-1-(2,2,2-trifluoroethyl)pyrazolo[4,3-c]pyridin-6-yl]-(3-endo-hydroxy-8-azabicyclo[3.2.1]octan-8-yl)methanone | 463.43 |
| 26 | 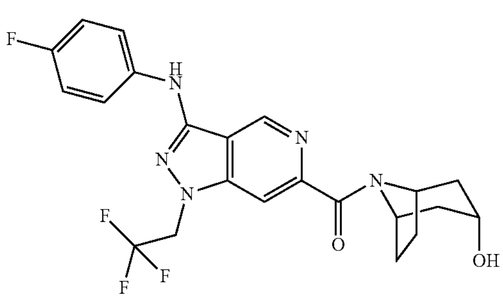 [SMILES: O=C(c1cc2c(cn1)c(Nc1ccc(F)cc1)nn2CC(F)(F)F)N1C2CCC1CC(O)C2] | [3-(4-fluoroanilino)-1-(2,2,2-trifluoroethyl)pyrazolo[4,3-c]pyridin-6-yl]-(3-endo-hydroxy-8-azabicyclo[3.2.1]octan-8-yl)methanone | 463.43 |

TABLE 2-continued examples of compounds of the present invention

| No. | Structure | IUPAC-Name | MW |
|---|---|---|---|
| 27 | 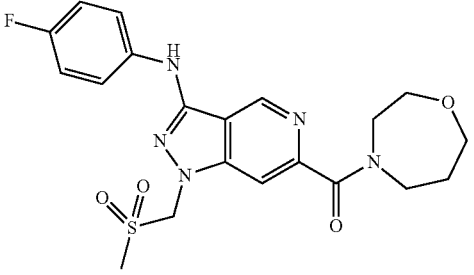 [SMILES: CS(=O)(=O)Cn1nc(Nc2ccc(F)cc2)c2cnc(C(=O)N3CCCOCC3)cc21] | [3-(4-fluoroanilino)-1-(methylsulfonylmethyl)pyrazolo[4,3-c]pyridin-6-yl]-(1,4-oxazepan-4-yl)methanone | 447.48 |
| 28 | 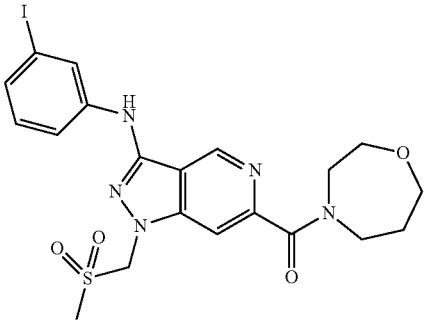 [SMILES: CS(=O)(=O)Cn1nc(Nc2cccc(I)c2)c2cnc(C(=O)N3CCCOCC3)cc21] | [3-(3-fluoroanilino)-1-(methylsulfonylmethyl)pyrazolo[4,3-c]pyridin-6-yl]-(1,4-oxazepan-4-yl)methanone | 447.48 |
| 29 | 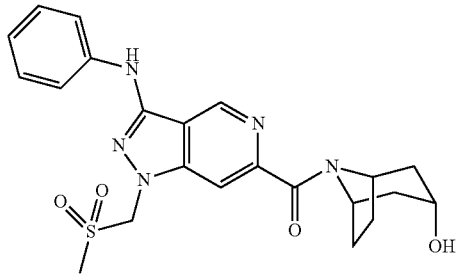 [SMILES: CS(=O)(=O)Cn1nc(Nc2ccccc2)c2cnc(C(=O)N3C4CCC3CC(O)C4)cc21] | [3-anilino-1-(methylsulfonylmethyl)pyrazolo[4,3-c]pyridin-6-yl]-(3-endo-hydroxy-8-azabicyclo[3.2.1]octan-8-yl)methanone | 455.53 |
| 30 | 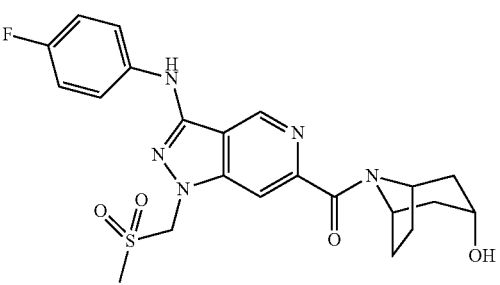 [SMILES: CS(=O)(=O)Cn1nc(Nc2ccc(F)cc2)c2cnc(C(=O)N3C4CCC3CC(O)C4)cc21] | [3-(4-fluoroanilino)-1-(methylsulfonylmethyl)pyrazolo[4,3-c]pyridin-6-yl]-(3-endo-hydroxy-8-azabicyclo[3.2.1]octan-8-yl)methanone | 473.52 |
| 31 | 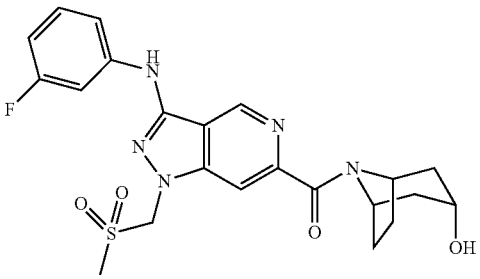 [SMILES: CS(=O)(=O)Cn1nc(Nc2cccc(F)c2)c2cnc(C(=O)N3C4CCC3CC(O)C4)cc21] | [3-(3-fluoroanilino)-1-(methylsulfonylmethyl)pyrazolo[4,3-c]pyridin-6-yl]-(3-endo-hydroxy-8-azabicyclo[3.2.1]octan-8-yl)methanone | 473.52 |

TABLE 2-continued examples of compounds of the present invention

| No. | Structure | IUPAC-Name | MW |
|---|---|---|---|
| 32 | 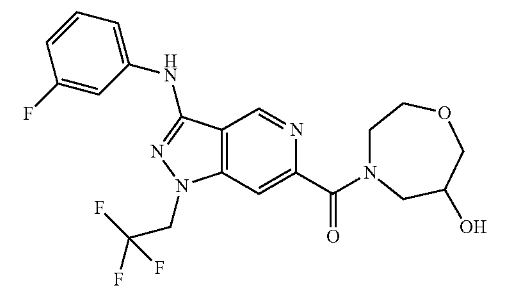 [SMILES: O=C(c1cc2c(cn1)c(Nc1cccc(F)c1)nn2CC(F)(F)F)N1CCOCC(O)C1] | [3-(3-fluoroanilino)-1-(2,2,2-trifluoroethyl)pyrazolo[4,3-c]pyridin-6-yl]-(6-hydroxy-1,4-oxazepan-4-yl)methanone | 453.39 |
| 33 | 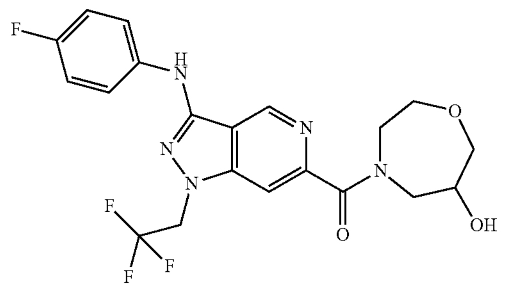 [SMILES: O=C(c1cc2c(cn1)c(Nc1ccc(F)cc1)nn2CC(F)(F)F)N1CCOCC(O)C1] | [3-(4-fluoroanilino)-1-(2,2,2-trifluoroethyl)pyrazolo[4,3-c]pyridin-6-yl]-(6-hydroxy-1,4-oxazepan-4-yl)methanone | 453.39 |
| 34 | 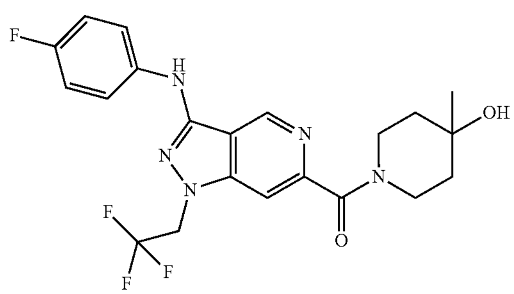 [SMILES: CC1(O)CCN(C(=O)c2cc3c(cn2)c(Nc2ccc(F)cc2)nn3CC(F)(F)F)CC1] | [3-(4-fluoroanilino)-1-(2,2,2-trifluoroethyl)pyrazolo[4,3-c]pyridin-6-yl]-(4-hydroxy-4-methyl-1-piperidyl)methanone | 451.42 |
| 35 | 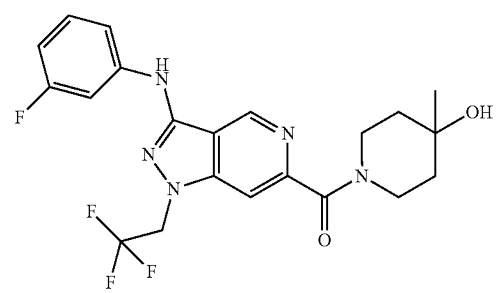 [SMILES: CC1(O)CCN(C(=O)c2cc3c(cn2)c(Nc2cccc(F)c2)nn3CC(F)(F)F)CC1] | [3-(3-fluoroanilino)-1-(2,2,2-trifluoroethyl)pyrazolo[4,3-c]pyridin-6-yl]-(4-hydroxy-4-methyl-1-piperidyl)methanone | 451.42 |
| 36 | 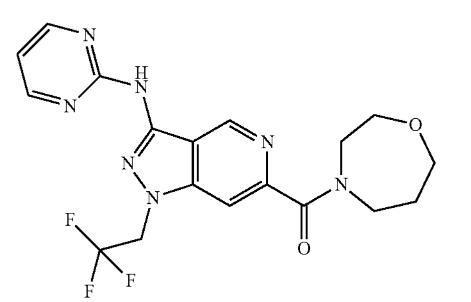 [SMILES: O=C(c1cc2c(cn1)c(Nc1ncccn1)nn2CC(F)(F)F)N1CCCOCC1] | 1,4-oxazepan-4-yl-[3-(pyrimidin-2-ylamino)-1-(2,2,2-trifluoroethyl)pyrazolo[4,3-c]pyridin-6-yl]methanone | 421.38 |

TABLE 2-continued examples of compounds of the present invention

| No. | Structure | IUPAC-Name | MW |
|---|---|---|---|
| 37 | 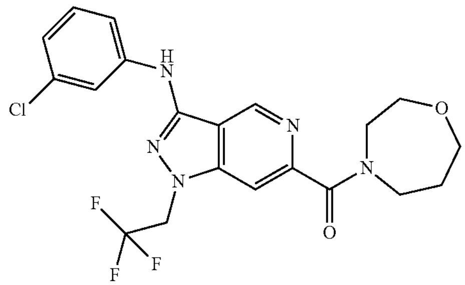 [SMILES: O=C(c1cc2c(cn1)c(Nc1cccc(Cl)c1)nn2CC(F)(F)F)N1CCCOCC1] | [3-(3-chloroanilino)-1-(2,2,2-trifluoroethyl)pyrazolo[4,3-c]pyridin-6-yl]-(1,4-oxazepan-4-yl)methanone | 453.86 |
| 48 | 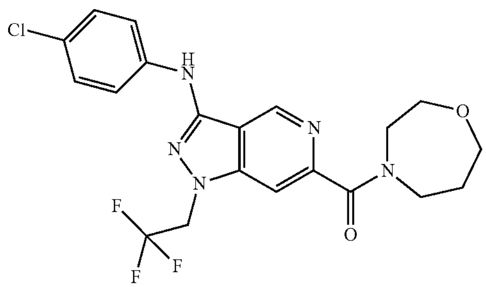 [SMILES: O=C(c1cc2c(cn1)c(Nc1ccc(Cl)cc1)nn2CC(F)(F)F)N1CCCOCC1] | [3-(4-chloroanilino)-1-(2,2,2-trifluoroethyl)pyrazolo[4,3-c]pyridin-6-yl]-(1,4-oxazepan-4-yl)methanone | 453.86 |
| 39 | 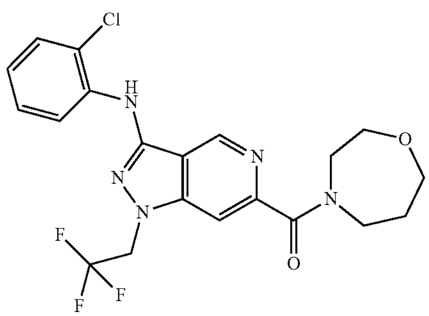 [SMILES: O=C(c1cc2c(cn1)c(Nc1ccccc1Cl)nn2CC(F)(F)F)N1CCCOCC1] | [3-(2-chloroanilino)-1-(2,2,2-trifluoroethyl)pyrazolo[4,3-c]pyridin-6-yl]-(1,4-oxazepan-4-yl)methanone | 453.86 |
| 40 | 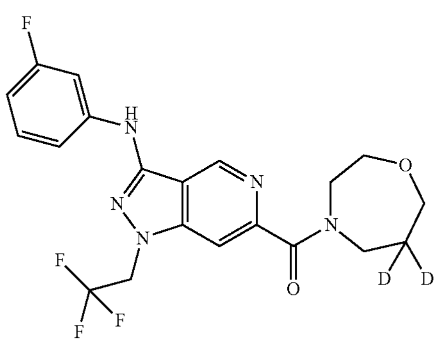 [SMILES: [2H]C1([2H])COCCN(C(=O)c2cc3c(cn2)c(Nc2cccc(F)c2)nn3CC(F)(F)F)C1] | (6,6-dideuterio-1,4-oxazepan-4-yl)-[3-(3-fluoroanilino)-1-(2,2,2-trifluoroethyl)pyrazolo[4,3-c]pyridin-6-yl]methanone | 439.40 |
| 41 | 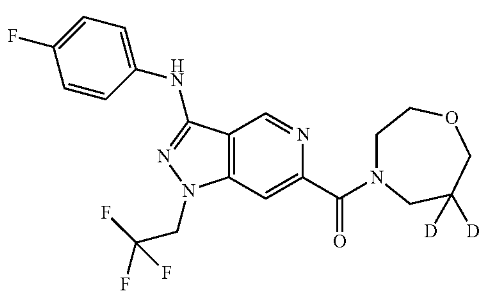 [SMILES: [2H]C1([2H])COCCN(C(=O)c2cc3c(cn2)c(Nc2ccc(F)cc2)nn3CC(F)(F)F)C1] | (6,6-dideuterio-1,4-oxazepan-4-yl)-[3-(4-fluoroanilino)-1-(2,2,2-trifluoroethyl)pyrazolo[4,3-c]pyridin-6-yl]methanone | 439.40 |

TABLE 2-continued examples of compounds of the present invention

| No. | Structure | IUPAC-Name | MW |
|---|---|---|---|
| 42 | 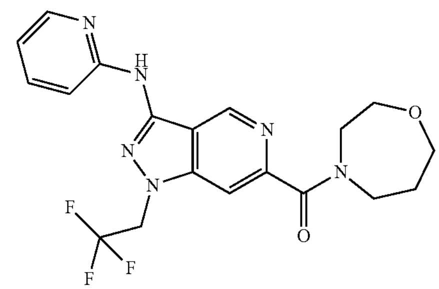 [SMILES: O=C(c1cc2c(cn1)c(Nc1ccccn1)nn2CC(F)(F)F)N1CCCOCC1] | 1,4-oxazepan-4-yl-[3-(2-pyridylamino)-1-(2,2,2-trifluoroethyl)pyrazolo[4,3-c]pyridin-6-yl]methanone | 420.39 |
| 43 | 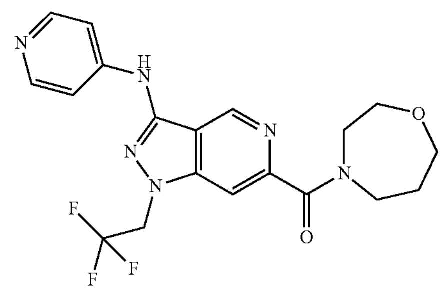 [SMILES: O=C(c1cc2c(cn1)c(Nc1ccncc1)nn2CC(F)(F)F)N1CCCOCC1] | 1,4-oxazepan-4-yl-[3-(4-pyridylamino)-1-(2,2,2-trifluoroethyl)pyrazolo[4,3-c]pyridin-6-yl]methanone | 420.39 |
| 44 | 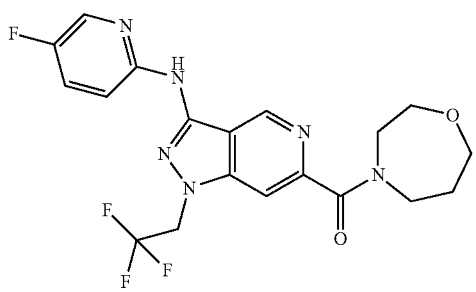 | [3-[(5-fluoro-2-pyridyl)amino]-1-(2,2,2-trifluoroethyl)pyrazolo[4,3-c]pyridin-6-yl]-(1,4-oxazepan-4-yl)methanone | 438.38 |
| 45 | 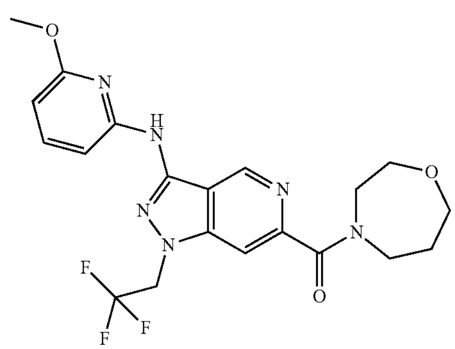 [SMILES: COc1cccc(Nc2nn(CC(F)(F)F)c3cc(C(=O)N4CCCOCC4)ncc23)n1] | [3-[(6-methoxy-2-pyridyl)amino]-1-(2,2,2-trifluoroethyl)pyrazolo[4,3-c]pyridin-6-yl]-(1,4-oxazepan-4-yl)methanone | 450.41 |
| 46 | 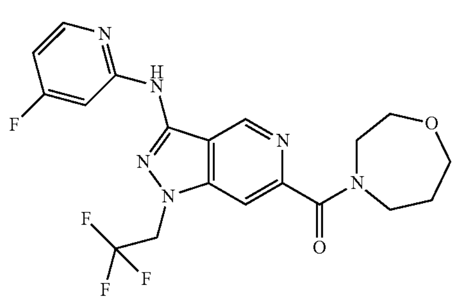 [SMILES: O=C(c1cc2c(cn1)c(Nc1cc(F)ccn1)nn2CC(F)(F)F)N1CCCOCC1] | [3-[(4-fluoro-2-pyridyl)amino]-1-(2,2,2-trifluoroethyl)pyrazolo[4,3-c]pyridin-6-yl]-(1,4-oxazepan-4-yl)methanone | 438.38 |

TABLE 2-continued examples of compounds of the present invention

| No. | Structure | IUPAC-Name | MW |
|-----|-----------|------------|-----|
| 47 | 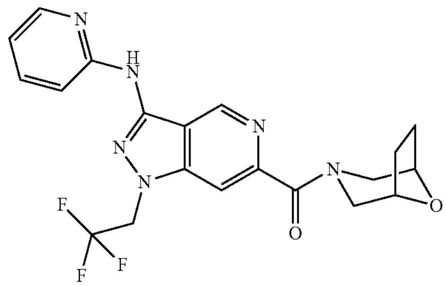 [SMILES: O=C(c1cc2c(cn1)c(Nc1ccccn1)nn2CC(F)(F)F)N1CC2CCC(C1)O2] | 8-oxa-3-azabicyclo[3.2.1]octan-3-yl-[3-(2-pyridylamino)-1-(2,2,2-trifluoroethyl) pyrazolo[4,3-c]pyridin-6-yl]methanone | 432.40 |
| 58 | 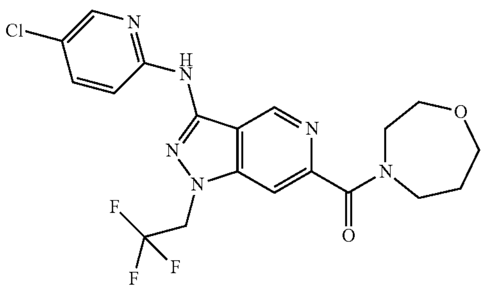 [SMILES: O=C(c1cc2c(cn1)c(Nc1ccc(Cl)cn1)nn2CC(F)(F)F)N1CCCOCC1] | [3-[(5-chloro-2-pyridyl)amino]-1-(2,2,2-trifluoroethyl)pyrazolo[4,3-c]pyridin-6-yl]-(1,4-oxazepan-4-yl)methanone | 454.83 |
| 49 | 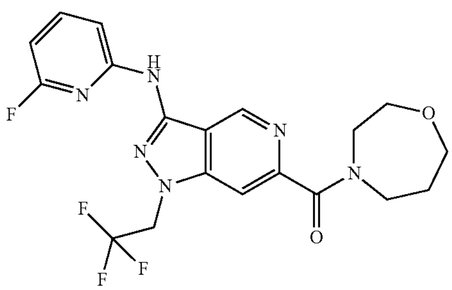 [SMILES: O=C(c1cc2c(cn1)c(Nc1cccc(F)n1)nn2CC(F)(F)F)N1CCCOCC1] | [3-[(6-fluoro-2-pyridyl)amino]-1-(2,2,2-trifluoroethyl)pyrazolo[4,3-c]pyridin-6-yl]-(1,4-oxazepan-4-yl)methanone | 438.38 |
| 50 | 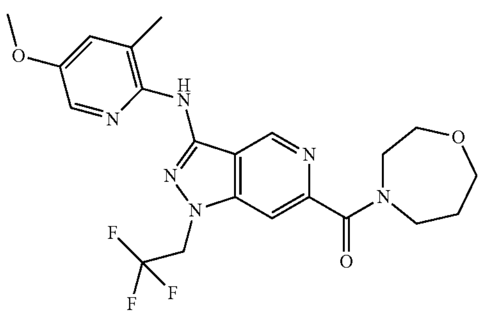 [SMILES: COc1cnc(Nc2nn(CC(F)(F)F)c3cc(C(=O)N4CCCOCC4)ncc23)c(C)c1] | [3-[(5-methoxy-3-methyl-2-pyridyl)amino]-1-(2,2,2-trifluoroethyl)pyrazolo[4,3-c]pyridin-6-yl]-(1,4-oxazepan-4-yl)methanone | 464.44 |
| 51 | 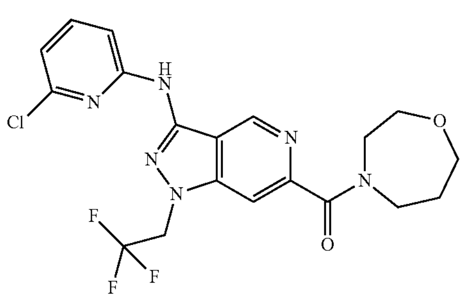 [SMILES: O=C(c1cc2c(cn1)c(Nc1cccc(Cl)n1)nn2CC(F)(F)F)N1CCCOCC1] | [3-[(6-chloro-2-pyridyl)amino]-1-(2,2,2-trifluoroethyl)pyrazolo[4,3-c]pyridin-6-yl]-(1,4-oxazepan-4-yl)methanone | 454.83 |

TABLE 2-continued examples of compounds of the present invention

| No. | Structure | IUPAC-Name | MW |
|---|---|---|---|
| 52 | 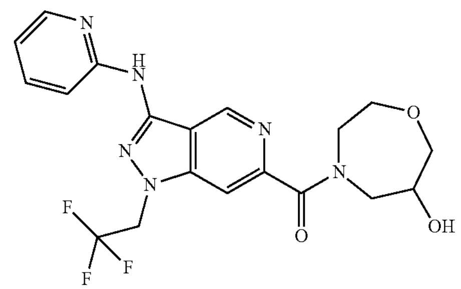 [SMILES: O=C(c1cc2c(cn1)c(Nc1ccccn1)nn2CC(F)(F)F)N1CCOCC(O)C1] | (6-hydroxy-1,4-oxazepan-4-yl)-[3-(2-pyridylamino)-1-(2,2,2-trifluoroethyl)pyrazolo[4,3-c]pyridin-6-yl]methanone | 436.39 |
| 53 | 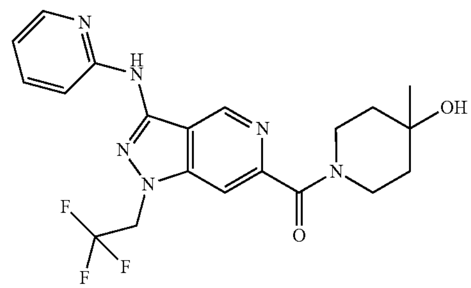 [SMILES: CC1(O)CCN(C(=O)c2cc3c(cn2)c(Nc2ccccn2)nn3CC(F)(F)F)CC1] | (4-hydroxy-4-methyl-1-piperidyl)-[3-(2-pyridylamino)-1-(2,2,2-trifluoroethyl)pyrazolo[4,3-c]pyridin-6-yl]methanone | 434.41 |
| 54 | 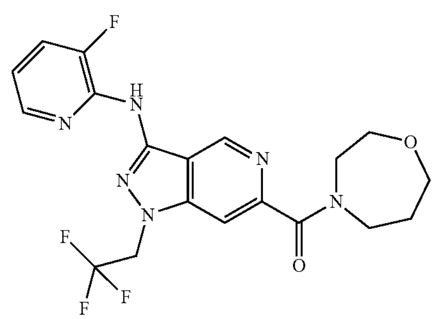 [SMILES: O=C(c1cc2c(cn1)c(Nc1ncccc1F)nn2CC(F)(F)F)N1CCCOCC1] | [3-[(3-fluoro-2-pyridyl)amino]-1-(2,2,2-trifluoroethyl)pyrazolo[4,3-c]pyridin-6-yl]-(1,4-oxazepan-4-yl)methanone | 438.38 |
| 55 | 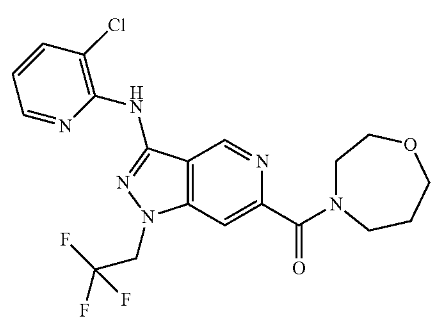 | [3-[(3-chloro-2-pyridyl)amino]-1-(2,2,2-trifluoroethyl)pyrazolo[4,3-c]pyridin-6-yl]-(1,4-oxazepan-4-yl)methanone | 438.38 |
| 56 | 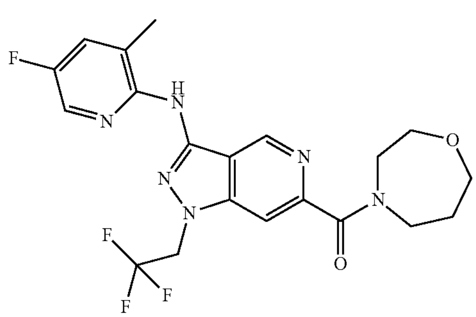 [SMILES: Cc1cc(F)cnc1Nc1nn(CC(F)(F)F)c2cc(C(=O)N3CCCOCC3)ncc12] | [3-[(5-fluoro-3-methyl-2-pyridyl)amino]-1-(2,2,2-trifluoroethyl)pyrazolo[4,3-c]pyridin-6-yl]-(1,4-oxazepan-4-yl)methanone | 452.41 |

TABLE 2-continued examples of compounds of the present invention

| No. | Structure | IUPAC-Name | MW |
|---|---|---|---|
| 57 | 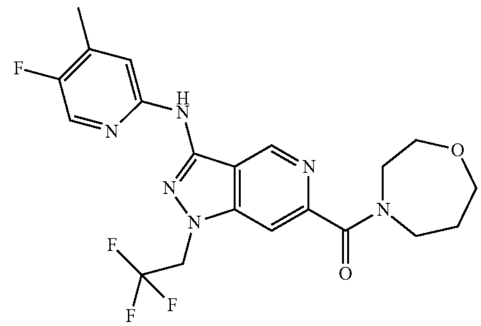 [SMILES: Cc1cc(Nc2nn(CC(F)(F)F)c3cc(C(=O)N4CCCOCC4)ncc23)ncc1F] | [3-[(5-fluoro-4-methyl-2-pyridyl)amino]-1-(2,2,2-trifluoroethyl)pyrazolo[4,3-c]pyridin-6-yl]-(1,4-oxazepan-4-yl)methanone | 452.41 |
| 58 | 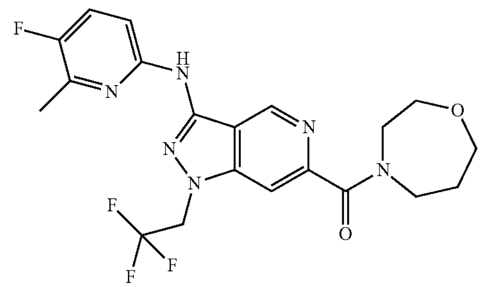 | [3-[(5-fluoro-6-methyl-2-pyridyl)amino]-1-(2,2,2-trifluoroethyl)pyrazolo[4,3-c]pyridin-6-yl]-(1,4-oxazepan-4-yl)methanone | 452.41 |
| 59 | 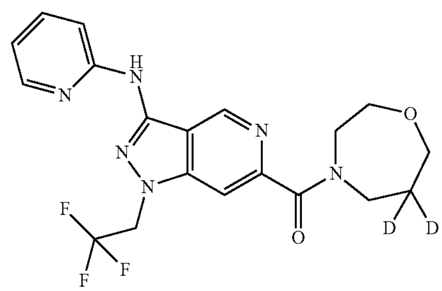 [SMILES: [2H]C1([2H])COCCN(C(=O)c2cc3c(cn2)c(Nc2ccccn2)nn3CC(F)(F)F)C1] | (6,6-dideuterio-1,4-oxazepan-4-yl)-[3-(2-pyridylamino)-1-(2,2,2-trifluoroethyl)pyrazolo[4,3-c]pyridin-6-yl]methanone | 422.40 |
| 60 | 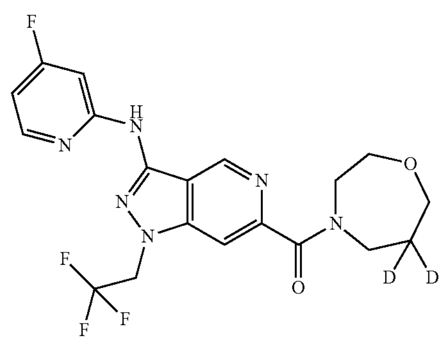 [SMILES: [2H]C1([2H])COCCN(C(=O)c2cc3c(cn2)c(Nc2cc(F)ccn2)nn3CC(F)(F)F)C1] | (6,6-dideuterio-1,4-oxazepan-4-yl)-[3-[(4-fluoro-2-pyridyl)amino]-1-(2,2,2-trifluoroethyl)pyrazolo[4,3-c]pyridin-6-yl]methanone | 440.39 |
| 61 | 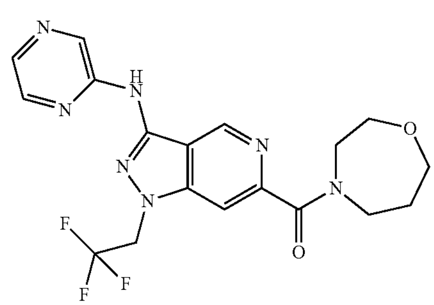 [SMILES: O=C(c1cc2c(cn1)c(Nc1cnccn1)nn2CC(F)(F)F)N1CCCOCC1] | 1,4-oxazepan-4-yl-[3-(pyrazin-2-ylamino)-1-(2,2,2-trifluoroethyl)pyrazolo[4,3-c]pyridin-6-yl]methanone | 421.38 |

TABLE 2-continued examples of compounds of the present invention

| No. | Structure | IUPAC-Name | MW |
|---|---|---|---|
| 62 | 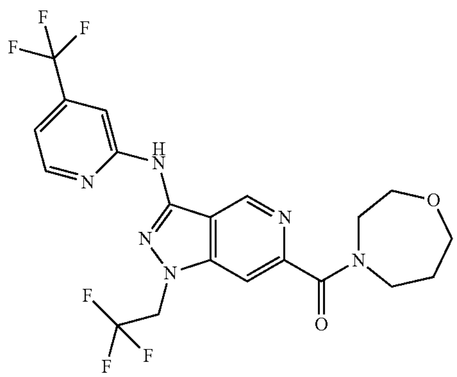 [SMILES: O=C(c1cc2c(cn1)c(Nc1cc(C(F)(F)F)ccn1)nn2CC(F)(F)F)N1CCCOCC1] | 1,4-oxazepan-4-yl-[1-(2,2,2-trifluoroethyl)-3-[[4-(trifluoromethyl)-2-pyridyl]amino]pyrazolo[4,3-c]pyridin-6-yl]methanone | 488.39 |
| 63 | 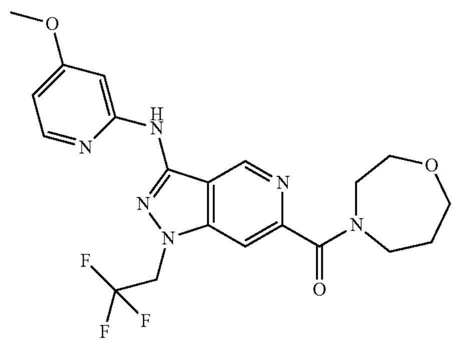 [SMILES: COc1ccnc(Nc2nn(CC(F)(F)F)c3cc(C(=O)N4CCCOCC4)ncc23)c1] | [3-[(4-methoxy-2-pyridyl)amino]-1-(2,2,2-trifluoroethyl)pyrazolo[4,3-c]pyridin-6-yl]-(1,4-oxazepan-4-yl)methanone | 450.41 |
| 64 | 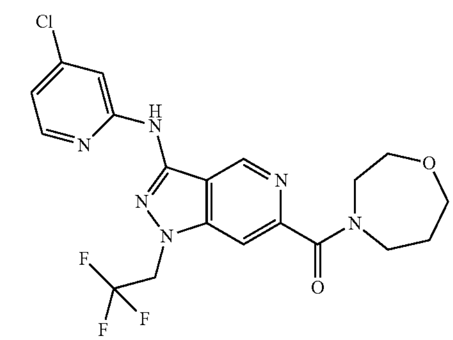 [SMILES: O=C(c1cc2c(cn1)c(Nc1cc(Cl)ccn1)nn2CC(F)(F)F)N1CCCOCC1] | [3-[(4-chloro-2-pyridyl)amino]-1-(2,2,2-trifluoroethyl)pyrazolo[4,3-c]pyridin-6-yl]-(1,4-oxazepan-4-yl)methanone | 454.83 |
| 65 | 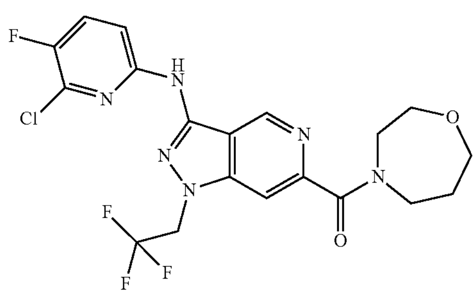 [SMILES: O=C(c1cc2c(cn1)c(Nc1ccc(F)c(Cl)n1)nn2CC(F)(F)F)N1CCCOCC1] | [3-[(6-chloro-5-fluoro-2-pyridyl)amino]-1-(2,2,2-trifluoroethyl)pyrazolo[4,3-c]pyridin-6-yl]-(1,4-oxazepan-4-yl)methanone | 472.82 |

TABLE 2-continued examples of compounds of the present invention

| No. | Structure | IUPAC-Name | MW |
|---|---|---|---|
| 66 | 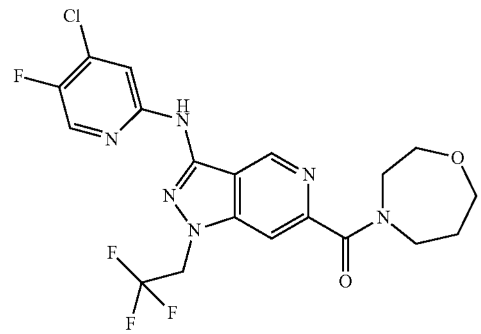 [SMILES: O=C(c1cc2c(cn1)c(Nc1cc(Cl)c(F)cn1)nn2CC(F)(F)F)N1CCCOCC1] | [3-[(4-chloro-5-fluoro-2-pyridyl)amino]-1-(2,2,2-trifluoroethyl)pyrazolo[4,3-c]pyridin-6-yl]-(1,4-oxazepan-4-yl)methanone | 472.82 |
| 67 | 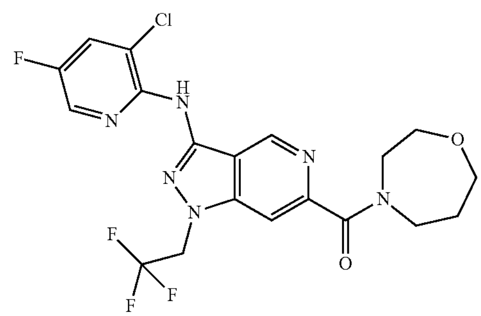 [SMILES: O=C(c1cc2c(cn1)c(Nc1ncc(F)cc1Cl)nn2CC(F)(F)F)N1CCCOCC1] | [3-[(3-chloro-5-fluoro-2-pyridyl)amino]-1-(2,2,2-trifluoroethyl)pyrazolo[4,3-c]pyridin-6-yl]-(1,4-oxazepan-4-yl)methanone | 472.82 |
| 68 | 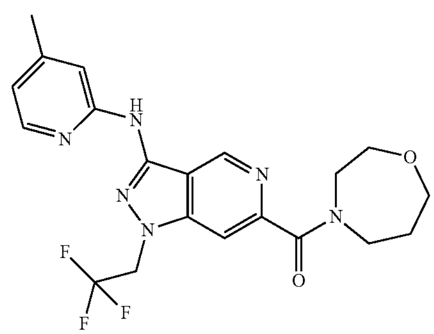 [SMILES: Cc1ccnc(Nc2nn(CC(F)(F)F)c3cc(C(=O)N4CCCOCC4)ncc23)c1] | [3-[(4-methyl-2-pyridyl)amino]-1-(2,2,2-trifluoroethyl)pyrazolo[4,3-c]pyridin-6-yl]-(1,4-oxazepan-4-yl)methanone | 434.41 |
| 69 | 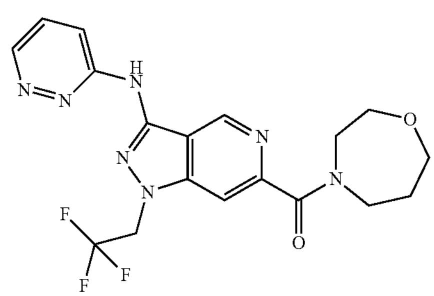 [SMILES: O=C(c1cc2c(cn1)c(Nc1cccnn1)nn2CC(F)(F)F)N1CCCOCC1] | 1,4-oxazepan-4-yl-[3-(pyridazin-3-ylamino)-1-(2,2,2-trifluoroethyl)pyrazolo[4,3-c]pyridin-6-yl]methanone | 421.38 |

TABLE 2-continued examples of compounds of the present invention

| No. | Structure | IUPAC-Name | MW |
|---|---|---|---|
| 70 | 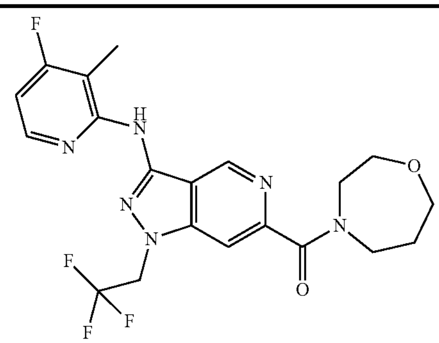 | [3-[(4-fluoro-3-methyl-2-pyridyl)amino]-1-(2,2,2-trifluoroethyl)pyrazolo[4,3-c]pyridin-6-yl]-(1,4-oxazepan-4-yl)methanone | 452.41 |
| 71 | 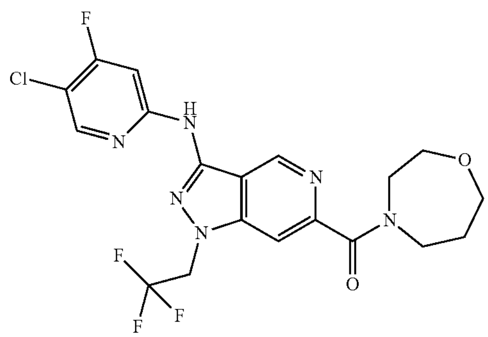 [SMILES: O=C(c1cc2c(cn1)c(Nc1cc(F)c(Cl)cn1)nn2CC(F)(F)F)N1CCCOCC1] | [3-[(5-chloro-4-fluoro-2-pyridyl)amino]-1-(2,2,2-trifluoroethyl)pyrazolo[4,3-c]pyridin-6-yl]-(1,4-oxazepan-4-yl)methanone | 472.82 |
| 72 | 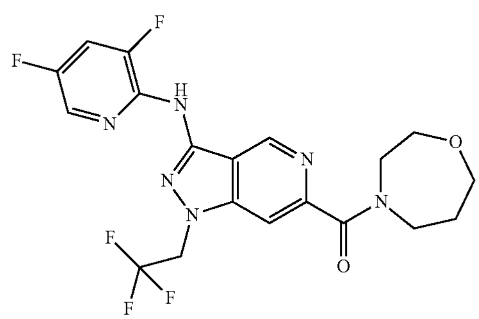 [SMILES: O=C(c1cc2c(cn1)c(Nc1ncc(F)cc1F)nn2CC(F)(F)F)N1CCCOCC1] | [3-[(3,5-difluoro-2-pyridyl)amino]-1-(2,2,2-trifluoroethyl)pyrazolo[4,3-c]pyridin-6-yl]-(1,4-oxazepan-4-yl)methanone | 456.37 |
| 73 | 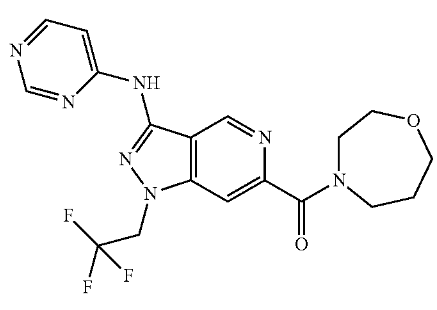 [SMILES: O=C(c1cc2c(cn1)c(Nc1ccncn1)nn2CC(F)(F)F)N1CCCOCC1] | [1,4]Oxazepan-4-yl-[3-(pyrimidin-4-ylamino)-1-(2,2,2-trifluoro-ethyl)-1H-pyrazolo[4,3-c]pyridin-6-yl]-methanone | 421.38 |
| 74 | 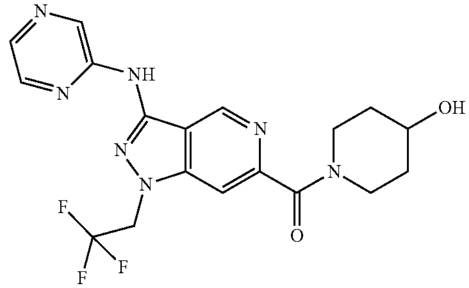 [SMILES: O=C(c1cc2c(cn1)c(Nc1cnccn1)nn2CC(F)(F)F)N1CCC(O)CC1] | (4-Hydroxy-piperidin-1-yl)-[3-(pyrazin-2-ylamino)-1-(2,2,2-trifluoro-ethyl)-1H-pyrazolo[4,3-c]pyridin-6-yl]-methanone | 421.38 |

TABLE 2-continued examples of compounds of the present invention

| No. | Structure | IUPAC-Name | MW |
|---|---|---|---|
| 75 | 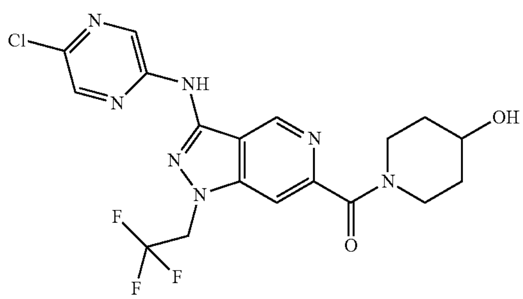 [SMILES: O=C(c1cc2c(cn1)c(Nc1cnc(Cl)cn1)nn2CC(F)(F)F)N1CCC(O)CC1] | [3-(5-Chloro-pyrazin-2-ylamino)-1-(2,2,2-trifluoro-ethyl)-1H-pyrazolo[4,3-c]pyridin-6-yl]-(4-hydroxy-piperidin-1-yl)-methanone | 455.83 |
| 76 | 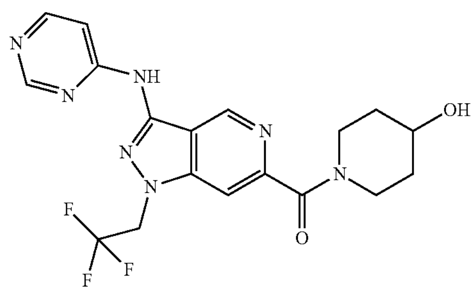 [SMILES: O=C(c1cc2c(cn1)c(Nc1ccncn1)nn2CC(F)(F)F)N1CCC(O)CC1] | (4-Hydroxy-piperidin-1-yl)-[3-(pyrimidin-4-ylamino)-1-(2,2,2-trifluoro-ethyl)-1H-pyrazolo[4,3-c]pyridin-6-yl]-methanone | 421.38 |
| 77 | 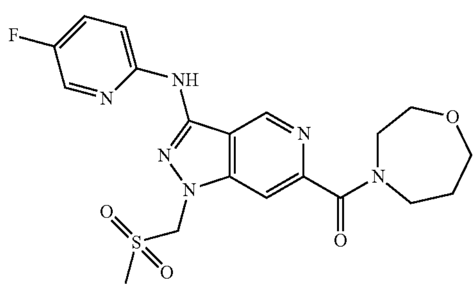 [SMILES: CS(=O)(=O)Cn1nc(Nc2ccc(F)cn2)c2cnc(C(=O)N3CCCOCC3)cc21] | [3-(5-Fluoro-pyridin-2-ylamino)-1-methanesulfonylmethyl-1H-pyrazolo[4,3-c]pyridin-6-yl]-[1,4]oxazepan-4-yl-methanone | 448.47 |
| 78 | 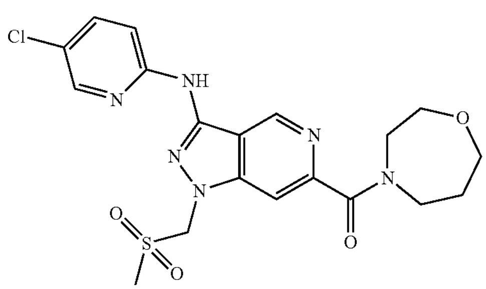 [SMILES: CS(=O)(=O)Cn1nc(Nc2ccc(Cl)cn2)c2cnc(C(=O)N3CCCOCC3)cc21] | [3-(5-Chloro-pyridin-2-ylamino)-1-methanesulfonylmethyl-1H-pyrazolo[4,3-c]pyridin-6-yl]-[1,4]oxazepan-4-yl-methanone | 464.93 |
| 79 | 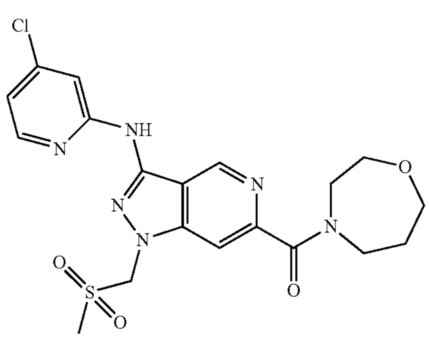 [SMILES: CS(=O)(=O)Cn1nc(Nc2cc(Cl)ccn2)c2cnc(C(=O)N3CCCOCC3)cc21] | [3-(4-Chloro-pyridin-2-ylamino)-1-methanesulfonylmethyl-1H-pyrazolo[4,3-c]pyridin-6-yl]-[1,4]oxazepan-4-yl-methanone | 464.93 |

TABLE 2-continued examples of compounds of the present invention

| No. | Structure | IUPAC-Name | MW |
|---|---|---|---|
| 80 | 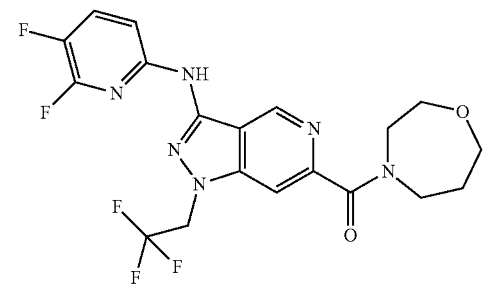 [SMILES: O=C(c1cc2c(cn1)c(Nc1ccc(F)c(F)n1)nn2CC(F)(F)F)N1CCCOCC1] | [3-[(5,6-difluoro-2-pyridyl)amino]-1-(2,2,2-trifluoroethyl)pyrazolo[4,3-c]pyridin-6-yl]-(1,4-oxazepan-4-yl)methanone | 456.38 |
| 81 | 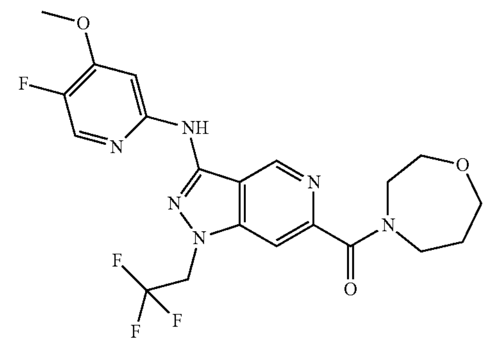 [SMILES: COc1cc(Nc2nn(CC(F)(F)F)c3cc(C(=O)N4CCCOCC4)ncc23)ncc1F] | [3-[(5-fluoro-4-methoxy-2-pyridyl)amino]-1-(2,2,2-trifluoroethyl)pyrazolo[4,3-c]pyridin-6-yl]-(1,4-oxazepan-4-yl)methanone | 468.41 |
| 82 | 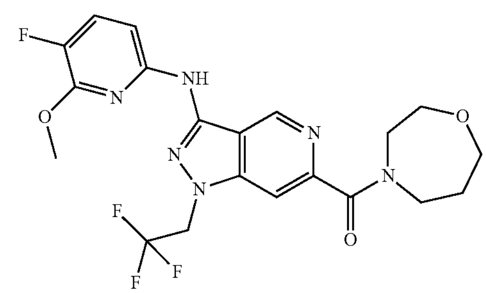 [SMILES: COc1nc(Nc2nn(CC(F)(F)F)c3cc(C(=O)N4CCCOCC4)ncc23)ccc1F] | [3-[(5-fluoro-6-methoxy-2-pyridyl)amino]-1-(2,2,2-trifluoroethyl)pyrazolo[4,3-c]pyridin-6-yl]-(1,4-oxazepan-4-yl)methanone | 468.41 |
| 83 | 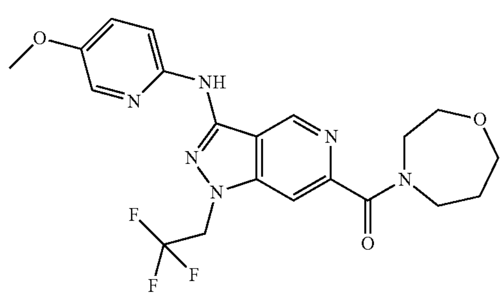 [SMILES: COc1ccc(Nc2nn(CC(F)(F)F)c3cc(C(=O)N4CCCOCC4)ncc23)nc1] | [3-(5-Methoxy-pyridin-2-ylamino)-1-(2,2,2-trifluoro-ethyl)-1H-pyrazolo[4,3-c]pyridin-6-yl]-[1,4]oxazepan-4-yl-methanone | 450.42 |
| 84 | 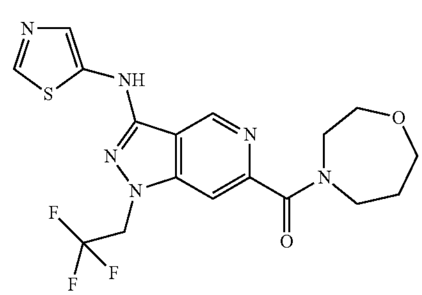 [SMILES: O=C(c1cc2c(cn1)c(Nc1cncs1)nn2CC(F)(F)F)N1CCCOCC1] | [1,4]Oxazepan-4-yl-[3-(thiazol-5-ylamino)-1-(2,2,2-trifluoro-ethyl)-1H-pyrazolo[4,3-c]pyridin-6-yl]-methanone | 426.42 |

TABLE 2-continued examples of compounds of the present invention

| No. | Structure | IUPAC-Name | MW |
|---|---|---|---|
| 85 | 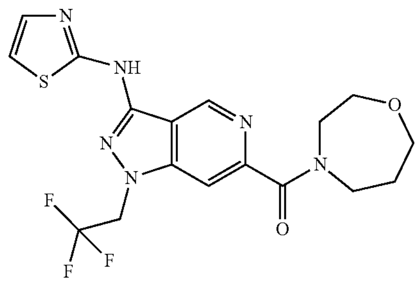 [SMILES: O=C(c1cc2c(cn1)c(Nc1nccs1)nn2CC(F)(F)F)N1CCCOCC1] | [1,4]Oxazepan-4-yl-[3-(thiazol-2-ylamino)-1-(2,2,2-trifluoro-ethyl)-1H-pyrazolo[4,3-c]pyridin-6-yl]-methanone | 426.42 |
| 86 | 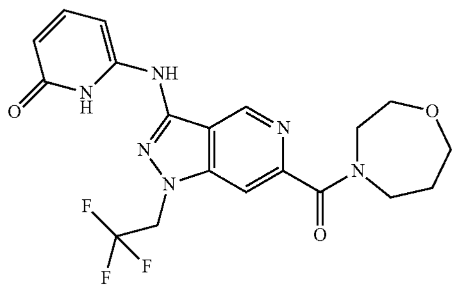 [SMILES: O=C(c1cc2c(cn1)c(Nc1cccc(=O)[nH]1)nn2CC(F)(F)F)N1CCCOCC1] | 6-[6-([1,4]Oxazepane-4-carbonyl)-1-(2,2,2-trifluoro-ethyl)-1H-pyrazolo[4,3-c]pyridin-3-ylamino]-1H-pyridin-2-one | 436.40 |
| 87 | 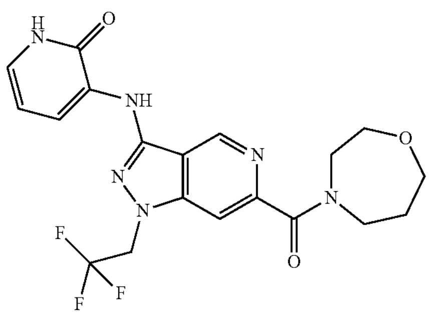 [SMILES: O=C(c1cc2c(cn1)c(Nc1ccc[nH]c1=O)nn2CC(F)(F)F)N1CCCOCC1] | 3-[[6-(1,4-oxazepane-4-carbonyl)-1-(2,2,2-trifluoroethyl)pyrazolo[4,3-c]pyridin-3-yl]amino]-1H-pyridin-2-one | 436.40 |
| 88 | 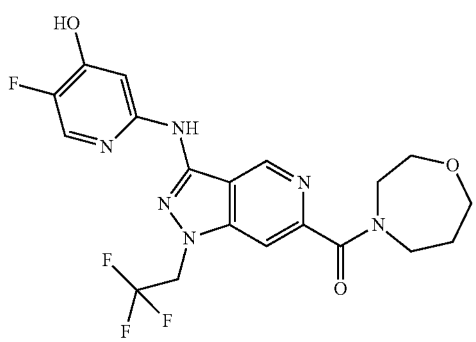 [SMILES: O=C(c1cc2c(cn1)c(Nc1cc(O)c(F)cn1)nn2CC(F)(F)F)N1CCCOCC1] | [3-[(5-fluoro-4-hydroxy-2-pyridyl)amino]-1-(2,2,2-trifluoroethyl)pyrazolo[4,3-c]pyridin-6-yl]-(1,4-oxazepan-4-yl)methanone | 454.39 |
| 89 | 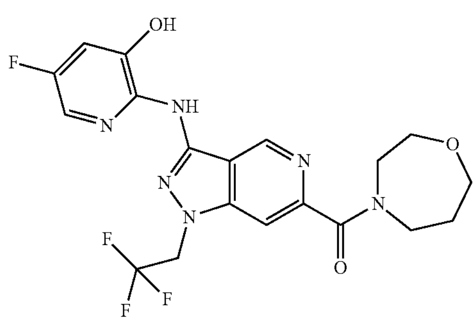 [SMILES: O=C(c1cc2c(cn1)c(Nc1ncc(F)cc1O)nn2CC(F)(F)F)N1CCCOCC1] | [3-[(5-fluoro-3-hydroxy-2-pyridyl)amino]-1-(2,2,2-trifluoroethyl)pyrazolo[4,3-c]pyridin-6-yl]-(1,4-oxazepan-4-yl)methanone | 454.39 |

TABLE 2-continued examples of compounds of the present invention

| No. | Structure | IUPAC-Name | MW |
|---|---|---|---|
| 90 | 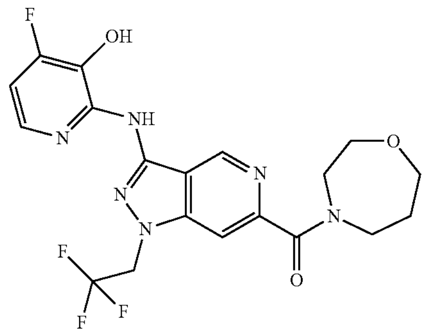 [SMILES: O=C(c1cc2c(cn1)c(Nc1nccc(F)c1O)nn2CC(F)(F)F)N1CCCOCC1] | [3-[(4-fluoro-3-hydroxy-2-pyridyl)amino]-1-(2,2,2-trifluoroethyl)pyrazolo[4,3-c]pyridin-6-yl]-(1,4-oxazepan-4-yl)methanone | 454.39 |
| 91 | 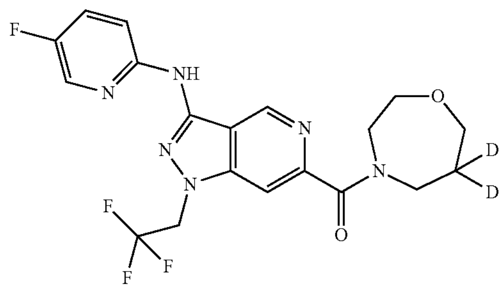 [SMILES: [2H]C1([2H])COCCN(C(=O)c2cc3c(cn2)c(Nc2ccc(F)cn2)nn3CC(F)(F)F)C1] | (6,6-dideuterio-1,4-oxazepan-4-yl)-[3-[(5-fluoro-2-pyridyl)amino]-1-(2,2,2-trifluoroethyl)pyrazolo[4,3-c]pyridin-6-yl]methanone | 440.40 |
| 92 | 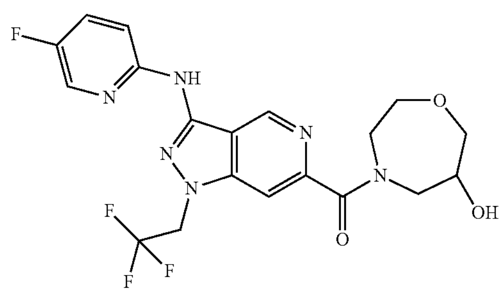 [SMILES: O=C(c1cc2c(cn1)c(Nc1ccc(F)cn1)nn2CC(F)(F)F)N1CCOCC(O)C1] | [3-[(5-fluoro-2-pyridyl)amino]-1-(2,2,2-trifluoroethyl)pyrazolo[4,3-c]pyridin-6-yl]-(6-hydroxy-1,4-oxazepan-4-yl)methanone | 454.39 |
| 93 | 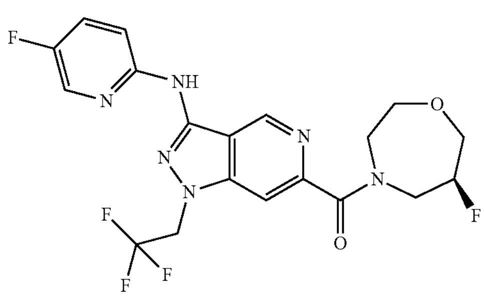 [SMILES: O=C(c1cc2c(cn1)c(Nc1ccc(F)cn1)nn2CC(F)(F)F)N1CCOC[C@@H](F)C1] | [(6S)-6-fluoro-1,4-oxazepan-4-yl]-[3-[(5-fluoro-2-pyridyl)amino]-1-(2,2,2-trifluoroethyl)pyrazolo[4,3-c]pyridin-6-yl]methanone | 456.38 |
| 94 | 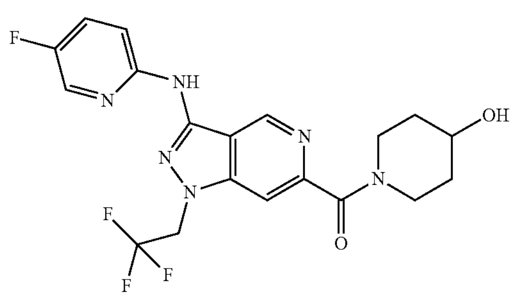 [SMILES: O=C(c1cc2c(cn1)c(Nc1ccc(F)cn1)nn2CC(F)(F)F)N1CCC(O)CC1] | [3-[(5-fluoro-2-pyridyl)amino]-1-(2,2,2-trifluoroethyl)pyrazolo[4,3-c]pyridin-6-yl]-(4-hydroxypiperidin-1-yl)methanone | 438.39 |

TABLE 2-continued examples of compounds of the present invention

| No. | Structure | IUPAC-Name | MW |
|---|---|---|---|
| 95 | 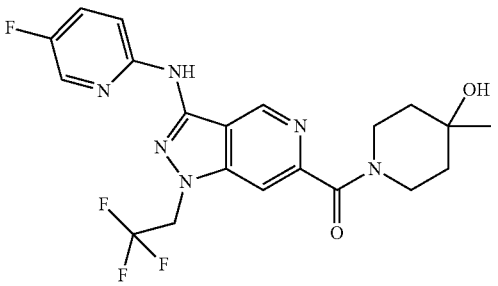 [SMILES: CC1(O)CCN(C(=O)c2cc3c(cn2)c(Nc2ccc(F)cn2)nn3CC(F)(F)F)CC1] | [3-(5-Fluoro-pyridin-2-ylamino)-1-(2,2,2-trifluoro-ethyl)-1H-pyrazolo[4,3-c]pyridin-6-yl]-(4-hydroxy-4-methyl-piperidin-1-yl)-methanone | 452.41 |
| 96 | 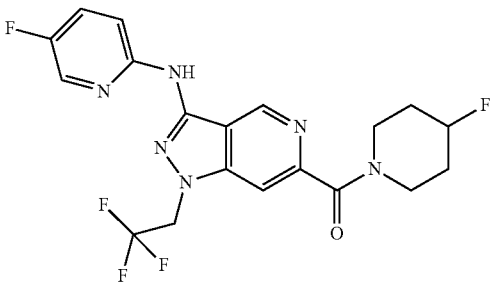 [SMILES: O=C(c1cc2c(cn1)c(Nc1ccc(F)cn1)nn2CC(F)(F)F)N1CCC(F)CC1] | (4-Fluoro-piperidin-1-yl)-[3-(5-fluoro-pyridin-2-ylamino)-1-(2,2,2-trifluoro-ethyl)-1H-pyrazolo[4,3-c]pyridin-6-yl]-methanone | 440.38 |
| 97 | 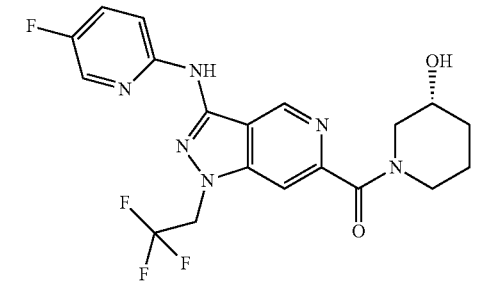 [SMILES: O=C(c1cc2c(cn1)c(Nc1ccc(F)cn1)nn2CC(F)(F)F)N1CCC[C@@H](O)C1] | [(3R)-3-hydroxy-piperidin-1-yl]-[3-(5-Fluoro-pyridin-2-ylamino)-1-(2,2,2-trifluoro-ethyl)-1H-pyrazolo[4,3-c]pyridin-6-yl]methanone | 438.39 |
| 98 | 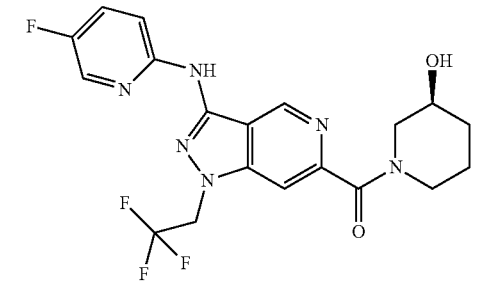 [SMILES: O=C(c1cc2c(cn1)c(Nc1ccc(F)cn1)nn2CC(F)(F)F)N1CCC[C@H](O)C1] | [(3S)-3-hydroxy-piperidin-1-yl]-3-(5-Fluoro-pyridin-2-ylamino)-1-(2,2,2-trifluoro-ethyl)-1H-pyrazolo[4,3-c]pyridin-6-yl]methanone | 438.39 |
| 99 | 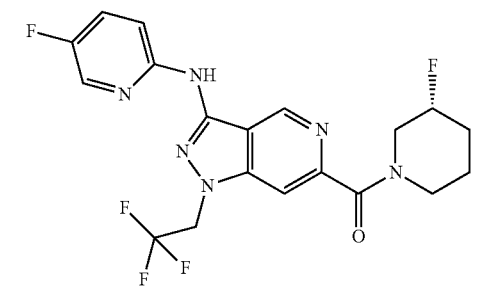 [SMILES: O=C(c1cc2c(cn1)c(Nc1ccc(F)cn1)nn2CC(F)(F)F)N1CCC[C@@H](F)C1] | [(3R)-3-fluoro-piperidin-1-yl]-3-(5-Fluoro-pyridin-2-ylamino)-1-(2,2,2-trifluoro-ethyl)-1H-pyrazolo[4,3-c]pyridin-6-yl]methanone | 440.38 |

TABLE 2-continued examples of compounds of the present invention

| No. | Structure | IUPAC-Name | MW |
|---|---|---|---|
| 100 | 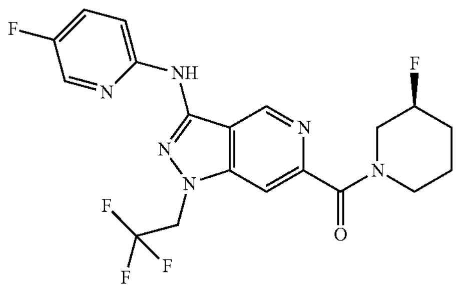 [SMILES: O=C(c1cc2c(cn1)c(Nc1ccc(F)cn1)nn2CC(F)(F)F)N1CCC[C@H](F)C1] | [(3S)-3-fluoro-piperidin-1-yl]-3-(5-Fluoro-pyridin-2-ylamino)-1-(2,2,2-trifluoro-ethyl)-1H-pyrazolo[4,3-c]pyridin-6-yl]methanone | 440.38 |
| 101 | 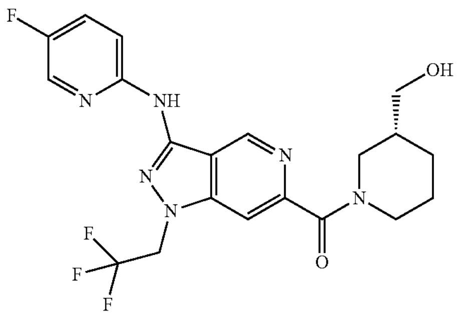 [SMILES: O=C(c1cc2c(cn1)c(Nc1ccc(F)cn1)nn2CC(F)(F)F)N1CCC[C@@H](CO)C1] | [3-[(5-fluoro-2-pyridyl)amino]-1-(2,2,2-trifluoroethyl)pyrazolo[4,3-c]pyridin-6-yl]-[(3R)-3-(hydroxymethyl)-1-piperidyl]methanone | 452.41 |
| 102 | 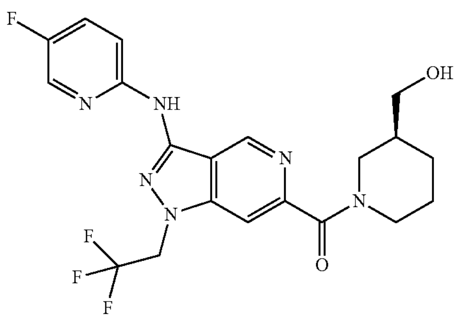 [SMILES: O=C(c1cc2c(cn1)c(Nc1ccc(F)cn1)nn2CC(F)(F)F)N1CCC[C@H](CO)C1] | [3-[(5-fluoro-2-pyridyl)amino]-1-(2,2,2-trifluoroethyl)pyrazolo[4,3-c]pyridin-6-yl]-[(3S)-3-(hydroxymethyl)-1-piperidyl]methanone | 452.41 |
| 103 | 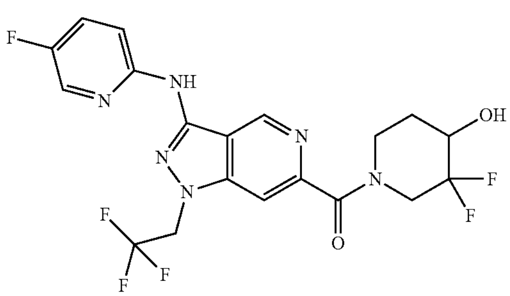 [SMILES: O=C(c1cc2c(cn1)c(Nc1ccc(F)cn1)nn2CC(F)(F)F)N1CCC(O)C(F)(F)C1] | (3,3-Difluoro-4-hydroxy-piperidin-1-yl)-[3-(5-fluoro-pyridin-2-ylamino)-1-(2,2,2-trifluoro-ethyl)-1H-pyrazolo[4,3-c]pyridin-6-yl]-methanone | 474.37 |
| 104 | 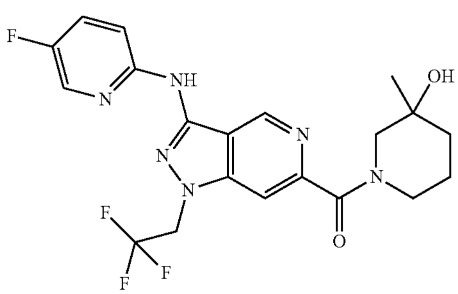 [SMILES: CC1(O)CCCN(C(=O)c2cc3c(cn2)c(Nc2ccc(F)cn2)nn3CC(F)(F)F)C1] | [3-[(5-fluoro-2-pyridyl)amino]-1-(2,2,2-trifluoroethyl)pyrazolo[4,3-c]pyridin-6-yl]-(3-hydroxy-3-methyl-piperidin-1-yl)methanone | 452.41 |

TABLE 2-continued examples of compounds of the present invention

| No. | Structure | IUPAC-Name | MW |
|---|---|---|---|
| 105 | 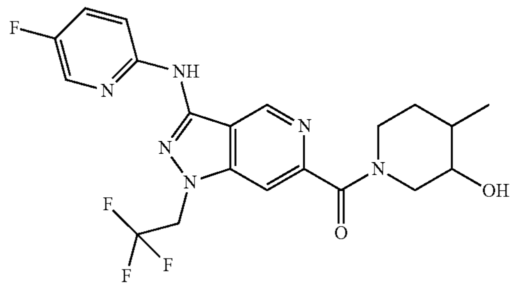 [SMILES: CC1CCN(C(=O)c2cc3c(cn2)c(Nc2ccc(F)cn2)nn3CC(F)(F)F)CC1O] | Cis-[3-(5-Fluoro-pyridin-2-ylamino)-1-(2,2,2-trifluoro-ethyl)-1H-pyrazolo[4,3-c]pyridin-6-yl]-(3-hydroxy-4-methyl-piperidin-1-yl)-methanone | 452.41 |
| 106 | 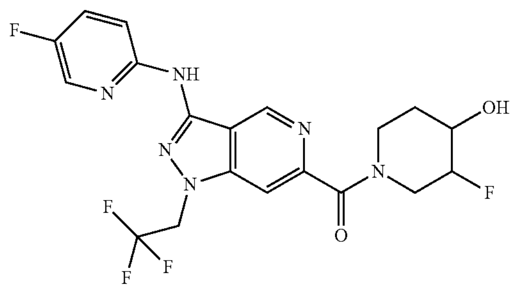 [SMILES: O=C(c1cc2c(cn1)c(Nc1ccc(F)cn1)nn2CC(F)(F)F)N1CCC(O)C(F)C1] | Cis-(3-Fluoro-4-hydroxy-piperidin-1-yl)-[3-(5-fluoro-pyridin-2-ylamino)-1-(2,2,2-trifluoro-ethyl)-1H-pyrazolo[4,3-c]pyridin-6-yl]-methanone | 456.38 |
| 107 | 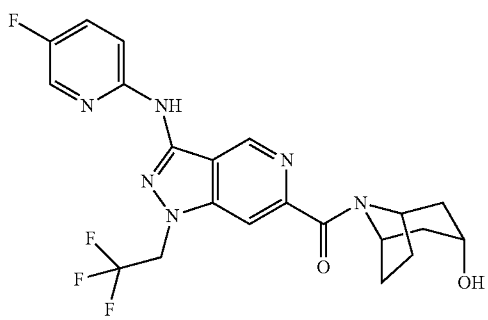 [SMILES: O=C(c1cc2c(cn1)c(Nc1ccc(F)cn1)nn2CC(F)(F)F)N1C2CCC1CC(O)C2] | [3-[(5-fluoro-2-pyridyl)amino]-1-(2,2,2-trifluoroethyl)pyrazolo[4,3-c]pyridin-6-yl]-(3-endo-hydroxy-8-azabicyclo[3.2.1]octan-8-yl)methanone | 464.42 |
| 108 | 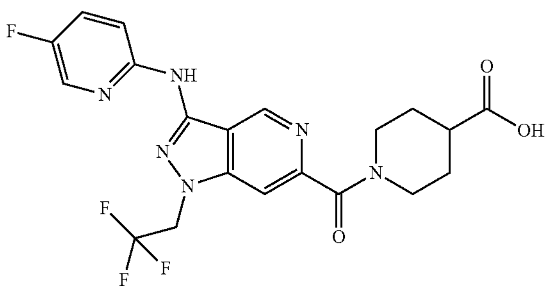 [SMILES: O=C(O)C1CCN(C(=O)c2cc3c(cn2)c(Nc2ccc(F)cn2)nn3CC(F)(F)F)CC1] | 1-[3-[(5-fluoro-2-pyridyl)amino]-1-(2,2,2-trifluoroethyl)pyrazolo[4,3-c]pyridine-6-carbonyl]pyridine-4-carboxylic acid | 466.40 |
| 109 | 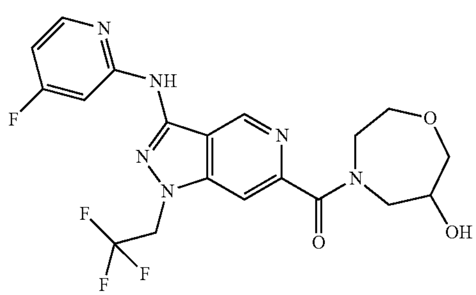 [SMILES: O=C(c1cc2c(cn1)c(Nc1cc(F)ccn1)nn2CC(F)(F)F)N1CCOCC(O)C1] | [3-[(4-fluoro-2-pyridyl)amino]-1-(2,2,2-trifluoroethyl)pyrazolo[4,3-c]pyridin-6-yl]-(6-hydroxy-1,4-oxazepan-4-yl)methanone | 454.39 |

TABLE 2-continued examples of compounds of the present invention

| No. | Structure | IUPAC-Name | MW |
|---|---|---|---|
| 110 | 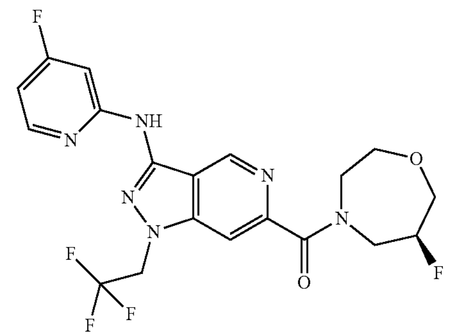 [SMILES: O=C(c1cc2c(cn1)c(Nc1cc(F)ccn1)nn2CC(F)(F)F)N1CCOC[C@@H](F)C1] | [(6S)-6-fluoro-1,4-oxazepan-4-yl]-[3-(4-fluoro-pyridin-2-ylamino)-1-(2,2,2-trifluoro-ethyl)-1H-pyrazolo[4,3-c]pyridin-6-yl]-methanone | 456.38 |
| 111 | 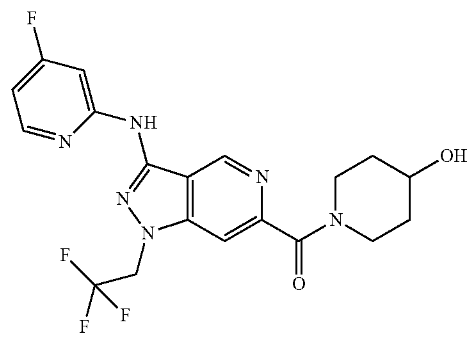 [SMILES: O=C(c1cc2c(cn1)c(Nc1cc(F)ccn1)nn2CC(F)(F)F)N1CCC(O)CC1] | [3-[(4-fluoro-2-pyridyl)amino]-1-(2,2,2-trifluoroethyl)pyrazolo[4,3-c]pyridin-6-yl]-(4-hydroxypiperidin-1-yl)methanone | 438.39 |
| 112 | 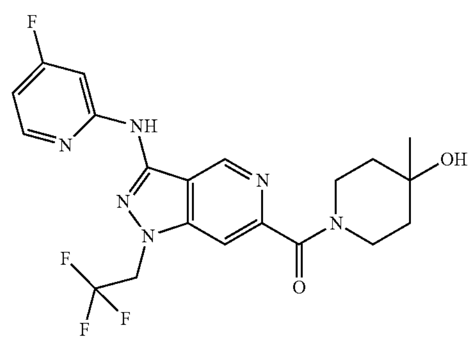 [SMILES: CC1(O)CCN(C(=O)c2cc3c(cn2)c(Nc2cc(F)ccn2)nn3CC(F)(F)F)CC1] | [3-(4-Fluoro-pyridin-2-ylamino)-1-(2,2,2-trifluoro-ethyl)-1H-pyrazolo[4,3-c]pyridin-6-yl]-(4-hydroxy-4-methyl-piperidin-1-yl)-methanone | 452.41 |
| 113 | 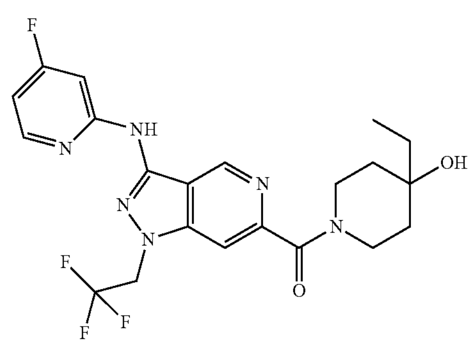 [SMILES: CCC1(O)CCN(C(=O)c2cc3c(cn2)c(Nc2cc(F)ccn2)nn3CC(F)(F)F)CC1] | [3-(4-Fluoro-pyridin-2-ylamino)-1-(2,2,2-trifluoro-ethyl)-1H-pyrazolo[4,3-c]pyridin-6-yl]-(4-ethyl-4-hydroxypiperidin-1-yl)-methanone | 466.44 |

TABLE 2-continued examples of compounds of the present invention

| No. | Structure | IUPAC-Name | MW |
|---|---|---|---|
| 114 | 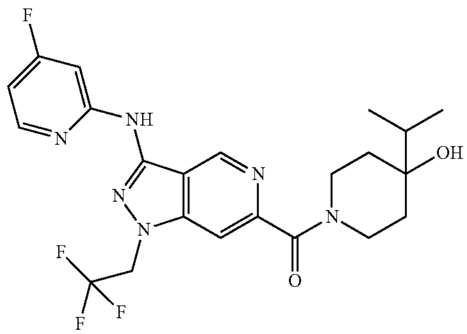 [SMILES: CC(C)C1(O)CCN(C(=O)c2cc3c(cn2)c(Nc2cc(F)ccn2)nn3CC(F)(F)F)CC1] | [3-(4-Fluoro-pyridin-2-ylamino)-1-(2,2,2-trifluoro-ethyl)-1H-pyrazolo[4,3-c]pyridin-6-yl]-(4-isopropyl-4-hydroxypiperidin-1-yl)-methanone | 480.47 |
| 115 | 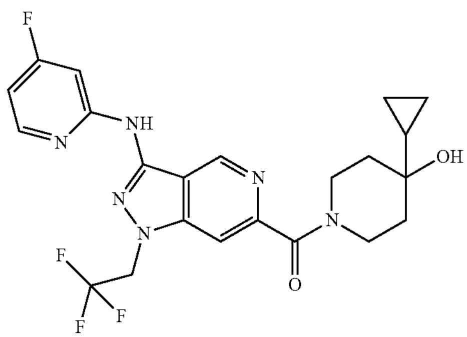 [SMILES: O=C(c1cc2c(cn1)c(Nc1cc(F)ccn1)nn2CC(F)(F)F)N1CCC(O)(C2CC2)CC1] | [3-(4-Fluoro-pyridin-2-ylamino)-1-(2,2,2-trifluoro-ethyl)-1H-pyrazolo[4,3-c]pyridin-6-yl]-(4-cyclopropyl-4-hydroxypiperidin-1-yl)-methanone | 478.45 |
| 116 | 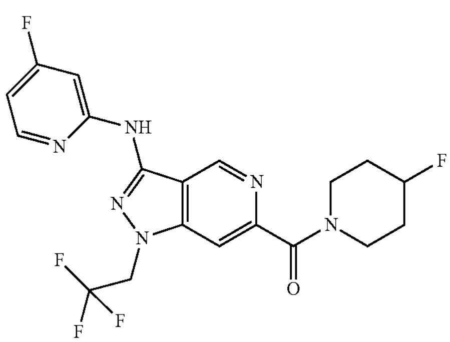 [SMILES: O=C(c1cc2c(cn1)c(Nc1cc(F)ccn1)nn2CC(F)(F)F)N1CCC(F)CC1] | (4-Fluoro-piperidin-1-yl)-[3-(4-fluoro-pyridin-2-ylamino)-1-(2,2,2-trifluoro-ethyl)-1H-pyrazolo[4,3-c]pyridin-6-yl]-methanone | 440.38 |
| 117 | 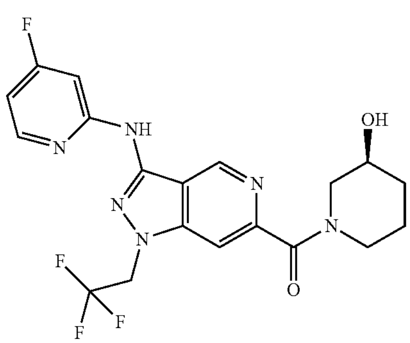 [SMILES: O=C(c1cc2c(cn1)c(Nc1cc(F)ccn1)nn2CC(F)(F)F)N1CCC[C@H](O)C1] | [(3S)-3-hydroxy-piperidin-1-yl]-[3-(4-fluoro-pyridin-2-ylamino)-1-(2,2,2-trifluoro-ethyl)-1H-pyrazolo[4,3-c]pyridin-6-yl]methanone | 438.39 |

TABLE 2-continued examples of compounds of the present invention

| No. | Structure | IUPAC-Name | MW |
|---|---|---|---|
| 118 | 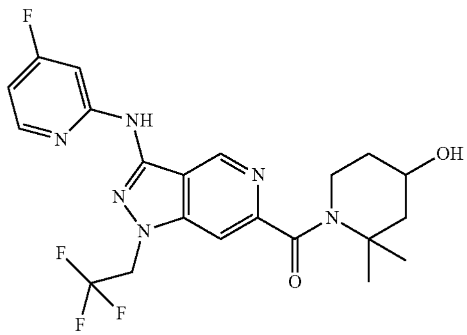 [SMILES: CC1(C)CC(O)CCN1C(=O)c1cc2c(cn1)c(Nc1cc(F)ccn1)nn2CC(F)(F)F] | [3-(4-Fluoro-pyridin-2-ylamino)-1-(2,2,2-trifluoro-ethyl)-1H-pyrazolo[4,3-c]pyridin-6-yl]-(4-hydroxy-2,2-dimethyl-piperidin-1-yl)-methanone | |
| 119 | 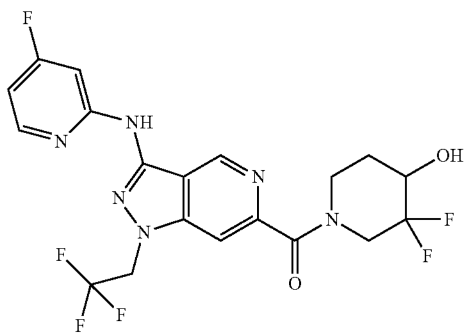 [SMILES: O=C(c1cc2c(cn1)c(Nc1cc(F)ccn1)nn2CC(F)(F)F)N1CCC(O)C(F)(F)C1] | (3,3-Difluoro-4-hydroxy-piperidin-1-yl)-[3-(4-fluoro-pyridin-2-ylamino)-1-(2,2,2-trifluoro-ethyl)-1H-pyrazolo[4,3-c]pyridin-6-yl]-methanone | 474.37 |
| 120 | 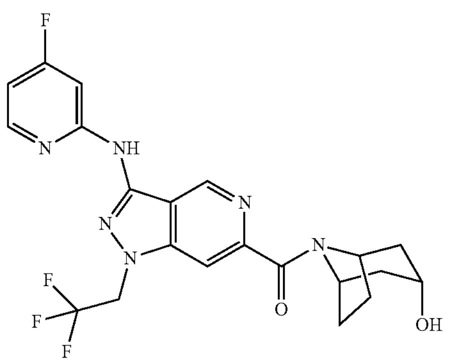 [SMILES: O=C(c1cc2c(cn1)c(Nc1cc(F)ccn1)nn2CC(F)(F)F)N1C2CCC1CC(O)C2] | [3-[(4-fluoro-2-pyridyl)amino]-1-(2,2,2-trifluoroethyl)pyrazolo[4,3-c]pyridin-6-yl]-(3-endo-hydroxy-8-azabicyclo[3.2.1]octan-8-yl)methanone | 464.42 |
| 121 | 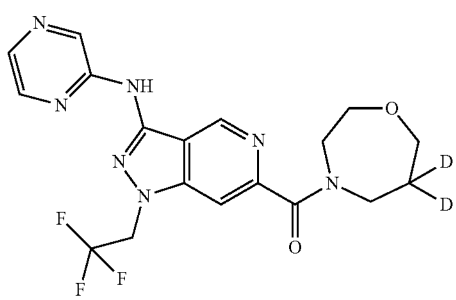 [SMILES: [2H]C1([2H])COCCN(C(=O)c2cc3c(cn2)c(Nc2cnccn2)nn3CC(F)(F)F)C1] | 6,6-dideuterio-1,4-oxazepan-4-yl)-[3-(pyrazin-2ylamino)-1-(2,2,2-trifluoroethyl)pyrazolo[4,3-c]pyridin-6-yl]methanone | 423.40 |

TABLE 2-continued examples of compounds of the present invention

| No. | Structure | IUPAC-Name | MW |
|---|---|---|---|
| 122 | 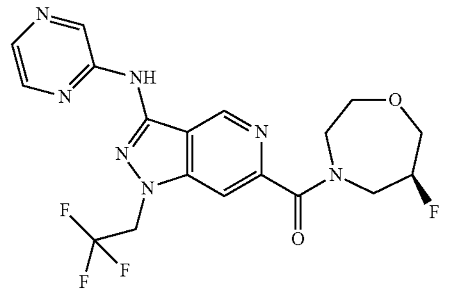 [SMILES: O=C(c1cc2c(cn1)c(Nc1cnccn1)nn2CC(F)(F)F)N1CCOC[C@@H](F)C1] | [(6S)-6-fluoro-1,4-oxazepan-4-yl]-[3-(pyrazin-2ylamino)-1-(2,2,2-trifluoro-ethyl)-1H-pyrazolo[4,3-c]pyridin-6-yl]-methanone | 439.37 |
| 123 | 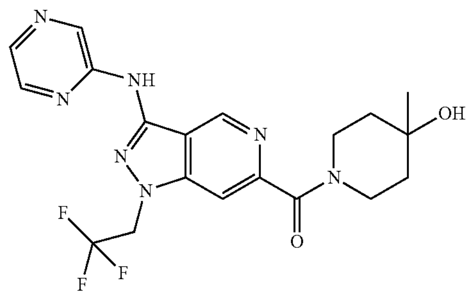 [SMILES: CC1(O)CCN(C(=O)c2cc3c(cn2)c(Nc2cnccn2)nn3CC(F)(F)F)CC1] | [3-(pyrazin-2ylamino)-1-(2,2,2-trifluoro-ethyl)-1H-pyrazolo[4,3-c]pyridin-6-yl]-(4-hydroxy-4-methyl-piperidin-1-yl)-methanone | 435.41 |
| 124 | 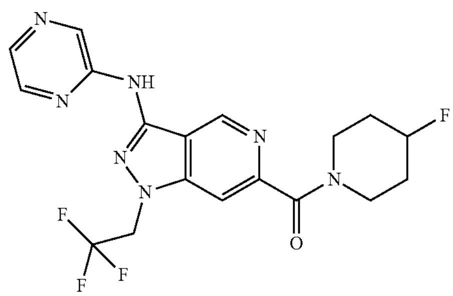 [SMILES: O=C(c1cc2c(cn1)c(Nc1cnccn1)nn2CC(F)(F)F)N1CCC(F)CC1] | [3-(pyrazin-2ylamino)-1-(2,2,2-trifluoro-ethyl)-1H-pyrazolo[4,3-c]pyridin-6-yl]-(4-fluoro-piperidin-1-yl)-methanone | 423.38 |
| 125 | 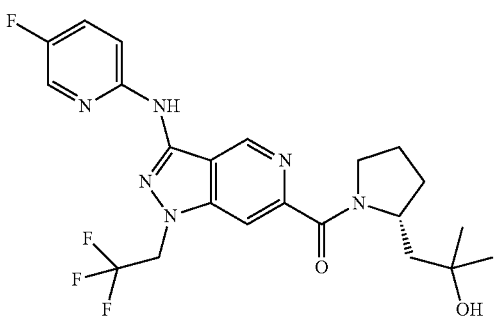 [SMILES: CC(C)(O)C[C@H]1CCCN1C(=O)c1cc2c(cn1)c(Nc1ccc(F)cn1)nn2CC(F)(F)F] | [3-[(5-fluoro-2-pyridyl)amino]-1-(2,2,2-trifluoroethyl)pyrazolo[4,3-c]pyridin-6-yl]-[(2R)-2-(2-hydroxy-2-methyl-propyl)pyrrolidin-1-yl]methanone | 480.47 |
| 126 | 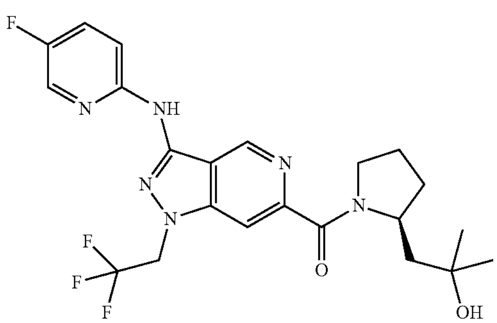 [SMILES: CC(C)(O)C[C@@H]1CCCN1C(=O)c1cc2c(cn1)c(Nc1ccc(F)cn1)nn2CC(F)(F)F] | [3-[(5-fluoro-2-pyridyl)amino]-1-(2,2,2-trifluoroethyl)pyrazolo[4,3-c]pyridin-6-yl]-[(2S)-2-(2-hydroxy-2-methyl-propyl)pyrrolidin-1-yl]methanone | 480.47 |

TABLE 2-continued examples of compounds of the present invention

| No. | Structure | IUPAC-Name | MW |
|---|---|---|---|
| 127 | 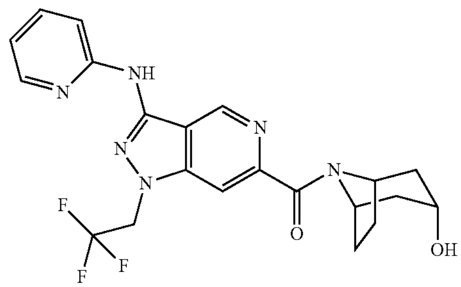 [SMILES: O=C(c1cc2c(cn1)c(Nc1ccccn1)nn2CC(F)(F)F)N1C2CCC1CC(O)C2] | (3-endo-hydroxy-8-azabicyclo[3.2.1]octan-8-yl)-[3-(2-pyridylamino)-1-(2,2,2-trifluoroethyl)pyrazolo[4,3-c]pyridin-6-yl]methanone | 446.43 |

Example 2: Preparation of the Compounds of the Present Invention and Analytical Methods The compounds of general formula (I) and their pharmaceutically acceptable salts can be synthesized according to methods described in the following scheme:

General Conditions:

All reagents were commercial grade and used without further purification. Reactions were typically run using anhydrous solvents under argon atmosphere. Thin layer chromatography was carried out using pre-coated silica gel F-254 plate. Flash column chromatography were performed

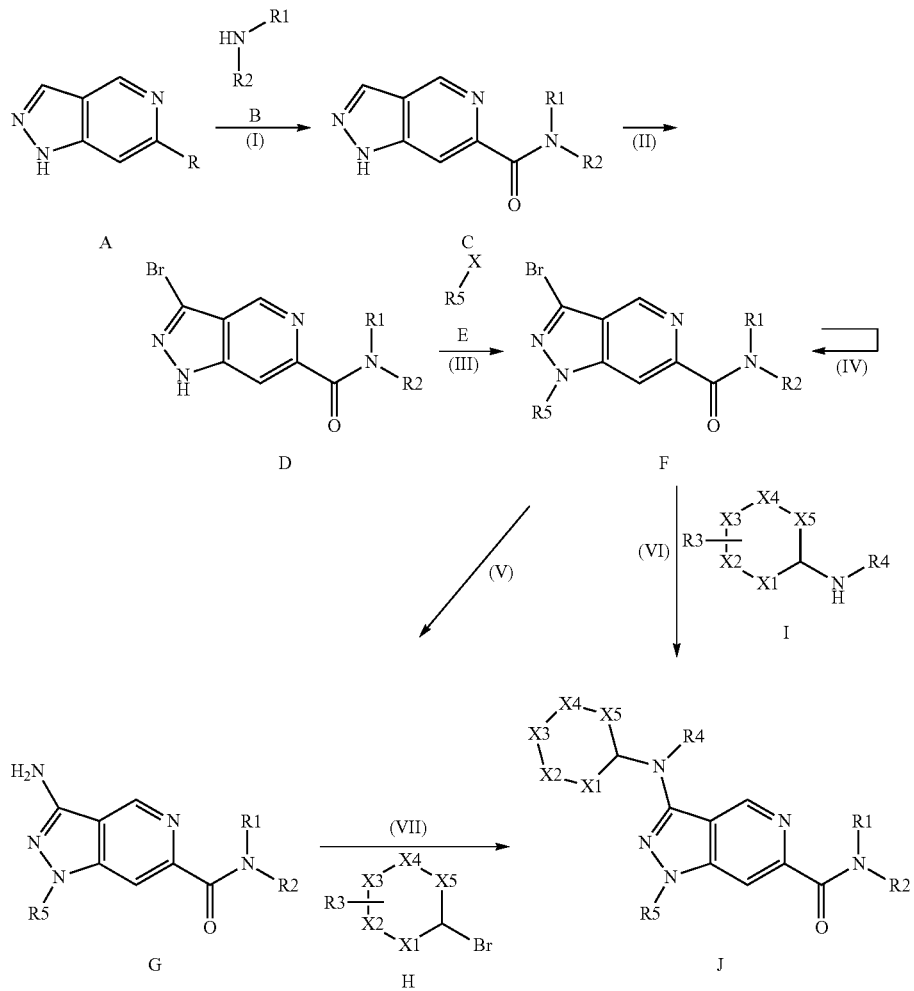

Scheme 1 Preparation of Compounds using a Biotage isolera 4 system, with the Biotage SNAP cartridge KP-SIL (40-60 μm) if not specified. Other cartridges like the Biotage SNAP cartridge KP—NH(40-60 μm) or the Interchim PF-15SIHP-F0025 cartridge (15 μm) were punctually used. After purification by flash chromatography, final compounds were usually triturated in Et₂O or iPr₂O then dried overnight under vacuum at 70° C. Final compounds were usually synthesized in 10 to 100 mg scale.

Reactions were monitored and molecules were characterized using a Waters Acquity UPLC H-class system with a photodiode array detector (190-400 nm). An Acquity CSH C18 1.7 μM 2.1×30 mm column was used. The mobile phase consisted in a gradient of A and B: A was water with 0.025% of trifluoroacetic acid and B was acetonitrile with 0.025% of trifluoroacetic acid. Flow rate was 0.8 ml per min. All analyses were performed at 55° C. The UPLC system was coupled to a Waters SQD2 platform. All mass spectra were full-scan experiments (mass range 100-800 amu). Mass spectra were obtained using positive electro spray ionisation.

Preparative HPLC were performed using a Waters HPLC system with a 2767 sample manager, a 2525 pump, a photodiode array detector (190-400 nm) enabling analytical and preparative modes. An Xselect CSH C18 3.5 μM 4.6×50 mm column was used in analytical mode and a Xselect CSH C18 5 μM 19×100 mm column in preparative mode. The mobile phase consisted in both cases in a gradient of A and B: A was water with 0.1% of formic acid and B was acetonitrile with 0.1% of formic acid. Flow rate was 1 ml per min in analytical mode and 25 ml per min in preparative mode. All LCMS analysis/purification were performed at room temperature. The HPLC system was coupled with a Waters Acquity QDa detector. All mass spectra were full-scan experiments (mass range 100-800 amu). Mass spectra were obtained using positive electro spray ionisation.

All NMR experiments were recorded on a Brucker AMX-400 spectrometer. Proton chemical shift are listed relative to residual DMSO (2.50 ppm). Splitting patterns are designated as s (singlet), d (doublet), dd (doublet of doublet), t (triplet), dt (doublet of triplet), td (triplet of doublet), tt (triplet of triplet), q (quartet), quint (quintuplet), m (multiplet), b (broad), bs (broad singlet). When compounds were characterized as rotamer mixtures at 25° C., some signals could be specifically assigned to a rotamer.

Compound B7: 6,6-dideuterio-1,4-oxazepane Hydrochloride

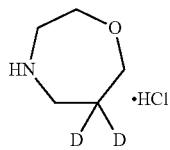

To a solution of 1,4-oxazepan-5-one (1 equiv.) in DMF (0.1M) at 0° C., was added sodium hydride (1.2 equiv.). The reaction mixture was stirred 15 min at 0° C., then p-methoxybenzyl chloride (1.1 equiv.) was added. The reaction mixture was stirred 3 h at rt, then quenched with a saturated bicarbonate solution. The reaction mixture was extracted with AcOEt, the organic phase was washed with brine, dried over magnesium sulfate then concentrated. The resulting solid was purified by flash chromatography (DCM/MeOH: 100/0 to 95/5) to afford 4-[(4-methoxyphenyl) methyl]-1,4-oxazepan-5-one as a colorless oil in 93% yield. M/Z (M+H)+: 236 To a suspension of 4-[(4-methoxyphenyl) methyl]-1,4-oxazepan-5-one (1 equiv.) in D2O (0.25M) was added potassium carbonate (2 equiv.). The reaction mixture was heated 72 h at reflux. The reaction mixture was diluted with a saturated sodium bicarbonate solution then extracted with DCM. The combined organic layers were filtered on an hydrophobic cartridge. Purification by flash chromatography (Cyclohexane/AcOEt: 8/2 to 0/10 then DCM/MeOH: 10/0 to 97/3) afforded 6,6-dideuterio-4-[(4-methoxyphenyl) methyl]-1,4-oxazepan-5-one as a colorless oil in 68% yield. M/Z (M+H)+: 238

To a solution of 6,6-dideuterio-4-[(4-methoxyphenyl) methyl]-1,4-oxazepan-5-one (1 equiv.) in THF (0.1M) at 0° C., was added LiAlH4 (2 equiv.). The reaction mixture was stirred overnight at rt. The reaction mixture was quenched with x μl of water (x is the number of mg of LiAlD4), 3× μl of a 3N NaOH solution, x μl of water, then diluted with Et2O. The resulting white suspension was filtered off, the filtrate was concentrated then purified by flash chromatography (DCM/MeOH: 100/0 to 92/8) to afford 6,6-dideuterio-4-[(4-methoxyphenyl)methyl]-1,4-oxazepane as a colorless oil in quantitative yield. M/Z (M+H)+: 224

To a solution of 6,6-dideuterio-4-[(4-methoxyphenyl) methyl]-1,4-oxazepane (1 equiv.) in DCE (0.2M) at 0° C., was added 1-chloroethyl chloroformate (2.5 equiv.). The reaction mixture was refluxed overnight, then concentrated. The resulting solid was dissolved in MeOH (0.1M). The reaction mixture was refluxed 3 h. HCl, 1.25N in MeOH, (1 equiv.) was added, then the reaction mixture was concentrated. The resulting residue was triturated in Et2O, then dried overnight under vacuum to afford 6,6-dideuterio-1,4-oxazepane hydrochloride B7 as a beige powder in 84% yield. M/Z (M+H)+: 104

General Procedure I: Synthesis of Compounds C from 6-bromo-1H-pyrazolo[4,3-c]-pyridine A (Scheme 1)

In a 2-chamber glassware system, a suspension of 6-bromo-1H-pyrazolo[4,3-c]-pyridine A (1 equiv.), amine B (2 equiv.), triethylamine (2 equiv.), and XantPhos Pd G3 precatalyst (2 mol %) in anhydrous dioxane (0.3M) was degassed under argon in the chamber 1. In the chamber 2, DBU (1.5 equiv.) was added to a solution of molybdenum hexacarbonyl (0.5 equiv.) in anhydrous dioxane (0.3M). Both chambers were immediately sealed, the reaction mixtures were heated overnight at 85° C. The chamber 1 reaction mixture was diluted with a DCM/MeOH mixture. Potassium carbonate (3 equiv.) was added. Silica was added to this solution in order to prepare a solid deposit for purification by flash chromatography to afford compound C.

Compound C1: 1,4-oxazepan-4-yl(1H-pyrazolo[4,3-c]pyridin-6-yl)methanone

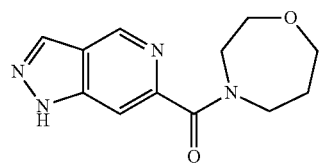 [SMILES: O=C(c1cc2[nH]ncc2cn1)N1CCCOCC1]

Compound C1 was obtained according to General Procedure I, using 1,4-oxazepane B1. Purification by flash chromatography (DCM/MeOH: 100/0 to 94/6) afforded C1 as a light yellow powder in 65% yield. M/Z (M+H)+: 247

Compound C2: 8-oxa-3-azabicyclo[3.2.1]octan-3-yl (1H-pyrazolo[4,3-c]pyridin-6-yl)-methanone

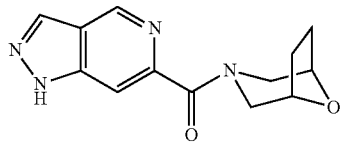 [SMILES: O=C(c1cc2[nH]ncc2cn1)N1CC2CCC(C1)O2]

Compound C2 was obtained according to General Procedure I, using 8-oxa-3-azabicyclo[3.2.1]octane hydrochloride B2. In that specific case, 3 equiv. of triethylamine and 5 equiv. of potassium carbonate were used. Purification by flash chromatography (DCM/MeOH: 10/0 to 9/1) afforded C2 as an orange oil in 89% yield. M/Z (M+H)+: 259

Compound C3: (4-hydroxy-1-piperidyl)-(1H-pyrazolo[4,3-c]pyridin-6-yl)methanone

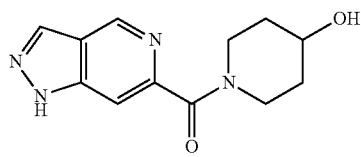 [SMILES: O=C(c1cc2[nH]ncc2cn1)N1CCC(O)CC1]

Compound C3 was obtained according to General Procedure I, using 4-hydroxy-piperidine B3. Purification by flash chromatography (DCM/MeOH: 10/0 to 9/1) afforded C3 as a yellow powder in 87% yield. M/Z (M+H)+: 247

Compound C4: (3-endo-hydroxy-8-azabicyclo[3.2.1]octan-8-yl)-(1H-pyrazolo[4,3-c]pyridin-6-yl)methanone

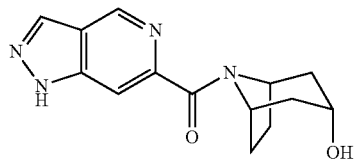 [SMILES: O=C(c1cc2[nH]ncc2cn1)N1C2CCC1CC(O)C2]

Compound C4 was obtained according to General Procedure I, using nortropine B4. Purification by flash chromatography (DCM/MeOH: 10/0 to 9/1) afforded C4 as a white powder in 63% yield. M/Z (M+H)+: 273

Compound C5: (6-hydroxy-1,4-oxazepan-4-yl)-(1H-pyrazolo[4,3-c]pyridin-6-yl)-methanone

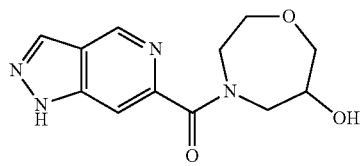 [SMILES: O=C(c1cc2[nH]ncc2cn1)N1CCOCC(O)C1]

Compound C5 was obtained according to General Procedure I, using 1,4-oxazepan-6-ol B5. Purification by flash chromatography (DCM/MeOH: 10/0 to 9/1) afforded C5 in 65% yield. M/Z (M+H)+: 263

Compound C6: (4-hydroxy-4-methyl-1-piperidyl)-(1H-pyrazolo[4,3-c]pyridin-6-yl)-methanone

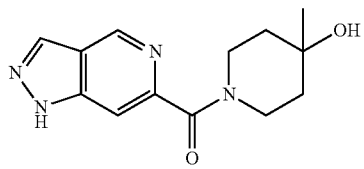 [SMILES: CC1(O)CCN(C(=O)c2cc3[nH]ncc3cn2)CC1]

Compound C6 was obtained according to General Procedure I, using 4-hydroxy-4-methyl-piperidine B6. Purification by flash chromatography (DCM/MeOH: 10/0 to 9/1) afforded C6 as an orange powder in 83% yield. M/Z (M+H)+: 261

Compound C7: (6,6-dideuterio-1,4-oxazepan-4-yl)-(1H-pyrazolo[4,3-c]pyridin-6-yl)-methanone

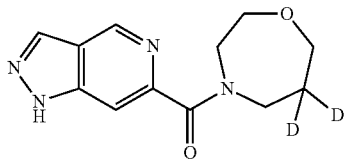 [SMILES: [2H]C1([2H])COCCN(C(=O)c2cc3[nH]ncc3cn2)C1]

Compound C7 was obtained according to General Procedure I, using 5,5-dideuterio-[1,4]oxazepane hydrochloride B7. In that specific case, 3 equiv. of triethylamine were used. Purification by flash chromatography (DCM/MeOH: 100/0 to 9/1) afforded C7 as a beige powder in quantitative yield. M/Z (M+H)+: 249

General Procedure II: Synthesis of Compounds D from Compounds C (Scheme 1)

To a solution of compound C (1 equiv.) in DCM (0.2M) was added NBS (1.05 equiv.). The reaction mixture was stirred 1 h at room temperature, concentrated, then purified by flash chromatography to afford compound D.

Compound D1: (3-bromo-1H-pyrazolo[4,3-c]pyridin-6-yl)-(1,4-oxazepan-4-yl)-methanone

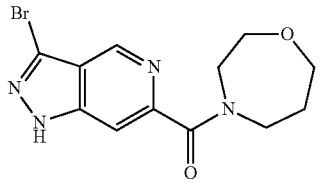 [SMILES: O=C(c1cc2[nH]nc(Br)c2cn1)N1CCCOCC1]

Compound D1 was obtained according to General Procedure II, starting from 1,4-oxazepan-4-yl(1H-pyrazolo[4,3-c]pyridin-6-yl)methanone C1. Purification by flash chromatography (DCM/MeOH: 10/0 to 9/1) afforded D1 as a light yellow powder in 95% yield. M/Z (M+H)$^+$: 325/327

Compound D2: (3-bromo-1H-pyrazolo[4,3-c]pyridin-6-yl)-(8-oxa-3-azabicyclo[3.2.1]-octan-3-yl)methanone

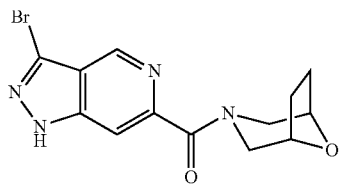 [SMILES: O=C(c1cc2[nH]nc(Br)c2cn1)N1CC2CCC(C1)O2]

Compound D2 was obtained according to General Procedure II, starting from 8-oxa-3-azabicyclo[3.2.1]octan-3-yl(1H-pyrazolo[4,3-c]pyridin-6-yl)methanone C2. Purification by flash chromatography (DCM/MeOH: 10/0 to 9/1) afforded D2 as a white powder in 99% yield. M/Z (M+H)$^+$: 337/339

Compound D3: (3-bromo-1H-pyrazolo[4,3-c]pyridin-6-yl)-(4-hydroxy-1-piperidyl)-methanone

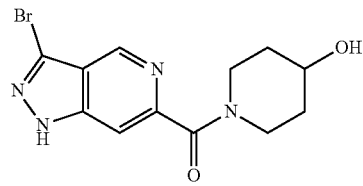 [SMILES: O=C(c1cc2[nH]nc(Br)c2cn1)N1CCC(O)CC1]

Compound D3 was obtained according to General Procedure II, starting from (4-hydroxy-1-piperidyl)-(1H-pyrazolo[4,3-c]pyridin-6-yl)methanone C3. Purification by flash chromatography (DCM/MeOH: 10/0 to 9/1) afforded D3 as a white powder in 83% yield. M/Z (M+H)$^+$: 325/327

Compound D4: (3-bromo-1H-pyrazolo[4,3-c]pyridin-6-yl)-(3-endo-hydroxy-8-aza-bicyclo[3.2.1]octan-8-yl)methanone

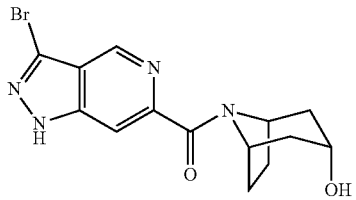 [SMILES: O=C(c1cc2[nH]nc(Br)c2cn1)N1C2CCC1CC(O)C2]

Compound D4 was obtained according to General Procedure II, starting from (3-endo-hydroxy-8-azabicyclo[3.2.1]octan-8-yl)-(1H-pyrazolo[4,3-c]pyridin-6-yl)methanone C4. Purification by flash chromatography (DCM/MeOH: 100/0 to 93/7) afforded D4 as a colorless oil in 72% yield. M/Z (M+H)$^+$: 351/353

Compound D5: (3-bromo-1H-pyrazolo[4,3-c]pyridin-6-yl)-(6-hydroxy-1,4-oxazepan-4-yl)methanone

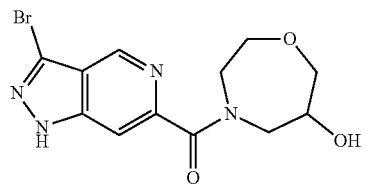 [SMILES: O=C(c1cc2[nH]nc(Br)c2cn1)N1CCOCC(O)C1]

Compound D5 was obtained according to General Procedure II, starting from (6-hydroxy-1,4-oxazepan-4-yl)-(1H-pyrazolo[4,3-c]pyridin-6-yl)methanone C5. Purification by flash chromatography (DCM/MeOH: 10/0 to 9/1) afforded D5 in 86% yield. M/Z (M+H)$^+$: 341/343

Compound D6: (3-bromo-1H-pyrazolo[4,3-c]pyridin-6-yl)-(4-hydroxy-4-methyl-1-piperidyl)methanone

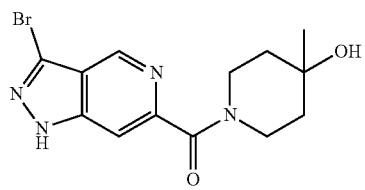 [SMILES: CC1(O)CCN(C(=O)c2cc3[nH]nc(Br)c3cn2)CC1]

Compound D6 was obtained according to General Procedure II, starting from (4-hydroxy-4-methyl-1-piperidyl)-(1H-pyrazolo[4,3-c]pyridin-6-yl)methanone C6. Purification by flash chromatography (DCM/MeOH: 10/0 to 9/1) afforded D6 as a white powder in 95% yield. M/Z (M+H)$^+$: 339/341

Compound D7: (3-bromo-1H-pyrazolo[4,3-c]pyridin-6-yl)-(6,6-dideuterio-1,4-oxazepan-4-yl)methanone

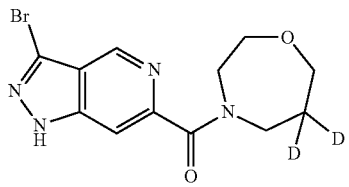 [SMILES: [2H]C1([2H])COCCN(C(=O)c2cc3[nH]nc(Br)c3cn2)C1]

Compound D7 was obtained according to General Procedure II, starting from (6,6-dideuterio-1,4-oxazepan-4-yl)-(1H-pyrazolo[4,3-c]pyridin-6-yl)methanone C7. Purification by flash chromatography (DCM/MeOH: 10/0 to 9/1) afforded D7 as a yellow powder in 96% yield. M/Z (M+H)$^+$: 327/329

General Procedure III: Synthesis of Compounds F from Compounds D (Scheme 1)

Alternative 1:

To a solution of compound D (1 equiv.) in DMF (0.15M) were added potassium carbonate (2 equiv.) and 2,2,2-trifluoroethyl trifluoromethanesulfonate E1 (1.2 equiv.). The reaction mixture was stirred 1 h at room temperature. The reaction mixture was diluted with AcOEt, washed with water, dried over magnesium sulfate then concentrated. The resulting oil was purified by flash chromatography to afford compound F.

Alternative 2:

To a solution of chloromethyl methyl sulfide E2 (1.5 equiv.) in acetone (0.15M) was added sodium iodide (1.5 equiv.). The reaction mixture was stirred 1 h at rt. Compound D (1 equiv.) and cesium carbonate (1.7 equiv.) were added. The reaction mixture was stirred 1 h at rt. The reaction mixture was diluted with AcOEt, washed with water, dried over magnesium sulfate, and concentrated. The resulting oil was purified by flash chromatography to afford compound F.

Compound F1: [3-bromo-1-(2,2,2-trifluoroethyl)pyrazolo[4,3-c]pyridin-6-yl]-(1,4-oxazepan-4-yl)methanone

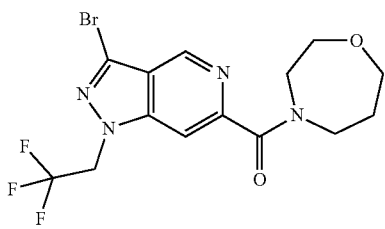 [SMILES: O=C(c1cc2c(cn1)c(Br)nn2CC(F)(F)F)N1CCCOCC1]

Compound F1 was obtained according to General Procedure III, Alternative 1, starting from (3-bromo-1H-pyrazolo[4,3-c]pyridin-6-yl)-(1,4-oxazepan-4-yl)methanone D1. Purification by flash chromatography (DCM/MeOH: 10/0 to 9/1) afforded F1 as a white powder in 70% yield. M/Z (M+H)$^+$: 407/409

Compound F2: [3-bromo-1-(2,2,2-trifluoroethyl)pyrazolo[4,3-c]pyridin-6-yl]-(8-oxa-3-azabicyclo[3.2.1]octan-3-yl)methanone

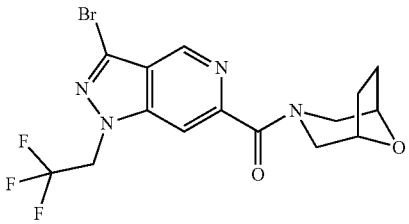 [SMILES: O=C(c1cc2c(cn1)c(Br)nn2CC(F)(F)F)N1CC2CCC(C1)O2]

Compound F2 was obtained according to General Procedure III, Alternative 1, starting from (3-bromo-1H-pyrazolo[4,3-c]pyridin-6-yl)-(8-oxa-3-azabicyclo[3.2.1]octan-3-yl)methanone D2. Purification by flash chromatography (DCM/MeOH: 10/0 to 9/1) afforded F2 as a white powder in 75% yield. M/Z (M+H)$^+$: 419/421

Compound F3: [3-bromo-1-(2,2,2-trifluoroethyl)pyrazolo[4,3-c]pyridin-6-yl]-(4-hydroxy-1-piperidyl)methanone

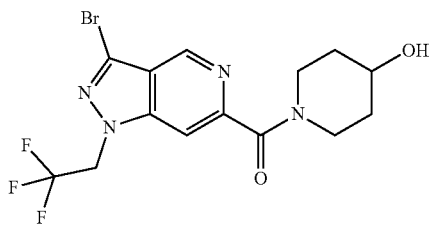

Compound F3 was obtained according to General Procedure III, Alternative 1, starting from (3-bromo-1H-pyrazolo[4,3-c]pyridin-6-yl)-(4-hydroxy-1-piperidyl)methanone D3. Purification by flash chromatography (DCM/MeOH: 10/0 to 9/1) afforded F3 as a white powder in 91% yield. M/Z (M+H)$^+$: 407/409

Compound F4: [3-bromo-1-(2,2,2-trifluoroethyl)pyrazolo[4,3-c]pyridin-6-yl]-(3-endo-hydroxy-8-azabicyclo[3.2.1]octan-8-yl)methanone

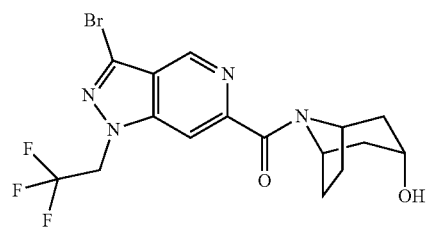 [SMILES: O=C(c1cc2c(cn1)c(Br)nn2CC(F)(F)F)N1C2CCC1CC(O)C2]

Compound F4 was obtained according to General Procedure III, Alternative 1, starting from (3-bromo-1H-pyrazolo[4,3-c]pyridin-6-yl)-(3-endo-hydroxy-8-azabicyclo[3.2.1]-octan-8-yl)methanone D4. Purification by flash chromatography (DCM/MeOH: 100/0 to 95/5) afforded F4 as a white foam in 93% yield. M/Z (M+H)$^+$: 433/435

Compound F5: [3-bromo-1-(methylsulfanylmethyl)pyrazolo[4,3-c]pyridin-6-yl]-(1,4-oxazepan-4-yl)methanone

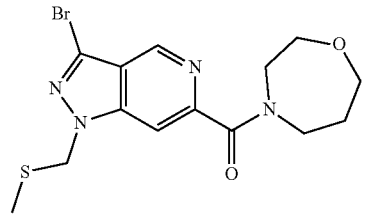 [SMILES: CSCn1nc(Br)c2cnc(C(=O)N3CCCOCC3)cc21]

Compound F5 was obtained according to General Procedure III, Alternative 2, starting from 3-bromo-1H-pyrazolo[4,3-c]pyridin-6-yl)-(1,4-oxazepan-4-yl)methanone D1. Purification by flash chromatography (DCM/MeOH: 10/0 to 9/1) afforded F5 as a yellow powder in 68% yield. M/Z (M+H)$^+$: 385/387

Compound F6: [3-bromo-1-(methylsulfanylmethyl)pyrazolo[4,3-c]pyridin-6-yl]-(3-endo-hydroxy-8-azabicyclo[3.2.1]octan-8-yl)methanone

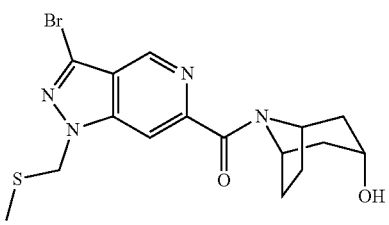 [SMILES: CSCn1nc(Br)c2cnc(C(=O)N3C4CCC3CC(O)C4)cc21]

Compound F6 was obtained according to General Procedure III, Alternative 2, starting from (3-bromo-1H-pyrazolo[4,3-c]pyridin-6-yl)-(3-endo-hydroxy-8-azabicyclo[3.2.1]octan-8-yl)methanone D4. Purification by flash chromatography (DCM/MeOH: 10/0 to 9/1) afforded F6 in 74% yield. M/Z (M+H)$^+$: 411/413

Compound F7: [3-bromo-1-(2,2,2-trifluoroethyl)pyrazolo[4,3-c]pyridin-6-yl]-(6-hydroxy-1,4-oxazepan-4-yl)methanone

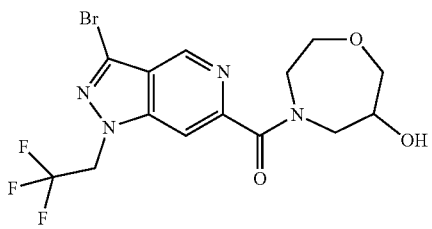 [SMILES: O=C(c1cc2c(cn1)c(Br)nn2CC(F)(F)F)N1CCOCC(O)C1]

Compound F7 was obtained according to General Procedure III, Alternative 1, starting from (3-bromo-1H-pyrazolo[4,3-c]pyridin-6-yl)-(6-hydroxy-1,4-oxazepan-4-yl)methanone D5. Purification by flash chromatography (DCM/MeOH: 10/0 to 9/1) afforded F7 in 76% yield. M/Z (M+H)$^+$: 423/425

Compound F8: [3-bromo-1-(2,2,2-trifluoroethyl)pyrazolo[4,3-c]pyridin-6-yl]-(4-hydroxy-4-methyl-1-piperidyl)methanone

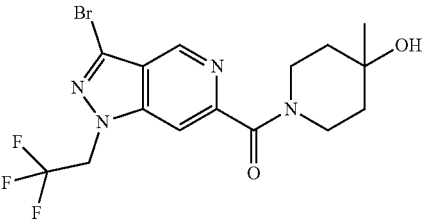 [SMILES: CC1(O)CCN(C(=O)c2cc3c(cn2)c(Br)nn3CC(F)(F)F)CC1]

Compound F8 was obtained according to General Procedure III, Alternative 1, starting from (3-bromo-1H-pyrazolo[4,3-c]pyridin-6-yl)-(4-hydroxy-4-methyl-1-piperidyl)methanone D6. Purification by flash chromatography (DCM/MeOH: 10/0 to 9/1) afforded F8 as a white powder in 68% yield. M/Z (M+H)$^+$: 421/423

Compound F9: [3-bromo-1-(2,2,2-trifluoroethyl)pyrazolo[4,3-c]pyridin-6-yl]-(6,6-dideuterio-1,4-oxazepan-4-yl)methanone

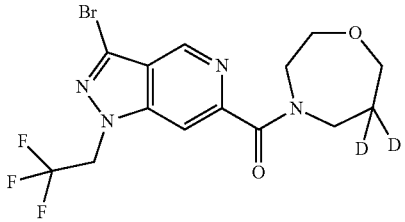 [SMILES: [2H]C1([2H])COCCN(C(=O)c2cc3c(cn2)c(Br)nn3CC(F)(F)F)C1]

Compound F9 was obtained according to General Procedure III, Alternative 1, starting from (3-bromo-1H-pyrazolo[4,3-c]pyridin-6-yl)-(6,6-dideuterio-1,4-oxazepan-4-yl)methanone D7. Purification by flash chromatography (DCM/MeOH: 10/0 to 9/1) then on a 15 μm silica cartridge (DCM/AcOEt: 10/0 to 5/5 then DCM/AcOEt 5/5 to DCM/MeOH 9/1) afforded F9 as a white powder in 39% yield. M/Z (M+H)$^+$: 409/411

General Procedure IV: Synthesis of Compounds F from Compounds F (Scheme 1)

To a solution of compound F (1 equiv.) in DCM (0.07M) was added mCPBA (2.5 equiv.). The reaction mixture was stirred 1 h at rt. The reaction mixture was diluted with AcOEt, washed with water, a saturated sodium thiosulfate solution and a saturated sodium bicarbonate solution, then concentrated. The resulting solid was purified by flash chromatography to afford compound F.

Compound F10: [3-bromo-1-(methylsulfonylmethyl)pyrazolo[4,3-c]pyridin-6-yl]-(1,4-oxazepan-4-yl)methanone

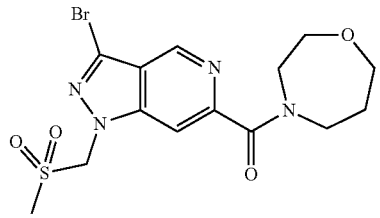 [SMILES: CS(=O)(=O)Cn1nc(Br)c2cnc(C(=O)N3CCCOCC3)cc21]

Compound F10 was obtained according to General Procedure IV, starting from [3-bromo-1-(methylsulfanylmethyl)pyrazolo[4,3-c]pyridin-6-yl]-(1,4-oxazepan-4-yl)methanone F5. Purification by flash chromatography (DCM/MeOH: 10/0 to 9/1) afforded F10 as a white solid in 74% yield. M/Z (M+H)$^+$: 417/419

Compound F11: [3-bromo-1-(methylsulfonylmethyl)pyrazolo[4,3-c]pyridin-6-yl]-(3-endo-hydroxy-8-azabicyclo[3.2.1]octan-8-yl)methanone

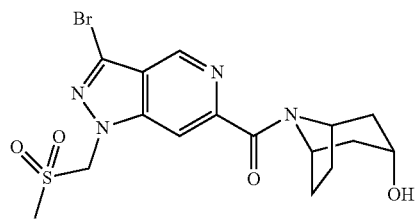 [SMILES: CS(=O)(=O)Cn1nc(Br)c2cnc(C(=O)N3C4CCC3CC(O)C4)cc21]

Compound F11 was obtained according to General Procedure IV, starting from [3-bromo-1-(methylsulfanylmethyl)pyrazolo[4,3-c]pyridin-6-yl]-(3-endo-hydroxy-8-azabicyclo[3.2.1]octan-8-yl)methanone F6. Purification by flash chromatography (DCM/MeOH: 10/0 to 9/1) afforded F11 in 73% yield. M/Z (M+H)$^+$: 443/445

General Procedure V: Synthesis of Compounds G from Compounds F (Scheme 1)

To a solution of compound F (1 equiv.) in dioxane (0.15M) were added benzophenone imine (1.3 equiv.), cesium carbonate (2.4 equiv.), and XantPhos Pd G3 precatalyst (10 mol %). The reaction mixture was stirred overnight at 90° C. The reaction mixture was cooled down, diluted with AcOEt, washed with water. The aqueous layer was extracted twice with DCM. The combined organic layers were dried over sodium sulfate and concentrated.

The resulting oil was dissolved in dioxane (0.05M). HCl 4N in dioxane (5 equiv.) was added dropwise at 0° C. The reaction mixture was stirred 1 h at 0° C. The reaction mixture was diluted with water, extracted twice with diethyl ether. The aqueous layer was basified with solid sodium bicarbonate to pH 9-10 then extracted 3 times with DCM. The combined organic layers were dried over magnesium sulfate and concentrated. The resulting oil was purified by flash chromatography to afford compound G.

Compound G1: [3-amino-1-(2,2,2-trifluoroethyl)pyrazolo[4,3-c]pyridin-6-yl]-(1,4-oxazepan-4-yl)methanone

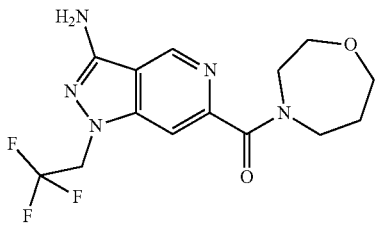 [SMILES: Nc1nn(CC(F)(F)F)c2cc(C(=O)N3CCCOCC3)ncc12]

Compound G1 was obtained according to General Procedure V, starting from [3-bromo-1-(2,2,2-trifluoroethyl)pyrazolo[4,3-c]pyridin-6-yl]-(1,4-oxazepan-4-yl)methanone F1. Purification by flash chromatography (DCM/MeOH: 10/0 to 9/1) afforded G1 as a yellow solid in 64% yield. M/Z (M+H)$^+$: 344

Compound G2: [3-amino-1-(2,2,2-trifluoroethyl)pyrazolo[4,3-c]pyridin-6-yl]-(8-oxa-3-azabicyclo[3.2.1]octan-3-yl)methanone

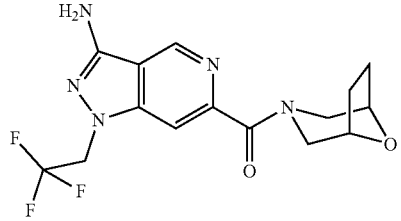 [SMILES: Nc1nn(CC(F)(F)F)c2cc(C(=O)N3CC4CCC(C3)O4)ncc12]

Compound G2 was obtained according to General Procedure V, starting from [3-bromo-1-(2,2,2-trifluoroethyl)pyrazolo[4,3-c]pyridin-6-yl]-(8-oxa-3-azabicyclo[3.2.1]octan-3-yl)methanone F2. Purification by flash chromatography (DCM/MeOH: 10/0 to 8/2) afforded G2 as a brown oil in 54% yield. M/Z (M+H)$^+$: 344

Compound G3: [3-amino-1-(2,2,2-trifluoroethyl)pyrazolo[4,3-c]pyridin-6-yl]-(6-hydroxy-1,4-oxazepan-4-yl)methanone

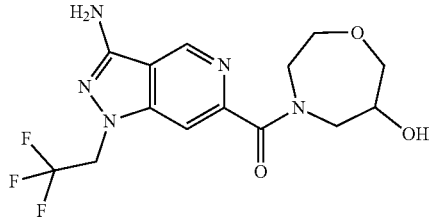 [SMILES: Nc1nn(CC(F)(F)F)c2cc(C(=O)N3CCOCC(O)C3)ncc12]

Compound G3 was obtained according to General Procedure V, starting from [3-bromo-1-(2,2,2-trifluoroethyl)pyrazolo[4,3-c]pyridin-6-yl]-(6-hydroxy-1,4-oxazepan-4-yl)methanone F7. Purification by flash chromatography (DCM/MeOH: 10/0 to 9/1) afforded G3 in 35% yield. M/Z (M+H)$^+$: 360

Compound G4: [3-amino-1-(2,2,2-trifluoroethyl)pyrazolo[4,3-c]pyridin-6-yl]-(4-hydroxy-4-methyl-1-piperidyl)methanone

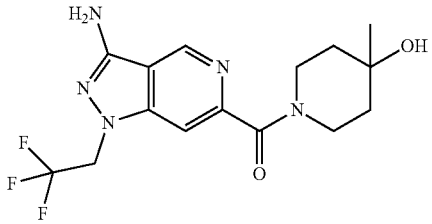 [SMILES: CC1(O)CCN(C(=O)c2cc3c(cn2)c(N)nn3CC(F)(F)F)CC1]

Compound G4 was obtained according to General Procedure V, starting from [3-bromo-1-(2,2,2-trifluoroethyl)pyrazolo[4,3-c]pyridin-6-yl]-(4-hydroxy-4-methyl-1-piperidyl)methanone F8. Purification by flash chromatography (DCM/MeOH: 10/0 to 8/2) afforded G4 as a brown oil in 79% yield. M/Z (M+H)+: 358

Compound G5: [3-amino-1-(2,2,2-trifluoroethyl)pyrazolo[4,3-c]pyridin-6-yl]-(6,6-dideuterio-1,4-oxazepan-4-yl)methanone

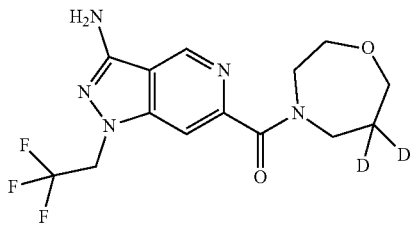 [SMILES: [2H]C1([2H])COCCN(C(=O)c2cc3c(cn2)c(N)nn3CC(F)(F)F)C1]

Compound G5 was obtained according to General Procedure V, starting from [3-bromo-1-(2,2,2-trifluoroethyl)pyrazolo[4,3-c]pyridin-6-yl]-(6,6-dideuterio-1,4-oxazepan-4-yl)methanone F9. Purification by flash chromatography (DCM/MeOH: 10/0 to 9/1) afforded G5 as a brown oil in 69% yield. M/Z (M+H)+: 346

General Procedure VI: Synthesis of Compounds from Compounds F and I (Scheme 1)

Alternative 1:
To a solution of compound F (1 equiv.) in toluene (0.1M) were added amine I (1.2 equiv.) and cesium carbonate (2.4 equiv.). The reaction mixture was degassed with argon, then RuPhos Pd G4 precatalyst (5 mol %) was added. The reaction mixture was stirred overnight at 90° C. Amine I (1.2 equiv.), cesium carbonate (2.4 equiv.) and RuPhos Pd G4 precatalyst (2.5 mol %) were added. The reaction mixture was then heated 4 h at 90° C. The reaction mixture was diluted with DCM, washed with sodium bicarbonate and brine, dried over magnesium sulfate then concentrated. The resulting oil was purified by flash chromatography to afford the compound.

Alternative 2:
To a solution of compound F (1 equiv.) in toluene (0.1M) were added amine I (1.2 equiv.) and cesium carbonate (2.4 equiv.). The reaction mixture was degassed with argon, then RuPhos Pd G4 precatalyst (5 mol %) was added. The reaction mixture was stirred overnight at 90° C. The reaction mixture was diluted with DCM, washed with sodium bicarbonate and brine, dried over magnesium sulfate then concentrated. The resulting oil was purified by flash chromatography to afford the compound.

Alternative 3:
To a solution of compound F (1 equiv.) in dioxane (0.1M) were added amine I (1.2 equiv.) and cesium carbonate (2.4 equiv.). The reaction mixture was degassed with argon, then BrettPhos Pd G1 precatalyst (5 mol %) was added. The reaction mixture was stirred 1 h at 90° C. The reaction mixture was diluted with DCM, washed with sodium bicarbonate and brine, dried over magnesium sulfate then concentrated. The resulting oil was purified by flash chromatography to afford the compound.

Compound 1: [3-(2-fluoroanilino)-1-(2,2,2-trifluoroethyl)pyrazolo[4,3-c]pyridin-6-yl]-(1,4-oxazepan-4-yl)methanone Compound 1 was obtained according to General Procedure VI, Alternative 1, starting from [3-bromo-1-(2,2,2-trifluoroethyl)pyrazolo[4,3-c]pyridin-6-yl]-(1,4-oxazepan-4-yl)-methanone F1 and 2-fluoroaniline I1. Purification by flash chromatography (DCM/MeOH: 100/0 to 95/5) afforded the compound 1 as a beige powder in 65% yield. $^1$H-NMR (DMSO-$d_6$, 400 MHz): 1.74 (quint, J 5.8 Hz, 1H, CH$_2$); 1.92 (quint, J 5.8 Hz, 1H, CH$_2$); 3.43-3.47 (m, 2H, N—CH$_2$); 3.61-3.64 (m, 1H, N—CH$_2$); 3.69-3.79 (m, 5H, CH$_2$); 5.37 (q, J 9.1 Hz, 2H, CH$_2$—CF$_3$); 6.96-7.01 (m, 1H, Ar); 7.18 (t, J 7.8 Hz, 1H, Ar); 7.27 (ddd, J 12.0, 8.1, 0.9 Hz, 1H, Ar); 7.91 (d, J 1.0 Hz, 1H, signal of a rotamer, Ar); 7.92 (d, J 1.0 Hz, 1H, signal of a rotamer, Ar); 8.21-8.26 (m, 1H, Ar); 9.18 (bs, 1H, NH); 9.35 (d, J 1.0 Hz, 1H, signal of a rotamer, Ar); 9.36 (d, J 1.0 Hz, 1H, signal of a rotamer, Ar). M/Z (M+H)+: 438

Compound 2: [3-anilino-1-(2,2,2-trifluoroethyl)pyrazolo[4,3-c]pyridin-6-yl]-(1,4-oxazepan-4-yl)methanone Compound 2 was obtained according to General Procedure VI, Alternative 1, starting from [3-bromo-1-(2,2,2-trifluoroethyl)pyrazolo[4,3-c]pyridin-6-yl]-(1,4-oxazepan-4-yl)-methanone F1 and aniline I2. Purification by flash chromatography (DCM/MeOH: 100/0 to 93/7) afforded the compound 2 as a light brown powder in 62% yield. $^1$H-NMR (DMSO-$d_6$, 400 MHz): 1.74 (quint, J 5.8 Hz, 1H, CH$_2$); 1.92 (quint, J 5.8 Hz, 1H, CH$_2$); 3.43-3.47 (m, 2H, N—CH$_2$); 3.61-3.64 (m, 1H, N—CH$_2$); 3.68-3.79 (m, 5H, CH$_2$); 5.37 (q, J 9.0 Hz, 2H, CH$_2$—CF$_3$); 6.92 (t, J 7.3 Hz, 1H, Ar); 7.33 (t, J 7.8 Hz, 1H, 2H, Ar); 7.72-7.74 (m, 2H, Ar); 7.89 (d, J 0.9 Hz, 1H, signal of a rotamer, Ar); 7.90 (d, J 0.9 Hz, 1H, signal of a rotamer, Ar); 9.27 (d, J 0.9 Hz, 1H, signal of a rotamer, Ar); 9.28 (d, J 0.9 Hz, 1H, signal of a rotamer, Ar); 9.52 (bs, 1H, NH). M/Z (M+H)+: 420

Compound 3: [3-(2-methoxyanilino)-1-(2,2,2-trifluoroethyl)pyrazolo[4,3-c]pyridin-6-yl]-(1,4-oxazepan-4-yl)methanone Compound 3 was obtained according to General Procedure VI, Alternative 1, starting from [3-bromo-1-(2,2,2-trifluoroethyl)pyrazolo[4,3-c]pyridin-6-yl]-(1,4-oxazepan-4-yl)-methanone F1 and 2-methoxyaniline I3. Purification by flash chromatography (DCM/MeOH: 100/0 to 95/5) afforded the compound 3 as a beige powder in 75% yield.

¹H-NMR (DMSO-d$_6$, 400 MHz): 1.74 (quint, J 5.8 Hz, 1H, CH$_2$); 1.92 (quint, J 5.8 Hz, 1H, CH$_2$); 3.43-3.47 (m, 2H, N—CH$_2$); 3.62-3.64 (m, 1H, N—CH$_2$); 3.68-3.79 (m, 5H, CH$_2$); 3.91 (s, 3H, CH$_3$); 5.36 (q, J 9.0 Hz, 2H, CH$_2$—CF$_3$); 6.92-6.97 (m, 2H, Ar); 7.03-7.07 (m, 1H, Ar); 7.88 (d, J 1.0 Hz, 1H, signal of a rotamer, Ar); 7.89 (d, J 1.0 Hz, 1H, signal of a rotamer, Ar); 8.16-9.19 (m, 1H, Ar); 8.54 (s, 1H, NH); 9.33 (d, J 1.0 Hz, 1H, signal of a rotamer, Ar); 9.34 (d, J 1.0 Hz, 1H, signal of a rotamer, Ar). M/Z (M+H)$^+$: 450

Compound 4: [3-(2-methylanilino)-1-(2,2,2-trifluoroethyl)pyrazolo[4,3-c]pyridin-6-yl]-(1,4-oxazepan-4-yl)methanone Compound 4 was obtained according to General Procedure VI, Alternative 2, starting from [3-bromo-1-(2,2,2-trifluoroethyl)pyrazolo[4,3-c]pyridin-6-yl]-(1,4-oxazepan-4-yl)-methanone F1 and 2-methylaniline I4. Purification by flash chromatography (DCM/MeOH: 100/0 to 95/5) afforded the compound 4 as a light beige powder in 51% yield. ¹H-NMR (DMSO-d$_6$, 400 MHz): 1.74 (quint, J 5.8 Hz, 1H, CH$_2$); 1.92 (quint, J 5.8 Hz, 1H, CH$_2$); 2.32 (s, 3H, CH$_3$); 3.44-3.48 (m, 2H, N—CH$_2$); 3.62-3.64 (m, 1H, N—CH$_2$); 3.68-3.78 (m, 5H, CH$_2$); 5.31 (q, J 9.0 Hz, 2H, CH$_2$—CF$_3$); 6.97 (td, J 7.4, 0.9 Hz, 1H, Ar); 7.17 (t, J 7.4 Hz, 1H, Ar); 7.22 (d, J 7.4 Hz, 1H, Ar); 7.70-7.75 (m, 1H, Ar); 7.88 (d, J 1.0 Hz, 1H, signal of a rotamer, Ar); 7.88 (d, J 1.0 Hz, 1H, signal of a rotamer, Ar); 8.39 (s, 1H, NH); 9.12 (d, J 1.0 Hz, 1H, signal of a rotamer, Ar); 9.13 (d, J 1.0 Hz, 1H, signal of a rotamer, Ar). M/Z (M+H)$^+$: 434

Compound 5: [3—(N-methylanilino)-1-(2,2,2-trifluoroethyl)pyrazolo[4,3-c]pyridin-6-yl]-(1,4-oxazepan-4-yl)methanone Compound 5 was obtained according to General Procedure VI, Alternative 2, starting from [3-bromo-1-(2,2,2-trifluoroethyl)pyrazolo[4,3-c]pyridin-6-yl]-(1,4-oxazepan-4-yl)-methanone F1 and N-methylaniline I5. Purification by flash chromatography (DCM/MeOH: 100/0 to 96/4) then by preparative HPLC afforded the compound 5 as a white powder in 26% yield. ¹H-NMR (DMSO-d$_6$, 400 MHz): 1.68 (quint, J 5.8 Hz, 1H, CH$_2$); 1.88 (quint, J 5.8 Hz, 1H, CH$_2$); 3.36-3.40 (m, 2H, N—CH$_2$); 3.45 (s, 3H, signal of a rotamer, CH$_3$); 3.46 (s, 3H, signal of a rotamer, CH$_3$); 3.54-3.57 (m, 1H, N—CH$_2$); 3.63-3.74 (m, 5H, CH$_2$); 5.37 (q, J 9.0 Hz, 2H, CH$_2$—CF$_3$); 7.25 (t, J 7.4 Hz, 1H, Ar); 7.31-7.34 (m, 2H, Ar); 7.41-7.47 (m, 2H, Ar); 7.77 (d, J 1.0 Hz, 1H, signal of a rotamer, Ar); 7.78 (d, J 1.0 Hz, 1H, signal of a rotamer, Ar); 7.89 (d, J 1.0 Hz, 1H, signal of a rotamer, Ar); 7.90 (d, J 1.0 Hz, 1H, signal of a rotamer, Ar). M/Z (M+H)$^+$: 434

Compound 6: [3-(3-fluoroanilino)-1-(2,2,2-trifluoroethyl)pyrazolo[4,3-c]pyridin-6-yl]-(1,4-oxazepan-4-yl)methanone Compound 6 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)-methanone F1 and 3-fluoroaniline I6. Purification by flash chromatography (DCM/MeOH: 10/0 to 9/1) afforded the compound 6 as a beige powder in 89% yield. ¹H-NMR (DMSO-d$_6$, 400 MHz): 1.74 (quint, J 5.8 Hz, 1H, CH$_2$); 1.92 (quint, J 5.8 Hz, 1H, CH$_2$); 3.42-3.48 (m, 2H, N—CH$_2$); 3.60-3.64 (m, 1H, N—CH$_2$); 3.67-3.79 (m, 5H, CH$_2$); 5.40 (q, J 9.0 Hz, 2H, CH$_2$—CF$_3$); 6.69-6.76 (m, 1H, Ar); 7.31-7.41 (m, 2H, Ar); 7.71-7.75 (m, 1H, Ar); 7.91 (bs, 1H, signal of a rotamer, Ar); 7.92 (bs, 1H, signal of a rotamer, Ar); 9.26 (d, J 1.0 Hz, 1H, signal of a rotamer, Ar); 9.28 (d, J 1.0 Hz, 1H, signal of a rotamer, Ar); 9.79 (s, 1H, NH). M/Z (M+H)$^+$: 438

Compound 7: [3-(3-methoxyanilino)-1-(2,2,2-trifluoroethyl)pyrazolo[4,3-c]pyridin-6-yl]-(1,4-oxazepan-4-yl)methanone Compound 7 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)-methanone F1 and 3-methoxyaniline I7. Purification by flash chromatography (DCM/MeOH: 10/0 to 9/1) afforded the compound 7 as a beige powder in 81% yield. ¹H-NMR (DMSO-d$_6$, 400 MHz): 1.74 (quint, J 5.8 Hz, 1H, CH$_2$); 1.92 (quint, J 5.8 Hz, 1H, CH$_2$); 3.41-3.48 (m, 2H, N—CH$_2$); 3.60-3.64 (m, 1H, N—CH$_2$); 3.67-3.79 (m, 5H, CH$_2$); 3.76 (s, 3H, O—CH$_3$); 5.36 (q, J 9.0 Hz, 2H, CH$_2$—CF$_3$); 6.48-6.53 (m, 1H, Ar); 7.20-7.24 (m, 2H, Ar); 7.49 (bs, 1H, Ar); 7.90 (d, J 1.0 Hz, 1H, signal of a rotamer, Ar); 7.91 (d, J 1.0 Hz, 1H, signal of a rotamer, Ar); 9.26 (d, J 1.0, 1 Hz, 1H, signal of a rotamer, Ar); 9.28 (d, J 1.0, 1 Hz, 1H, signal of a rotamer, Ar); 9.53 (s, 1H, NH). M/Z (M+H)$^+$: 450

Compound 8: 3-[[6-(1,4-oxazepane-4-carbonyl)-1-(2,2,2-trifluoroethyl)pyrazolo[4,3-c]pyridin-3-yl]amino]benzonitrile Compound 8 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)-methanone F1 and 3-aminobenzonitrile I8. Purification by flash chromatography (DCM/MeOH: 10/0 to 9/1) afforded the compound 8 as a white powder in 79% yield. ¹H-NMR (DMSO-d$_6$, 400 MHz): 1.75 (quint, J 5.8 Hz, 1H, CH$_2$); 1.92 (quint, J 5.8 Hz, 1H, CH$_2$); 3.44-3.48 (m, 2H, N—CH$_2$); 3.61-3.65 (m, 1H, N—CH$_2$); 3.68-3.80 (m, 5H, CH$_2$); 5.44 (q, J 9.0 Hz, 2H, CH$_2$—CF$_3$); 7.35-7.39 (d, J 7.7 Hz, 1H, Ar); 7.56 (t, J 7.7 Hz, 1H, Ar); 7.87-7.92 (m, 1H, Ar); 7.95 (d, J 1.0 Hz, 1H, signal of a rotamer, Ar); 7.96 (d, J 1.0 Hz, 1H, signal of a rotamer, Ar); 8.22-8.25 (m, 1H, Ar); 9.26 (d, J 1.0 Hz, 1H, signal of a rotamer, Ar); 9.28 (d, J 1.0 Hz, 1H, signal of a rotamer, Ar); 9.99 (s, 1H, NH). M/Z (M+H)$^+$: 445

Compound 9: 3-[[6-(1,4-oxazepane-4-carbonyl)-1-(2,2,2-trifluoroethyl)pyrazolo[4,3-c]pyridin-3-yl]amino]benzamide To a solution of Compound 8 in DMSO (0.05M) were added H$_2$O$_2$, 30% in water (2 equiv.) and potassium carbonate (0.2 equiv.). The reaction mixture was stirred overnight at rt. Water was added to the reaction mixture, the resulting precipitate was filtered and dried under vacuum to afford the compound 9 as a white powder in 58% yield. ¹H-NMR (DMSO-d$_6$, 400 MHz): 1.74 (quint, J 5.8 Hz, 1H, CH$_2$); 1.92 (quint, J 5.8 Hz, 1H, CH$_2$); 3.42-3.49 (m, 2H, N—CH$_2$); 3.60-3.64 (m, 1H, N—CH$_2$); 3.69-3.81 (m, 5H, CH$_2$); 5.37 (q, J 9.0 Hz, 2H, CH$_2$—CF$_3$); 7.30 (bs, 1H, NH$_2$); 7.36-7.43 (m, 2H, Ar); 7.88 (bs, 1H, NH$_2$); 7.90 (bs, 1H, signal of a rotamer); 7.90 (bs, 1H, signal of a rotamer, Ar); 8.01-8.09 (m, 2H, Ar); 9.26 (d, J 1.0 Hz, 1H, signal of a rotamer, Ar); 9.28 (d, J 1.0 Hz, 1H, signal of a rotamer, Ar); 9.68 (s, 1H, NH). M/Z (M+H)$^+$: 463

Compound 10: [3-(4-fluoroanilino)-1-(2,2,2-trifluoroethyl)pyrazolo[4,3-c]pyridin-6-yl]-(1,4-oxazepan-4-yl)methanone Compound 10 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 4-fluoroaniline I9. Purification by flash chromatography (DCM/MeOH: 10/0 to 9/1) afforded the compound 10 as a yellow powder in 63% yield. $^1$H-NMR (DMSO-$d_6$, 400 MHz): 1.74 (quint, J 5.8 Hz, 1H, $CH_2$); 1.92 (quint, J 5.8 Hz, 1H, $CH_2$); 3.42-3.48 (m, 2H, N—$CH_2$); 3.60-3.64 (m, 1H, N—$CH_2$); 3.67-3.79 (m, 5H, $CH_2$); 5.36 (q, J 9.0 Hz, 2H, $CH_2$—$CF_3$); 7.18 (t, J 9.0 Hz, 2H, Ar); 7.74 (ddd, J 9.0, 4.7, 0.8 Hz, 2H, Ar); 7.89 (d, J 1.0 Hz, 1H, signal of a rotamer, Ar); 7.90 (d, J 1.0 Hz, 1H, signal of a rotamer, Ar); 9.24 (d, J 1.0 Hz, 1H, signal of a rotamer, Ar); 9.25 (d, J 1.0 Hz, 1H, signal of a rotamer, Ar); 9.55 (s, 1H, NH). M/Z (M+H)$^+$: 438

Compound 11: [3-(4-methoxyanilino)-1-(2,2,2-trifluoroethyl)pyrazolo[4,3-c]pyridin-6-yl]-(1,4-oxazepan-4-yl)methanone Compound 11 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 4-methoxyaniline I10. Purification by flash chromatography (DCM/MeOH: 10/0 to 9/1) afforded the compound 11 as a beige powder in 75% yield. $^1$H-NMR (DMSO-$d_6$, 400 MHz): 1.74 (quint, J 5.8 Hz, 1H, $CH_2$); 1.92 (quint, J 5.8 Hz, 1H, $CH_2$); 3.42-3.48 (m, 2H, N—$CH_2$); 3.60-3.64 (m, 1H, N—$CH_2$); 3.67-3.80 (m, 8H, O—$CH_3$, $CH_2$); 5.32 (q, J 9.0 Hz, 2H, $CH_2$—$CF_3$); 6.91 (d, J 9.0 Hz, 2H); 7.65 (d, J 9.0 Hz, 2H); 7.86 (d, J 1.0 Hz, 1H, signal of a rotamer, Ar); 7.87 (d, J 1.0 Hz, 1H, signal of a rotamer, Ar); 9.21 (d, J 1.0 Hz, 1H, signal of a rotamer, Ar); 9.22 (d, J 1.0 Hz, 1H, signal of a rotamer, Ar); 9.33 (s, 1H, NH). M/Z (M+H)$^+$: 450

Compound 12: 1,4-oxazepan-4-yl-[3-(3-pyridylamino)-1-(2,2,2-trifluoroethyl)pyrazolo-[4,3-c]pyridin-6-yl]methanone Compound 12 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 3-aminopyridine I11. Purification by flash chromatography (DCM/MeOH: 10/0 to 9/1) afforded the compound 12 as a beige powder in 52% yield. $^1$H-NMR (DMSO-$d_6$, 400 MHz): 1.74 (quint, J 5.8 Hz, 1H, $CH_2$); 1.92 (quint, J 5.8 Hz, 1H, $CH_2$); 3.43-3.48 (m, 2H, N—$CH_2$); 3.60-3.64 (m, 1H, N—$CH_2$); 3.68-3.80 (m, 5H, $CH_2$); 5.40 (q, J 9.0 Hz, 2H, $CH_2$—$CF_3$); 7.39 (dd, J 8.3, 4.7 Hz, 1H, Ar); 7.93 (d, J 1.0 Hz, 1H, signal of a rotamer, Ar); 7.94 (d, J 1.0 Hz, 1H, signal of a rotamer, Ar); 8.14-8.22 (m, 2H, Ar); 8.92 (d, J 2.7 Hz, 1H, Ar); 9.28 (d, J 1.0 Hz, 1H, Ar); 9.29 (d, J 1.0 Hz, 1H, Ar); 9.82 (s, 1H, NH). M/Z (M+H)$^+$: 421

Compound 13: 4-[[6-(1,4-oxazepane-4-carbonyl)-1-(2,2,2-trifluoroethyl)pyrazolo[4,3-c]pyridin-3-yl]amino]benzonitrile Compound 13 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 4-benzonitrile I12. Purification by flash chromatography (DCM/MeOH: 10/0 to 9/1) afforded the compound 13 as a grey powder in 82% yield. $^1$H-NMR (DMSO-$d_6$, 400 MHz): 1.74 (quint, J 5.8 Hz, 1H, $CH_2$); 1.92 (quint, J 5.8 Hz, 1H, $CH_2$); 3.41-3.47 (m, 2H, N—$CH_2$); 3.60-3.64 (m, 1H, N—$CH_2$); 3.67-3.79 (m, 5H, $CH_2$); 5.44 (q, J 9.0 Hz, 2H, $CH_2$—$CF_3$); 7.78 (d, J 8.5 Hz, 2H, Ar); 7.86 (d, J 8.5 Hz, 2H, Ar); 7.95-7.97 (m, 1H, Ar); 9.28 (d, J 1.0 Hz, 1H, signal of a rotamer, Ar); 9.29 (d, J 1.0 Hz, 1H, signal of a rotamer, Ar); 10.14 (s, 1H, NH). M/Z (M+H)$^+$: 445

Compound 14: 4-[[6-(1,4-oxazepane-4-carbonyl)-1-(2,2,2-trifluoroethyl)pyrazolo[4,3-c]pyridin-3-yl]amino]benzamide To a solution of Compound 13 4-[[6-(1,4-oxazepane-4-carbonyl)-1-(2,2,2-trifluoro-ethyl)pyrazolo[4,3-c]pyridin-3-yl]amino]benzonitrile (1 equiv.) in DMSO (0.05M) were added $H_2O_2$, 30% in water (2 equiv.) and potassium carbonate (0.2 equiv.). The reaction mixture was stirred overnight at rt. Water was added, then the reaction mixture was extracted with AcOEt. The organic layer was dried over magnesium sulfate. The aqueous layer was extracted with DCM. The resulting organic layer was filtered through an hydrophobic cartridge. The combined organic layers were concentrated, the resulting solid was triturated in a minimum amount of water. Purification by preparative HPLC afforded the compound 14 as a white powder in 22% yield. $^1$H-NMR (DMSO-$d_6$, 400 MHz): 1.74 (quint, J 5.8 Hz, 1H, $CH_2$); 1.92 (quint, J 5.8 Hz, 1H, $CH_2$); 3.42-3.48 (m, 2H, N—$CH_2$); 3.60-3.64 (m, 2H, N—$CH_2$); 3.67-3.79 (m, 4H, 2O—$CH_2$); 5.41 (q, J 9.0 Hz, 2H, $CH_2$—$CF_3$); 7.12 (bs, 1H, $NH_2$); 7.73-7.79 (m, 3H, Ar, $NH_2$); 7.87 (d, J 8.7 Hz, 2H, Ar); 7.93 (d, J 1.0 Hz, 1H, signal of a rotamer, Ar); 7.94 (d, J 1.0 Hz, 1H, signal of a rotamer, Ar); 9.28 (d, J 1.0 Hz, 1H, signal of a rotamer, Ar); 9.29 (d, J 1.0 Hz, 1H, signal of a rotamer, Ar); 9.84 (s, 1H, NH). M/Z (M+H)$^+$: 463

Compound 15: [3-(3,5-difluoroanilino)-1-(2,2,2-trifluoroethyl)pyrazolo[4,3-c]pyridin-6-yl]-(1,4-oxazepan-4-yl)methanone Compound 15 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 3,5-difluoroaniline I14. Purification by flash chromatography (DCM/MeOH: 10/0 to 9/1) afforded the compound 15 as a white powder in 42% yield. $^1$H-NMR (DMSO-$d_6$, 400 MHz): 1.74 (quint, J 5.8 Hz, 1H, $CH_2$); 1.92 (quint, J 5.8 Hz, 1H, $CH_2$); 3.41-3.49 (m, 2H, N—$CH_2$); 3.60-3.64 (m, 1H, N—$CH_2$); 3.67-3.81 (m, 5H, $CH_2$); 5.43 (q, J 9.0 Hz, 2H, $CH_2$—$CF_3$); 6.73 (td, J 9.4, 4.3 Hz, 1H, Ar); 7.37-7.45 (m, 2H, Ar); 7.94 (d, J 0.9 Hz, 1H, signal of a rotamer, Ar); 7.95 (d, J 0.9 Hz, 1H, signal of a rotamer, Ar); 9.23 (d, J 0.9 Hz, 1H, signal of a rotamer, Ar); 9.24 (d, J 0.9 Hz, 1H, signal of a rotamer, Ar); 10.01 (s, 1H, NH). M/Z (M+H)$^+$: 456

Compound 16: [3-(3-fluoro-4-methylanilino)-1-(2,2,2-trifluoroethyl)pyrazolo[4,3-c]-pyridin-6-yl]-(1,4-oxazepan-4-yl)methanone Compound 16 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 3-fluoro-4-methylaniline I16. Purification by flash chromatography (DCM/MeOH: 10/0 to 9/1) afforded the compound 17 as a beige powder in 66% yield. ¹H-NMR (DMSO-d₆, 400 MHz): 1.74 (quint, J 5.8 Hz, 1H, CH₂); 1.92 (quint, J 5.8 Hz, 1H, CH₂); 2.18 (s, 3H, CH₃); 3.41-3.49 (m, 2H, N—CH₂); 3.60-3.65 (m, 1H, N—CH₂); 3.68-3.80 (m, 5H, CH₂); 5.38 (q, J 9.0 Hz, 2H, CH₂—CF₃); 7.21 (t, J 8.4 Hz, 1H, Ar); 7.3 (d, J 8.4 Hz, 2H, Ar); 7.69 (d, J 12.9 Hz, 1H, Ar); 7.90 (d, J 0.9 Hz, 1H, signal of a rotamer, Ar); 7.91 (d, J 0.9 Hz, 1H, signal of a rotamer, Ar); 9.23 (d, J 0.9 Hz, 1H, signal of a rotamer, Ar); 9.25 (d, J 0.9 Hz, 1H, signal of a rotamer, Ar); 9.65 (s, 1H, NH). M/Z (M+H)⁺: 452

Compound 17: [3-(3,4-difluoroanilino)-1-(2,2,2-trifluoroethyl)pyrazolo[4,3-c]pyridin-6-yl]-(1,4-oxazepan-4-yl)methanone Compound 17 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 3,4-difluoroaniline 116. Purification by flash chromatography (DCM/MeOH: 10/0 to 9/1) afforded the compound 17 as a beige powder in 60% yield. ¹H-NMR (DMSO-d₆, 400 MHz): 1.74 (quint, J 5.8 Hz, 1H, CH₂); 1.92 (quint, J 5.8 Hz, 1H, CH₂); 3.42-3.49 (m, 2H, N—CH₂); 3.60-3.63 (m, 1H, N—CH₂); 3.66-3.81 (m, 5H, CH₂); 5.39 (q, J 9.0 Hz, 2H, CH₂—CF₃); 7.29-7.47 (m, 2H, Ar); 7.87-7.95 (m, 2H, Ar); 9.23 (d, J 0.9 Hz, 1H, signal of a rotamer, Ar); 9.24 (d, J 0.9 Hz, 1H, signal of a rotamer, Ar); 9.79 (s, 1H, NH). M/Z (M+H)⁺: 456

Compound 18: [3-(3-chloro-4-fluoroanilino)-1-(2,2,2-trifluoroethyl)pyrazolo[4,3-c]-pyridin-6-yl]-(1,4-oxazepan-4-yl)methanone Compound 18 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 3-chloro-4-fluoroaniline 117. Purification by flash chromatography (DCM/MeOH: 10/0 to 9/1) then by preparative HPLC afforded the compound 18 as a white powder in 26% yield. ¹H-NMR (DMSO-d₆, 400 MHz): 1.74 (quint, J 5.8 Hz, 1H, CH₂); 1.92 (quint, J 5.8 Hz, 1H, CH₂); 3.42-3.49 (m, 2H, N—CH₂); 3.60-3.63 (m, 1H, N—CH₂); 3.66-3.81 (m, 5H, CH₂); 5.39 (q, J 9.0 Hz, 2H, CH₂—CF₃); 7.40 (t, J 9.1 Hz, 1H, Ar); 7.56-7.62 (m, 1H, Ar); 7.92 (d, J 0.9 Hz, 1H, signal of a rotamer, Ar); 7.93 (d, J 0.9 Hz, 1H, signal of a rotamer, Ar); 8.03 (ddd, J 6.6, 2.7, 0.9 Hz, 1H, Ar); 9.23 (d, J 0.9 Hz, 1H, signal of a rotamer, Ar); 9.24 (d, J 0.9 Hz, 1H, signal of a rotamer, Ar); 9.75 (s, 1H, NH). M/Z (M+H)⁺: 472/474

Compound 19: [3-(4-chloro-3-fluoroanilino)-1-(2,2,2-trifluoroethyl)pyrazolo[4,3-c]-pyridin-6-yl]-(1,4-oxazepan-4-yl)methanone Compound 19 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 4-chloro-3-fluoroaniline 118 (1.1 equiv.). Purification by flash chromatography (DCM/MeOH: 10/0 to 9/1) then by preparative HPLC afforded the compound 19 as a white powder in 18% yield. ¹H-NMR (DMSO-ak, 400 MHz): 1.74 (quint, J 5.8 Hz, 1H, CH₂); 1.92 (quint, J 5.8 Hz, 1H, CH₂); 3.41-3.49 (m, 2H, N—CH₂); 3.58-3.65 (m, 1H, N—CH₂); 3.67-3.80 (m, 5H, CH₂); 5.41 (q, J 9.0 Hz, 2H, CH₂—CF₃); 7.40-7.43 (m, 1H, Ar); 7.51 (t, J 8.7 Hz, 1H, Ar); 7.90-7.95 (m, 2H, Ar); 9.24 (d, J 0.9 Hz, 1H, signal of a rotamer, Ar); 9.25 (d, J 0.9 Hz, 1H, signal of a rotamer, Ar); 9.95 (s, 1H, NH). M/Z (M+H)⁺: 472/474

Compound 20: [3-(3-fluoroanilino)-1-(2,2,2-trifluoroethyl)pyrazolo[4,3-c]pyridin-6-yl]-(8-oxa-3-azabicyclo[3.2.1]octan-3-yl)methanone Compound 20 was obtained according to General Procedure VI, Alternative 3, starting from [3-bromo-1-(2,2,2-trifluoroethyl)pyrazolo[4,3-c]pyridin-6-yl]-(8-oxa-3-azabicyclo[3.2.1]octan-3-yl)methanone F2 and 3-fluoroaniline I6 (1.3 equiv.). In that specific case, 10 mol % of BrettPhos Pd G1 precatalyst was used. Purification by flash chromatography (DCM/MeOH: 10/0 to 9/1) afforded the compound 20 as a beige powder in 64% yield. ¹H-NMR (DMSO-d6,400 MHz): 1.68-1.92 (m, 4H, CH₂); 3.03 (dd, J 13.2, 2.3 Hz, 1H, N—CH₂); 3.26-3.33 (m, 2H, N—CH₂); 4.15-4.24 (m, 2H, N—CH₂, O—CH); 4.38-4.43 (m, 1H, O—CH); 5.41 (m, 2H, CH₂—CF₃); 6.70-6.75 (m, 1H, Ar); 7.31-7.41 (m, 2H, Ar); 7.74 (dt, J 12.1, 2.0 Hz, 1H, Ar); 7.94 (bs, 1H, Ar); 9.26 (d, J 1.0 Hz, 1H, Ar); 9.79 (bs, 1H, NH). M/Z (M+H)⁺: 450

Compound 21: [3-(4-fluoroanilino)-1-(2,2,2-trifluoroethyl)pyrazolo[4,3-c]pyridin-6-yl]-(8-oxa-3-azabicyclo[3.2.1]octan-3-yl)methanone Compound 21 was obtained according to General Procedure VI, Alternative 3, starting from [3-bromo-1-(2,2,2-trifluoroethyl)pyrazolo[4,3-c]pyridin-6-yl]-(8-oxa-3-azabicyclo[3.2.1]octan-3-yl)methanone F2 and 4-fluoroaniline I9. In that specific case, mol % of BrettPhos Pd G1 precatalyst was used. Purification by flash chromatography (DCM/MeOH: 10/0 to 9/1) afforded the compound 21 as a beige powder in 60% yield. ¹H-NMR (DMSO-d₆, 400 MHz): 1.68-1.92 (m, 4H, CH₂); 3.03 (dd, J 13.2, 2.3 Hz, 1H, N—CH₂); 3.26-3.33 (m, 2H, N—CH₂); 4.17-4.24 (m, 2H, N—CH₂, O—CH); 4.38-4.43 (m, 1H, O—CH); 5.21 (m, 2H, CH₂—CF₃); 7.18 (t, J 9.0 Hz, 2H, Ar); 7.73 (dd, J 9.0, 4.8 Hz, 2H, Ar); 7.91 (bs, 1H, Ar); 9.24 (d, J 1.0 Hz, 1H, Ar); 9.55 (bs, 1H, N—H). M/Z (M+H)⁺: 450

Compound 22: [3-(4-fluoroanilino)-1-(2,2,2-trifluoroethyl)pyrazolo[4,3-c]pyridin-6-yl]-(4-hydroxy-1-piperidyl)methanone Compound 22 was obtained according to General Procedure VI, Alternative 3, starting from [3-bromo-1-(2,2,2-trifluoroethyl)pyrazolo[4,3-c]pyridin-6-yl]-(4-hydroxy-1-piperidyl)methanone F3 and 4-fluoroaniline I9. Purification by flash chromatography (DCM/MeOH: 100/0 to 95/5) afforded the compound 22 as a yellow powder in 49% yield. ¹H-NMR (DMSO-d₆, 400 MHz): 1.30-1.49 (m, 2H, CH₂); 1.63-1.72 (m, 1H, CH₂); 1.78-1.88 (m, 1H, CH₂); 3.10 (ddd, J 13.1, 9.9, 3.3 Hz, 1H, N—CH₂); 3.25 (ddd, J 13.1, 9.9, 3.3 Hz, 1H, N—CH₂); 3.43-3.53 (m, 1H, N—CH₂); 3.71-3.81 (m, 1H, N—CH₂); 4.01-4.14 (m, 1H, CH—OH); 4.78 (d, J 4.2 Hz, 1H, OH); 5.34 (q, J 9.0 Hz, 2H, CH₂—CF₃); 7.18 (t, J 9.1 Hz, 2H, Ar); 7.73 (dd, J 9.1, 4.8 Hz, 2H, Ar); 7.85 (bs, 1H, Ar); 9.24 (d, J 0.9 Hz, 1H, Ar); 9.54 (s, 1H, NH). M/Z (M+H)⁺: 438

Compound 23: [3-(3-fluoroanilino)-1-(2,2,2-trifluoroethyl)pyrazolo[4,3-c]pyridin-6-yl]-(4-hydroxy-1-piperidyl)methanone Compound 23 was obtained according to General Procedure VI, Alternative 3, starting from [3-bromo-1-(2,2,2- trifluoroethyl)pyrazolo[4,3-c]pyridin-6-yl]-(4-hydroxy-1-piperidyl)methanone F3 and 3-fluoroaniline I6. Purification by flash chromatography (DCM/MeOH: 100/0 to 95/5), then by preparative HPLC afforded the compound 23 as a white powder in 26% yield. $^1$H-NMR (DMSO-d$_6$, 400 MHz): 1.30-1.47 (m, 2H, CH$_2$); 1.64-1.73 (m, 1H, CH$_2$); 1.78-1.88 (m, 1H, CH$_2$); 3.03-3.15 (m, 1H, N—CH$_2$); 3.18-3.26 (m, 1H, N—CH$_2$); 3.43-3.54 (m, 1H, N—CH$_2$); 3.69-3.83 (m, 1H, N—CH$_2$); 4.02-4.15 (d, J 4.0 Hz, 1H, CH—OH); 4.79 (d, J 4.1 Hz, 1H, OH); 5.39 (q, J 9.0 Hz, 2H, CH$_2$—CF$_3$); 6.69-6.77 (m, 1H, Ar); 7.28-7.45 (m, 2H, Ar); 7.74 (td, J 12.5, 2.0 Hz, 1H, Ar); 7.88 (bs, 1H, Ar); 9.26 (d, J 0.6 Hz, 1H, Ar); 9.80 (s, 1H, NH). M/Z (M+H)$^+$: 438

Compound 24: (4-hydroxy-1-piperidyl)-[3-(2-pyridylamino)-1-(2,2,2-trifluoroethyl)-pyrazolo[4,3-c]pyridin-6-yl]methanone Compound 24 was obtained according to General Procedure VI, Alternative 3, starting from [3-bromo-1-(2,2,2-trifluoroethyl)pyrazolo[4,3-c]pyridin-6-yl]-(4-hydroxy-1-piperidyl)methanone F3 and 2-aminopyridine I19. Purification by flash chromatography (DCM/MeOH: 100/0 to 95/5), then by preparative HPLC afforded the compound 24 as a white powder in 22% yield. $^1$H-NMR (DMSO-d6, 400 MHz): 1.29-1.49 (m, 2H, CH$_2$); 1.64-1.74 (m, 1H, CH$_2$); 1.77-1.88 (m, 1H, CH$_2$); 3.11 (ddd, J 13.0, 9.4, 3.1 Hz, 1H, N—CH$_2$); 3.25 (ddd, J 13.0, 9.4, 3.1 Hz, 1H, N—CH$_2$); 3.46-3.55 (m, 1H, N—CH$_2$); 3.71-3.81 (m, 1H, N—CH$_2$); 4.04-4.13 (m, 1H, CH—OH); 4.78 (d, J 4.1 Hz, 1H, OH); 5.39 (q, J 9.2 Hz, 2H, CH$_2$—CF$_3$); 6.93 (ddd, J 6.8, 4.9, 0.7 Hz, 1H, Ar); 7.77 (ddd, J 8.7, 6.8, 1.9 Hz, 1H, Ar); 7.89 (bs, 1H, Ar); 7.94 (d, J 8.7 Hz, 1H, Ar); 8.26-8.29 (m, 1H, Ar); 9.40 (d, J 1.0 Hz, 1H, Ar); 10.32 (s, 1H, NH). M/Z (M+H)$^+$: 421

Compound 25: [3-(3-fluoroanilino)-1-(2,2,2-trifluoroethyl)pyrazolo[4,3-c]pyridin-6-yl]-(3-endo-hydroxy-8-azabicyclo[3.2.1]octan-8-yl)methanone Compound 25 was obtained according to General Procedure VI, Alternative 3, starting from [3-bromo-1-(2,2,2-trifluoroethyl)pyrazolo[4,3-c]pyridin-6-yl]-(3-endo-hydroxy-8-azabicyclo[3.2.1]octan-8-yl)methanone F4 and 3-fluoroaniline I6. Purification by flash chromatography (DCM/MeOH: 100/0 to 92/8) then by preparative HPLC afforded the compound 25 as a white powder in 21% yield. $^1$H-NMR (DMSO-d$_6$, 400 MHz): 1.61-1.70 (m, 1H, CH$_2$); 1.76-1.94 (m, 3H, CH$_2$); 1.98-2.10 (m, 2H, CH$_2$); 2.15-2.32 (m, 2H, CH$_2$); 3.98 (bs, 1H, N—CH); 4.31-4.36 (m, 1H, N—CH); 4.60-4.66 (m, 2H, CH, OH); 5.41 (q, 2H, J 9.3 Hz, CH$_2$—CF$_3$); 6.68-6.76 (m, 1H, Ar); 7.31-7.41 (m, 2H, Ar); 7.731 (dt, J 12.4, 2.1 Hz, 1H, Ar); 8.00 (d, J 1.0 Hz, 1H, Ar); 9.26 (d, J 1.0 Hz, 1H, Ar); 9.79 (s, 1H, NH). M/Z (M+H)$^+$: 464

Compound 26: [3-(4-fluoroanilino)-1-(2,2,2-trifluoroethyl)pyrazolo[4,3-c]pyridin-6-yl]-(3-endo-hydroxy-8-azabicyclo[3.2.1]octan-8-yl)methanone Compound 26 was obtained according to General Procedure VI, Alternative 3, starting from [3-bromo-1-(2,2,2-trifluoroethyl)pyrazolo[4,3-c]pyridin-6-yl]-(3-endo-hydroxy-8-azabicyclo[3.2.1]octan-8-yl)methanone F4 and 4-fluoroaniline I9. Purification by flash chromatography (DCM/MeOH: 100/0 to 92/8) then by preparative HPLC afforded the compound 26 as a beige powder in 26% yield. $^1$H-NMR (DMSO-d$_6$, 400 MHz): 1.62-1.70 (m, 1H, CH$_2$); 1.75-1.94 (m, 3H, CH$_2$); 1.98-2.08 (m, 2H, CH$_2$); 2.16-2.30 (m, 2H, CH$_2$); 3.99 (bs, 1H, N—CH); 4.31-4.36 (m, 1H, N—CH); 4.59-4.65 (m, 2H, CH, OH); 5.37 (q, J 9.2 Hz, 2H, CH$_2$—CF$_3$); 7.18 (d, J 8.9 Hz, 2H, Ar); 7.74 (dd, J 8.9, 4.8 Hz, 2H, Ar); 7.97 (bs, 1H, Ar); 9.24 (d, J 1.0 Hz, 1H, Ar); 9.54 (bs, 1H, NH). M/Z (M+H)$^+$: 464

Compound 27: [3-(4-fluoroanilino)-1-(methylsulfonylmethyl)pyrazolo[4,3-c]pyridin-6-yl]-(1,4-oxazepan-4-yl)methanone Compound 27 was obtained according to General Procedure VI, Alternative 3, starting from [3-bromo-1-(methylsulfonylmethyl)pyrazolo[4,3-c]pyridin-6-yl]-(1,4-oxazepan-4-yl)methanone F10 and 4-fluoroaniline I9. Purification by flash chromatography (DCM/MeOH: 10/0 to 9/1) afforded the compound 27 as a beige powder in 69% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 3.09 (s, 3H, S—CH$_3$); 3.41-3.48 (m, 2H, N—CH$_2$); 3.60-3.64 (m, 1H, N—CH$_2$); 3.67-3.79 (m, 5H, CH$_2$); 6.02 (s, 2H, CH$_2$—SO$_2$CH$_3$); 7.18 (t, J 8.9 Hz, 2H, Ar); 7.75 (ddd, J 8.9, 4.9, 1.0 Hz, 2H, Ar); 7.92 (d, J 0.1 Hz, 1H, signal of a rotamer, Ar); 7.93 (d, J 0.1 Hz, 1H, signal of a rotamer, Ar); 9.25 (d, J 0.1 Hz, 1H, signal of a rotamer, Ar); 9.27 (d, J 0.1 Hz, 1H, signal of a rotamer, Ar); 9.97 (s, 1H, NH). M/Z (M+H)$^+$: 448

Compound 28: [3-(3-fluoroanilino)-1-(methylsulfonylmethyl)pyrazolo[4,3-c]pyridin-6-yl]-(1,4-oxazepan-4-yl)methanone Compound 28 was obtained according to General Procedure VI, Alternative 3, starting from [3-bromo-1-(methylsulfonylmethyl)pyrazolo[4,3-c]pyridin-6-yl]-(1,4-oxazepan-4-yl)methanone F10 and 3-fluoroaniline I6. Purification by flash chromatography (DCM/MeOH: 10/0 to 9/1) afforded the compound 28 as a beige powder in 32% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 3.11 (s, 3H, S—CH$_3$); 3.40-3.46 (m, 2H, N—CH$_2$); 3.60-3.64 (m, 1H, N—CH$_2$); 3.67-3.79 (m, 4H, CH$_2$); 6.03 (s, 2H, CH$_2$—SO$_2$CH$_3$); 6.71-6.77 (m, 1H, Ar); 7.34-7.43 (m, 2H, Ar); 7.71-7.77 (m, 1H, Ar); 7.94 (d, J 0.1 Hz, 1H, signal of a rotamer, Ar); 7.95 (d, J 0.1 Hz, 1H, signal of a rotamer, Ar); 9.28 (d, J 0.1 Hz, 1H, signal of a rotamer, Ar); 9.29 (d, J 0.1 Hz, 1H, signal of a rotamer, Ar); 9.87 (s, 1H, NH). M/Z (M+H)$^+$: 448

Compound 29: [3-anilino-1-(methylsulfonylmethyl)pyrazolo[4,3-c]pyridin-6-yl]-(3-endo-hydroxy-8-azabicyclo[3.2.1]octan-8-yl)methanone Compound 29 was obtained according to General Procedure VI, Alternative 3, starting from [3-bromo-1-(methylsulfonylmethyl)pyrazolo[4,3-c]pyridin-6-yl]-(3-endo-hydroxy-8-azabicyclo[3.2.1]octan-8-yl)methanone F11 and aniline I2. In that specific case, 10 mol % of BrettPhos Pd G1 precatalyst was used. Purification by flash chromatography (DCM/MeOH: 10/0 to 9/1) then by preparative HPLC afforded the compound 29 as a yellow powder in 12% yield. $^1$H-NMR (DMSO-d$_6$, 400 MHz): 1.63-1.69 (m, 1H, CH$_2$); 1.78-1.91 (m, 3H, CH$_2$); 2.00-2.08 (m, 2H, CH$_2$); 2.17-2.29 (m, 2H, CH$_2$); 3.11 (s, 3H, SO$_2$CH$_3$); 3.96-4.00 (m, 1H, N—CH); 4.32-4.36 (m, 1H, N—CH); 4.62-4.65 (m, 2H, CH, OH); 6.00 (s, 2H, CH$_2$SO$_2$); 6.94 (t, J 7.6 Hz, 1H, Ar);

7.34 (t, J 7.6 Hz, 2H, Ar); 7.75 (d, J 7.6 Hz, 2H, Ar); 8.00 (d, J 0.9 Hz, 1H, Ar); 9.28 (d, J 0.9 Hz, 1H, Ar); 9.57 (s, 1H, NH). M/Z (M+H)$^+$: 456

Compound 30: [3-(4-fluoroanilino)-1-(methylsulfonylmethyl)pyrazolo[4,3-c]pyridin-6-yl]-(3-endo-hydroxy-8-azabicyclo[3.2.1]octan-8-yl)methanone Compound 30 was obtained according to General Procedure VI, Alternative 3, starting from [3-bromo-1-(methylsulfonylmethyl)pyrazolo[4,3-c]pyridin-6-yl]-(3-endo-hydroxy-8-azabicyclo[3.2.1]octan-8-yl)methanone F11 and 4-fluoroaniline I9. In that specific case, 10 mol % of Brett-Phos Pd G1 precatalyst was used. Purification by flash chromatography (DCM/MeOH: 10/0 to 9/1) afforded the compound 30 as a yellow powder in 56% yield. $^1$H-NMR (DMSO-d$_6$, 400 MHz): 1.63-1.69 (m, 1H, CH$_2$); 1.78-1.91 (m, 3H, CH$_2$); 2.00-2.08 (m, 2H, CH$_2$); 2.17-2.29 (m, 2H, CH$_2$); 3.09 (s, 3H, SO$_2$CH$_3$); 3.96-4.01 (m, 1H, N—CH); 4.31-4.36 (m, 1H, N—CH); 4.61-4.66 (m, 2H, CH, OH); 5.97 (s, 2H, CH$_2$SO$_2$); 7.18 (t, J 9.0 Hz, 2H, Ar); 7.75 (dd, J 9.0, 4.8 Hz, 2H, Ar); 8.00 (d, J 0.9 Hz, 1H, Ar); 9.25 (d, J 0.9 Hz, 1H, Ar); 9.61 (s, 1H, NH). M/Z (M+H)$^+$: 474

Compound 31: [3-(3-fluoroanilino)-1-(methylsulfonylmethyl)pyrazolo[4,3-c]pyridin-6-yl]-(3-endo-hydroxy-8-azabicyclo[3.2.1]octan-8-yl)methanone Compound 31 was obtained according to General Procedure VI, Alternative 3, starting from [3-bromo-1-(methylsulfonylmethyl)pyrazolo[4,3-c]pyridin-6-yl]-(3-endo-hydroxy-8-azabicyclo[3.2.1]octan-8-yl)methanone F11 and 3-fluoroaniline I6. In that specific case, 10 mol % of Brett-Phos Pd G1 precatalyst was used. Purification by flash chromatography (DCM/MeOH: 10/0 to 9/1), then by preparative HPLC afforded the compound 31 as a white powder in 86% yield. $^1$H-NMR (DMSO-d$_6$, 400 MHz): 1.63-1.69 (m, 1H, CH$_2$); 1.78-1.91 (m, 3H, CH$_2$); 2.00-2.08 (m, 2H, CH$_2$); 2.17-2.29 (m, 2H, CH$_2$); 3.11 (s, 3H, SO$_2$CH$_3$); 3.96-4.01 (m, 1H, N—CH); 4.31-4.36 (m, 1H, N—CH); 4.61-4.66 (m, 2H, CH, OH); 6.03 (m, 2H, CH$_2$SO$_2$); 6.71-6.77 (m, 1H, Ar); 7.33-7.42 (m, 2H, Ar); 7.75 (dt, J 12.1, 2.1 Hz, 1H, Ar); 8.03 (d, J 0.9 Hz, 1H, Ar); 9.27 (d, J 0.9 Hz, 1H, Ar); 9.85 (s, 1H, NH). M/Z (M+H)$^+$: 474

Compound 32: [3-(3-fluoroanilino)-1-(2,2,2-trifluoroethyl)pyrazolo[4,3-c]pyridin-6-yl]-(6-hydroxy-1,4-oxazepan-4-yl)methanone Compound 32 was obtained according to General Procedure VI, Alternative 3, starting from [3-bromo-1-(2,2,2-trifluoroethyl)pyrazolo[4,3-c]pyridin-6-yl]-(6-hydroxy-1,4-oxazepan-4-yl)methanone F7 and 3-fluoroaniline I6. Purification by flash chromatography (DCM/MeOH: 10/0 to 9/1) afforded the compound 32 in 52% yield. $^1$H-NMR (DMSO-d$_6$, 400 MHz): 3.19-3.42 (m, 1H, CH$_2$); 3.47-3.80 (m, 6H, CH, CH$_2$); 3.80-3.98 (m, 1H, signal of a rotamer, CH$_2$); 3.94-4.02 (m, 1H, CH$_2$); 4.19-4.26 (m, 1H, signal of a rotamer, CH); 5.06 (d, J 4.9 Hz, 1H, OH, major rotamer); 5.12 (d, J 4.9 Hz, 1H, OH, minor rotamer); 5.36-5.46 (m, 2H, CH$_2$—CF$_3$); 6.69-6.76 (m, 1H, Ar); 7.31-7.41 (m, 2H, Ar); 7.71-7.78 (m, 1H, Ar); 7.94 (bs, 1H, signal of a rotamer, Ar); 7.96 (bs, 1H, signal of a rotamer, Ar); 9.26 (d, J 0.9 Hz, 1H, signal of a rotamer, Ar); 9.27 (d, J 0.9 Hz, 1H, signal of a rotamer, Ar); 9.80 (s, 1H, signal of a rotamer, NH); 9.82 (s, 1H, signal of a rotamer, NH). M/Z (M+H)$^+$: 454

Compound 33: [3-(4-fluoroanilino)-1-(2,2,2-trifluoroethyl)pyrazolo[4,3-c]pyridin-6-yl]-(6-hydroxy-1,4-oxazepan-4-yl)methanone Compound 33 was obtained according to General Procedure VI, Alternative 3, starting from [3-bromo-1-(2,2,2-trifluoroethyl)pyrazolo[4,3-c]pyridin-6-yl]-(6-hydroxy-1,4-oxazepan-4-yl)methanone F7 and 4-fluoroaniline I9. Purification by flash chromatography (DCM/MeOH: 10/0 to 9/1) afforded the compound 33 in 53% yield. $^1$H-NMR (DMSO-d$_6$, 400 MHz): 3.18-3.41 (m, 1H, CH$_2$); 3.47-3.79 (m, 6H, CH, CH$_2$); 3.80-3.88 (m, 1H, signal of a rotamer, CH$_2$); 3.93-4.02 (m, 1H, CH$_2$); 4.17-4.25 (m, 1H, signal of a rotamer, CH); 5.08 (d, J 4.8 Hz, 1H, OH, major rotamer); 5.12 (d, J 4.8 Hz, 1H, OH, minor rotamer); 5.30-5.40 (m, 2H, CH$_2$—CF$_3$); 7.14-7.22 (m, 2H, Ar); 7.70-7.77 (m, 2H, Ar); 7.91 (bs, 1H, signal of a rotamer, Ar); 7.93 (bs, 1H, signal of a rotamer, Ar); 9.24 (d, J 0.9 Hz, 1H, signal of a rotamer, Ar); 9.25 (d, J 0.9 Hz, 1H, signal of a rotamer, Ar); 9.55 (s, 1H, signal of a rotamer, NH); 9.57 (s, 1H, signal of a rotamer, NH). M/Z (M+H)$^+$: 454

Compound 34: [3-(4-fluoroanilino)-1-(2,2,2-trifluoroethyl)pyrazolo[4,3-c]pyridin-6-yl]-(4-hydroxy-4-methyl-1-piperidyl)methanone Compound 34 was obtained according to General Procedure VI, Alternative 3, starting from [3-bromo-1-(2,2,2-trifluoroethyl)pyrazolo[4,3-c]pyridin-6-yl]-(4-hydroxy-4-methyl-1-piperidyl)methanone F8 and 4-fluoroaniline I9. Purification by flash chromatography (DCM/MeOH: 10/0 to 9/1) afforded the compound 34 as a white powder in 68% yield. $^1$H-NMR (DMSO-d$_6$, 400 MHz): 1.16 (s, 3H, CH$_3$); 1.37-1.63 (m, 4H, CH$_2$); 3.22-3.32 (m, 3H, N—CH$_2$); 4.08-4.14 (m, 1H, N—CH$_2$); 4.43 (s, 1H, OH); 5.34 (q, J 9.0 Hz, 2H, CH$_2$—CF$_3$); 7.18 (t, J 9.1 Hz, 2H, Ar); 7.74 (dd, J 9.1, 4.8 Hz, 2H, Ar); 7.84 (bs, 1H, Ar); 9.23 (d, J 0.9 Hz, 1H, Ar); 9.55 (s, 1H, NH). M/Z (M+H)$^+$: 452

Compound 35: [3-(3-fluoroanilino)-1-(2,2,2-trifluoroethyl)pyrazolo[4,3-c]pyridin-6-yl]-4-hydroxy-4-methyl-1-piperidyl)methanone Compound 35 was obtained according to General Procedure VI, Alternative 3, starting from [3-bromo-1-(2,2,2-trifluoroethyl)pyrazolo[4,3-c]pyridin-6-yl]-(4-hydroxy-4-methyl-1-piperidyl)methanone F8 and 3-fluoroaniline I6. Purification by flash chromatography (DCM/MeOH: 10/0 to 9/1) afforded the compound 35 as a white powder in 66% yield. $^1$H-NMR (DMSO-d$_6$, 400 MHz): 1.17 (s, 3H, CH$_3$); 1.39-1.62 (m, 4H, CH$_2$); 3.22-3.32 (m, 3H, N—CH$_2$); 4.07-4.15 (m, 1H, N—CH$_2$); 4.44 (s, 1H, OH); 5.38 (q, J 9.0 Hz, 2H, CH$_2$—CF$_3$); 6.69-6.76 (m, 1H, Ar); 7.328-7.42 (m, 2H, Ar); 7.74 (td, J 12.5, 2.0 Hz, 1H, Ar); 7.87 (bs, 1H, Ar); 9.25 (d, J 1.0 Hz, 1H, Ar); 9.79 (s, 1H, NH). M/Z (M+H)$^+$: 452

Compound 36: 1,4-oxazepan-4-yl-[3-(pyrimidin-2-ylamino)-1-(2,2,2-trifluoroethyl)-pyrazolo[4,3-c]pyridin-6-yl]methanone Compound 36 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 2-aminopyrimidine I20 (2.4 equiv.). In that specific case, the reaction mixture was stirred overnight at 100° C. Purification by flash chromatography (DCM/MeOH: 100/0 to 95/5) afforded the compound 36 as a yellow powder in 31% yield. $^1$H-NMR (DMSO-d$_6$, 400 MHz): 1.75 (quint, J 6.2 Hz, 1H, CH$_2$); 1.92 (quint, J 6.2 Hz, 1H, CH$_2$); 3.46-3.50 (m, 2H, N—CH$_2$); 3.62-3.65 (m, 1H, N—CH$_2$); 3.68-3.78 (m, 5H, CH$_2$); 5.42 (q, J 9.0 Hz, 2H, CH$_2$—CF$_3$); 6.94 (t, J 4.8 Hz, 1H, Ar); 8.00 (bs, 1H, signal of a rotamer, Ar); 8.01 (bs, 1H, signal of a rotamer, Ar); 8.50 (d, J 4.8 Hz, 1H, Ar); 9.11 (d, J 0.8 Hz, 1H, signal of a rotamer, Ar); 9.12 (d, J 0.8 Hz, 1H, signal of a rotamer, Ar); 10.36 (bs, 1H, NH). M/Z (M+H)$^+$: 422

Compound 37: [3-(3-chloroanilino)-1-(2,2,2-trifluoroethyl)pyrazolo[4,3-c]pyridin-6-yl]-(1,4-oxazepan-4-yl)methanone Compound 37 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 3-chloroaniline I21. Purification by flash chromatography (DCM/MeOH: 100/0 to 95/5), then by preparative LCMS afforded the compound 37 as a yellow powder in 14% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 3.42-3.48 (m, 2H, N—CH$_2$); 3.60-3.64 (m, 1H, N—CH$_2$); 3.68-3.81 (m, 5H, CH$_2$); 5.41 (q, J 9.0 Hz, 2H, CH$_2$—CF$_3$); 6.97 (ddd, J 8.0, 1.9, 0.6 Hz, 1H, Ar); 7.36 (t, J 8.0 Hz, 1H, Ar); 7.57-7.61 (m, 1H, Ar); 7.91-7.94 (m, 1H, Ar); 7.97 (bs, 1H, signal of a rotamer, Ar); 7.98 (bs, 1H, signal of a rotamer, Ar); 9.32 (bs, 1H, signal of a rotamer, Ar); 9.33 (bs, 1H, signal of a rotamer, Ar); 9.88 (s, 1H, NH). M/Z (M+H)$^+$: 454/456

Compound 38: [3-(4-chloroanilino)-1-(2,2,2-trifluoroethyl)pyrazolo[4,3-c]pyridin-6-yl]-(1,4-oxazepan-4-yl)methanone Compound 38 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 4-chloroaniline I22. Purification by flash chromatography (DCM/MeOH: 10/0 to 95/5), then by preparative HPLC, afforded the compound 38 as a yellow powder in 50% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 3.42-3.48 (m, 2H, N—CH$_2$); 3.60-3.64 (m, 1H, N—CH$_2$); 3.67-3.79 (m, 5H, CH$_2$); 5.36 (q, J 9.0 Hz, 2H, CH$_2$—CF$_3$); 7.38 (d, J 8.8 Hz, 2H, Ar); 7.75 (dd, J 8.8, 1.0 Hz, 2H, Ar); 7.91 (bs, 1H, signal of a rotamer, Ar); 7.92 (bs, 1H, signal of a rotamer, Ar); 9.25 (d, J 1.0 Hz, 1H, signal of a rotamer, Ar); 9.26 (d, J 1.0 Hz, 1H, signal of a rotamer, Ar); 9.69 (s, 1H, NH). M/Z (M+H)$^+$: 454/456

Compound 39: [3-(2-chloroanilino)-1-(2,2,2-trifluoroethyl)pyrazolo[4,3-c]pyridin-6-yl]-(1,4-oxazepan-4-yl)methanone Compound 39 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 2-chloroaniline I23. Purification by flash chromatography (DCM/MeOH: 10/0 to 95/5), then by preparative HPLC, afforded the compound 39 as a yellow powder in 21% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 3.42-3.48 (m, 2H, N—CH$_2$); 3.60-3.64 (m, 1H, N—CH$_2$); 3.67-3.79 (m, 5H, CH$_2$); 5.36 (q, J 9.0 Hz, 2H, CH$_2$—CF$_3$); 7.03 (td, J 7.9, 1.5 Hz, 1H, Ar); 7.32 (td, J 7.9, 1.5 Hz, 1H, Ar); 7.49 (dd, J 7.9, 1.5 Hz, 1H, Ar); 7.92 (bs, 1H, signal of a rotamer, Ar); 7.93 (bs, 1H, signal of a rotamer, Ar); 8.05 (dt, J 7.9, 1.5 Hz, 1H, Ar); 8.72 (s, 1H, NH); 9.22 (d, J 1.0 Hz, 1H, signal of a rotamer, Ar); 9.23 (d, J 1.0 Hz, 1H, signal of a rotamer, Ar). M/Z (M+H)$^+$: 454/456

Compound 40: (6,6-dideuterio-1,4-oxazepan-4-yl)-[3-(3-fluoroanilino)-1-(2,2,2-trifluoroethyl)pyrazolo[4,3-c]pyridin-6-yl]methanone Compound 40 was obtained according to General Procedure VI, Alternative 3, starting from [3-bromo-1-(2,2,2-trifluoroethyl)pyrazolo[4,3-c]pyridin-6-yl]-(6,6-dideuterio-1,4-oxazepan-4-yl)methanone F9 and 3-fluoroaniline I6. Purification by flash chromatography (DCM/MeOH: 10/0 to 9/1) afforded the compound 40 as a beige powder in 73% yield. $^1$H-NMR (DMSO-d$_6$, 400 MHz): 3.41-3.48 (m, 2H, N—CH$_2$); 3.60-3.64 (m, 1H, N—CH$_2$); 3.69 (s, 1H, N—CH$_2$); 3.71-3.80 (m, 4H, CH$_2$); 5.40 (q, J 9.0 Hz, 2H, CH$_2$—CF$_3$); 6.69-6.76 (m, 1H, Ar); 7.32-7.42 (m, 2H, Ar); 7.74 (d, J 12.3 Hz, 1H, Ar); 7.92 (bs, 1H, signal of a rotamer, Ar); 7.93 (bs, 1H, signal of a rotamer, Ar); 9.26 (d, J 1.0 Hz, 1H, signal of a rotamer, Ar); 9.27 (d, J 1.0 Hz, 1H, signal of a rotamer, Ar); 9.80 (s, 1H, NH). M/Z (M+H)$^+$: 440

Compound 41: (6,6-dideuterio-1,4-oxazepan-4-yl)-[3-(4-fluoroanilino)-1-(2,2,2-trifluoroethyl)pyrazolo[4,3-c]pyridin-6-yl]methanone Compound 41 was obtained according to General Procedure VI, Alternative 3, starting from [3-bromo-1-(2,2,2-trifluoroethyl)pyrazolo[4,3-c]pyridin-6-yl]-(6,6-dideuterio-1,4-oxazepan-4-yl)methanone F9 and 4-fluoroaniline I9. Purification by flash chromatography (DCM/MeOH: 10/0 to 9/1) afforded the compound 41 as a beige powder in 88% yield. $^1$H-NMR (DMSO-d$_6$, 400 MHz): 3.41-3.48 (m, 2H, N—CH$_2$); 3.60-3.64 (m, 1H, N—CH$_2$); 3.69 (s, 1H, N—CH$_2$); 3.71-3.80 (m, 4H, CH$_2$); 5.35 (q, J 9.0 Hz, 2H, CH$_2$—CF$_3$); 7.18 (t, J 8.9 Hz, 2H, Ar); 7.74 (ddd, J 8.9, 4.7, 0.9 Hz, 2H, Ar); 7.89 (bs, 1H, signal of a rotamer, Ar); 7.90 (bs, 1H, signal of a rotamer, Ar); 9.24 (d, J 1.0 Hz, 1H, signal of a rotamer, Ar); 9.25 (d, J 1.0 Hz, 1H, signal of a rotamer, Ar); 9.55 (s, 1H, NH). M/Z (M+H)$^+$: 440

Compound 73: [1,4]Oxazepan-4-yl-[3-(pyrimidin-4-ylamino)-1-(2,2,2-trifluoro-ethyl)-1H-pyrazolo[4,3-c]pyridin-6-yl]-methanone Compound 73 was obtained according to General Procedure VI, Alternative 3, starting from [3-bromo-1-(2,2,2-trifluoroethyl)pyrazolo[4,3-c]pyridin-6-yl]-(1,4-oxazepan-4-yl)methanone F1 and 4-aminopyrimidine I24. In this specific case, DBU and AlPhos Pd G3 precatalyst were used instead of cesium carbonate and BrettPhos Pd G1 precatalyst respectively. Purification by flash chromatography (DCM/MeOH: 100/0 to 92/8) afforded the compound 73 as a white powder in 21% yield. 1H-NMR (DMSO-d6, 400 MHz) 5: 1.72-1.77 (m, 1H, CH2); 1.89-1.95 (m, 1H, CH2); 3.44-3.49 (m, 2H, N—CH2); 3.61-3.64 (m, 1H, N—CH2); 3.68-3.79 (m, 5H, CH2); 5.47 (q, J 9.0 Hz, 2H, CH2-CF3); 7.82 (dd, J 6.0, 0.8 Hz, 1H, Ar); 8.00 (d, J 0.8 Hz, 1H, Ar, signal of a rotamer); 8.01 (d, J 0.8 Hz, 1H, Ar, signal of a rotamer); 8.55 (d, J 6.0 Hz, 1H, Ar); 8.77 (bs, 1H, Ar); 9.39 (d, J 0.8 Hz, 1H, Ar, signal of a rotamer); 9.40 (d, J 0.8 Hz, 1H, Ar, signal of a rotamer); 10.93 (s, 1H, NH); OH signal not observed. M/Z (M+H)+: 422

Compound 74: (4-Hydroxy-piperidin-1-yl)-[3-(pyrazin-2-ylamino)-1-(2,2,2-trifluoro-ethyl)-1H-pyrazolo[4,3-c]pyridin-6-yl]-methanone Compound 74 was obtained according to General Procedure VI, Alternative 3, starting from [3-bromo-1-(2,2,2-trifluoroethyl)pyrazolo[4,3-c]pyridin-6-yl]-(4-hydroxy-1-piperidyl)methanone F3 and 2-aminopyrazine I25. In this specific case, XantPhos Pd G3 precatalyst was used instead of BrettPhos Pd G1 precatalyst. Purification by flash chromatography (DCM/MeOH: 10/0 to 9/1) afforded the compound 74 as a white powder in 10% yield. 1H-NMR (DMSO-d6, 400 MHz): 1.29-1.46 (m, 2H, CH2); 1.65-1.74 (m, 1H, CH2); 1.78-1.88 (m, 1H, CH2); 3.13 (ddd, J 13.6, 9.4, 3.6 Hz, 1H, N—CH2); 3.27 (ddd, J 13.6, 9.4, 3.6 Hz, 1H, N—CH2); 3.46-3.55 (m, 1H, N—CH2); 3.77 (sext, J 4.0 Hz, 1H, CH); 4.04-4.12 (m, 1H, N—CH2); 5.45 (q, J 9.0 Hz, 2H, N-CH2-CF3); 7.98 (bs, 1H, Ar); 8.20 (d, J 2.6 Hz, 1H, Ar); 8.32 (dd, J 2.6, 1.6 Hz, 1H); 9.23 (d, J 1.6 Hz, 1H, Ar); 9.41 (bs, 1H, Ar); 10.72 (s, 1H, NH). M/Z (M+H)+: 422

Compound 75: [3-(5-Chloro-pyrazin-2-ylamino)-1-(2,2,2-trifluoro-ethyl)-1H-pyrazolo[4,3-c]pyridin-6-yl]-(4-hydroxy-piperidin-1-yl)-methanone Compound 75 was obtained according to General Procedure VI, Alternative 3, starting from [3-bromo-1-(2,2,2-trifluoroethyl)pyrazolo[4,3-c]pyridin-6-yl]-(4-hydroxy-1-piperidyl)methanone F3 and 2-amino-5-chloro-pyrazine I26. In this specific case, DBU and AlPhos Pd G3 precatalyst were used instead of cesium carbonate and BrettPhos Pd G1 precatalyst respectively. Purification by flash chromatography (DCM/MeOH: 10/0 to 9/1) afforded the compound 75 as a white powder in 18% yield. 1H-NMR (DMSO-d6, 400 MHz) δ: 1.31-1.46 (m, 2H, CH2); 1.67-1.71 (m, 1H, CH2); 1.81-1.86 (m, 1H, CH2); 3.07-3.14 (m, 1H, N—CH2); 3.22-3.26 (m, 1H, N—CH2); 3.46-3.52 (m, 1H, N—CH2); 3.73-3.79 (m, 1H, CH); 4.05-4.11 (m, 1H, N—CH2); 4.79 (bs, 1H, OH); 5.45 (q, J 9.0 Hz, 2H, CH2-CF3); 7.95 (d, J 0.8 Hz, 1H Ar); 8.46 (d, J 1.2 Hz, 1H, Ar); 9.04 (d, J 1.2 Hz, 1H Ar); 9.36 (d, J 0.8 Hz, 1H, Ar); 10.92 (s, 1H, NH). M/Z (M+H)+: 456

Compound 76: (4-Hydroxy-piperidin-1-yl)-[3-(pyrimidin-4-ylamino)-1-(2,2,2-trifluoro-ethyl)-1H-pyrazolo[4,3-c]pyridin-6-yl]-methanone Compound 76 was obtained according to General Procedure VI, Alternative 3, starting from [3-bromo-1-(2,2,2-trifluoroethyl)pyrazolo[4,3-c]pyridin-6-yl]-(4-hydroxy-1-piperidyl)methanone F3 and 4-aminopyrimidine I27. In this specific case, DBU and AlPhos Pd G3 precatalyst were used instead of cesium carbonate and BrettPhos Pd G1 precatalyst respectively. Purification by flash chromatography (DCM/MeOH: 10/0 to 9/1), then by preparative HPLC afforded the compound 76 as a white powder in 16% yield. 1H-NMR (DMSO-d6, 400 MHz) δ: 1.31-1.46 (m, 2H, CH2); 1.67-1.71 (m, 1H, CH2); 1.81-1.86 (m, 1H, CH2); 3.12 (ddd, J 12.8, 9.6, 3.2 Hz, 1H, N—CH2); 3.27 (ddd, J 12.8, 9.6, 3.2 Hz, 1H, N—CH2); 3.47-3.52 (m, 1H, N—CH2); 3.76 (sept, J 4.0 Hz, 1H, CH); 4.05-4.11 (m, 1H, N—CH2); 5.49 (q, J 9.0 Hz, 2H, CH2-CF3); 7.80 (d, J 6.0 Hz, 1H, Ar); 8.00 (d, J 0.8 Hz, 1H Ar); 8.59 (d, J 6.0 Hz, 1H, Ar); 8.86 (s, 1H, Ar); 9.39 (d, J 0.8 Hz, 1H Ar); 11.32 (s, 1H, NH); OH signal not observed. M/Z (M+H)+: 422

Compound 77: [3-(5-Fluoro-pyridin-2-ylamino)-1-methanesulfonylmethyl-1H-pyrazolo[4,3-c]pyridin-6-yl]-[1,4]oxazepan-4-yl-methanone Compound 77 was obtained according to General Procedure VI, Alternative 3, starting from [3-bromo-1-(methylsulfonylmethyl)pyrazolo[4,3-c]pyridin-6-yl]-(1,4-oxazepan-4-yl)methanone F10 and 2-amino-5-fluoropyridine I28. Purification by flash chromatography (DCM/MeOH: 100/0 to 95/5) afforded the compound 77 as a beige powder in 5% yield. 1H-NMR (DMSO-d6, 400 MHz): 1.74 (quint, J 5.8 Hz, 1H, CH2); 1.92 (quint, J 5.8 Hz, 1H, CH2); 3.09 (s, 3H, CH3-SO2); 3.43-3.48 (m, 2H, N—CH2); 3.59-3.63 (m, 1H, N—CH2); 3.68-3.79 (m, 5H, CH2); 6.01 (s, 2H, CH2-SO2); 7.75 (dt, J 8.7, 3.0 Hz, 1H, Ar); 7.95 (d, J 1.0 Hz, 1H, Ar, signal of a rotamer); 7.97 (d, J 1.0 Hz, 1H, Ar, signal of a rotamer); 8.03 (dd, J 9.2, 3.7 Hz, 1H, Ar); 8.29 (d, J 3.0 Hz, 1H, Ar); 9.38 (d, J 1.0 Hz, 1H, Ar, signal of a rotamer); 9.40 (d, J 1.0 Hz, 1H, Ar, signal of a rotamer); 10.49 (s, 1H, NH). M/Z (M+H)+: 449

Compound 78: [3-(5-Chloro-pyridin-2-ylamino)-1-methanesulfonylmethyl-1H-pyrazolo[4,3-c]pyridin-6-yl]-[1,4]oxazepan-4-yl-methanone Compound 78 was obtained according to General Procedure VI, Alternative 3, starting from [3-bromo-1-(methylsulfonylmethyl)pyrazolo[4,3-c]pyridin-6-yl]-(1,4-oxazepan-4-yl)methanone F10 and 2-amino-5-chloropyridine I29. Purification by flash chromatography (DCM/MeOH: 100/0 to 95/5) afforded the compound 78 as a beige powder in 4% yield. 1H-NMR (DMSO-d6, 400 MHz): 1.74 (quint, J 5.8 Hz, 1H, CH2); 1.92 (quint, J 5.8 Hz, 1H, CH2); 3.09 (s, 3H, CH3-SO2); 3.43-3.48 (m, 2H, N—CH2); 3.60-3.63 (m, 1H, N—CH2); 3.67-3.79 (m, 5H, CH2); 6.02 (s, 2H, CH2-SO2); 7.75 (dd, J 9.0, 2.5 Hz, 1H, Ar); 7.96 (d, J 1.0 Hz, 1H, Ar, signal of a rotamer); 7.97 (d, J 1.0 Hz, 1H, Ar, signal of a rotamer); 7.99 (d, J 9.0 Hz, 1H, Ar); 8.29 (d, J 2.5 Hz, 1H, Ar); 9.38 (d, J 1.0 Hz, 1H, Ar, signal of a rotamer); 9.39 (d, J 1.0 Hz, 1H, Ar, signal of a rotamer); 10.62 (bs, 1H, NH). M/Z (M+H)+: 465

Compound 79: [3-(4-Chloro-pyridin-2-ylamino)-1-methanesulfonylmethyl-1H-pyrazolo[4,3-c]pyridin-6-yl]-[1,4]oxazepan-4-yl-methanone Compound 79 was obtained according to General Procedure VI, Alternative 3, starting from [3-bromo-1-(methylsulfonylmethyl)pyrazolo[4,3-c]pyridin-6-yl]-(1,4-oxazepan-4-yl)methanone F10 and 2-amino-4-chloropyridine I30. Purification by flash chromatography (DCM/MeOH: 100/0 to 95/5) afforded the compound 79 as a beige powder in 4% yield. 1H-NMR (DMSO-d6, 400 MHz): 1.74 (quint, J 5.8 Hz, 1H, CH2); 1.92 (quint, J 5.8 Hz, 1H, CH2); 3.12 (s, 3H, CH3-SO2); 3.43-3.48 (m, 2H, N—CH2); 3.60-3.64 (m, 1H, N—CH2); 3.67-3.79 (m, 5H, CH2); 6.07 (s, 2H, CH2-SO2); 7.08 (dd, J 5.3, 1.8 Hz, 1H, Ar); 7.98 (d, J 1.0 Hz, 1H, Ar, signal of a rotamer); 7.99 (d, J 0.9 Hz, 1H, Ar, signal of a rotamer); 8.08 (bs, 1H, Ar); 8.28 (d, J 5.3 Hz, 1H, Ar); 9.41 (d, J 0.9 Hz, 1H, Ar, signal of a rotamer); 9.42 (d, J 0.9 Hz, 1H, Ar, signal of a rotamer); 10.74 (bs, 1H, NH). M/Z (M+H)+: 465

General Procedure VII: Synthesis of Compounds from Compounds G and H (Scheme 1)

Alternative 1:
To a degassed suspension of compound G (1 equiv.) in dioxane (0.1M) were added halogenated (hetero)aromatic H, cesium carbonate (2.4 equiv.) and BrettPhos Pd G1 precatalyst (10 mol %). The reaction mixture was stirred 24 h at 90° C. The reaction mixture was diluted with DCM, washed with water, the aqueous layer was extracted with DCM. The combined organic layers were dried over sodium sulfate, concentrated. The resulting residue was purified by flash chromatography to afford the compound.

Alternative 2:
To a degassed suspension of compound G (1 equiv.) in dioxane (0.1M) were added halogenated (hetero)aromatic H, cesium carbonate (2.4 equiv.), $Pd_2(dba)_3$ (10 mol %) and BINAP (20 mol %). The reaction mixture was stirred 3 h at 90° C. The reaction mixture was diluted with DCM, washed with water, the aqueous layer was extracted with DCM. The combined organic layers were dried over sodium sulfate, concentrated. The resulting residue was purified by flash chromatography to afford the compound.

Alternative 3:
To a degassed suspension of compound G (1 equiv.) in dioxane (0.1M) were added halogenated (hetero)aromatic H, cesium carbonate (2.4 equiv.) and XantPhos Pd G3 precatalyst (10 mol %). The reaction mixture was stirred 2 h at 90° C. The reaction mixture was diluted with DCM, washed with water, the aqueous layer was extracted with DCM. The combined organic layers were dried over sodium sulfate, concentrated. The resulting residue was purified by flash chromatography to afford the compound.

Compound 42: 1,4-oxazepan-4-yl-[3-(2-pyridylamino)-1-(2,2,2-trifluoroethyl)pyrazolo[4,3-c] pyridin-6-yl]methanone Compound 42 was obtained according to General Procedure VII, Alternative 1, starting from [3-amino-1-(2,2,2-trifluoroethyl)pyrazolo[4,3-c]pyridin-6-yl]-(1,4-oxazepan-4-yl)methanone G1 and 2-bromopyridine H1 (1.7 equiv.). In that specific case, 5 mol % of BrettPhos Pd G1 precatalyst were used. Purification by flash chromatography (DCM/MeOH: 100/0 to 93/7) afforded the compound 42 as a yellow powder in 37% yield. $^1$H-NMR (DMSO-$d_6$, 400 MHz): 1.74 (quint, J 6.1 Hz, 1H, $CH_2$); 1.92 (quint, J 6.1 Hz, 1H, $CH_2$); 3.44-3.49 (m, 2H, N—$CH_2$); 3.60-3.64 (m, 1H, N—$CH_2$); 3.68-3.78 (m, 5H, $CH_2$); 5.40 (q, J 9.2 Hz, 2H, $CH_2$—$CF_3$); 6.94 (dd, J 6.8, 5.2 Hz, 1H, Ar); 7.75-7.79 (m, 1H, Ar); 7.92-7.96 (m, 2H, Ar); 8.27 (d, J 1.0 Hz, 1H, signal of a rotamer, Ar); 8.29 (d, J 1.0 Hz, 1H, signal of a rotamer, Ar); 9.39 (d, J 1.0 Hz, 1H, signal of a rotamer, Ar); 9.40 (d, J 1.0 Hz, 1H, signal of a rotamer, Ar); 10.30 (bs, 1H, NH). M/Z (M+H)$^+$: 421

Compound 43: 1,4-oxazepan-4-yl-[3-(4-pyridylamino)-1-(2,2,2-trifluoroethyl)-pyrazolo[4,3-c]pyridin-6-yl]methanone Compound 43 was obtained according to General Procedure VII, Alternative 1, starting from [3-amino-1-(2,2,2-trifluoroethyl)pyrazolo[4,3-c]pyridin-6-yl]-(1,4-oxazepan-4-yl)methanone G1 and 4-bromopyridine H2 (1.2 equiv.). Purification by flash chromatography (DCM/MeOH: 100/0 to 93/7) afforded the compound 43 as a yellow powder in 30% yield. $^1$H-NMR (DMSO-$d_6$, 400 MHz): 1.74 (quint, J 6.1 Hz, 1H, $CH_2$); 1.92 (quint, J 6.1 Hz, 1H, $CH_2$); 3.42-3.48 (m, 2H, N—$CH_2$); 3.60-3.64 (m, 1H, N—$CH_2$); 3.67-3.80 (m, 5H, $CH_2$); 5.44 (q, J 8.8 Hz, 2H, $CH_2$—$CF_3$); 7.66 (d, J 5.5 Hz, 2H, Ar); 7.97 (bs, 1H, Ar); 8.39 (d, J 5.5 Hz, 2H, Ar); 9.28 (s, 1H, Ar, signal of a rotamer, Ar); 9.29 (s, 1H, signal of a rotamer, Ar); 10.40 (bs, 1H, NH). M/Z (M+H)$^+$: 421

Compound 44: [3-[(5-fluoro-2-pyridyl)amino]-1-(2,2,2-trifluoroethyl)pyrazolo[4,3-c]-pyridin-6-yl]-(1,4-oxazepan-4-yl)methanone Compound 44 was obtained according to General Procedure VII, Alternative 1, starting from [3-amino-1-(2,2,2-trifluoroethyl)pyrazolo[4,3-c]pyridin-6-yl]-(1,4-oxazepan-4-yl)methanone G1 and 2-bromo-5-fluoropyridine H3 (3 equiv.). Purification by flash chromatography (DCM/MeOH: 100/0 to 95/5) afforded the compound 44 as a white powder in 29% yield. $^1$H-NMR (DMSO-$d_6$, 400 MHz): 1.74 (quint, J 5.8 Hz, 1H, $CH_2$); 1.92 (quint, J 5.8 Hz, 1H, $CH_2$); 3.43-3.48 (m, 2H, N—$CH_2$); 3.60-3.64 (m, 1H, N—$CH_2$); 3.69-3.80 (m, 5H, $CH_2$); 5.39 (q, J 9.1 Hz, 2H, $CH_2$—$CF_3$); 7.76 (td, J 8.9, 3.0 Hz, 1H, Ar); 7.93 (bs, 1H, signal of a rotamer, Ar); 7.94 (bs, 1H, signal of a rotamer, Ar); 8.01 (dd, J 8.9, 3.8 Hz, 1H, Ar); 8.28 (d, J 3.0 Hz, 1H, Ar); 9.37 (d, J 0.9 Hz, 1H, signal of a rotamer, Ar); 9.39 (d, J 0.9 Hz, 1H, signal of a rotamer, Ar); 10.42 (s, 1H, NH). M/Z (M+H)$^+$: 439

Compound 45: [3-[(6-methoxy-2-pyridyl)amino]-1-(2,2,2-trifluoroethyl)pyrazolo[4,3-c]-pyridin-6-yl]-(1,4-oxazepan-4-yl)methanone Compound 45 was obtained according to General Procedure VII, Alternative 1, starting from [3-amino-1-(2,2,2-trifluoroethyl)pyrazolo[4,3-c]pyridin-6-yl]-(1,4-oxazepan-4-yl)methanone G1 and 2-bromo-6-methoxypyridine H4 (1.2 equiv.). Purification by flash chromatography (DCM/MeOH: 100/0 to 95/5), then by preparative HPLC afforded the compound 45 as a white powder in 17% yield. $^1$H-NMR (DMSO-$d_6$, 400 MHz): 1.74 (quint, J 5.8 Hz, 1H, $CH_2$); 1.92 (quint, J 5.8 Hz, 1H, $CH_2$); 3.42-3.50 (m, 2H, N—$CH_2$); 3.60-3.65 (m, 1H, N—$CH_2$); 3.67-3.80 (m, 5H, $CH_2$); 3.84 (s, 3H, $CH_3$); 5.40 (q, J 9.0 Hz, 2H, $CH_2$—$CF_3$); 6.35 (d, J 8.0 Hz, 1H, Ar); 7.50 (d, J 8.0 Hz, 1H, Ar); 7.67 (t, J 8.0 Hz, 1H, Ar); 7.92 (bs, 1H, signal of a rotamer, Ar); 7.94 (bs, 1H, signal of a rotamer, Ar); 9.39 (d, J 0.9 Hz, 1H, signal of a rotamer, Ar); 9.40 (d, J 0.9 Hz, 1H, signal of a rotamer, Ar); 10.11 (s, 1H, NH). M/Z (M+H)$^+$: 451

Compound 46: [3-[(4-fluoro-2-pyridyl)amino]-1-(2,2,2-trifluoroethyl)pyrazolo[4,3-c]-pyridin-6-yl]-(1,4-oxazepan-4-yl)methanone Compound 46 was obtained according to General Procedure VII, Alternative 1, starting from [3-amino-1-(2,2,2-trifluoroethyl)pyrazolo[4,3-c]pyridin-6-yl]-(1,4-oxazepan-4-yl)methanone G1 and 2-bromo-4-fluoropyridine H5 (2.0 equiv.). Purification by flash chromatography (DCM/MeOH: 10/0 to 9/1) afforded the compound 46 as a beige powder in 37% yield. $^1$H-NMR (DMSO-$d_6$, 400 MHz): 1.74 (m, 1H, $CH_2$); 1.92 (m, 1H, $CH_2$); 3.43-3.50 (m, 2H, N—$CH_2$); 3.60-3.64 (m, 1H, N—$CH_2$); 3.66-3.80 (m, 5H, $CH_2$); 5.46 (q, J 9.1 Hz, 2H, $CH_2$—$CF_3$); 6.87 (ddd, J 8.3, 5.7, 2.4 Hz, 1H, Ar); 7.76 (dd, J 12.8, 2.4 Hz, 1H, Ar); 7.96 (bs, 1H, signal of a rotamer, Ar); 7.97 (bs, 1H, signal of a rotamer, Ar); 8.33 (dd, J 9.1, 5.7 Hz, 1H, Ar); 9.41 (d, J 1.0

Hz, 1H, signal of a rotamer, Ar); 9.42 (d, J 1.0 Hz, 1H, signal of a rotamer, Ar); 10.78 (s, 1H, NH). M/Z (M+H)$^+$: 439

Compound 47: 8-oxa-3-azabicyclo[3.2.1]octan-3-yl-[3-(2-pyridylamino)-1-(2,2,2-trifluoroethyl) pyrazolo[4,3-c]pyridin-6-yl]methanone Compound 47 was obtained according to General Procedure VII, Alternative 1, starting from [3-amino-1-(2,2,2-trifluoroethyl)pyrazolo[4,3-c]pyridin-6-yl]-(8-oxa-3-aza-bicyclo[3.2.1]octan-3-yl)methanone G2 and 2-bromopyridine H1 (1.6 equiv.). Purification by flash chromatography (DCM/MeOH: 10/0 to 8/2) afforded the compound 47 as a orange powder in 41% yield. $^1$H-NMR (DMSO-d6,400 MHz): 1.69-1.91 (m, 4H, CH$_2$); 3.04 (dd, J 13.2, 2.3 Hz, 1H, N—CH$_2$); 3.27-3.38 (m, 2H, N—CH$_2$); 4.17-4.24 (m, 2H, N—CH$_2$, O—CH); 4.39-4.43 (m, 1H, O—CH); 5.43 (m, 2H, CH$_2$—CF$_3$); 6.92-6.96 (m, 1H, Ar); 7.74-7.80 (m, 1H, Ar); 7.93-7.97 (m, 2H, Ar); 8.26-8.29 (m, 1H, Ar); 9.41 (d, J 1.0 Hz, 1H); 10.35 (bs, 1H, NH). M/Z (M+H)$^+$: 433

Compound 48: [3-[(5-chloro-2-pyridyl)amino]-1-(2,2,2-trifluoroethyl)pyrazolo[4,3-c]pyridin-6-yl]-(1,4-oxazepan-4-yl)methanone Compound 48 was obtained according to General Procedure VII, Alternative 1, starting from [3-amino-1-(2,2,2-trifluoroethyl)pyrazolo[4,3-c]pyridin-6-yl]-(1,4-oxazepan-4-yl)methanone G1 and 2-bromo-5-chloropyridine H6 (3 equiv.). Purification by flash chromatography (DCM/MeOH: 10/0 to 9/1) afforded the compound 48 as a beige powder in 36% yield. $^1$H-NMR (DMSO-d6,400 MHz): 1.74 (quint, J 5.8 Hz, 1H, CH$_2$); 1.92 (quint, J 5.8 Hz, 1H, CH$_2$); 3.43-3.48 (m, 2H, N—CH$_2$); 3.60-3.64 (m, 1H, N—CH$_2$); 3.67-3.79 (m, 5H, CH$_2$); 5.42 (q, J 9.1 Hz, 2H, CH$_2$—CF$_3$); 7.88 (dd, J 9.0, 2.6 Hz, 1H, Ar); 7.92-7.99 (m, 2H, Ar); 8.31 (d, J 2.6 Hz, 1H, Ar); 9.38 (d, J 1.0 Hz, 1H, signal of a rotamer, Ar); 9.39 (d, J 1.0 Hz, 1H, signal of a rotamer, Ar); 10.56 (s, 1H, NH). M/Z (M+H)$^+$: 455/457

Compound 49: [3-[(6-fluoro-2-pyridyl)amino]-1-(2,2,2-trifluoroethyl)pyrazolo[4,3-c]-pyridin-6-yl]-(1,4-oxazepan-4-yl)methanone Compound 49 was obtained according to General Procedure VII, Alternative 1, starting from [3-amino-1-(2,2,2-trifluoroethyl)pyrazolo[4,3-c]pyridin-6-yl]-(1,4-oxazepan-4-yl)methanone G1 and 2-bromo-6-fluoropyridine H7 (3 equiv.). Purification by flash chromatography (DCM/MeOH: 100/0 to 95/5) afforded the compound 49 as a beige powder in 46% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 3.43-3.48 (m, 2H, N—CH$_2$); 3.60-3.64 (m, 1H, N—CH$_2$); 3.67-3.79 (m, 5H, CH$_2$); 5.43 (q, J 9.1 Hz, 2H, CH$_2$—CF$_3$); 6.65 (dd, J 7.7, 2.1 Hz, 1H, Ar); 7.87 (dd, J 8.1, 2.4 Hz, 1H, Ar); 7.91-7.99 (m, 2H, Ar); 9.39 (d, J 0.9 Hz, 1H, signal of a rotamer, Ar); 9.40 (d, J 0.9 Hz, 1H, signal of a rotamer, Ar); 10.63 (s, 1H, NH). M/Z (M+H)+: 439

Compound 50: [3-[(5-methoxy-3-methyl-2-pyridyl)amino]-1-(2,2,2-trifluoroethyl)-pyrazolo[4,3-c]pyridin-6-yl]-(1,4-oxazepan-4-yl)methanone Compound 50 was obtained according to General Procedure VII, Alternative 1, starting from [3-amino-1-(2,2,2-trifluoroethyl)pyrazolo[4,3-c]pyridin-6-yl]-(1,4-oxazepan-4-yl)methanone G1 and 2-bromo-5-methoxy-3-methylpyridine H8 (3 equiv.). Purification by flash chromatography (DCM/MeOH: 100/0 to 95/5) afforded the compound 50 as a beige powder in 12% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 2.28 (s, 3H, CH$_3$); 3.43-3.49 (m, 2H, N—CH$_2$); 3.60-3.64 (m, 1H, N—CH$_2$); 3.66-3.77 (m, 5H, CH$_2$); 3.79 (s, 3H, O—CH$_3$); 5.33 (q, J 9.0 Hz, 2H, CH$_2$—CF$_3$); 7.30 (d, J 2.8 Hz, 1H, Ar); 7.76 (d, J 2.8 Hz, 1H, Ar); 7.91 (bs, 1H, signal of a rotamer, Ar); 7.92 (bs, 1H, signal of a rotamer, Ar); 8.73 (d, J 1.0 Hz, 1H, signal of a rotamer, Ar); 8.74 (d, J 1.0 Hz, 1H, signal of a rotamer, Ar); 8.94 (s, 1H, NH). M/Z (M+H)$^+$: 465

Compound 51: [3-[(6-chloro-2-pyridyl)amino]-1-(2,2,2-trifluoroethyl)pyrazolo[4,3-c]pyridin-6-yl]-(1,4-oxazepan-4-yl)methanone Compound 51 was obtained according to General Procedure VII, Alternative 1, starting from [3-amino-1-(2,2,2-trifluoroethyl)pyrazolo[4,3-c]pyridin-6-yl]-(1,4-oxazepan-4-yl)methanone G1 and 2-bromo-6-chloropyridine H9 (3 equiv.). Purification by preparative HPLC afforded the compound 51 as a white powder in 10% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 3.42-3.49 (m, 2H, N—CH$_2$); 3.59-3.64 (m, 1H, N—CH$_2$); 3.67-3.79 (m, 5H, CH$_2$); 5.42 (q, J 9.1 Hz, 2H, CH$_2$—CF$_3$); 7.02 (d, J 7.8 Hz, 1H, Ar); 7.83 (t, J 7.8 Hz, 1H, Ar); 7.93-7.98 (m, 2H, Ar); 9.40 (d, J 1.0 Hz, 1H, signal of a rotamer, Ar); 9.42 (d, J 1.0 Hz, 1H, signal of a rotamer, Ar); 10.74 (s, 1H, NH). M/Z (M+H)$^+$: 455/457

Compound 52: (6-hydroxy-1,4-oxazepan-4-yl)-[3-(2-pyridylamino)-1-(2,2,2-trifluoro-ethyl)pyrazolo[4,3-c]pyridin-6-yl]methanone Compound 52 was obtained according to General Procedure VII, Alternative 1, starting from [3-amino-1-(2,2,2-trifluoroethyl)pyrazolo[4,3-c]pyridin-6-yl]-(6-hydroxy-1,4-oxazepan-4-yl)methanone G3 and 2-bromopyridine H1 (1.7 equiv.). In that specific case, 5 mol % of BrettPhos Pd G1 precatalyst were used. Purification by flash chromatography (DCM/MeOH: 100/0 to 93/7) afforded the compound 52 in 81% yield. $^1$H-NMR (DMSO-d$_6$, 400 MHz): 3.19-3.42 (m, 1H, CH$_2$); 3.47-3.80 (m, 6H, CH, CH$_2$); 3.80-3.88 (m, 1H, signal of a rotamer, CH$_2$); 3.94-4.03 (m, 1H, CH$_2$); 4.19-4.26 (m, 1H, signal of a rotamer, CH); 5.06 (d, J 4.7 Hz, 1H, OH, major rotamer); 5.11 (d, J 4.7 Hz, 1H, OH, minor rotamer); 5.35-5.46 (m, 2H, CH$_2$—CF$_3$); 6.92-6.96 (m, 1H, Ar); 7.74-7.81 (m, 1H, Ar); 7.93-7.98 (m, 2H, Ar); 8.26-8.30 (m, 1H, Ar); 9.39 (d, J 1.0 Hz, 1H, signal of a rotamer, Ar); 9.41 (d, J 1.0 Hz, 1H, signal of a rotamer, Ar); 10.34 (bs, 1H, signal of a rotamer, NH); 10.36 (bs, 1H, signal of a rotamer, NH). M/Z (M+H)$^+$: 437

Compound 53: (4-hydroxy-4-methyl-1-piperidyl)-[3-(2-pyridylamino)-1-(2,2,2-trifluoro-ethyl) pyrazolo[4,3-c]pyridin-6-yl]methanone Compound 53 was obtained according to General Procedure VII, Alternative 1, starting from [3-amino-1-(2,2,2-trifluoroethyl)pyrazolo[4,3-c]pyridin-6-yl]-(4-hydroxy-4-methyl-1-piperidyl)methanone G4 and 2-bromopyridine H1 (1.6 equiv.). Purification by flash chromatography (DCM/MeOH: 10/0 to 9/1) afforded the compound 53 as a white powder in 43% yield. $^1$H-NMR (DMSO-d$_6$, 400 MHz): 1.18 (s, 3H, CH$_3$); 1.37-1.62 (m, 4H, CH$_2$); 3.22-3.32 (m, 3H, N—CH$_2$); 4.07-4.15 (m, 1H, N—CH$_2$); 4.44 (s, 1H, OH);

5.39 (q, J 9.0 Hz, 2H, CH$_2$—CF$_3$); 6.94 (ddd, J 7.2, 4.9, 0.7 Hz, 1H, Ar); 7.77 (ddd, J 8.7, 7.2, 1.9 Hz, 1H, Ar); 7.89 (d, J 0.9 Hz, 1H, Ar); 7.94 (d, J 8.7 Hz, 1H, Ar); 8.26-8.29 (m, 1H, Ar); 9.39 (d, J 0.9 Hz, 1H, Ar); 10.33 (s, 1H, NH). M/Z (M+H)$^+$: 435

Compound 54: [3-[(3-fluoro-2-pyridyl)amino]-1-(2,2,2-trifluoroethyl)pyrazolo[4,3-c]pyridin-6-yl]-(1,4-oxazepan-4-yl)methanone Compound 54 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-3-fluoropyridine H10 (1.5 equiv.). Purification by flash chromatography (DCM/MeOH: 10/0 to 9/1) afforded the compound 54 as a white powder in 67% yield. $^1$H-NMR (DMSO-d6,400 MHz): 1.75 (quint, J 5.8 Hz, 1H, CH$_2$); 1.92 (quint, J 5.8 Hz, 1H, CH$_2$); 3.45-3.51 (m, 2H, N—CH$_2$); 3.60-3.65 (m, 1H, N—CH$_2$); 3.67-3.79 (m, 5H, CH$_2$); 5.42 (q, J 9.0 Hz, 2H, CH$_2$—CF$_3$); 6.96 (ddd, J 8.0, 4.8, 3.4 Hz, 1H, Ar); 7.64 (ddd, J 11.2, 8.0, 1.0 Hz, 1H, Ar); 7.96 (dd, J 4.8, 1.0 Hz, 1H, Ar); 7.99 (bs, 1H, signal of a rotamer, Ar); 8.00 (bs, 1H, signal of a rotamer, Ar); 8.95 (d, J 1.0 Hz, 1H, signal of a rotamer, Ar); 8.96 (d, J 1.0 Hz, 1H, signal of a rotamer, Ar); 9.80 (bs, 1H, NH). M/Z (M+H)$^+$: 439

Compound 55: [3-[(3-chloro-2-pyridyl)amino]-1-(2,2,2-trifluoroethyl)pyrazolo[4,3-c]-pyridin-6-yl]-(1,4-oxazepan-4-yl)methanone Compound 55 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 3-chloro-2-iodo pyridine H11 (1.3 equiv.). Purification by flash chromatography (DCM/MeOH: 10/0 to 9/1) then by preparative HPLC afforded the compound 55 as a yellow powder in 20% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 3.43-3.48 (m, 2H, N—CH$_2$); 3.61-3.65 (m, 1H, N—CH$_2$); 3.67-3.80 (m, 5H, CH$_2$); 5.40 (q, J 9.0 Hz, 2H, CH$_2$—CF$_3$); 7.43 (dd, J 8.1, 4.5 Hz, 1H, Ar); 7.97 (bs, 1H, signal of a rotamer, Ar); 7.98 (bs, 1H, signal of a rotamer, Ar); 8.03 (dd, J 4.5, 1.7 Hz, 1H, Ar); 8.47 (dt, J 8.1, 1.7 Hz, 1H, Ar); 8.95 (bs, 1H, NH); 9.31 (d, J 1.0 Hz, 1H, signal of a rotamer, Ar); 9.32 (d, J 1.0 Hz, 1H, signal of a rotamer, Ar). M/Z (M+H)$^+$: 455/457

Compound 56: [3-[(5-fluoro-3-methyl-2-pyridyl)amino]-1-(2,2,2-trifluoroethyl)pyrazolo-[4,3-c] pyridin-6-yl]-(1,4-oxazepan-4-yl)methanone Compound 56 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-5-fluoro-3-methylpyridine H12 (1.2 equiv.). Purification by flash chromatography (DCM/MeOH: 10/0 to 9/1) then by preparative HPLC afforded the compound 56 as a yellow powder in 55% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 2.32 (s, 3H, CH$_3$); 3.44-3.50 (m, 2H, N—CH$_2$); 3.61-3.65 (m, 1H, N—CH$_2$); 3.67-3.79 (m, 5H, CH$_2$); 5.39 (q, J 9.0 Hz, 2H, CH$_2$—CF$_3$); 7.58 (dd, J 9.0, 2.4 Hz, 1H, Ar); 7.96-8.00 (m, 2H, Ar); 8.78 (d, J 1.0 Hz, 1H, signal of a rotamer, Ar); 8.79 (d, J 1.0 Hz, 1H, signal of a rotamer, Ar); 9.16 (bs, 1H, NH). M/Z (M+H)$^+$: 453

Compound 57: [3-[(5-fluoro-4-methyl-2-pyridyl)amino]-1-(2,2,2-trifluoroethyl)pyrazolo-[4,3-c] pyridin-6-yl]-(1,4-oxazepan-4-yl)methanone Compound 57 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-5-fluoro-4-methylpyridine H13 (1.5 equiv.). Purification by flash chromatography (DCM/MeOH: 10/0 to 9/1) afforded the compound 57 as a beige powder in 52% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 2.29 (s, 3H, CH$_3$); 3.43-3.49 (m, 2H, N—CH$_2$); 3.61-3.65 (m, 1H, N—CH$_2$); 3.67-3.79 (m, 5H, CH$_2$); 5.39 (q, J 9.0 Hz, 2H, CH$_2$—CF$_3$); 7.86 (d, J 5.6 Hz, 1H, Ar); 7.93 (bs, 1H, signal of a rotamer, Ar); 7.94 (bs, 1H, signal of a rotamer, Ar); 8.16 (bs, 1H, Ar); 9.35 (d, J 1.0 Hz, 1H, signal of a rotamer, Ar); 9.36 (d, J 1.0 Hz, 1H, signal of a rotamer, Ar); 10.28 (bs, 1H, NH). M/Z (M+H)$^+$: 453

Compound 58: [3-[(5-fluoro-6-methyl-2-pyridyl)amino]-1-(2,2,2-trifluoroethyl)pyrazolo-[4,3-c] pyridin-6-yl]-(1,4-oxazepan-4-yl)methanone Compound 58 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-5-fluoro-3-methylpyridine H12 (1.5 equiv.). Purification by flash chromatography (DCM/MeOH: 10/0 to 9/1) afforded the compound 58 as a beige powder in 60% yield. $^1$H-NMR (DMSO-d$_6$,400 MHz): 1.74 (quint, J 5.8 Hz, 1H, CH$_2$); 1.92 (quint, J 5.8 Hz, 1H, CH$_2$); 2.40 (d, J 2.8 Hz, 3H, CH$_3$); 3.42-3.49 (m, 2H, N—CH$_2$); 3.60-3.64 (m, 1H, N—CH$_2$); 3.67-3.80 (m, 5H, CH$_2$); 5.39 (q, J 9.0 Hz, 2H, CH$_2$—CF$_3$); 7.65 (t, J 9.0 Hz, 1H, Ar); 7.89 (dd, J 9.0, 3.0 Hz, 1H, Ar); 7.92 (bs, 1H, signal of a rotamer, Ar); 7.93 (bs, 1H, signal of a rotamer, Ar); 9.40 (d, J 0.9 Hz, 1H, signal of a rotamer, Ar); 9.41 (d, J 0.9 Hz, 1H, signal of a rotamer, Ar); 10.37 (bs, 1H, NH). M/Z (M+H)$^+$: 453

Compound 59: (6,6-dideuterio-1,4-oxazepan-4-yl)-[3-(2-pyridylamino)-1-(2,2,2-trifluoroethyl)pyrazolo[4,3-c]pyridin-6-yl]methanone Compound 59 was obtained according to General Procedure VII, Alternative 1, starting from [3-amino-1-(2,2,2-trifluoroethyl)pyrazolo[4,3-c]pyridin-6-yl]-(6,6-dideuterio-1,4-oxazepan-4-yl)methanone G5 and 2-bromopyridine H1 (1.6 equiv.). Purification by flash chromatography (DCM/MeOH: 100/0 to 9/1) afforded the compound 59 as a beige powder in 47% yield. $^1$H-NMR (DMSO-d$_6$,400 MHz): 3.43-3.49 (m, 2H, N—CH$_2$); 3.60-3.64 (m, 1H, N—CH$_2$); 3.69 (s, 1H, N—CH$_2$); 3.71-3.79 (m, 4H, CH$_2$); 5.40 (q, J 9.2 Hz, 2H, CH$_2$—CF$_3$); 6.94 (dd, J 6.7, 4.9 Hz, 1H, Ar); 7.74-7.79 (m, 1H, Ar); 7.92-7.97 (m, 2H, Ar); 8.26-8.29 (m, 1H, Ar); 9.39 (d, J 0.9 Hz, 1H, signal of a rotamer, Ar); 9.40 (d, J 0.9 Hz, 1H, signal of a rotamer, Ar); 10.33 (bs, 1H, NH). M/Z (M+H)$^+$: 423

Compound 60: (6,6-dideuterio-1,4-oxazepan-4-yl)-[3-[(4-fluoro-2-pyridyl)amino]-1-(2,2,2-trifluoroethyl)pyrazolo[4,3-c]pyridin-6-yl]methanone Compound 60 was obtained according to General Procedure VII, Alternative 3, starting from [3-amino-1-(2,2,2-trifluoroethyl)pyrazolo[4,3-c]pyridin-6-yl]-(6,6-dideuterio- 1,4-oxazepan-4-yl)methanone G5 and 2-bromo-4-fluoropyridine H5 (1.5 equiv.). Purification by flash chromatography (DCM/MeOH: 100/0 to 9/1) afforded the compound 60 as a beige powder in 56% yield. $^1$H-NMR (DMSO-d$_6$, 400 MHz): 3.42-3.49 (m, 2H, N—CH$_2$); 3.60-3.64 (m, 1H, N—CH$_2$); 3.68 (s, 1H, N—CH$_2$); 3.70-3.79 (m, 4H, CH$_2$); 5.44 (q, J 9.1 Hz, 2H, CH$_2$—CF$_3$); 6.87 (ddd, J 8.2, 5.7, 2.2 Hz, 1H, Ar); 7.83 (dd, J 12.4, 2.2, 1H, Ar); 7.95 (bs, 1H, signal of a rotamer, Ar); 7.96 (bs, 1H, signal of a rotamer, Ar); 8.32 (dd, J 9.5, 5.7 Hz, 1H, Ar); 9.41 (d, J 1.0 Hz, 1H, signal of a rotamer, Ar); 9.42 (d, J 1.0 Hz, 1H, signal of a rotamer, Ar); 10.73 (bs, 1H, NH). M/Z (M+H)$^+$: 441

Compound 61: 1,4-oxazepan-4-yl-[3-(pyrazin-2-ylamino)-1-(2,2,2-trifluoroethyl)-pyrazolo[4,3-c]pyridin-6-yl]methanone Compound 61 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-chloropyrazine H15 (1.2 equiv.). Purification by flash chromatography (DCM/MeOH: 100/0 to 96/4) afforded the compound 61 as a yellow powder in 30% yield. $^1$H-NMR (DMSO-d$_6$, 400 MHz): 1.74 (quint, J 5.4 Hz, 1H, CH$_2$); 1.92 (quint, J 5.4 Hz, 1H, CH$_2$); 3.43-3.50 (m, 2H, N—CH$_2$); 3.60-3.65 (m, 1H, N—CH$_2$); 3.67-3.80 (m, 5H, CH$_2$); 5.46 (q, J 9.0 Hz, 2H, CH$_2$—CF$_3$); 7.99 (d, J 2.3 Hz, 1H, Ar); 8.18 (bs, 1H, signal of a rotamer, Ar); 8.19 (bs, 1H, signal of a rotamer, Ar); 8.31 (bs, 1H, Ar); 9.23 (bs, 1H, Ar); 9.37 (bs, 1H, signal of a rotamer, Ar); 9.38 (bs, 1H, signal of a rotamer, Ar); 10.68 (bs, 1H, NH). M/Z (M+H)$^+$: 422

Compound 62: 1,4-oxazepan-4-yl-[1-(2,2,2-trifluoroethyl)-3-[[4-(trifluoromethyl)-2-pyridyl]amino]pyrazolo[4,3-c]pyridin-6-yl]methanone Compound 62 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-4-trifluoromethylpyridine H16 (1.2 equiv.). Purification by flash chromatography (DCM/MeOH: 10/0 to 9/1) afforded the compound 62 as a white powder in 37% yield. $^1$H-NMR (DMSO-d$_6$, 400 MHz): 1.75 (quint, J 5.7 Hz, 1H, CH$_2$); 1.92 (quint, J 5.7 Hz, 1H, CH$_2$); 3.43-3.50 (m, 2H, N—CH$_2$); 3.60-3.65 (m, 1H, N—CH$_2$); 3.67-3.80 (m, 5H, CH$_2$); 5.44 (q, J 9.0 Hz, 2H, CH$_2$—CF$_3$); 7.27 (dd, J 5.3, 1.1 Hz, 1H, Ar); 8.00 (bs, 1H, signal of a rotamer, Ar); 8.01 (bs, 1H, signal of a rotamer, Ar); 8.28 (bs, 1H, Ar); 8.55 (d, J 5.3 Hz, 1H, Ar); 9.40 (d, J 0.9 Hz, 1H, signal of a rotamer, Ar); 9.41 (d, J 0.9 Hz, 1H, signal of a rotamer, Ar); 10.88 (bs, 1H, NH). M/Z (M+H)$^+$: 489

Compound 63: [3-[(4-methoxy-2-pyridyl)amino]-1-(2,2,2-trifluoroethyl)pyrazolo[4,3-c]pyridin-6-yl]-(1,4-oxazepan-4-yl)methanone Compound 63 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-4-methyoxypyridine H17 (1.2 equiv.). Purification by flash chromatography (DCM/MeOH: 10/0 to 9/1) afforded the compound 63 as a white powder in 22% yield. $^1$H-NMR (DMSO-d$_6$, 400 MHz): 1.74 (quint, J 5.8 Hz, 1H, CH$_2$); 1.92 (quint, J 5.8 Hz, 1H, CH$_2$); 3.43-3.50 (m, 2H, N—CH$_2$); 3.61-3.64 (m, 1H, N—CH$_2$); 3.67-3.80 (m, 5H, CH$_2$); 3.93 (s, 3H, CH$_3$); 5.47 (q, J 9.0 Hz, 2H, CH$_2$—CF$_3$); 6.76 (m, 1H, Ar); 7.53 (d, J 1.4 Hz, 1H, Ar); 8.02 (bs, 1H, signal of a rotamer, Ar); 8.03 (bs, 1H, signal of a rotamer, Ar); 8.20 (d, J 6.3 Hz, 1H, Ar); 9.42 (d, J 1.0 Hz, 1H, signal of a rotamer, Ar); 9.44 (d, J 1.0 Hz, 1H, signal of a rotamer, Ar); 10.97-11.49 (m, 1H, NH). M/Z (M+H)$^+$: 451

Compound 64: [3-[(4-chloro-2-pyridyl)amino]-1-(2,2,2-trifluoroethyl)pyrazolo[4,3-c]-pyridin-6-yl]-(1,4-oxazepan-4-yl)methanone Compound 64 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-4-chloropyridine H18 (1.2 equiv.). Purification by flash chromatography (DCM/MeOH: 10/0 to 9/1) afforded the compound 64 as a white powder in 12% yield. $^1$H-NMR (DMSO-d$_6$, 400 MHz): 1.75 (quint, J 5.7 Hz, 1H, CH$_2$); 1.92 (quint, J 5.7 Hz, 1H, CH$_2$); 3.44-3.50 (m, 2H, N—CH$_2$); 3.60-3.65 (m, 1H, N—CH$_2$); 3.67-3.80 (m, 5H, CH$_2$); 5.46 (q, J 9.0 Hz, 2H, CH$_2$—CF$_3$); 7.07 (dd, J 5.3, 1.8 Hz, 1H, Ar); 8.00 (bs, 1H, signal of a rotamer, Ar); 8.01 (bs, 1H, signal of a rotamer, Ar); 8.05 (d, J 1.8 Hz, 1H, Ar); 8.28 (d, J 5.3 Hz, 1H, Ar); 9.43 (bs, 1H, signal of a rotamer, Ar); 9.44 (bs, 1H, signal of a rotamer, Ar); 10.73 (bs, 1H, NH). M/Z (M+H)$^+$: 455

Compound 65: [3-[(6-chloro-5-fluoro-2-pyridyl)amino]-1-(2,2,2-trifluoroethyl)pyrazolo[-4,3-c]pyridin-6-yl]-(1,4-oxazepan-4-yl)methanone Compound 65 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-6-chloro-5-fluoropyridine H19 (1.2 equiv.). Purification by preparative HPLC afforded the compound 65 as a white powder in 17% yield. $^1$H-NMR (DMSO-d$_6$, 400 MHz): 1.74 (quint, J 5.9 Hz, 1H, CH$_2$); 1.92 (quint, J 5.9 Hz, 1H, CH$_2$); 3.43-3.49 (m, 2H, N—CH$_2$); 3.60-3.64 (m, 1H, N—CH$_2$); 3.67-3.80 (m, 5H, CH$_2$); 5.42 (q, J 9.0 Hz, 2H, CH$_2$—CF$_3$); 7.94-8.03 (m, 3H, Ar); 9.39 (bs, 1H, signal of a rotamer, Ar); 9.40 (bs, 1H, signal of a rotamer, Ar); 10.78 (bs, 1H, NH). M/Z (M+H)$^+$: 473

Compound 66: [3-[(4-chloro-5-fluoro-2-pyridyl)amino]-1-(2,2,2-trifluoroethyl)pyrazolo-[4,3-c] pyridin-6-yl]-(1,4-oxazepan-4-yl)methanone Compound 66 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-4-chloro-5-fluoropyridine H20 (1.2 equiv.). Purification by preparative HPLC afforded the compound 66 as a white powder in 21% yield. $^1$H-NMR (DMSO-d$_6$, 400 MHz): 1.74 (quint, J 5.9 Hz, 1H, CH$_2$); 1.92 (quint, J 5.9 Hz, 1H, CH$_2$); 3.43-3.49 (m, 2H, N—CH$_2$); 3.60-3.64 (m, 1H, N—CH$_2$); 3.67-3.80 (m, 5H, CH$_2$); 5.45 (q, J 9.1 Hz, 2H, CH$_2$—CF3); 7.96 (bs, 1H, signal of a rotamer, Ar); 7.97 (bs, 1H, signal of a rotamer, Ar); 8.20 (d, J 5.3 Hz, 1H, Ar); 8.46 (bs, 1H, Ar); 9.38 (d, J 1.1 Hz, 1H, signal of a rotamer, Ar); 9.39 (d, J 1.1 Hz, 1H, signal of a rotamer, Ar); 10.70 (bs, 1H, NH). M/Z (M+H)$^+$: 473

Compound 67: [3-[(3-chloro-5-fluoro-2-pyridyl) amino]-1-(2,2,2-trifluoroethyl)pyrazolo-[4,3-c] pyridin-6-yl]-(1,4-oxazepan-4-yl)methanone Compound 67 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-3-chloro-5-fluoropyridine H21 (1.2 equiv.). Purification by preparative HPLC afforded the compound 67 as a white powder in 54% yield. $^1$H-NMR (DMSO-$d_6$, 400 MHz): 1.74 (quint, J 5.9 Hz, 1H, $CH_2$); 1.92 (quint, J 5.9 Hz, 1H, $CH_2$); 3.44-3.50 (m, 2H, N—$CH_2$); 3.61-3.65 (m, 1H, N—$CH_2$); 3.67-3.80 (m, 5H, $CH_2$); 5.43 (q, J 9.0 Hz, 2H, $CH_2$—$CF_3$); 8.01-8.03 (m, 1H, Ar); 8.05-8.08 (m, 1H, Ar); 8.12-8.14 (m, 1H, Ar); 8.83 (bs, 1H, signal of a rotamer, Ar); 8.84 (bs, 1H, signal of a rotamer, Ar); 9.42 (bs, 1H, NH). M/Z $(M+H)^+$: 473

Compound 68: [3-[(4-methyl-2-pyridyl)amino]-1-(2,2,2-trifluoroethyl)pyrazolo[4,3-c]-pyridin-6-yl]-(1,4-oxazepan-4-yl)methanone Compound 68 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-4-methylpyridine H22 (1.2 equiv.). Purification by flash chromatography (DCM/MeOH: 100/0 to 93/7) then by preparative HPLC afforded the compound 68 as a white powder in 40% yield. $^1$H-NMR (DMSO-$d_6$, 400 MHz): 1.75 (quint, J 5.7 Hz, 1H, $CH_2$); 1.92 (quint, J 5.7 Hz, 1H, $CH_2$); 2.40 (s, 3H, $CH_3$); 3.44-3.50 (m, 2H, N—$CH_2$); 3.61-3.65 (m, 1H, N—$CH_2$); 3.68-3.80 (m, 5H, $CH_2$); 5.47 (q, J 8.8 Hz, 2H, $CH_2$—$CF_3$); 6.95 (bs, 1H, Ar); 7.71 (bs, 1H, Ar); 8.02 (bs, 1H, Ar); 8.19 (d, J 5.3 Hz, 1H, Ar); 9.44 (bs, 1H, Ar); 10.93-11.31 (bs, 1H, NH). M/Z $(M+H)^+$: 435

Compound 69: 1,4-oxazepan-4-yl-[3-(pyridazin-3-ylamino)-1-(2,2,2-trifluoroethyl)pyrazolo[4,3-c]pyridin-6-yl]methanone Compound 69 was obtained according to General Procedure VII, Alternative 3, starting from [3-amino-1-(2,2,2-trifluoroethyl)pyrazolo[4,3-c]pyridin-6-yl]-(1,4-oxazepan-4-yl)methanone G1 and 3-bromopyridazine H23 (1.2 equiv.). Purification by flash chromatography (DCM/MeOH: 100/0 to 95/5) then by preparative HPLC afforded the compound 69 as a white powder in 12% yield. 1H-NMR (DMSO-d6, 400 MHz): 1.74 (quint, J 5.4 Hz, 1H, CH2); 1.92 (quint, J 5.4 Hz, 1H, CH2); 3.45-3.51 (m, 2H, N—CH2); 3.60-3.65 (m, 1H, N—CH2); 3.67-3.80 (m, 5H, CH2); 5.43 (q, J 9.1 Hz, 2H, CH2-CF3); 7.66 (dd, J 9.1, 4.7 Hz, 1H, Ar); 7.98 (d, J 0.9 Hz, 1H, signal of a rotamer, Ar); 7.99 (d, J 0.9 Hz, 1H, signal of a rotamer, Ar); 8.17 (dd, J 9.1, 1.3 Hz, 1H, Ar); 8.82 (dd, J 4.7, 1.3 Hz, 1H, Ar); 9.41 (d, J 0.9 Hz, 1H, signal of a rotamer, Ar); 9.42 (d, J 0.9 Hz, 1H, signal of a rotamer, Ar); 10.91 (bs, 1H, NH). M/Z (M+H)+: 422

Compound 70: [3-[(4-fluoro-3-methyl-2-pyridyl) amino]-1-(2,2,2-trifluoroethyl)pyrazolo-[4,3-c] pyridin-6-yl]-(1,4-oxazepan-4-yl)methanone Compound 70 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-4-fluoro-3-methylpyridine H24 (1.2 equiv.). Purification by preparative HPLC afforded the compound 70 as a white powder in 53% yield. $^1$H-NMR (DMSO-d6,400 MHz): 1.75 (quint, J 5.9 Hz, 1H, $CH_2$); 1.92 (quint, J 5.9 Hz, 1H, $CH_2$); 2.21 (s, 3H, $CH_3$); 3.44-3.50 (m, 2H, N—$CH_2$); 3.61-3.65 (m, 1H, N—$CH_2$); 3.68-3.80 (m, 5H, $CH_2$); 5.42 (q, J 9.1 Hz, 2H, $CH_2$—$CF_3$); 6.84 (dd, J 8.8, 5.4 Hz, 1H, Ar); 7.97 (dd, J 8.8, 5.7 Hz, 1H, Ar); 7.99 (bs, 1H, signal of a rotamer, Ar); 8.00 (bs, 1H, signal of a rotamer, Ar); 8.79 (d, J 1.0 Hz, 1H, signal of a rotamer, Ar); 8.80 (d, J 1.0 Hz, 1H, signal of a rotamer, Ar); 9.33 (bs, 1H, NH). M/Z $(M+H)^+$: 453

Compound 71: [3-[(5-chloro-4-fluoro-2-pyridyl) amino]-1-(2,2,2-trifluoroethyl)pyrazolo-[4,3-c] pyridin-6-yl]-(1,4-oxazepan-4-yl)methanone Compound 71 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-4-chloro-5-fluoropyridine H25 (1.2 equiv.). Purification by preparative HPLC afforded the compound 71 as a white powder in 47% yield. $^1$H-NMR (DMSO-$d_6$, 400 MHz): 1.74 (quint, J 5.9 Hz, 1H, $CH_2$); 1.92 (quint, J 5.9 Hz, 1H, $CH_2$); 3.43-3.49 (m, 2H, N—$CH_2$); 3.60-3.64 (m, 1H, N—$CH_2$); 3.67-3.80 (m, 5H, $CH_2$); 5.46 (q, J 9.0 Hz, 2H, $CH_2$—$CF_3$); 7.97 (bs, 1H, signal of a rotamer, Ar); 7.98 (bs, 1H, signal of a rotamer, Ar); 8.00 (d, J 12.1 Hz, 1H, Ar); 8.46 (d, J 10.2 Hz, 1H, Ar); 9.39 (d, J 1.1 Hz, 1H, signal of a rotamer, Ar); 9.40 (d, J 1.1 Hz, 1H, signal of a rotamer, Ar); 10.92 (bs, 1H, NH). M/Z $(M+H)^+$: 473

Compound 72: [3-[(3,5-difluoro-2-pyridyl)amino]-1-(2,2,2-trifluoroethyl)pyrazolo[4,3-c]pyridin-6-yl]-(1,4-oxazepan-4-yl)methanone Compound 72 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-3,5-difluoropyridine H26 (1.2 equiv.). Purification by flash chromatography (DCM/MeOH: 100/0 to 95/5) then by preparative HPLC afforded the compound 72 as a white powder in 34% yield. $^1$H-NMR (DMSO-$d_6$, 400 MHz): 1.74 (quint, J 5.9 Hz, 1H, $CH_2$); 1.92 (quint, J 5.9 Hz, 1H, $CH_2$); 3.43-3.49 (m, 2H, N—$CH_2$); 3.60-3.64 (m, 1H, N—$CH_2$); 3.67-3.80 (m, 5H, $CH_2$); 5.41 (q, J 9.0 Hz, 2H, $CH_2$—$CF_3$); 7.92 (ddd, J 10.9, 8.5, 2.5 Hz, 1H, Ar); 7.98 (bs, 1H, signal of a rotamer, Ar); 7.99 (bs, 1H, signal of a rotamer, Ar); 8.07 (dd, J 2.5, 1.1 Hz, 1H, Ar); 8.93 (d, J 1.0 Hz, 1H, signal of a rotamer, Ar); 8.94 (d, J 1.0 Hz, 1H, signal of a rotamer, Ar); 9.83 (bs, 1H, NH). M/Z $(M+H)^+$: 457

Scheme 2: Preparation of Compounds

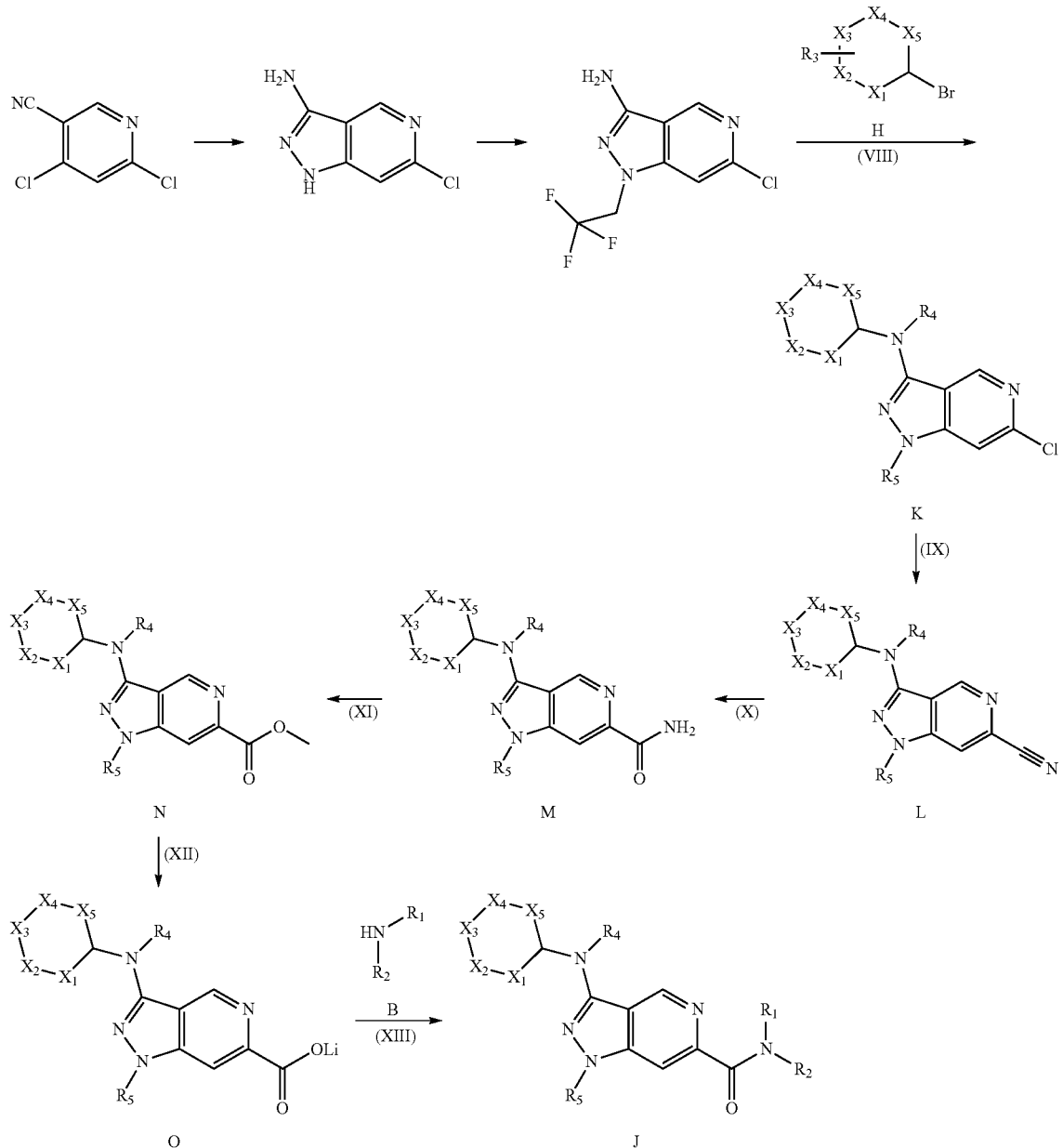

Compound 80: [3-[(5,6-difluoro-2-pyridyl)amino]-1-(2,2,2-trifluoroethyl)pyrazolo[4,3-c]pyridin-6-yl]-(1,4-oxazepan-4-yl)methanone Compound 80 was obtained according to General Procedure VII, Alternative 3, starting from [3-amino-1-(2,2,2-trifluoroethyl)pyrazolo[4,3-c]pyridin-6-yl]-(1,4-oxazepan-4-yl)methanone G1 and 6-bromo-2,3-difluoropyridine H27 (1.2 equiv.). Purification by flash chromatography (DCM/MeOH: 100/0 to 95/5) afforded the compound 80 as a pale orange powder in 61% yield. 1H-NMR (DMSO-d6, 400 MHz) δ: 1.74 (quint, J 5.6 Hz, 1H, CH2); 1.91 (quint, J 5.6 Hz, 1H, CH2); 3.42-3.49 (m, 2H, N—CH2); 3.60-3.63 (m, 1H, N—CH2); 3.68-3.79 (m, 5H, CH2); 5.40 (q, J 9.0 Hz, 2H, N-CH2-CF3); 7.89 (dd, J 9.2, 2.4 Hz, 1H, Ar); 7.96 (d, J 0.8 Hz, 1H, Ar, signal of a rotamer); 7.96 (d, J 0.8 Hz, 1H, Ar, signal of a rotamer); 8.03 (q, J 9.2 Hz, 1H, Ar); 9.36 (d, J 0.8 Hz, 1H, Ar, signal of a rotamer); 9.37 (d, J 0.8 Hz, 1H, Ar, signal of a rotamer); 10.65 (s, 1H, NH). M/Z (M+H)+: 457

Compound 81: [3-[(5-fluoro-4-methoxy-2-pyridyl)amino]-1-(2,2,2-trifluoroethyl)pyrazolo[4,3-c]pyridin-6-yl]-(1,4-oxazepan-4-yl)methanone Compound 81 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-5-fluoro-4-methoxypyridine H28. Purification by flash chromatography (DCM/MeOH: 100/0 to 95/5) afforded the compound 81 as a white powder in 76% yield. 1H-NMR (DMSO-d6, 400 MHz): 1.74 (quint, J 5.8 Hz, 1H, CH2); 1.92 (quint, J 5.8 Hz, 1H, CH2); 3.43-3.50 (m, 2H, N—CH2); 3.60-3.65 (m, 1H, N—CH2); 3.66-3.79 (m, 5H, CH2); 3.93 (s, 3H, CH3); 5.41 (q, J 9.1 Hz, 2H, CH2-CF3); 7.90 (d, J 6.6 Hz, 1H, Ar); 7.95 (bs, 1H, signal of a rotamer, Ar); 7.96 (bs, 1H, signal of a rotamer, Ar); 8.13 (d, J 3.0 Hz, 1H, Ar); 9.37 (bs, 1H, signal of a rotamer, Ar); 9.38 (bs, 1H, signal of a rotamer, Ar); 10.37 (s, 1H, NH). M/Z (M+H)+: 469

Compound 82: [3-[(5-fluoro-6-methoxy-2-pyridyl)amino]-1-(2,2,2-trifluoroethyl)pyrazolo[4,3-c]pyridin-6-yl]-(1,4-oxazepan-4-yl)methanone Compound 82 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-5-fluoro-6-methoxypyridine H29. Purification by flash chromatography (DCM/MeOH: 100/0 to 95/5) afforded the compound 82 as a white powder in 86% yield. 1H-NMR (DMSO-d6, 400 MHz): 1.74 (quint, J 5.8 Hz, 1H, CH2); 1.92 (quint, J 5.8 Hz, 1H, CH2); 3.43-3.50 (m, 2H, N—CH2); 3.60-3.65 (m, 1H, N—CH2); 3.66-3.79 (m, 5H, CH2); 3.95 (s, 3H, CH3); 5.41 (q, J 9.1 Hz, 2H, CH2-CF3); 7.49 (d, J 8.6, 2.3 Hz, 1H, Ar); 7.66 (d, J 10.1, 8.6 Hz, 1H, Ar); 7.92 (bs, 1H, signal of a rotamer, Ar); 7.93 (bs, 1H, signal of a rotamer, Ar); 9.37 (d, J 1.0 Hz, 1H, signal of a rotamer, Ar); 9.38 (d, J 1.0 Hz, 1H, signal of a rotamer, Ar); 10.14 (s, 1H, NH). M/Z (M+H)+: 469

Compound 83: [3-(5-Methoxy-pyridin-2-ylamino)-1-(2,2,2-trifluoro-ethyl)-1H-pyrazolo[4,3-c]pyridin-6-yl]-[1,4]oxazepan-4-yl-methanone Compound 83 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-bromo-5-methoxypyridine H30. Purification by flash chromatography (DCM/MeOH: 10/0 to 9/1) then by preparative HPLC afforded the compound 83 as a white powder in 69% yield. 1H-NMR (DMSO-d6, 400 MHz): 1.74 (quint, J 5.8 Hz, 1H, CH2); 1.92 (quint, J 5.8 Hz, 1H, CH2); 3.42-3.49 (m, 2H, N—CH2); 3.60-3.64 (m, 1H, N—CH2); 3.67-3.80 (m, 5H, CH2); 3.81 (s, 3H, CH3); 5.37 (q, J 8.9 Hz, 2H, CH2-CF3); 7.47 (dd, J 9.0, 3.1 Hz, 1H, Ar); 7.90 (bs, 1H, Ar, signal of a rotamer); 7.91 (bs, 1H, Ar, signal of a rotamer); 7.97 (d, J 9.0 Hz, 1H, Ar); 8.03 (d, J 3.1 Hz, 1H, Ar); 9.37 (d, J 1.0 Hz, 1H, Ar, signal of a rotamer); 9.38 (d, J 1.0 Hz, 1H, Ar, signal of a rotamer); 10.14 (s, 1H, NH). M/Z (M+H)+: 451

Compound 84: [1,4]Oxazepan-4-yl-[3-(thiazol-5-ylamino)-1-(2,2,2-trifluoro-ethyl)-1H-pyrazolo[4,3-c]pyridin-6-yl]-methanone Compound 84 was obtained according to General Procedure VII, Alternative 3, starting from [3-amino-1-(2,2,2-trifluoroethyl)pyrazolo[4,3-c]pyridin-6-yl]-(1,4-oxazepan-4-yl)methanone G1 and 5-bromo-thiazole H31 (1.2 equiv.). Purification by flash chromatography (DCM/MeOH: 100/0 to 9/1) on a 15 µm silica cartridge afforded the compound 84 as an orange powder in 48% yield. 1H-NMR (DMSO-d6, 400 MHz): 1.75 (quint, J 5.7 Hz, 1H, CH2); 1.92 (quint, J 5.7 Hz, 1H, CH2); 3.44-3.49 (m, 2H, N—CH2); 3.60-3.65 (m, 1H, N—CH2); 3.67-3.80 (m, 5H, CH2); 5.36 (q, J 9.0 Hz, 2H, N-CH2-CF3); 7.50-7.52 (m, 1H, Ar); 7.91 (bs, 1H, Ar, signal of a rotamer); 7.92 (bs, 1H, Ar, signal of a rotamer); 9.01-9.03 (m, 1H, Ar); 9.37 (d, J 0.9 Hz, 1H, Ar, signal of a rotamer); 9.38 (d, J 0.9 Hz, 1H, Ar, signal of a rotamer); 10.87 (bs, 1H, NH). M/Z (M+H)+: 427

Compound 85: [1,4]Oxazepan-4-yl-[3-(thiazol-2-ylamino)-1-(2,2,2-trifluoro-ethyl)-1H-pyrazolo[4,3-c]pyridin-6-yl]-methanone Compound 85 was obtained according to General Procedure VII, Alternative 3, starting from [3-amino-1-(2,2,2-trifluoroethyl)pyrazolo[4,3-c]pyridin-6-yl]-(1,4-oxazepan-4-yl)methanone G1 and 2-bromo-thiazole H32 (1.2 equiv.). Purification by flash chromatography (Cyclohexane/AcOEt: 10/0 to 0/10) afforded the compound 85 as an beige powder in 27% yield. 1H-NMR (DMSO-d6, 400 MHz): 1.74 (quint, J 5.6 Hz, 1H, CH2); 1.92 (quint, J 5.6 Hz, 1H, CH2); 3.42-3.49 (m, 2H, N—CH2); 3.60-3.64 (m, 1H, N—CH2); 3.67-3.80 (m, 5H, CH2); 5.40 (q, J 9.0 Hz, 2H, N-CH2-CF3); 7.12 (bs, 1H, Ar); 7.42 (bs, 1H, Ar); 7.97 (bs, 1H, Ar, signal of a rotamer); 7.98 (bs, 1H, Ar, signal of a rotamer); 9.38 (bs, 1H, Ar); 12.00 (bs, 1H, NH). M/Z (M+H)+: 427

Compound 86: 6-[6-([1,4]Oxazepane-4-carbonyl)-1-(2,2,2-trifluoro-ethyl)-1H-pyrazolo[4,3-c]pyridin-3-ylamino]-1H-pyridin-2-one Compound 86 was obtained according to General Procedure VII, Alternative 3, starting from [3-amino-1-(2,2,2-trifluoroethyl)pyrazolo[4,3-c]pyridin-6-yl]-(1,4-oxazepan-4-yl)methanone G1 and 6-bromo-1,2-dihydropyridin-2-one H33 (1.2 equiv.). Purification by preparative HPLC afforded the compound 86 as an beige powder in 54% yield. 1H-NMR (DMSO-d6, 400 MHz): 1.74 (quint, J 5.8 Hz, 1H, CH2); 1.92 (quint, J 5.8 Hz, 1H, CH2); 3.43-3.48 (m, 2H, N—CH2); 3.59-3.63 (m, 1H, N—CH2); 3.68-3.79 (m, 5H, CH2); 5.41 (q, J 8.7 Hz, 2H, CH2-CF3); 6.06-6.17 (m, 1H, Ar); 6.93-7.43 (m, 1H, NH); 7.54 (t, J 7.8 Hz, 1H, Ar); 7.94 (s, 1H, Ar, signal of a rotamer); 7.95 (s, 1H, Ar, signal of a rotamer); 9.34 (bs, 1H, Ar); 10.04-10.17 (m, 1H, Ar); 10.16-10.62 (m, 1H, NH). M/Z (M+H)+: 437

Compound 87: 3-[[6-(1,4-oxazepane-4-carbonyl)-1-(2,2,2-trifluoroethyl)pyrazolo[4,3-c]pyridin-3-yl]amino]-1H-pyridin-2-one Compound 87 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 2-(benzyloxy)-3-bromopyridine H34. Purification by flash chromatography (DCM/MeOH: 100/0 to 97/3) afforded a white powder in 82% yield. The powder was dissolved in a MeOH/AcOEt (3/1, 0.05M) mixture, then Pd/C (10% w/w) was added. The reaction mixture was stirred at rt for 1.5 h under H2 atmosphere. The reaction mixture was then filtered on a celite pad, concentrated, purified by flash chromatography (DCM/MeOH: 10/0 to 9/1) to afford the compound 87 as a pale green powder in 56% yield. 1H-NMR (DMSO-d6, 400 MHz) δ: 1.74 (quint, J 5.6 Hz, 1H, CH2); 1.92 (quint, J 5.6 Hz, 1H, CH2); 3.44-3.47 (m, 2H, N—CH2); 3.61-3.63 (m, 1H, N—CH2); 3.68-3.79 (m, 5H, CH2); 5.38 (q, J 9.0 Hz, 2H, CH2-CF3); 6.28 (t, J 7.2 Hz, 1H, Ar); 6.95-6.99 (m, 1H, Ar); 7.90 (bs, 1H, Ar, signal of a rotamer); 7.91 (bs, 1H, Ar, signal of a rotamer); 8.22 (dt, J 7.2, 1.4 Hz, 1H, Ar); 9.06 (s, 1H, NH);

9.43 (d, J 0.8 Hz, 1H, Ar, signal of a rotamer); 9.45 (d, J 0.8 Hz, 1H, Ar, signal of a rotamer); 11.87 (bs, 1H, NH). M/Z (M+H)+: 437

Compound 88: [3-[(5-fluoro-4-hydroxy-2-pyridyl)amino]-1-(2,2,2-trifluoroethyl)pyrazolo[4,3-c]pyridin-6-yl]-(1,4-oxazepan-4-yl)methanone Compound 88 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 4-(benzyloxy)-2-bromo-5-fluoropyridine H35. Purification by flash chromatography (DCM/MeOH: 100/0 to 95/5) afforded a white powder in 79% yield. The powder was dissolved in a MeOH (0.07M), then Pd/C (10% w/w) was added. The reaction mixture was stirred at rt for 1 h under H2 atmosphere. The reaction mixture was then filtered on a celite pad, concentrated, purified by flash chromatography (DCM/MeOH: 10/0 to 9/1) to afford the compound 88 as a yellow powder in 94% yield. 1H-NMR (DMSO-d6, 400 MHz): 1.74 (quint, J 5.8 Hz, 1H, CH2); 1.92 (quint, J 5.8 Hz, 1H, CH2); 3.43-3.50 (m, 2H, N—CH2); 3.60-3.65 (m, 1H, N—CH2); 3.66-3.79 (m, 5H, CH2); 5.35 (q, J 9.1 Hz, 2H, CH2-CF3); 7.55 (bs, 1H, Ar); 7.92 (bs, 1H, signal of a rotamer, Ar); 7.93 (bs, 1H, signal of a rotamer, Ar); 8.04 (bs, 1H, Ar); 9.35 (bs, 1H, signal of a rotamer, Ar); 9.36 (bs, 1H, signal of a rotamer, Ar); 10.13 (s, 1H, NH), 11.18 (bs, 1H, OH). M/Z (M+H)+: 455

Compound 89: [3-[(5-fluoro-3-hydroxy-2-pyridyl)amino]-1-(2,2,2-trifluoroethyl)pyrazolo[4,3-c]pyridin-6-yl]-(1,4-oxazepan-4-yl)methanone Compound 89 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 3-(benzyloxy)-2-bromo-5-fluoropyridine H36. Purification by flash chromatography (DCM/MeOH: 100/0 to 95/5) afforded a white powder. The powder was dissolved in a MeOH (0.04M), then Pd/C (10% w/w) was added. The reaction mixture was stirred at rt for 1 h under H2 atmosphere. The reaction mixture was then filtered on a celite pad, concentrated, purified by flash chromatography (DCM/MeOH: 10/0 to 9/1) to afford the compound 89 as a beige powder in 85% yield over 2 steps. 1H-NMR (DMSO-d6, 400 MHz): 1.74 (quint, J 5.8 Hz, 1H, CH2); 1.92 (quint, J 5.8 Hz, 1H, CH2); 3.42-3.49 (m, 2H, N—CH2); 3.60-3.64 (m, 1H, N—CH2); 3.67-3.80 (m, 5H, CH2); 5.39 (q, J 8.9 Hz, 2H, CH2-CF3); 7.04 (dd, J 9.5, 2.8 Hz, 1H, Ar); 7.63-7.65 (m, 1H, Ar); 7.95 (bs, 1H, Ar, signal of a rotamer); 7.96 (bs, 1H, Ar, signal of a rotamer); 8.73 (s, 1H, OH); 9.01 (d, J 0.9 Hz, 1H, Ar, signal of a rotamer); 9.02 (d, J 0.9 Hz, 1H, Ar, signal of a rotamer); 10.73 (s, 1H, NH). M/Z (M+H)+: 455

Compound 90: [3-[(4-fluoro-3-hydroxy-2-pyridyl)amino]-1-(2,2,2-trifluoroethyl)pyrazolo[4,3-c]pyridin-6-yl]-(1,4-oxazepan-4-yl)methanone Compound 90 was obtained according to General Procedure VII, Alternative 2, starting from [3-amino-1-(2,2,2-trifluoroethyl)pyrazolo[4,3-c]pyridin-6-yl]-(1,4-oxazepan-4-yl)methanone G1 and 3-(benzyloxy)-2-bromo-4-fluoropyridine H37. Purification by flash chromatography (DCM/AcOEt: 10/0 to 3/7) afforded a yellow powder. The powder was dissolved in a MeOH (0.07M), then Pd/C (10% w/w) was added. The reaction mixture was stirred at rt for 1 h under H2 atmosphere. The reaction mixture was then filtered on a celite pad, concentrated, purified by flash chromatography (DCM/MeOH: 100/0 to 95/5) to afford the compound 90 as a white powder in 46% yield over 2 steps. 1H-NMR (DMSO-d6, 400 MHz) 5: 1.75 (quint, J 5.8 Hz, 1H, CH2); 1.92 (quint, J 5.8 Hz, 1H, CH2); 3.44-3.52 (m, 2H, N—CH2); 3.61-3.64 (m, 1H, N—CH2); 3.66-3.79 (m, 5H, CH2); 5.42 (q, J 9.2 Hz, 2H, CH2-CF3); 6.84 (d, J 10.0, 5.6 Hz, 1H, Ar); 7.64 (dd, J 10.0, 7.3 Hz, Ar); 7.98 (bs, 1H, Ar, signal of a rotamer); 7.99 (bs, 1H, Ar, signal of a rotamer); 9.01-9.10 (m, 2H, Ar); 10.18 (bs, 1H, NH). M/Z (M+H)+: 455

General Procedure VIII: Synthesis of Compounds K (Scheme 2)

To a solution of 2,4-dichloro-5-cyanopyridine (1 equiv.) in THF (0.2M) was added hydrazine monohydrate (2.5 equiv.). The reaction mixture was heated at 60° C. for 30 min, then allowed to cool down to rt. Trifluoroacetic acid (3 equiv.) was added. The reaction mixture was stirred at rt for 15 min, then quenched by adding potassium carbonate (6 equiv.). The reaction mixture was diluted with a DCM/MeOH (7/3) mixture. The resulting precipitate was filtered off. The filtrate was concentrated, then purified by flash chromatography (DCM/MeOH: 10/0 to 9/1) to afford 6-chloro-1H-pyrazolo[4,3-c]pyridin-3-amine as a brown solid in 39% yield. M/Z (M+H)+: 169 To a solution of 6-chloro-1H-pyrazolo[4,3-c]pyridin-3-amine (1 equiv.) in DMF (0.15M) at 0° C. was added sodium hydride (1.2 equiv.). The reaction mixture was stirred at 0° C. for 10 min. 2,2,2-trifluoroethyl trifluoromethanesulfonate E1 (1.5 equiv.) was added. The reaction mixture was stirred at rt for 15 min. The reaction mixture was diluted with AcOEt, washed with water, dried over magnesium sulfate then concentrated. The resulting oil was purified by flash chromatography (Cyclohexane/AcOEt: 10/0 to 4/6) to afford 6-chloro-1-(2,2,2-trifluoroethyl)-1H-pyrazolo[4,3-c]pyridin-3-amine as a brown solid in 71% yield. M/Z (M+H)+: 251 To a degassed suspension of 6-chloro-1-(2,2,2-trifluoroethyl)-1H-pyrazolo[4,3-c]pyridin-3-amine (1 equiv.) in dioxane (0.1M) were added halogenated (hetero)aromatic H, cesium carbonate (2.4 equiv.), Pd2(dba)3 (10 mol %) and BINAP (20 mol %). The reaction mixture was stirred 2 h at 100° C. The reaction mixture was allowed to cool down to rt, diluted with AcOEt, filtered on a celite pad, then purified by flash chromatography to afford compound K.

Compound K1: 6-chloro-N-(5-fluoropyridin-2-yl)-1-(2,2,2-trifluoroethyl)-1H-pyrazolo[4,3-c]pyridin-3-amine Compound K1 was obtained according to General Procedure VIII, by using 2-bromo-5-fluoropyridine H3. Purification by flash chromatography (Cyclohexane/AcOEt: 10/0 to 5/5) afforded K1 as an orange powder in 58% yield. M/Z (M+H)+: 346/348

Compound K2: 6-chloro-N-(4-fluoropyridin-2-yl)-1-(2,2,2-trifluoroethyl)-1H-pyrazolo[4,3-c]pyridin-3-amine Compound K2 was obtained according to General Procedure VIII, by using 2-bromo-4-fluoropyridine H5. Purification by flash chromatography (Cyclohexane/AcOEt: 10/0 to 5/5) afforded K2 as a yellow powder in 45% yield. M/Z (M+H)+: 346/348

Compound K3: 6-chloro-N-(pyrazin-2-yl)-1-(2,2,2-trifluoroethyl)-1H-pyrazolo[4,3-c]pyridin-3-amine Compound K3 was obtained according to General Procedure VIII, by using 2-bromo-pyrazine H38. Purification by flash chromatography (Cyclohexane/AcOEt: 10/0 to 5/5) afforded K3 as a yellow powder in 81% yield. M/Z (M+H)+: 329/331

General Procedure IX: Synthesis of Compounds L from Compounds K (Scheme 2)

Under argon atmosphere, to a solution of compound K (1 equiv.) in anhydrous DMA (0.2M) was added zinc cyanide (1.2 equiv.). The reaction mixture was degassed with argon. Pd(PPh3)4 (10 mol %) was added. The reaction mixture was heated 25 min at 130° C. under microwave irradiation. The reaction mixture was diluted with AcOEt, washed with water and brine, dried over magnesium sulfate then concentrated. The resulting crude was purified by flash chromatography (Cyclohexane/AcOEt: 10/0 to 5/5) to afford compound L.

Compound L1: 3-((5-fluoropyridin-2-yl)amino)-1-(2,2,2-trifluoroethyl)-1H-pyrazolo[4,3-c]pyridine-6-carbonitrile Compound L1 was obtained according to General Procedure IX, starting from compound K1. Purification by flash chromatography (Cyclohexane/AcOEt: 10/0 to 6/4) afforded L1 as a yellow powder in 72% yield. M/Z (M+H)+: 337

Compound L2: 3-((4-fluoropyridin-2-yl)amino)-1-(2,2,2-trifluoroethyl)-1H-pyrazolo[4,3-c]pyridine-6-carbonitrile Compound L2 was obtained according to General Procedure IX, starting from compound K2. Purification by flash chromatography (Cyclohexane/AcOEt: 10/0 to 5/5) afforded L2 as a yellow powder in 66% yield. M/Z (M+H)+: 337

Compound L3: 3-((pyrazin-2-yl)amino)-1-(2,2,2-trifluoroethyl)-1H-pyrazolo[4,3-c]pyridine-6-carbonitrile Compound L3 was obtained according to General Procedure IX, starting from compound K3. Purification by flash chromatography (DCM/MeOH: 100/0 to 96/4) afforded L3 as a beige powder in 79% yield. M/Z (M+H)+: 320

General Procedure X: Synthesis of Compounds M from Compounds L (Scheme 2)

To a solution of compound L (1 equiv.) in DMSO (0.1M) were added a solution of H2O2, 30% in water, (1.5 equiv.) and potassium carbonate (0.2 equiv.). The reaction mixture was stirred overnight at rt. Water was added to the reaction mixture. The resulting precipitate was filtered then dried under vacuum at 70° C. with phosphorus pentoxide to afford compound M.

Compound M1: 3-((5-fluoropyridin-2-yl)amino)-1-(2,2,2-trifluoroethyl)-1H-pyrazolo[4,3-c]pyridine-6-carboxamide Compound M1 was obtained according to General Procedure X, starting from compound L1, as a yellow powder in 98% yield. M/Z (M+H)+: 355

Compound M2: 3-((4-fluoropyridin-2-yl)amino)-1-(2,2,2-trifluoroethyl)-1H-pyrazolo[4,3-c]pyridine-6-carboxamide Compound M2 was obtained according to General Procedure X, starting from compound L2, as a yellow powder in 94% yield. M/Z (M+H)+: 355

Compound M3: 3-((pyrazin-2-yl)amino)-1-(2,2,2-trifluoroethyl)-1H-pyrazolo[4,3-c]pyridine-6-carboxamide Compound M3 was obtained according to General Procedure X, starting from compound L3, as a yellow powder in 74% yield. M/Z (M+H)+: 338

General Procedure XI: Synthesis of Compounds N from Compounds M (Scheme 2)

To a solution of compound M (1 equiv.) in MeOH (0.1M) was added DMF-DMA (6 equiv.). The reaction mixture was heated overnight at 50° C. The reaction mixture was concentrated to dryness, then purified by flash chromatography to afford compound N.

Compound N1: methyl 3-((5-fluoropyridin-2-yl)amino)-1-(2,2,2-trifluoroethyl)-1H-pyrazolo[4,3-c]pyridine-6-carboxylate Compound N1 was obtained according to General Procedure XI, starting from compound M1. Purification by flash chromatography (DCM/MeOH: 100/0 to 97.5/2.5) afforded compound N1 as a yellow powder in 84% yield. M/Z (M+H)+: 370

Compound N2: methyl 3-((4-fluoropyridin-2-yl)amino)-1-(2,2,2-trifluoroethyl)-1H-pyrazolo[4,3-c]pyridine-6-carboxylate Compound N2 was obtained according to General Procedure XI, starting from compound M2. Purification by flash chromatography (DCM/MeOH: 100/0 to 95/5) afforded compound N1 as a white powder in 65% yield. M/Z (M+H)+: 370

Compound N3: methyl 3-((pyrazin-2-yl)amino)-1-(2,2,2-trifluoroethyl)-1H-pyrazolo[4,3-c]pyridine-6-carboxylate Compound N3 was obtained according to General Procedure XI, starting from compound M3. Purification by flash chromatography (DCM/MeOH: 100/0 to 97.5/2.5) afforded compound N3 as a white powder in 80% yield. M/Z (M+H)+: 353

General Procedure XII: Synthesis of Compounds O from Compounds N (Scheme 2)

To a solution of compound N (1 equiv.) in THF (0.1M) were added LiOH, 1N in water (1.1 equiv.). The reaction mixture was stirred 2 h at rt. The reaction mixture was concentrated to dryness to afford compound O.

Compound O1: lithium 3-((5-fluoropyridin-2-yl)amino)-1-(2,2,2-trifluoroethyl)-1H-pyrazolo[4,3-c]pyridine-6-carboxylate Compound O1 was obtained according to General Procedure XII, starting from compound N1, as a yellow powder in 89% yield. M/Z (M+H)+: 356

Compound O2: lithium 3-((4-fluoropyridin-2-yl)amino)-1-(2,2,2-trifluoroethyl)-1H-pyrazolo[4,3-c]pyridine-6-carboxylate Compound O2 was obtained according to General Procedure XII, starting from compound N2, as a white powder in 92% yield. M/Z (M+H)+: 370

Compound O3: lithium 3-((pyrazin-2-yl)amino)-1-(2,2,2-trifluoroethyl)-1H-pyrazolo[4,3-c]pyridine-6-carboxylate Compound O3 was obtained according to General Procedure XII, starting from compound N3, as a yellow powder in 95% yield. M/Z (M+H)+: 339

General Procedure XIII: Synthesis of Compounds from Compounds O (Scheme 2)

To a solution of compound O (1 equiv.) in DMF (0.1M) were added amine B (1.1 equiv.), diisopropylethylamine (3 equiv.) and HATU (1.3 equiv.). The reaction mixture was stirred 1 h at rt. The reaction mixture was diluted with AcOEt, washed with a saturated ammonium chloride solution and brine, dried over magnesium sulfate, then concentrated. The resulting crude mixture was purified by flash chromatography to afford the compound.

Compound 91: (6,6-dideuterio-1,4-oxazepan-4-yl)-[3-[(5-fluoro-2-pyridyl)amino]-1-(2,2,2-trifluoroethyl)pyrazolo[4,3-c]pyridin-6-yl]methanone Compound 91 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and 6,6-dideuterio-1,4-oxazepane hydrochloride B7. Purification by preparative HPLC afforded the compound 91 as a beige powder in 50% yield. 1H-NMR (DMSO-d6, 400 MHz): 3.44-3.49 (m, 2H, N—CH2); 3.60-3.64 (m, 1H, N—CH2); 3.68 (s, 1H, N—CH2); 3.70-3.79 (m, 4H, CH2); 5.40 (q, J 9.1 Hz, 2H, CH2-CF3); 7.76 (td, J 8.7, 3.0 Hz, 1H, Ar); 7.93 (bs, 1H, signal of a rotamer, Ar); 7.94 (bs, 1H, signal of a rotamer, Ar); 8.01 (dd, J 9.2, 3.9 Hz, 1H, Ar); 8.28 (d, J 3.0, 1H, Ar); 9.38 (d, J 1.0 Hz, 1H, signal of a rotamer, Ar); 9.39 (d, J 1.0 Hz, 1H, signal of a rotamer, Ar); 10.43 (bs, 1H, NH). M/Z (M+H)+: 441

Compound 92: [3-[(5-fluoro-2-pyridyl)amino]-1-(2,2,2-trifluoroethyl)pyrazolo[4,3-c]pyridin-6-yl]-(6-hydroxy-1,4-oxazepan-4-yl)methanone Compound 92 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and 1,4-oxazepan-6-ol B5. Purification by flash chromatography (DCM/MeOH: 100/0 to 93/7) afforded the compound 92 as a beige powder in 54% yield. 1H-NMR (DMSO-d6, 400 MHz): 3.19-3.42 (m, 1H, CH2); 3.47-3.80 (m, 6H, CH, CH2); 3.80-3.88 (m, 1H, signal of a rotamer, CH2); 3.94-4.03 (m, 1H, CH2); 4.19-4.26 (m, 1H, signal of a rotamer, CH); 5.06 (d, J 4.7 Hz, 1H, OH, major rotamer); 5.11 (d, J 4.7 Hz, 1H, OH, minor rotamer); 5.35-5.46 (m, 2H, CH2-CF3); 7.72-7.80 (m, 1H, Ar); 7.96 (bs, 1H, Ar, signal of a rotamer); 7.97 (bs, 1H, Ar, signal of a rotamer); 7.98-8.04 (m, 1H, Ar); 8.26-8.30 (m, 1H, Ar); 9.37 (bs, 1H, Ar, signal of a rotamer); 9.39 (bs, 1H, Ar, signal of a rotamer); 10.43 (s, 1H, NH, signal of a rotamer); 10.45 (s, 1H, NH, signal of a rotamer). M/Z (M+H)+: 455

Compound 93: [(6S)-6-fluoro-1,4-oxazepan-4-yl]-[3-[(5-fluoro-2-pyridyl)amino]-1-(2,2,2-trifluoroethyl)pyrazolo[4,3-c]pyridin-6-yl]methanone Compound 93 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and 6-fluoro-1,4-oxazepane hydrochloride B8. Purification by flash chromatography (DCM/MeOH: 10/0 to 9/1) then by preparative HPLC afforded the compound 93 as a beige powder in 52% yield. 1H-NMR (DMSO-d6, 400 MHz) 80° C.: 3.42-3.53 (m, 1H, CH2, signal of a rotamer); 3.54-3.67 (m, 2H, CH2); 3.73-3.92 (m, 3H, CH2); 3.95-4.10 (m, 2H, CH2); 4.14-4.24 (m, 1H, CH2, signal of a rotamer); 4.79-5.15 (m, 1H, CH—F); 5.34-5.46 (m, 2H, CH2CF3); 7.69 (td, J 8.6, 3.2 Hz, 1H, Ar); 7.98-8.02 (m, 2H, Ar); 8.28 (d, J 2.9 Hz, 1H, Ar); 9.39 (d, J 1.0 Hz, 1H, Ar); 10.44 (s, 1H, NH). M/Z (M+H)+: 457

Compound 94: [3-[(5-fluoro-2-pyridyl)amino]-1-(2,2,2-trifluoroethyl)pyrazolo[4,3-c]pyridin-6-yl]-(4-hydroxypiperidin-1-yl)methanone Compound 94 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and 4-hydroxy-piperidine B3. Purification by flash chromatography (DCM/MeOH: 10/0 to 9/1) afforded the compound 94 as a beige powder in 96% yield. 1H-NMR (DMSO-d6, 400 MHz): 1.29-1.46 (m, 2H, CH2); 1.65-1.74 (m, 1H, CH2); 1.78-1.88 (m, 1H, CH2); 3.05-3.15 (m, 1H, N—CH2); 3.45-3.55 (m, 1H, N—CH2); 3.45-3.54 (m, 1H, N—CH2); 3.75 (sext, J 4.2 Hz, 1H, CH); 4.04-4.12 (m, 1H, N—CH2); 4.78 (d, J 4.2 Hz, 1H, OH); 5.39 (q, J 9.2 Hz, 2H, N-CH2-CF3); 7.76 (td, J 9.0, 3.0 Hz, 1H, Ar); 7.90 (bs, 1H, Ar); 8.03 (dd, J 9.0, 3.6 Hz 1H, Ar); 8.28 (d, J 3.0 Hz, 1H, Ar); 9.37 (d, J 1.0 Hz, 1H, Ar); 10.42 (s, 1H, NH). M/Z (M+H)+: 439

Compound 95: [3-(5-Fluoro-pyridin-2-ylamino)-1-(2,2,2-trifluoro-ethyl)-1H-pyrazolo[4,3-c]pyridin-6-yl]-(4-hydroxy-4-methyl-piperidin-1-yl)-methanone Compound 95 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and 4-hydroxy-4-methyl-piperidine B6. Purification by flash chromatography (DCM/MeOH: 10/0 to 9/1) afforded the compound 95 as a beige powder in 80% yield. 1H-NMR (DMSO-d6, 400 MHz): 1.17 (s, 3H, CH3), 1.40-1.64 (m, 4H, CH2), 3.20-3.40 (m, 4H, CH2), 4.06-4.14 (m, 1H, CH2), 4.40 (s, 1H, OH), 5.38 (q, J 9.0 Hz, 2H, N-CH2-CF3); 7.76 (td, J 9.0, 3.0 Hz, 1H, Ar); 7.88 (bs, 1H, Ar); 8.00 (dd, J 9.0, 3.9 Hz, 1H, Ar); 8.28 (d, J 3.0 Hz, 1H, Ar); 9.37 (d, J 1.0 Hz, 1H, Ar); 10.42 (s, 1H, NH). M/Z (M+H)+: 453

Compound 96: (4-Fluoro-piperidin-1-yl)-[3-(5-fluoro-pyridin-2-ylamino)-1-(2,2,2-trifluoro-ethyl)-1H-pyrazolo[4,3-c]pyridin-6-yl]-methanone Compound 96 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and 4-fluoro-piperidine hydrochloride B9. Purification by flash chromatography (DCM/MeOH: 100/0 to 95/5) afforded the compound 96 as a beige powder in 63% yield. 1H-NMR (DMSO-d6, 400 MHz): 1.62-2.06 (m, 4H, CH2), 3.33-3.52 (m, 2H, N—CH2), 3.65-3.80 (m, 2H, N—CH2), 4.84-5.04 (m, 1H, CH—F), 5.39 (q, J 9.2 Hz, 2H, CH2-CF3); 7.76 (td, J 8.6, 3.0 Hz, 1H, Ar); 7.94 (bs, 1H, Ar); 8.01 (dd, J 9.2, 3.7 Hz, 1H, Ar); 8.28 (d, J 3.0 Hz, 1H, Ar); 9.39 (d, J 1.0 Hz, 1H, Ar); 10.43 (s, 1H, NH). M/Z (M+H)+: 441

Compound 97: [(3R)-3-hydroxy-piperidin-1-yl]-[3-(5-Fluoro-pyridin-2-ylamino)-1-(2,2,2-trifluoro-ethyl)-1H-pyrazolo[4,3-c]pyridin-6-yl]methanone Compound 97 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and (3R)-3-hydroxy-piperidine hydrochloride B10. Purification by flash chromatography (DCM/MeOH: 100/0 to 95/5) afforded the compound 97 as a pale yellow powder in 50% yield. 1H-NMR (DMSO-d6, 400 MHz): 1.34-1.50 (m, 2H, CH2); 1.58-1.96 (m, 2H, CH2); 2.79-2.90 (m, 1H, N—CH2, signal of a rotamer), 2.92-3.02 (m, 1H, N—CH2); 3.15-3.24 (m, 1H, N—CH2, signal of a rotamer); 3.38-3.60 (m, 2H, CH2), 3.91-3.98 (m, 1H, CH—OH, signal of a rotamer), 4.25-3.34 (m, 1H, CH—OH, signal of a rotamer), 4.70-4.90 (m, 1H, CH—OH, signal of a rotamer), 4.95-5.10 (m, 1H, CH—OH, signal of a rotamer), 5.39 (q, J 8.2 Hz, 2H, N-CH2-CF3); 7.76 (td, J 8.8, 3.6 Hz, 1H, Ar); 7.90 (d, J 12.2, 1H, Ar); 8.06 (dd, J 8.6 Hz, J 4.2 Hz, 1H, Ar); 8.28 (d, J 3.0 Hz, 1H, Ar); 9.38 (d, J 3.0 Hz, 1H, Ar); 10.43 (d, J 6.6 Hz 1H, NH). M/Z (M+H)+: 439

Compound 98: [(3S)-3-hydroxy-piperidin-1-yl]-[3-(5-Fluoro-pyridin-2-ylamino)-1-(2,2,2-trifluoro-ethyl)-1H-pyrazolo[4,3-c]pyridin-6-yl]methanone Compound 98 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and (3S)-3-hydroxy-piperidine hydrochloride B11. Purification by flash chromatography (DCM/MeOH: 100/0 to 94/6) afforded the compound 98 as a pale yellow powder in 24% yield. 1H-NMR (DMSO-d6, 400 MHz): 1.34-1.50 (m, 2H, CH2); 1.58-1.96 (m, 2H, CH2); 2.79-2.90 (m, 1H, N—CH2, signal of a rotamer), 2.92-3.02 (m, 1H, N—CH2); 3.15-3.24 (m, 1H, N—CH2, signal of a rotamer); 3.38-3.60 (m, 2H, CH2), 3.91-3.98 (m, 1H, CH—OH, signal of a rotamer), 4.25-3.34 (m, 1H, CH—OH, signal of a rotamer), 4.70-4.90 (m, 1H, CH—OH, signal of a rotamer), 4.95-5.10 (m, 1H, CH—OH, signal of a rotamer), 5.39 (q, J 8.2 Hz, 2H, N-CH2-CF3); 7.76 (td, J 8.8, 3.6 Hz, 1H, Ar); 7.90 (d, J 12.2, 1H, Ar); 8.06 (dd, J 8.6 Hz, J 4.2 Hz, 1H, Ar); 8.28 (d, J 3.0 Hz, 1H, Ar); 9.38 (d, J 3.0 Hz, 1H, Ar); 10.43 (d, J 6.6 Hz 1H, NH). M/Z (M+H)+: 439

Compound 99: [(3R)-3-fluoro-piperidin-1-yl]-[3-(5-Fluoro-pyridin-2-ylamino)-1-(2,2,2-trifluoro-ethyl)-1H-pyrazolo[4,3-c]pyridin-6-yl]methanone Compound 99 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and (3R)-3-fluoro-piperidine hydrochloride B12. Purification by flash chromatography (DCM/MeOH: 100/0 to 95/5) afforded the compound 99 as a pale yellow powder in 79% yield. 1H-NMR (DMSO-d6, 400 MHz): 1.40-1.50 (m, 1H, CH2, signal of a rotamer); 1.53-1.63 (m, 1H, CH2, signal of a rotamer) 1.66-1.95 (m, 3H, CH2); 3.15-3.27 (m, 1H, N—CH2); 3.40-3.49 (m, 1H, N—CH2, signal of a rotamer); 3.49-3.61 (m, 1H, N—CH2); 3.66-3.78 (m, 1H, N—CH2, signal of a rotamer); 4.05-4.13 (m, 1H, N—CH2, signal of a rotamer); 4.18-4.28 (m, 1H, N—CH2, signal of a rotamer); 4.58-4.93 (m, 1H, CHF); 5.39 (q, J 9.0 Hz, 2H, CH2-CF3); 7.76 (td, J 9.0, 3.0 Hz, 1H, Ar); 7.91 (s, 1H, Ar, signal of a rotamer); 7.95 (s, 1H, Ar, signal of a rotamer); 8.01 (dd, J 9.0, 3.8 Hz 1H, Ar); 8.28 (d, J 3.0 Hz, 1H, Ar); 9.39 (bs, 1H, Ar); 10.43 (s, 1H, NH). M/Z (M+H)+: 441

Compound 100: [(3S)-3-fluoro-piperidin-1-yl]-[3-(5-Fluoro-pyridin-2-ylamino)-1-(2,2,2-trifluoro-ethyl)-1H-pyrazolo[4,3-c]pyridin-6-yl]methanone Compound 100 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and (3S)-3-fluoro-piperidine hydrochloride B13. Purification by flash chromatography (DCM/MeOH: 100/0 to 95/5) then by preparative HPLC afforded the compound 100 as a pale yellow powder in 79% yield. 1H-NMR (DMSO-d6, 400 MHz): 1.40-1.50 (m, 1H, CH2, signal of a rotamer); 1.53-1.63 (m, 1H, CH2, signal of a rotamer) 1.66-1.95 (m, 3H, CH2); 3.15-3.27 (m, 1H, N—CH2); 3.40-3.49 (m, 1H, N—CH2, signal of a rotamer); 3.49-3.61 (m, 1H, N—CH2); 3.66-3.78 (m, 1H, N—CH2, signal of a rotamer); 4.05-4.13 (m, 1H, N—CH2, signal of a rotamer); 4.18-4.28 (m, 1H, N—CH2, signal of a rotamer); 4.58-4.93 (m, 1H, CHF); 5.39 (q, J 9.0 Hz, 2H, CH2-CF3); 7.76 (td, J 9.0, 3.0 Hz, 1H, Ar); 7.91 (s, 1H, Ar, signal of a rotamer); 7.95 (s, 1H, Ar, signal of a rotamer); 8.01 (dd, J 9.0, 3.8 Hz 1H, Ar); 8.28 (d, J 3.0 Hz, 1H, Ar); 9.39 (bs, 1H, Ar); 10.43 (s, 1H, NH). M/Z (M+H)+: 441

Compound 101: [3-[(5-fluoro-2-pyridyl)amino]-1-(2,2,2-trifluoroethyl)pyrazolo[4,3-c]pyridin-6-yl]-[(3R)-3-(hydroxymethyl)-1-piperidyl]methanone Compound 101 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and (3R)-3-(hydroxymethyl)-piperidine B14. Purification by preparative HPLC afforded the compound 101 as a yellow powder in 52% yield. 1H-NMR (DMSO-d6, 400 MHz): 1.17-1.30 (m, 1H, CH2); 1.37-1.52 (m, 1H, CH2); 1.54-1.80 (m, 3H, CH, CH2); 2.59-3.66 (m, 6H, CH2); 4.31-4.38 (m, 1H, OH, signal of a rotamer); 4.45-4.52 (m, 1H, OH, signal of a rotamer); 5.40 (q, J 9.0 Hz, 2H, CH2-CF3); 7.77 (td, J 8.7, 3.0 Hz, 1H, Ar);

7.91 (bs, 1H, Ar); 7.99-8.04 (m, 1H, Ar); 8.29 (d, J 3.0 Hz, 1H, Ar); 9.40 (bs, 1H, Ar); 10.47 (s, 1H, NH). M/Z (M+H)+: 453

Compound 102: [3-[(5-fluoro-2-pyridyl)amino]-1-(2,2,2-trifluoroethyl)pyrazolo[4,3-c]pyridin-6-yl]-[(3S)-3-(hydroxymethyl)-1-piperidyl]methanone Compound 102 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and (3S)-3-(hydroxymethyl)-piperidine B15. Purification by flash chromatography (DCM/MeOH: 100/0 to 9/1) then by preparative HPLC afforded the compound 102 as a yellow powder in 36% yield. 1H-NMR (DMSO-d6, 400 MHz): 1.17-1.30 (m, 1H, CH2); 1.37-1.52 (m, 1H, CH2); 1.54-1.80 (m, 3H, CH, CH2); 2.59-3.66 (m, 6H, CH2); 4.31-4.38 (m, 1H, OH, signal of a rotamer); 4.45-4.52 (m, 1H, OH, signal of a rotamer); 5.40 (q, J 9.0 Hz, 2H, CH2-CF3); 7.77 (td, J 8.7, 3.0 Hz, 1H, Ar); 7.91 (bs, 1H, Ar); 7.99-8.04 (m, 1H, Ar); 8.29 (d, J 3.0 Hz, 1H, Ar); 9.40 (bs, 1H, Ar); 10.47 (s, 1H, NH). M/Z (M+H)+: 453

Compound 103: (3,3-Difluoro-4-hydroxy-piperidin-1-yl)-[3-(5-fluoro-pyridin-2-ylamino)-1-(2,2,2-trifluoro-ethyl)-1H-pyrazolo[4,3-c]pyridin-6-yl]-methanone Compound 103 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and 3,3-Difluoro-4-hydroxypiperidine B16. Purification by flash chromatography (DCM/MeOH: 100/0 to 9/1) afforded the compound 103 as a pale orange powder in 97% yield. 1H-NMR (DMSO-d6, 400 MHz): 1.60-1.74 (m, 1H, CH2); 1.78-1.94 (m, 1H, CH2); 3.34-3.41 (m, 1H, CH2, signal of a rotamer); 3.48-3.65 (m, 1H, N—CH2); 3.75-4.00 (m, 3H, N—CH2, CH—OH); 4.05-4.16 (m, 1H, N—CH2, single of a rotamer); 5.36-5.48 (m, 2H, N-CH2-CF3); 5.76-5.84 (m, 1H, OH); 7.76 (td, J 9.0, 3.0 Hz, 1H, Ar); 7.94-8.06 (m, 2H, Ar); 8.28 (d, J 3.0 Hz, 1H, Ar); 9.40 (bs, 1.0 Hz, 1H, Ar); 10.45 (s, 1H, NH). M/Z (M+H)+: 439

Compound 104: [3-[(5-fluoro-2-pyridyl)amino]-1-(2,2,2-trifluoroethyl)pyrazolo[4,3-c]pyridin-6-yl]-(3-hydroxy-3-methyl-piperidin-1-yl)methanone Compound 104 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and 3-hydroxy-3-methyl-piperidine B16. Purification by flash chromatography (DCM/MeOH: 100/0 to 9/1) afforded the compound 104 as a pale orange powder in 97% yield. 1H-NMR (DMSO-d6, 400 MHz): 0.97 (s, 3H, CH3 signal of a rotamer); 1.19 (s, 3H, CH3 signal of a rotamer); 1.20-1.86 (m, 4H, CH2); 3.13 (d, J 13.2 Hz, 1H, N—CH2, signal of a rotamer); 3.17-3.22 (m, 1H, N—CH2); 3.29 (d, J 13.2 Hz, 1H, N—CH2, signal of a rotamer); 3.31-3.36 (m, 1H, N—CH2, signal of a rotamer); 3.43 (d, J 12.4 Hz, 1H, N—CH2, signal of a rotamer); 3.54 (d, J 12.4 Hz, 1H, N—CH2, signal of a rotamer); 3.82-3.90 (m, 1H, CH2, signal of a rotamer); 4.58 (s, 1H, OH, signal of a rotamer); 4.63 (s, 1H, OH, signal of a rotamer); 5.33-5.47 (m, 2H, CH2-CF3); 7.76 (dd, J 8.6, 3.0 Hz, 1H, Ar); 7.86 (bs, 1H, Ar, signal of a rotamer); 7.93 (bs, 1H, Ar, signal of a rotamer); 8.01 (dd, J 9.2, 3.8 Hz, 1H, Ar); 8.29 (d, J 3.0 Hz, 1H, Ar); 9.36 (d, J 0.9 Hz, 1H, Ar, signal of a rotamer); 9.38 (d, J 0.9 Hz, 1H, Ar, signal of a rotamer); 10.42 (s, 1H, NH). M/Z (M+H)+: 455

Compound 105: Cis-[3-(5-Fluoro-pyridin-2-ylamino)-1-(2,2,2-trifluoro-ethyl)-1H-pyrazolo[4,3-c]pyridin-6-yl]-(3-hydroxy-4-methyl-piperidin-1-yl)-methanone Compound 105 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and cis-3-hydroxy-4-methyl-piperidine B17. Purification by flash chromatography (DCM/MeOH: 100/0 to 9/1) afforded the compound 105 as a yellow oil in 46% yield. 1H-NMR (DMSO-d6, 400 MHz): 0.87-0.95 1.20-1.30 (m, 3H, CH3, signal of a diastereoisomer); (m, 3H, CH3, signal of a diastereoisomer); 1.36-1.59 (m, 2H, CH2); 1.67-1.82 (m, 1H, CH); 2.87-3.16 (m, 2H, N—CH2); 3.41-3.49 (m, 1H, N—CH2); 3.61-3.69 (m, 1H, N—CH2); 4.18-4.24 (m, 1H, CH—OH, signal of a diastereoisomer); 4.30-4.36 (m, 1H, CH—OH, signal of a diastereoisomer); 4.70 (d, J 4.2 Hz, 1H, OH); 4.78 (d, J 3.9 Hz, 1H, OH); 5.39 (q, J 9.0 Hz, 2H, CH2-CF3); 7.76 (dd, J 9.0, 2.9 Hz, 1H, Ar); 7.84 (bs, 1H, Ar, signal of a diastereoisomer); 7.94 (bs, 1H, Ar, signal of a diastereoisomer); 8.01 (dd, J 9.0, 3.8 Hz, 1H, Ar); 8.29 (d, J 2.9 Hz, 1H, Ar); 9.36 (bs, 1H, Ar, signal of a diastereoisomer); 9.37 (bs, 1H, Ar, signal of a diastereoisomer); 10.41 (s, 1H, NH, signal of a diastereoisomer); 10.43 (s, 1H, NH, signal of a diastereoisomer). M/Z (M+H)+: 453

Compound 106: Cis-(3-Fluoro-4-hydroxy-piperidin-1-yl)-[3-(5-fluoro-pyridin-2-ylamino)-1-(2,2,2-trifluoro-ethyl)-1H-pyrazolo[4,3-c]pyridin-6-yl]-methanone Compound 106 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and cis-3-fluoro-4-hydroxypiperidine B18. Purification by flash chromatography (DCM/MeOH: 100/0 to 9/1) afforded the compound 106 as a yellow oil in 82% yield. 1H-NMR (DMSO-d6, 400 MHz): 1.54-1.77 (m, 2H, CH2); 3.05-3.18 (m, 1H, N—CH2); 3.34-3.93 (m, 3H, N—CH2); 4.21-4.47 (m, 1H, CH); 4.45-4.82 (m, 1H, OH); 5.07-5.19 (m, 1H, CH); 5.41 (q, J 9.0 Hz, 2H, CH2-CF3); 7.75 (td, J 8.6, 3.2 Hz, 1H, Ar); 7.95 (bs, 1H, Ar); 8.01 (dd, J 9.2, 3.9 Hz, 1H, Ar); 8.29 (d, J 3.2 Hz, 1H, Ar); 9.39 (bs, 1H, Ar); 10.44 (bs, 1H, NH). M/Z (M+H)+: 457

Compound 107: [3-[(5-fluoro-2-pyridyl)amino]-1-(2,2,2-trifluoroethyl)pyrazolo[4,3-c]pyridin-6-yl]-(3-endo-hydroxy-8-azabicyclo[3.2.1]octan-8-yl)methanone Compound 107 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and nortropine B4. Purification by flash chromatography (DCM/MeOH: 100/0 to 9/1) afforded the compound 107 as a beige powder in 80% yield. 1H-NMR (DMSO-d6, 400 MHz): 1.64-1.70 (m, 1H, CH2); 1.77-1.94 (m, 3H, CH2); 1.98-2.09 (m, 2H, CH2); 2.16-2.30 (m, 2H, CH2); 3.95-4.00 (m, 1H, N—CH); 4.37-4.42 (m, 1H, N—CH); 4.51-4.76 (m, 1H, CH, OH); 5.42 (q, J 9.2 Hz, 2H, CH2-CF3); 7.69 (ddd, J 8.5, 3.0 Hz, 1H, Ar); 8.00 (dd, J 9.2, 3.8 Hz, 1H, Ar); 7.04 (bs, 1H, Ar); 8.29 (d, J 3.0 Hz, 1H, Ar); 9.38 (d, J 0.9 Hz, 1H, Ar); 10.43 (s, 1H, NH). M/Z (M+H)+: 465

Compound 108: 1-[3-[(5-fluoro-2-pyridyl)amino]-1-(2,2,2-trifluoroethyl)pyrazolo[4,3-c]pyridine-6-carbonyl]pyridine-4-carboxylic acid Compound 108 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and ethyl piperidine-4-carboxylate B19. Purification by flash chromatography (DCM/MeOH: 100/0 to 95/5) afforded a beige powder in 79% yield. The powder was dissolved in THF (0.1M). LiOH, 1N in water (4 equiv.) was added. The reaction mixture was stirred overnight at rt, then acidified to pH 6-7 with HCl 6N and concentrated. The resulting solid was dissolved in DMSO. Water was added to afford a precipitate. Filtration of the precipitate, then drying under reduced pressure in presence of P2O5, afforded compound 108 as a white powder in 34% yield. 1H-NMR (DMSO-d6, 400 MHz): 1.46-1.61 (m, 2H, CH2); 1.72-1.81 (m, 1H, CH2); 1.90-1.99 (m, 1H, CH2); 2.53-2.61 (m, 1H, CH); 2.98 (t, J 12.0 Hz, 1H, N—CH2); 3.10 (t, J 12.0 Hz, 1H, N—CH2); 3.53-3.62 (m, 1H, N—CH2); 4.34-4.43 (m, 1H, N—CH2); 5.33-5.46 (m, 2H, CH2-CF3); 7.76 (td, J 8.6, 2.8 Hz, 1H, Ar); 7.91 (bs, 1H, Ar); 8.00 (dd, J 9.2, 3.6 Hz, 1H, Ar); 8.28 (d, J 2.8 Hz, 1H, Ar) 9.39 (bs, 1H, Ar); 10.43 (s, 1H, NH); 12.18-12.40 (m, 1H, COOH,). M/Z (M+H)+: 467

Compound 109: [3-[(4-fluoro-2-pyridyl)amino]-1-(2,2,2-trifluoroethyl)pyrazolo[4,3-c]pyridin-6-yl]-(6-hydroxy-1,4-oxazepan-4-yl)methanone Compound 109 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and 1,4-oxazepan-6-ol B5. Purification by flash chromatography (DCM/MeOH: 100/0 to 70/30) then by preparative HPLC afforded the compound 109 as a beige powder in 64% yield. 1H-NMR (DMSO-d6, 400 MHz): 3.19-3.42 (m, 1H, CH2); 3.47-3.80 (m, 6H, CH, CH2); 3.80-3.88 (m, 1H, signal of a rotamer, CH2); 3.94-4.03 (m, 1H, CH2); 4.19-4.26 (m, 1H, signal of a rotamer, CH); 5.41-5.50 (m, 2H, CH2-CF3); 6.85-6.91 (m, 1H, Ar); 7.82 (dd, J 12.5, 2.4 Hz, 1H, Ar, signal of a rotamer); 7.84 (dd, J 12.5, 2.4 Hz, 1H, Ar, signal of a rotamer); 7.99 (bs, 1H, Ar, signal of a rotamer); 8.00 (bs, 1H, Ar, signal of a rotamer); 8.30-8.35 (m, 1H, Ar); 9.41 (d, J 1.0 Hz, 1H, Ar, signal of a rotamer); 9.43 (d, J 1.0 Hz, 1H, Ar, signal of a rotamer); 10.74 (s, 1H, NH, signal of a rotamer); 10.77 (s, 1H, NH, signal of a rotamer). M/Z (M+H)+: 455

Compound 110: [(6S)-6-fluoro-1,4-oxazepan-4-yl]-[3-(4-fluoro-pyridin-2-ylamino)-1-(2,2,2-trifluoroethyl)-1H-pyrazolo[4,3-c]pyridin-6-yl]-methanone Compound 110 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and 6-fluoro-1,4-oxazepane hydrochloride B8. Purification by flash chromatography (DCM/MeOH: 100/0 to 94/6) then by preparative HPLC afforded the compound 110 as a yellow powder in 40% yield. 1H-NMR (DMSO-d6, 400 MHz): 3.42-3.53 (m, 1H, CH2, signal of a rotamer); 3.54-3.67 (m, 2H, CH2); 3.73-3.92 (m, 3H, CH2); 3.95-4.10 (m, 2H, CH2); 4.14-4.24 (m, 1H, CH2, signal of a rotamer); 4.79-5.15 (m, 1H, CH—F); 5.40-5.52 (m, 2H, CH2-CF3); 6.88 (ddd, J 8.2, 5.7, 2.3 Hz, 1H, Ar); 7.83 (dd, J 12.3, 2.3 Hz, 1H, Ar); 8.02 (s, 1H, Ar, signal of a rotamer); 8.04 (s, 1H, Ar, signal of a rotamer); 8.33 (dd, J 9.4, 5.7 Hz, 1H, Ar); 9.43 (d, J 1.0 Hz, 1H, Ar); 10.77 (s, 1H, NH). M/Z (M+H)+: 457

Compound 111: [3-[(4-fluoro-2-pyridyl)amino]-1-(2,2,2-trifluoroethyl)pyrazolo[4,3-c]pyridin-6-yl]-(4-hydroxypiperidin-1-yl)methanone Compound 111 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and 4-hydroxy-piperidine B3. Purification by flash chromatography (DCM/MeOH: 10/0 to 9/1) afforded the compound 111 as a beige powder in 39% yield. 1H-NMR (DMSO-d6, 400 MHz): 1.29-1.46 (m, 2H, CH2); 1.63-1.74 (m, 1H, CH2); 1.78-1.89 (m, 1H, CH2); 3.11 (ddd, J 13.5, 9.4, 3.2 Hz, 1H, N—CH2); 3.21-3.30 (m, 1H, N—CH2); 3.45-3.54 (m, 1H, N—CH2); 3.70-3.81 (m, 1H, CH); 4.04-4.12 (dt, J 13.0, 4.6 Hz, 1H, N—CH2); 4.79 (d, 4.0 Hz, 1H, OH); 5.44 (q, J 9.2 Hz, 2H, CH2-CF3); 6.88 (ddd, J 8.3, 5.8, 2.4 Hz, 1H, Ar); 7.83 (dd, J 12.5, 2.4 Hz, 1H, Ar); 7.92 (d, J 1.0 Hz, 1H, Ar); 8.33 (d, J 9.6, 6.0 Hz, 1H, Ar); 9.41 (d, J 1.0 Hz, 1H, Ar,); 10.43 (s, 1H, NH). M/Z (M+H)+: 439

Compound 112: [3-(4-Fluoro-pyridin-2-ylamino)-1-(2,2,2-trifluoro-ethyl)-1H-pyrazolo[4,3-c]pyridin-6-yl]-(4-hydroxy-4-methyl-piperidin-1-yl)-methanone Compound 112 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and 4-hydroxy-4-methyl-piperidine B6. Purification by flash chromatography (DCM/MeOH: 10/0 to 9/1) afforded the compound 112 as a white powder in 56% yield. 1H-NMR (DMSO-d6, 400 MHz): 1.17 (s, 3H, CH3); 1.37-1.62 (m, 4H, CH2); 3.22-3.32 (m, 3H, N—CH2); 4.07-4.15 (m, 1H, N—CH2); 4.44 (s, 1H, OH); 5.43 (q, J 9.0 Hz, 2H, CH2-CF3); 6.87 (ddd, J 8.3, 5.7, 2.4 Hz, 1H, Ar); 7.83 (dd, J 12.3, 2.4 Hz, 1H, Ar); 7.91 (bs, 1H, Ar); 8.32 (dd, J 9.5, 5.7 Hz, 1H, Ar); 9.41 (d, J 0.8 Hz, 1H, Ar); 10.73 (bs, 1H, NH). M/Z (M+H)+: 453

Compound 113: [3-(4-Fluoro-pyridin-2-ylamino)-1-(2,2,2-trifluoro-ethyl)-1H-pyrazolo[4,3-c]pyridin-6-yl]-(4-ethyl-4-hydroxypiperidin-1-yl)-methanone Compound 113 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and 4-ethyl-4-hydroxy-piperidine B20. Purification by flash chromatography (DCM/MeOH: 10/0 to 9/1) afforded the compound 113 as a light brown powder in 50% yield. 1H NMR (400 MHz, DMSO-d6) δ: 0.85 (t, J 7.4 Hz, 3H, CH3); 1.34-1.50 (m, 5H, CH2); 1.53-1.61 (m, 1H, CH2); 3.19 (td, J 12.4, 3.0 Hz, 1H, N—CH2); 3.25-3.41 (m, 2H, N—CH2); 4.19-4.28 (m, 2H, OH+N—CH2); 5.43 (q, J 8.8 Hz, 2H, F3C—CH2); 6.87 (ddd, J 8.2, 5.6, 2.3 Hz, 1H, Ar); 7.83 (dd, J 12.4, 2.3 Hz, 1H, Ar); 7.91 (d, J 1 Hz, 1H, Ar); 8.32 (dd, J 9.5, 5.6 Hz, 1H, Ar); 9.41 (d, J 1.0 Hz, 1H, Ar); 10.73 (s, 1H, NH). M/Z (M+H)+: 467

Compound 114: [3-(4-Fluoro-pyridin-2-ylamino)-1-(2,2,2-trifluoro-ethyl)-1H-pyrazolo[4,3-c]pyridin-6-yl]-(4-isopropyl-4-hydroxypiperidin-1-yl)-methanone Compound 114 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and 4-isopropyl-4-hydroxy-piperidine B21. Purification by flash chromatography (DCM/MeOH: 10/0 to 9/1) afforded the compound 114 as a light brown powder in 65% yield. 1H NMR (400 MHz, DMSO-d6) δ: 0.85 (d, J 6.8 Hz, 3H, CH3); 0.86 (d, J 6.8 Hz, 3H, CH3); 1.33-1.63 (m, 5H, CH2, CH); 3.08 (td, J 12.4, 3.0 Hz, 1H, N—CH2); 3.23-3.30 (m, 1H, N—CH2); 3.38-3.47 (m, 1H, N—CH2); 4.13 (s, 1H, OH); 4.33-4.39 (m, 1H, N—CH2); 5.43 (q, J 8.8 Hz, 2H, F3C—CH2); 6.87 (ddd, J 8.2, 5.7, 2.3 Hz, 1H, Ar); 7.83 (dd, J 12.4, 2.3 Hz, 1H, Ar); 7.91 (bs, 1H, Ar); 8.32 (dd, J 9.6, 5.6 Hz, 1H, Ar); 9.41 (bs, 1H, Ar); 10.72 (s, 1H, NH). M/Z (M+H)+: 481

Compound 115: [3-(4-Fluoro-pyridin-2-ylamino)-1-(2,2,2-trifluoro-ethyl)-1H-pyrazolo[4,3-c]pyridin-6-yl]-(4-cyclopropyl-4-hydroxypiperidin-1-yl)-methanone Compound 115 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and 4-cyclopropyl-4-hydroxy-piperidine B22. Purification by flash chromatography (DCM/MeOH: 10/0 to 9/1) afforded the compound 115 as a light brown powder in 80% yield. 1H NMR (400 MHz, DMSO-d6) δ: 0.16-0.26 (m, 2H, CH—(CH2-CH2)); 0.30-0.40 (m, 2H, CH—(CH2-CH2)); 0.82-0.90 (m, 1H, CH—(CH2-CH2)); 1.35-1.44 (m, 1H, CH2); 1.48-1.61 (m, 3H, CH2); 3.15 (td, J 12.4, 3.6 Hz, 1H, N—CHa-Hb); 3.22-3.29 (m, 1H, N—CH2); 3.36-3.45 (m, 1H, N—CH2); 4.04 (s, 1H, OH) 4.24-4.32 (m, 1H, N—CH2); 5.43 (q, J 8.8 Hz, 2H, F3C—CH2); 6.87 (ddd, J 8.2, 5.7, 2.4 Hz, 1H, Ar); 7.83 (dd, J 12.4, 2.3 Hz, 1H, Ar); 7.92 (d, J 1.1 Hz, 1H, Ar); 8.32 (dd, J 9.5, 5.7 Hz, 1H, Ar); 9.41 (d, J 1.1 Hz, 1H, Ar); 10.73 (s, 1H, NH). M/Z (M+H)+: 479

Compound 116: (4-Fluoro-piperidin-1-yl)-[3-(4-fluoro-pyridin-2-ylamino)-1-(2,2,2-trifluoro-ethyl)-1H-pyrazolo[4,3-c]pyridin-6-yl]-methanone Compound 116 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and 4-fluoro-piperidine hydrochloride B9. Purification by flash chromatography (DCM/MeOH: 10/0 to 9/1) afforded the compound 116 as a white powder in 66% yield. 1H-NMR (DMSO-d6, 400 MHz): 1.62-2.04 (m, 4H, CH2); 3.28-3.37 (m, 1H, N—CH2); 3.39-3.51 (m, 1H, N—CH2); 3.65-3.79 (m, 2H, N—CH2); 4.84-5.03 (m, 1H, CH); 5.44 (q, J 9.0 Hz, 2H, N-CH2-CF3); 6.87 (ddd, J 8.3, 5.7, 2.3 Hz, 1H, Ar); 7.82 (dd, J 12.4, 2.3 Hz, 1H, Ar); 7.97 (d, J 0.9 Hz, 1H, Ar); 8.33 (dd, J 9.5, 5.7 Hz, 1H, Ar); 9.42 (d, J 0.9 Hz, 1H, Ar); 10.74 (bs, 1H, NH). M/Z (M+H)+: 441

Compound 117: [(3S)-3-hydroxy-piperidin-1-yl]-[3-(4-Fluoro-pyridin-2-ylamino)-1-(2,2,2-trifluoro-ethyl)-1H-pyrazolo[4,3-c]pyridin-6-yl]methanone Compound 117 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and (3S)-3-hydroxy-piperidine hydrochloride B11. Purification by preparative HPLC afforded the compound 117 as a pale yellow powder in 69% yield. 1H-NMR (DMSO-d6, 400 MHz): 1.34-1.50 (m, 2H, CH2); 1.58-1.93 (m, 2H, CH2); 2.79-2.86 (m, 1H, N—CH2, signal of a rotamer), 2.92-3.02 (m, 1H, N—CH2); 3.15-3.24 (m, 1H, N—CH2, signal of a rotamer); 3.38-3.58 (m, 2H, CH2), 3.91-3.98 (m, 1H, CH—OH, signal of a rotamer), 4.25-3.32 (m, 1H, CH—OH, signal of a rotamer), 5.39-5.49 (m, 2H, N-CH2-CF3); 6.85-6.91 (m, 1H, Ar); 7.80-7.86 (m, 1H, Ar); 7.92 (s, 1H, Ar, signal of a rotamer); 7.95 (s, 1H, Ar, signal of a rotamer); 8.33 (dd, J 9.3, 5.7 Hz 1H, Ar); 9.42 (bs, 1H, Ar, signal of a rotamer); 9.43 (bs, 1H, Ar, signal of a rotamer); 10.74 (s, 1H, NH, signal of a rotamer); 10.76 (s, 1H, NH, signal of a rotamer). M/Z (M+H)+: 439

Compound 118: [3-(4-Fluoro-pyridin-2-ylamino)-1-(2,2,2-trifluoro-ethyl)-1H-pyrazolo[4,3-c]pyridin-6-yl]-(4-hydroxy-2,2-dimethyl-piperidin-1-yl)-methanone Compound 118 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and 4-hydroxy-2,2-dimethyl-piperidine B23. Purification by flash chromatography (DCM/MeOH: 10/0 to 9/1) afforded the compound 118 as a white powder in 70% yield. 1H-NMR (DMSO-d6, 400 MHz): 1.32-1.42 (m, 1H, CH2); 1.46 (s, 3H, CH3); 1.54-1.64 (m, 4H, CH3, CH2); 1.72-1.81 (m, 1H, CH2); 1.80-1.91 (m, 1H, CH2); 2.94-3.05 (m, 1H, N—CH2); 3.33-3.43 (m, 1H, N—CH2); 3.78-3.88 (m, 1H, CH); 4.70 (d, J 4.4 Hz, 1H, OH); 5.43 (q, J 9.1 Hz, 2H, CH2-CF3); 6.87 (ddd, J 8.2, 5.7, 2.3 Hz, 1H, Ar); 7.83 (dd, J 12.4, 2.1 Hz, 1H, Ar); 7.87 (s, 1H, Ar); 8.32 (dd, J 9.5, 5.7 Hz, 1H, Ar); 9.39 (d, J 0.9 Hz, 1H, Ar); 10.72 (bs, 1H, NH). M/Z (M+H)+: 467

Compound 119: (3,3-Difluoro-4-hydroxy-piperidin-1-yl)-[3-(4-fluoro-pyridin-2-ylamino)-1-(2,2,2-trifluoro-ethyl)-1H-pyrazolo[4,3-c]pyridin-6-yl]-methanone Compound 119 was obtained according to General Procedure XIII, starting from lithium 3-((4-fluoropyridin-2-yl)amino)-1-(2,2,2-trifluoroethyl)-1H-pyrazolo[4,3-c]pyridine-6-carboxylate O2 and 3,3-Difluoro-4-hydroxypiperidine B16. Purification by flash chromatography (DCM/MeOH: 100/0 to 9/1) afforded the compound 119 as a beige powder in 50% yield. 1H-NMR (DMSO-d6, 400 MHz): 1.61-1.73 (m, 1H, CH2); 1.78-1.93 (m, 1H, CH2); 3.47-4.15 (m, 5H, N—CH2, CH); 5.42-5.51 (m, 2H, N-CH2-CF3); 5.76-5.82 (m, 1H, OH); 6.88 (ddd, J 8.3, 5.7, 2.3 Hz, 1H, Ar); 7.80-7.85 (m, 1H, Ar); 8.00 (bs, 1H, Ar, signal of a rotamer); 8.09 (bs, 1H, Ar, signal of a rotamer); 8.32 (dd, J 9.5, 5.7 Hz, 1H, Ar); 9.44 (d, J 0.9 Hz, 1H, Ar); 10.75 (bs, 1H, NH). M/Z (M+H)+: 475

Compound 120: [3-[(4-fluoro-2-pyridyl)amino]-1-(2,2,2-trifluoroethyl)pyrazolo[4,3-c]pyridin-6-yl]-(3-endo-hydroxy-8-azabicyclo[3.2.1]octan-8-yl)methanone Compound 120 was obtained according to General Procedure XIII, starting from lithium 3-((4-fluoropyridin-2-yl)

amino)-1-(2,2,2-trifluoroethyl)-1H-pyrazolo[4,3-c]pyridine-6-carboxylate O2 and nortropine B4. Purification by flash chromatography (DCM/MeOH: 100/0 to 9/1) afforded the compound 120 as a white powder in 30% yield. 1H-NMR (DMSO-d6, 400 MHz): 1.64-1.70 (m, 1H, CH2); 1.77-1.94 (m, 3H, CH2); 1.98-2.09 (m, 2H, CH2); 2.16-2.30 (m, 2H, CH2); 3.95-4.00 (m, 1H, N—CH); 4.37-4.42 (m, 1H, N—CH); 4.51-4.76 (m, 1H, CH, OH); 5.46 (q, J 9.2 Hz, 2H, CH2-CF3); 6.88 (ddd, J 8.3, 5.7, 2.4 Hz, 1H, Ar); 7.83 (dd, J 12.4, 2.4 Hz, 1H, Ar); 8.06 (bs, 1H, Ar); 8.32 (dd, J 9.5, 5.7 Hz, 1H, Ar); 9.41 (d, J 0.9 Hz, 1H, Ar); 10.76 (bs, 1H, NH). M/Z (M+H)+: 465

Compound 121: (6,6-dideuterio-1,4-oxazepan-4-yl)-[3-(pyrazin-2ylamino)-1-(2,2,2-trifluoroethyl)pyrazolo[4,3-c]pyridin-6-yl]methanone Compound 121 was obtained according to General Procedure XIII, starting from lithium 3-((pyrazin-2-yl)amino)-1-(2,2,2-trifluoroethyl)-1H-pyrazolo[4,3-c]pyridine-6-carboxylate O3 and 6,6-dideuterio-1,4-oxazepane hydrochloride B7. Purification by preparative HPLC afforded the compound 121 as a yellow powder in 55% yield. 1H-NMR (DMSO-d6, 400 MHz): 3.40-3.50 (m, 2H, CH2); 3.60-3.64 (m, 1H, CH2); 3.69 (s, 1H, CH2); 3.72-3.79 (m, 2H, CH2); 5.46 (q, J 9.2 Hz, 2H, N-CH2-CF3); 7.99 (bs, 1H, Ar, signal of a rotamer); 8.00 (bs, 1H, Ar, signal of a rotamer); 8.19 (d, J 2.6 Hz, 1H, Ar); 8.31 (dd, J 2.6, 1.4 Hz, 1H, Ar); 9.23 (d, J 1.4 Hz, 1H, Ar); 9.38 (s, 1H, Ar, signal of a rotamer); 9.39 (s, 1H, Ar, signal of a rotamer); 10.69 (s, 1H, NH). M/Z (M+H)+: 424

Compound 122: [(6S)-6-fluoro-1,4-oxazepan-4-yl]-[3-(pyrazin-2ylamino)-1-(2,2,2-trifluoro-ethyl)-1H-pyrazolo[4,3-c]pyridin-6-yl]-methanone Compound 122 was obtained according to General Procedure XIII, starting from lithium 3-((pyrazin-2-yl)amino)-1-(2,2,2-trifluoroethyl)-1H-pyrazolo[4,3-c]pyridine-6-carboxylate O3 and 6-fluoro-1,4-oxazepane hydrochloride B8. Purification by flash chromatography (Cyclohexane/AcOEt: 10/0 to 5/5) then by preparative HPLC afforded the compound 122 as a yellow powder in 18% yield. 1H-NMR (DMSO-d6, 400 MHz): 3.42-3.53 (m, 1H, CH2, signal of a rotamer); 3.54-3.67 (m, 2H, CH2); 3.73-3.92 (m, 3H, CH2); 3.95-4.10 (m, 2H, CH2); 4.14-4.24 (m, 1H, CH2, signal of a rotamer); 4.79-5.15 (m, 1H, CH—F); 5.40-5.52 (m, 2H, CH2-CF3); 8.04 (s, 1H, Ar, signal of a rotamer); 8.06 (s, 1H, Ar, signal of a rotamer); 8.20 (d, 2.6 Hz, 1H, Ar); 8.32 (bs, 1H, Ar); 9.23 (bs, 1H, Ar); 9.39 (bs, 1H, Ar); 10.71 (s, 1H, NH). M/Z (M+H)+: 440

Compound 123: [3-(pyrazin-2ylamino)-1-(2,2,2-trifluoro-ethyl)-1H-pyrazolo[4,3-c]pyridin-6-yl]-(4-hydroxy-4-methyl-piperidin-1-yl)-methanone Compound 123 was obtained according to General Procedure XIII, starting from lithium 3-((pyrazin-2-yl)amino)-1-(2,2,2-trifluoroethyl)-1H-pyrazolo[4,3-c]pyridine-6-carboxylate O3 and 4-hydroxy-4-methyl-piperidine B6. Purification by flash chromatography (DCM/MeOH: 100/0 to 93/7; then on a 15 μm cartridge, DCM/MeOH: 100/0 to 96/4) afforded the compound 123 as a white powder in 60% yield. 1H-NMR (DMSO-d6, 400 MHz): 1.17 (s, 3H, CH3), 1.40-1.55 (m, 3H, CH2), 1.55-1.64 (m, 1H, CH2), 3.26-3.36 (m, 3H, N—CH2), 4.07-4.15 (m, 1H, N—CH2); 5.45 (q, J 9.0 Hz, 2H, CH2-CF3); 7.95 (s, 1H, Ar); 8.19 (d, J 2.6 Hz, 1H, Ar); 8.31 (dd, J 2.6, 1.6 Hz, 1H, Ar); 9.23 (d, J 1.6 Hz, 1H, Ar); 9.38 (bs, 1H, Ar); 10.69 (s, 1H, NH). M/Z (M+H)+: 436

Compound 124: (4-Fluoro-piperidin-1-yl)-[3-(pyrazin-2ylamino)-1-(2,2,2-trifluoro-ethyl)-1H-pyrazolo[4,3-c]pyridin-6-yl]-methanone Compound 124 was obtained according to General Procedure XIII, starting from lithium 3-((pyrazin-2-yl)amino)-1-(2,2,2-trifluoroethyl)-1H-pyrazolo[4,3-c]pyridine-6-carboxylate O3 and 4-fluoro-piperidine hydrochloride B9. Purification by flash chromatography (DCM/MeOH: 100/0 to 95/57; then on a 15 μm cartridge, Cyclohexane/AcOEt: 10/0 to 5/5) afforded the compound 124 as a yellow powder in 53% yield. 1H-NMR (DMSO-d6, 400 MHz): 1.60-2.06 (m, 4H, CH2); 3.39-3.31 (m, 1H, N—CH2); 3.42-3.52 (m, 1H, N—CH2); 3.68-3.80 (m, 2H, N—CH2), 4.84-4.91 (m, 1H, CHF, signal of a rotamer), 4.96-5.04 (m, 1H, CHF, signal of a rotamer), 5.45 (q, J 9.0 Hz, 2H, N-CH2-CF3); 7.98 (bs, 1H, Ar); 8.19 (d, 2.6 Hz, 1H, Ar); 8.31 (dd, J 2.6, 1.6 Hz, 1H, Ar); 9.23 (d, J 1.6 Hz, 1H, Ar); 9.39 (d, J 0.8 Hz, 1H, Ar); 10.68 (s, 1H, NH). M/Z (M+H)+: 424

Compound 125: [3-[(5-fluoro-2-pyridyl)amino]-1-(2,2,2-trifluoroethyl)pyrazolo[4,3-c]pyridin-6-yl]-[(2R)-2-(2-hydroxy-2-methyl-propyl)pyrrolidin-1-yl]methanone Compound 125 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and (R)-2-methyl-1-(pyrrolidin-2-yl)propan-2-ol B24. Purification by flash chromatography (DCM/MeOH: 100/0 to 93/7) afforded the compound 125 as a beige powder in 44% yield. 1H-NMR (DMSO-d6, 400 MHz, 80° C.): 0.63-1.36 (m, 6H, CH3); 1.51-1.62 (m, 1H, CH2); 1.75-2.10 (m, 5H, CH2); 3.46-3.68 (m, 2H, N—CH2); 3.92-4.12 (m, 1H, OH); 4.33-4.492 (m, 1H, N—CH); 5.24-5.34 (m, 2H, CH2-CF3); 7.57 (td, J 9.0, 2.8 Hz, 1H, Ar); 7.89 (dd, J 9.0, 3.8 Hz, 1H, Ar); 7.94 (bs, 1H, Ar); 8.23 (d, J 2.8 Hz, 1H, Ar); 9.35 (bs, 1H, Ar); 9.98 (bs, 1H, NH). M/Z (M+H)+: 481

Compound 126: [3-[(5-fluoro-2-pyridyl)amino]-1-(2,2,2-trifluoroethyl)pyrazolo[4,3-c]pyridin-6-yl]-[(2S)-2-(2-hydroxy-2-methyl-propyl)pyrrolidin-1-yl]methanone Compound 126 was obtained according to General Procedure XIII, starting from lithium 3-((5-fluoropyridin-2-yl)amino)-1-(2,2,2-trifluoroethyl)-1H-pyrazolo[4,3-c]pyridine-6-carboxylate O1 and (S)-2-methyl-1-(pyrrolidin-2-yl)propan-2-ol B25. Purification by preparative HPLC afforded the compound 126 as a beige powder in 23% yield. 1H-NMR (DMSO-d6, 400 MHz, 80° C.): 0.63-1.36 (m, 6H, CH3); 1.51-1.62 (m, 1H, CH2); 1.75-2.10 (m, 5H, CH2); 3.46-3.68 (m, 2H, N—CH2); 3.92-4.12 (m, 1H, OH); 4.33-4.492 (m, 1H, N—CH); 5.24-5.34 (m, 2H, CH2-CF3); 7.57 (td, J 9.0, 2.8 Hz, 1H, Ar); 7.89 (dd, J 9.0, 3.8 Hz, 1H, Ar); 7.94 (bs, 1H, Ar); 8.23 (d, J 2.8 Hz, 1H, Ar); 9.35 (bs, 1H, Ar); 9.98 (bs, 1H, NH). M/Z (M+H)+: 481

Compound 127: (3-endo-hydroxy-8-azabicyclo[3.2.1]octan-8-yl)-[3-(2-pyridylamino)-1-(2,2,2-trifluoroethyl)pyrazolo[4,3-c]pyridin-6-yl]methanone Under argon atmosphere, to a solution of 6-bromo-1H-pyrazolo[4,3-c]pyridine A (1 equiv.) in anhydrous DMA (0.2M) was added zinc cyanide (1.5 equiv.). The reaction mixture was degassed with argon. Pd(PPh3)4 (10 mol %) was added. The reaction mixture was heated 3 h at 130° C. The reaction mixture was diluted with AcOEt, washed with water and brine, dried over magnesium sulfate then concentrated. The resulting crude mixture was triturated in DCM. The precipitate was filtered, then purified by flash chromatography (DCM/MeOH: 10/0 to 0/10) to afford 1H-pyrazolo[4,3-c]pyridine-6-carbonitrile as a white powder in 61% yield. M/Z (M+H)+: 145

To a solution of 1H-pyrazolo[4,3-c]pyridine-6-carbonitrile (1 equiv.) in ACN (0.1M) was added NBS (1.05 equiv.). The reaction mixture was stirred 1 h at 80° C. The reaction mixture was diluted with AcOEt, washed with water and brine, dried over magnesium sulfate, then concentrated. The resulting crude mixture was triturated in DCM. The precipitate was filtered to afford 3-bromo-1H-pyrazolo[4,3-c]pyridine-6-carbonitrile as a white powder in 97% yield. M/Z (M+H)+: 223/225

To a solution of 3-bromo-1H-pyrazolo[4,3-c]pyridine-6-carbonitrile (1 equiv.) in DMF (0.15M) at 0° C. was added sodium hydride (1.2 equiv.). The reaction mixture was stirred 10 min at 0° C. 2,2,2-trifluoroethyl p-toluenesulfonate E2 (1.2 equiv.) was added. The reaction mixture was stirred 4 h at room temperature. The reaction mixture was quenched at 0° C. with a saturated sodium bicarbonate solution and extracted with AcOEt. The organic phase was washed with brine, dried over magnesium sulfate then concentrated. The resulting oil was purified by flash chromatography (Cyclohexane/AcOEt: 10/0 to 7/3) to afford 3-bromo-1-(2,2,2-trifluoroethyl)pyrazolo[4,3-c]pyridine-6-carbonitrile as a white powder in 50% yield. M/Z (M+H)+: 305/307

To a solution of 3-bromo-1-(2,2,2-trifluoroethyl)pyrazolo[4,3-c]pyridine-6-carbonitrile (1 equiv.) in dioxane (0.15M) were added benzophenone imine (1.3 equiv.), cesium carbonate (2.4 equiv.), and XantPhos Pd G3 precatalyst (10 mol %). The reaction mixture was stirred overnight at 90° C. The reaction mixture was cooled down, diluted with AcOEt, washed with water. The aqueous layer was extracted twice with DCM. The combined organic layers were dried over sodium sulfate and concentrate. The resulting oil was dissolved in dioxane (0.05M). HCl 4N in dioxane (5 equiv.) was added dropwise at 0° C. The reaction mixture was stirred 1 h at 0° C. The reaction mixture was diluted with water, extracted twice with diethyl ether. The aqueous layer was basified with solid sodium bicarbonate to pH 9-10 then extracted 3 times with DCM. The combined organic layers were dried over magnesium sulfate and concentrated. The resulting oil was purified by flash chromatography (Cyclohexane/AcOEt: 10/0 to 0/10) to afford 3-amino-1-(2,2,2-trifluoroethyl)pyrazolo[4,3-c]pyridine-6-carbonitrile as a pale yellow power in 52% yield. M/Z (M+H)+: 242

To a solution of 3-amino-1-(2,2,2-trifluoroethyl)pyrazolo[4,3-c]pyridine-6-carbonitrile (1 equiv.) in dioxane (0.1M) were added 2-bromopyridine H1 (1.2 equiv.) and cesium carbonate (2.4 equiv.). The reaction mixture was degassed with argon, then BrettPhos Pd G1 precatalyst (5 mol %) was added. The reaction mixture was stirred 1 h at 90° C. The reaction mixture was diluted with DCM, washed with sodium bicarbonate and brine, dried over magnesium sulfate then concentrated. The resulting oil was purified by flash chromatography (Cyclohexane/AcOEt: 10/0 to 2/8) to afford 3-(pyridin-2-ylamino)-1-(2,2,2-trifluoroethyl)-1H-pyrazolo[4,3-c]pyridine-6-carbonitrile as a yellow solid in 37% yield.

A solution of 3-(pyridin-2-ylamino)-1-(2,2,2-trifluoroethyl)-1H-pyrazolo[4,3-c]pyridine-6-carbonitrile in concentrated HCl (0.05M) was heated overnight at reflux. The reaction mixture was concentrated. The resulting solid was dissolved in water. A saturated sodium bicarbonate solution was added until reaching pH 7. The formed precipitate was filtered, washed with water, then dried. The resulting powder was dissolved in DMF (0.1M). Nortropine B4 (1.2 equiv.), diisopropylethylamine (3 equiv.) and HATU (1.5 equiv.) were added. The reaction mixture was stirred 1 h at rt. The reaction mixture was diluted with AcOEt, washed with a saturated ammonium chloride solution and brine, dried over magnesium sulfate, then concentrated. The resulting crude mixture was purified by flash chromatography (DCM/MeOH: 100/0 to 95/5) to afford compound 127 as a beige powder in 15% yield. 1H-NMR (DMSO-d6, 400 MHz): 1.63-1.72 (m, 1H, CH2); 1.77-1.94 (m, 3H, CH2); 1.98-2.10 (m, 2H, CH2); 2.16-2.32 (m, 2H, CH2); 3.98 (bs, 1H, N—CH); 4.38-4.45 (m, 1H, N—CH); 4.60-4.68 (m, 2H, CH, OH); 5.41 (q, J 9.3 Hz, 2H, CH2-CF3); 6.91-6.98 (m, 1H, Ar); 7.74-7.80 (m, 1H, Ar); 7.90-7.97 (m, 1H, Ar); 8.03 (bs, 1H, Ar); 8.26-8.31 (m, 1H, Ar); 9.38 (d, J 1.0 Hz, 1H); 10.33 (bs, 1H, NH). M/Z (M+H)+: 447

Example 3: Testing Compounds of the Present Invention for Inhibitory Activities Against Human Adenosine Receptors in Recombinant Cells The functional activities of human $A_{2A}$ and $A_{2B}$ receptors were determined by quantification of cAMP, being the second messenger for adenosine receptors.

For this purpose, recombinant HEK293 cells, expressing either human $A_{2A}$ or $A_{2B}$ receptors (both Gs coupled) were seeded into 394-well microtiter plates, test compounds and agonist (NECA) were added. After a 15 min incubation, HTRF reagents (cAMP dynamic 2, Cis Bio) were added and the cellular cAMP levels were determined using the ENVISION (Perkin Elmer) plate reader.

The compounds of the present invention show a high selectivity for adenosine $A_{2A}$ and $A_{2B}$ receptors, as also reflected by the $IC_{50}$ data of the exemplary compounds of formula (I) according to the present invention shown in table 3 below.

Particularly, in contrast to the known adenosine $A_{2A}$ receptor antagonists, the compounds of the present invention surprisingly show an $A_{2A}/A_{2B}$ dual activity (see table 3) which is highly advantageous for the treatment and/or prevention of hyperproliferative and infectious diseases and disorders as it is disclosed above.

TABLE 3

| No. | A2A (Category) | A2B (Category) |
|---|---|---|
| 1 | A | B |
| 2 | A | B |
| 6 | A | A |
| 7 | A | A |
| 8 | A | B |
| 10 | A | A |
| 11 | A | B |
| 13 | A | B |
| 15 | A | B |
| 16 | A | A |
| 17 | A | B |

TABLE 3-continued

| No. | A2A (Category) | A2B (Category) |
|---|---|---|
| 18 | A | B |
| 19 | A | A |
| 20 | A | B |
| 21 | A | A |
| 22 | A | A |
| 23 | A | A |
| 24 | A | A |
| 25 | A | A |
| 26 | A | B |
| 27 | A | B |
| 28 | A | A |
| 29 | A | A |
| 30 | A | B |
| 31 | A | A |
| 32 | A | B |
| 33 | A | B |
| 34 | A | B |
| 35 | A | B |
| 37 | A | B |
| 38 | A | A |
| 40 | A | A |
| 41 | A | B |
| 42 | A | A |
| 44 | A | A |
| 46 | A | A |
| 47 | A | A |
| 48 | A | A |
| 49 | A | A |
| 51 | A | B |
| 52 | A | A |
| 53 | A | A |
| 59 | A | A |
| 60 | A | A |
| 61 | A | A |
| 62 | A | B |
| 63 | A | A |
| 64 | A | A |
| 65 | A | B |
| 66 | A | B |
| 68 | A | B |
| 71 | A | A |
| 73 | A | B |
| 74 | A | A |
| 75 | A | A |
| 76 | A | B |
| 77 | A | A |
| 78 | A | A |
| 79 | A | A |
| 80 | A | A |
| 81 | A | B |
| 83 | A | A |
| 84 | A | A |
| 85 | A | A |
| 86 | A | B |
| 91 | A | A |
| 93 | A | A |
| 94 | A | A |
| 95 | A | B |
| 96 | A | B |
| 97 | A | B |
| 98 | A | B |
| 99 | A | B |
| 100 | A | B |
| 101 | A | A |
| 102 | A | A |
| 107 | A | A |
| 110 | A | A |
| 111 | A | A |
| 112 | A | A |
| 113 | A | A |
| 114 | A | A |
| 115 | A | A |
| 116 | A | A |
| 117 | A | A |
| 120 | A | A |
| 121 | A | B |
| 122 | A | A |
| 123 | B | B |
| 124 | A | B |
| 125 | A | B |
| 127 | A | A |

"A" means $IC_{50}$ value is <100 nM,
"B" means $IC_{50}$ value is <1 µM.

Example 4: Testing the Effects of the Compounds of the Present Invention Against Endogenous Human $A_{2A}$ Receptor—Human T Cell Assay The endogenous functional activity of the Gs-coupled human $A_{2A}$ receptor was measured in T cells, where this receptor is highly expressed. Determination of receptor activity was done by quantification of cAMP, which is a second messenger for adenosine receptors.

In short, human pan T cells were isolated from human PBMC (MACS Pan T Cell Isolation Kit, Miltenyi Biotec) that have been derived from fresh whole blood. The T cells were seeded in 384-well microtiter plates and treated with test compounds. After 10 min incubation at room temperature, the $A_{2A}$ adenosine receptor agonist NECA was added, and the plates were incubated for another 45 min. Finally, HTRF reagents (cAMP Femto Kit, CisBio) were added to the wells, and after 1 h cellular cAMP levels were determined using the ENVISION (Perkin Elmer) plate reader.

The obtained raw data were normalized against the inhibitor control and the neutral control (DMSO) and the normalized data were fitted using Genedata Screener software.

The compounds of the present invention show that they are able to inhibit the $A_{2A}$ receptor expressed in human T cells which incubated with the $A_{2A}$ adenosine receptor agonist NECA (as measured by quantification of cAMP), which is preferred for the treatment and/or prevention of hyperproliferative and infectious diseases and disorders as it is disclosed above. Therefore, the compounds of the present invention surprisingly are able to prevent immunosuppression and thus are able to support anti-tumor T cell induced inhibition of tumor growth, reduction or destruction of metastases and prevention of neovascularization.

TABLE 4

| No. | | Human T cell cAMP IC$_{50}$ (nM) | Human T cell IL-2 IC$_{50}$ (nM) |
|---|---|---|---|
| 10 | (structure) | A | A |

"A" means IC$_{50}$ value is <100 nM, "B" means IC$_{50}$ value is <1 µM.

Example 5: Testing the Effect of the Compounds of the Present Invention on Mouse T Cells Background:

Adenosine (Ado) in tumor microenvironment can inhibit T cell activity by signaling through A$_{2A}$ receptors and suppress cytokine secretion by T cells. A$_{2A}$ specific agonists like NECA does similar job of inhibition of T cell cytokine secretion in vitro and in vivo. Potential A$_{2A}$ antagonists or A$_{2A}$/A$_{2B}$ dual antagonists can rescue T cells from this inhibition. Herein, we describe the in vitro system we established using Pan T cells from mouse spleens to screen potential A$_{2A}$ antagonists or A$_{2A}$/A$_{2B}$ dual antagonists for their activity. The method described involves the use of CD3/CD28 pre-coated beads to stimulate Pan T cells purified from mouse splenocytes, combined with the addition of A$_{2A}$ agonist along with potential A$_{2A}$ or A$_{2A}$/A$_{2B}$ dual antagonists to evaluate potentiation of T cell cytokine production.

Assay Description:

Mouse T Cells

Briefly, mouse Pan T cells are purified from spleens of BALB/c mice using Pan T cell isolation kit Mouse II (MACS Miltenyi biotech Cat # Order no. 130-095-130) according to manufacturer's protocol. The purified T cells are seeded in Nunc™ 96-Well Polystyrene Round Bottom Microwell Plates in RPMI medium with 10% heat inactivated fetal bovine serum. The cells are rested at 37° C. for 1 h before activating with CD3/CD28 pre-coated beads (Dynabeads™ Mouse T-Activator CD3/CD28; Cat #11456D). After 30 min the cells are treated with varying doses of test antagonist(s). The cells are incubated for additional 30 min at 37° C. before treating with A$_{2A}$ agonist NECA (1 µM) or neutral control (DMSO). After 24 h incubation IL-2 levels in the supernatants are measured by ELISAs according to manufacturer's protocol (R&D systems Cat # DY402 (IL-2)). Once the concentrations are calculated, the difference of cytokine concentration of DMSO control and agonist alone control is calculated and the percentage of rescue by each concentration of antagonist is calculated by using Microsoft Excel. These percentages of cytokine rescue in a dose dependent manner of antagonist is plotted in GraphPad Prism software and IC$_{50}$ is calculated.

The compounds of the present invention show that they are able to rescue T cells from inhibition and are able to prevent the suppression of cytokine secretion as induced by adenosine or A$_{2A}$ specific agonists like NECA, which is preferred for the treatment and/or prevention of hyperproliferative and infectious diseases and disorders as it is disclosed above. Therefore, the compounds of the present invention surprisingly are able to prevent immunosuppression and thus are able to support anti-tumor T cell induced inhibition of tumor growth, reduction or destruction of metastases and prevention of neovascularization.

TABLE 5

| No. | Mouse T cell IL-2 IC$_{50}$ (nM) |
|---|---|
| 10 | B |

"A" means IC$_{50}$ value is <100 nM,
"B" means IC$_{50}$ value is <1 µM.

The following examples relate to pharmaceutical compositions comprising an active ingredient according to the invention, i.e. a compound of formula (I) or a pharmaceutically acceptable salt, solvate or prodrug thereof:

Example 6: Injection Vials

A solution of 100 g of an active ingredient according to the invention and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

Example 7: Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

Example 8: Solution

A solution is prepared from 1 g of an active ingredient according to the invention, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example 9: Ointment 500 mg of an active ingredient according to the invention are mixed with 99.5 g of Vaseline under aseptic conditions.

Example 10: Tablets

A mixture of 1 kg of active ingredient, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

Example 11: Coated Tablets

Tablets are pressed analogously to Example 10 and subsequently coated in a conventional manner with a coating of sucrose, potato starch, talc, tragacanth and dye.

Example 12: Capsules 2 kg of active ingredient are introduced into hard gelatine capsules in a conventional manner in such a way that each capsule contains 20 mg of the active ingredient.

Example 13: Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula (I)

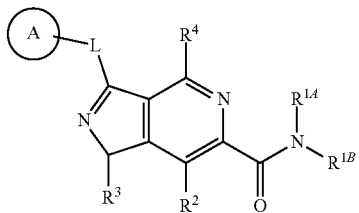

(I)

wherein:
$R^{1A}$ and $R^{1B}$ are mutually linked to form, together with the nitrogen atom that they are attached to, a group which is selected from

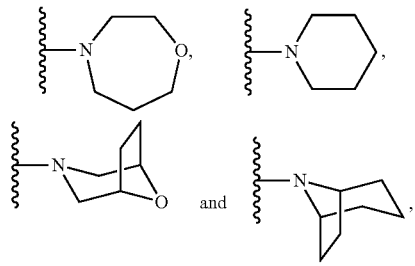

wherein each one of the above-depicted groups is optionally substituted with one or more groups $R^{11}$;

each $R^{11}$ is independently selected from $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, ($C_{0-3}$ alkylene)-O($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl)($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-SO—($C_{1-5}$ alkyl), —($C_{0-3}$ alkylene)-SO$_2$—($C_{1-5}$ alkyl), —($C_{0-3}$ alkylene)-carbocyclyl, and —($C_{0-3}$ alkylene)-heterocyclyl, wherein the carbocyclyl moiety of said —($C_{0-3}$ alkylene)-carbocyclyl and the heterocyclyl moiety of said —($C_{0-3}$ alkylene)-heterocyclyl are each optionally substituted with one or more groups independently selected from $C_{1-5}$ alkyl, $C_{2-5}$ alkenyl, $C_{2-5}$ alkynyl, —OH, —O($C_{1-5}$ alkyl), —O($C_{1-5}$ alkylene)-OH, —O($C_{1-5}$ alkylene)-O ($C_{1-5}$ alkyl), —SH, —S($C_{1-5}$ alkyl), —NH$_2$, —NH($C_{1-5}$ alkyl), —N($C_{1-5}$ alkyl)($C_{1-5}$ alkyl), halogen, $C_{1-5}$ haloalkyl, —O—($C_{1-5}$ haloalkyl), —CF$_3$, —CN, —NO$_2$, —CHO, —CO—($C_{1-5}$ alkyl), —COOH, —CO—O—($C_{1-5}$ alkyl), —O—CO—($C_{1-5}$ alkyl), —CO—NH$_2$, —CO—NH($C_{1-5}$ alkyl), —CO—N($C_{1-5}$ alkyl)($C_{1-5}$ alkyl), —NH—CO—($C_{1-5}$ alkyl), —N($C_{1-5}$ alkyl)-CO—($C_{1-5}$ alkyl), —SO$_2$—NH$_2$, —SO$_2$—NH ($C_{1-5}$ alkyl), —SO$_2$—N($C_{1-5}$ alkyl)($C_{1-5}$ alkyl), —NH—SO$_2$—($C_{1-5}$ alkyl), —N($C_{1-5}$ alkyl)-SO$_2$—($C_{1-5}$ alkyl), —SO—($C_{1-5}$ alkyl), —SO$_2$—($C_{1-5}$ alkyl), cycloalkyl, and heterocycloalkyl;

$R^2$ and $R^4$ are each independently selected from hydrogen, $C_{1-5}$ alkyl, $C_{2-5}$ alkenyl, $C_{2-5}$ alkynyl, —($C_{0-3}$ alkylene)-OH, —($C_{0-3}$ alkylene)-O($C_{1-5}$ alkyl), —($C_{0-3}$ alkylene)-O($C_{1-5}$ alkylene)-OH, —($C_{0-3}$ alkylene)-O ($C_{1-5}$ alkylene)-O($C_{1-5}$ alkyl), —($C_{0-3}$ alkylene)-SH, —($C_{0-3}$ alkylene)-S($C_{1-5}$ alkyl), —($C_{0-3}$ alkylene)-NH$_2$, —($C_{0-3}$ alkylene)-NH($C_{1-5}$ alkyl), —($C_{0-3}$ alkylene)-N($C_{1-5}$ alkyl)($C_{1-5}$ alkyl), —($C_{0-3}$ alkylene)-halogen, —($C_{0-3}$ alkylene)-($C_{1-5}$ haloalkyl), —($C_{0-3}$ alkylene)-O—($C_{1-5}$ haloalkyl), —($C_{0-3}$ alkylene)-CF$_3$, —($C_{0-3}$ alkylene)-CN, —($C_{0-3}$ alkylene)-NO$_2$, —($C_{0-3}$ alkylene)-CHO, —($C_{0-3}$ alkylene)-CO—($C_{1-5}$ alkyl), —($C_{0-3}$ alkylene)-COOH, —($C_{0-3}$ alkylene)-CO—O—($C_{1-5}$ alkyl), —($C_{0-3}$ alkylene)-O—CO—($C_{1-5}$ alkyl), —($C_{0-3}$ alkylene)-CO—NH$_2$, —($C_{0-3}$ alkylene)-CO—NH($C_{1-5}$ alkyl), —($C_{0-3}$ alkylene)-CO—N($C_{1-5}$ alkyl) ($C_{1-5}$ alkyl), —($C_{0-3}$ alkylene)-NH—CO—($C_{1-5}$ alkyl), —($C_{0-3}$ alkylene)-N($C_{1-5}$ alkyl)-CO—($C_{1-5}$ alkyl), —($C_{0-3}$ alkylene)-SO$_2$—NH$_2$, —($C_{0-3}$ alkylene)-SO$_2$—NH($C_{1-5}$ alkyl), —($C_{0-3}$ alkylene)-SO$_2$—N($C_{1-5}$ alkyl)($C_{1-5}$ alkyl), —($C_{0-3}$ alkylene)-NH—SO$_2$—($C_{1-5}$ alkyl), —($C_{0-3}$ alkylene)-N($C_{1-5}$ alkyl)-SO$_2$—($C_{1-5}$ alkyl), —($C_{0-3}$ alkylene)-SO—($C_{1-5}$ alkyl), —($C_{0-3}$ alkylene)-SO$_2$—($C_{1-5}$ alkyl), —($C_{0-3}$ alkylene)-carbocyclyl, and —(C$_{0-3}$ alkylene)-heterocyclyl, wherein the carbocyclyl moiety of said —(C$_{0-3}$ alkylene)-carbocyclyl and the heterocyclyl moiety of said —(C$_{0-3}$ alkylene)-heterocyclyl are each optionally substituted with one or more groups independently selected from C$_{1-5}$ alkyl, C$_{2-5}$ alkenyl, C$_{2-5}$ alkynyl, —OH, —O(C$_{1-5}$ alkyl), —O(C$_{1-5}$ alkylene)-OH, —O(C$_{1-5}$ alkylene)-O (C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —O—(C$_{1-5}$ haloalkyl), —CF$_3$, —CN, —NO$_2$, —CHO, —CO—(C$_{1-5}$ alkyl), —COOH, —CO—O—(C$_{1-5}$ alkyl), —O—CO—(C$_{1-5}$ alkyl), —CO—NH$_2$, —CO—NH(C$_{1-5}$ alkyl), —CO—N(C$_{1-5}$ alkyl)(C$_{1-5}$ alkyl), —NH—CO—(C$_{1-5}$ alkyl), —N(C$_{1-5}$ alkyl)-CO—(C$_{1-5}$ alkyl), —SO$_2$—NH$_2$, —SO$_2$—NH (C$_{1-5}$ alkyl), —SO$_2$—N(C$_{1-5}$ alkyl)(C$_{1-5}$ alkyl), —NH—SO$_2$—(C$_{1-5}$ alkyl), —N(C$_{1-5}$ alkyl)-SO$_2$—(C$_{1-5}$ alkyl), —SO—(C$_{1-5}$ alkyl), —SO$_2$—(C$_{1-5}$ alkyl), cycloalkyl, and heterocycloalkyl;

R$^3$ is —CH$_2$—CF$_3$ or —CH$_2$—SO$_2$—CH$_3$;

L is C$_{1-5}$ alkylene, wherein one or more —CH$_2$— units in said alkylene are each optionally replaced by a group independently selected from —N(R$^L$)—, —N(R$^L$)—CO—, —CO—N(R$^L$)—, —CO—, —O—, —CO—O—, —O—CO—, —S—, —SO—, —SO$_2$—, —SO$_2$—N(R$^L$)—, and —N(R$^L$)—SO$_2$—;

each R$^L$ is independently selected from hydrogen and C$_{1-5}$ alkyl;

ring A is aryl or monocyclic heteroaryl, wherein said aryl or said monocyclic heteroaryl is optionally substituted with one or more groups R$^A$; and each R$^A$ is independently selected from C$_{1-5}$ alkyl, C$_{2-5}$ alkenyl, C$_{2-5}$ alkynyl, —(C$_{0-3}$ alkylene)-OH, —(C$_{0-3}$ alkylene)-O(C$_{1-5}$ alkyl), —(C$_{0-3}$ alkylene)-O(C$_{1-5}$ alkylene)-OH, (C$_{0-3}$ alkylene)-O(C$_{1-5}$ alkylene)-O(C$_{1-5}$ alkyl), —(C$_{0-3}$ alkylene)-SH, —(C$_{0-3}$ alkylene)-S(C$_{1-5}$ alkyl), —(C$_{0-3}$ alkylene)-NH$_2$, —(C$_{0-3}$ alkylene)-NH(C$_{1-5}$ alkyl), —(C$_{0-3}$ alkylene)-N(C$_{1-5}$ alkyl)(C$_{1-5}$ alkyl), —(C$_{0-3}$ alkylene)-halogen, —(C$_{0-3}$ alkylene)-(C$_{1-5}$ haloalkyl), —(C$_{0-3}$ alkylene)-O—(C$_{1-5}$ haloalkyl), —(C$_{0-3}$ alkylene)-CF$_3$, —(C$_{0-3}$ alkylene)-CN, —(C$_{0-3}$ alkylene)-NO$_2$, —(C$_{0-3}$ alkylene)-CHO, —(C$_{0-3}$ alkylene)-CO—(C$_{1-5}$ alkyl), —(C$_{0-3}$ alkylene)-COOH, —(C$_{0-3}$ alkylene)-CO—O—(C$_{1-5}$ alkyl), —(C$_{0-3}$ alkylene)-O—CO—(C$_{1-5}$ alkyl), —(C$_{0-3}$ alkylene)-CO—NH$_2$, —(C$_{0-3}$ alkylene)-CO—NH(C$_{1-5}$ alkyl), —(C$_{0-3}$ alkylene)-CO—N(C$_{1-5}$ alkyl)(C$_{1-5}$ alkyl), —(C$_{0-3}$ alkylene)-NH—CO—(C$_{1-5}$ alkyl), —(C$_{0-3}$ alkylene)-N(C$_{1-5}$ alkyl)-CO—(C$_{1-5}$ alkyl), —(C$_{0-3}$ alkylene)-SO$_2$—NH$_2$, —(C$_{0-3}$ alkylene)-SO$_2$—NH(C$_{1-5}$ alkyl), —(C$_{0-3}$ alkylene)-SO$_2$—N(C$_{1-5}$ alkyl)(C$_{1-5}$ alkyl), —(C$_{0-3}$ alkylene)-NH—SO$_2$—(C$_{1-5}$ alkyl), —(C$_{0-3}$ alkylene)-N(C$_{1-5}$ alkyl)-SO$_2$—(C$_{1-5}$ alkyl), —(C$_{0-3}$ alkylene)-SO—(C$_{1-5}$ alkyl), —(C$_{0-3}$ alkylene)-SO$_2$—(C$_{1-5}$ alkyl), —(C$_{0-3}$ alkylene)-carbocyclyl, and —(C$_{0-3}$ alkylene)-heterocyclyl, wherein the carbocyclyl moiety of said —(C$_{0-3}$ alkylene)-carbocyclyl and the heterocyclyl moiety of said —(C$_{0-3}$ alkylene)-heterocyclyl are each optionally substituted with one or more groups independently selected from C$_{1-5}$ alkyl, C$_{2-5}$ alkenyl, C$_{2-5}$ alkynyl, —OH, —O(C$_{1-5}$ alkyl), —O(C$_{1-5}$ alkylene)-OH, —O(C$_{1-5}$ alkylene)-O (C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —O—(C$_{1-5}$ haloalkyl), —CF$_3$, —CN, —NO$_2$, —CHO, —CO—(C$_{1-5}$ alkyl), —COOH, —CO—O—(C$_{1-5}$ alkyl), —O—CO—(C$_{1-5}$ alkyl), —CO—NH$_2$, —CO—NH(C$_{1-5}$ alkyl), —CO—N(C$_{1-5}$ alkyl)(C$_{1-5}$ alkyl), —NH—CO—(C$_{1-5}$ alkyl), —N(C$_{1-5}$ alkyl)-CO—(C$_{1-5}$ alkyl), —SO$_2$—NH$_2$, —SO$_2$—NH (C$_{1-5}$ alkyl), —SO$_2$—N(C$_{1-5}$ alkyl)(C$_{1-5}$ alkyl), —NH—SO$_2$—(C$_{1-5}$ alkyl), —N(C$_{1-5}$ alkyl)-SO$_2$—(C$_{1-5}$ alkyl), —SO—(C$_{1-5}$ alkyl), —SO$_2$—(C$_{1-5}$ alkyl), cycloalkyl, and heterocycloalkyl;

or a pharmaceutically acceptable salt or solvate thereof.

2. The compound of claim 1, wherein R$^2$ and R$^4$ are each independently selected from hydrogen, C$_{1-5}$ alkyl, —OH, —O(C$_{1-5}$ alkyl), —O(C$_{1-5}$ alkylene)-OH, —O(C$_{1-5}$ alkylene)-O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —CF$_3$, and —CN.

3. The compound of claim 1, wherein L is C$_{1-3}$ alkylene, wherein one —CH$_2$— unit in said alkylene is optionally replaced by a group selected from —N(R$^L$)—, —N(R$^L$)—CO—, —CO—N(R$^L$)—, and —CO—, and further wherein each R$^L$ is independently selected from hydrogen, methyl and ethyl.

4. The compound of claim 1, wherein L is —NH—.

5. The compound of claim 1, wherein ring A is phenyl or a 6-membered monocyclic heteroaryl, wherein said phenyl or said monocyclic heteroaryl is optionally substituted with one or more groups R$^A$.

6. The compound of claim 1, wherein ring A is phenyl or pyridin-2-yl, wherein said phenyl or said pyridin-2-yl is optionally substituted with one or more groups R$^A$.

7. The compound of claim 1, wherein each R$^A$ is independently selected from C$_{1-5}$ alkyl, —OH, —O(C$_{1-5}$ alkyl), —O(C$_{1-5}$ alkylene)-OH, —O(C$_{1-5}$ alkylene)-O(C$_{1-5}$ alkyl), —SH, —S(C$_{1-5}$ alkyl), —NH$_2$, —NH(C$_{1-5}$ alkyl), —N(C$_{1-5}$ alkyl)(C$_{1-5}$ alkyl), halogen, C$_{1-5}$ haloalkyl, —CF$_3$, and —CN.

8. A compound, wherein said compound is selected from:

| | |
|---|---|
| 1 | [3-(2-fluoroanilino)-1-(2,2,2-trifluoroethyl)pyrazolo[4,3-c]pyridin-6-yl]-(1,4-oxazepan-4-yl)methanone |
| 2 | [3-anilino-1-(2,2,2-trifluoroethyl)pyrazolo[4,3-c]pyridin-6-yl]-(1,4-oxazepan-4-yl)methanone |
| 3 | [3-(2-methoxyanilino)-1-(2,2,2-trifluoroethyl)pyrazolo[4,3-c]pyridin-6-yl]-(1,4-oxazepan-4-yl)methanone |
| 4 | [3-(2-methylanilino)-1-(2,2,2-trifluoroethyl)pyrazolo[4,3-c]pyridin-6-yl]-(1,4-oxazepan-4-yl)methanone |
| 5 | [3-(N-methylanilino)-1-(2,2,2-trifluoroethyl)pyrazolo[4,3-c]pyridin-6-yl]-(1,4-oxazepan-4-yl)methanone |
| 6 | [3-(3-fluoroanilino)-1-(2,2,2-trifluoroethyl)pyrazolo[4,3-c]pyridin-6-yl]-(1,4-oxazepan-4-yl)methanone |
| 7 | [3-(3-methoxyanilino)-1-(2,2,2-trifluoroethyl)pyrazolo[4,3-c]pyridin-6-yl]-(1,4-oxazepan-4-yl)methanone |
| 8 | 3-[[6-(1,4-oxazepane-4-carbonyl)-1-(2,2,2-trifluoroethyl)pyrazolo[4,3-c]pyridin-3-yl]amino]benzonitrile |

| | |
|---|---|
| 9 | 3-[[6-(1,4-oxazepane-4-carbonyl)-1-(2,2,2-trifluoroethyl)pyrazolo[4,3-c]pyridin-3-yl]amino]benzamide |
| 10 | [3-(4-fluoroanilino)-1-(2,2,2-trifluoroethyl)pyrazolo[4,3-c]pyridin-6-yl]-(1,4-oxazepan-4-yl)methanone |
| 11 | [3-(4-methoxyanilino)-1-(2,2,2-trifluoroethyl)pyrazolo[4,3-c]pyridin-6-yl]-(1,4-oxazepan-4-yl)methanone |
| 12 | 1,4-oxazepan-4-yl-[3-(3-pyridylamino)-1-(2,2,2-trifluoroethyl)pyrazolo[4,3-c]pyridin-6-yl]methanone |
| 13 | 4-[[6-(1,4-oxazepane-4-carbonyl)-1-(2,2,2-trifluoroethyl)pyrazolo[4,3-c]pyridin-3-yl]amino]benzonitrile |
| 14 | 4-[[6-(1,4-oxazepane-4-carbonyl)-1-(2,2,2-trifluoroethyl)pyrazolo[4,3-c]pyridin-3-yl]amino]benzamide |
| 15 | [3-(3,5-difluoroanilino)-1-(2,2,2-trifluoroethyl)pyrazolo[4,3-c]pyridin-6-yl]-(1,4-oxazepan-4-yl)methanone |
| 16 | [3-(3-fluoro-4-methylanilino)-1-(2,2,2-trifluoroethyl)pyrazolo[4,3-c]pyridin-6-yl]-(1,4-oxazepan-4-yl)methanone |
| 17 | [3-(3,4-difluoroanilino)-1-(2,2,2-trifluoroethyl)pyrazolo[4,3-c]pyridin-6-yl]-(1,4-oxazepan-4-yl)methanone |
| 18 | [3-(3-chloro-4-fluoroanilino)-1-(2,2,2-trifluoroethyl)pyrazolo[4,3-c]pyridin-6-yl]-(1,4-oxazepan-4-yl)methanone |
| 19 | [3-(4-chloro-3-fluoroanilino)-1-(2,2,2-trifluoroethyl)pyrazolo[4,3-c]pyridin-6-yl]-(1,4-oxazepan-4-yl)methanone |
| 20 | [3-(3-fluoroanilino)-1-(2,2,2-trifluoroethyl)pyrazolo[4,3-c]pyridin-6-yl]-(8-oxa-3-azabicyclo[3.2.1]octan-3-yl)methanone |
| 21 | [3-(4-fluoroanilino)-1-(2,2,2-trifluoroethyl)pyrazolo[4,3-c]pyridin-6-yl]-(8-oxa-3-azabicyclo[3.2.1]octan-3-yl)methanone |
| 22 | [3-(4-fluoroanilino)-1-(2,2,2-trifluoroethyl)pyrazolo[4,3-c]pyridin-6-yl]-(4-hydroxy-1-piperidyl)methanone |
| 23 | [3-(3-fluoroanilino)-1-(2,2,2-trifluoroethyl)pyrazolo[4,3-c]pyridin-6-yl]-(4-hydroxy-1-piperidyl)methanone |
| 24 | (4-hydroxy-1-piperidyl)-[3-(2-pyridylamino)-1-(2,2,2-trifluoroethyl)pyrazolo[4,3-c]pyridin-6-yl]methanone |
| 25 | [3-(3-fluoroanilino)-1-(2,2,2-trifluoroethyl)pyrazolo[4,3-c]pyridin-6-yl]-(3-endo-hydroxy-8-azabicyclo[3.2.1]octan-8-yl)methanone |
| 26 | [3-(4-fluoroanilino)-1-(2,2,2-trifluoroethyl)pyrazolo[4,3-c]pyridin-6-yl]-(3-endo-hydroxy-8-azabicyclo[3.2.1]octan-8-yl)methanone |
| 27 | [3-(4-fluoroanilino)-1-(methylsulfonylmethyl)pyrazolo[4,3-c]pyridin-6-yl]-(1,4-oxazepan-4-yl)methanone |
| 28 | [3-(3-fluoroanilino)-1-(methylsulfonylmethyl)pyrazolo[4,3-c]pyridin-6-yl]-(1,4-oxazepan-4-yl)methanone |
| 29 | [3-anilino-1-(methylsulfonylmethyl)pyrazolo[4,3-c]pyridin-6-yl]-(3-endo-hydroxy-8-azabicyclo[3.2.1]octan-8-yl)methanone |
| 30 | [3-(4-fluoroanilino)-1-(methylsulfonylmethyl)pyrazolo[4,3-c]pyridin-6-yl]-(3-endo-hydroxy-8-azabicyclo[3.2.1]octan-8-yl)methanone |
| 31 | [3-(3-fluoroanilino)-1-(methylsulfonylmethyl)pyrazolo[4,3-c]pyridin-6-yl]-(3-endo-hydroxy-8-azabicyclo[3.2.1]octan-8-yl)methanone |
| 32 | [3-(3-fluoroanilino)-1-(2,2,2-trifluoroethyl)pyrazolo[4,3-c]pyridin-6-yl]-(6-hydroxy-1,4-oxazepan-4-yl)methanone |
| 33 | [3-(4-fluoroanilino)-1-(2,2,2-trifluoroethyl)pyrazolo[4,3-c]pyridin-6-yl]-(6-hydroxy-1,4-oxazepan-4-yl)methanone |
| 34 | [3-(4-fluoroanilino)-1-(2,2,2-trifluoroethyl)pyrazolo[4,3-c]pyridin-6-yl]-(4-hydroxy-4-methyl-1-piperidyl)methanone |
| 35 | [3-(3-fluoroanilino)-1-(2,2,2-trifluoroethyl)pyrazolo[4,3-c]pyridin-6-yl]-(4-hydroxy-4-methyl-1-piperidyl)methanone |
| 36 | 1,4-oxazepan-4-yl-[3-(pyrimidin-2-ylamino)-1-(2,2,2-trifluoroethyl)pyrazolo[4,3-c]pyridin-6-yl]methanone |
| 37 | [3-(3-chloroanilino)-1-(2,2,2-trifluoroethyl)pyrazolo[4,3-c]pyridin-6-yl]-(1,4-oxazepan-4-yl)methanone |
| 38 | [3-(4-chloroanilino)-1-(2,2,2-trifluoroethyl)pyrazolo[4,3-c]pyridin-6-yl]-(1,4-oxazepan-4-yl)methanone |
| 39 | [3-(2-chloroanilino)-1-(2,2,2-trifluoroethyl)pyrazolo[4,3-c]pyridin-6-yl]-(1,4-oxazepan-4-yl)methanone |
| 40 | (6,6-dideuterio-1,4-oxazepan-4-yl)-[3-(3-fluoroanilino)-1-(2,2,2-trifluoroethyl)pyrazolo[4,3-c]pyridin-6-yl]methanone |
| 41 | (6,6-dideuterio-1,4-oxazepan-4-yl)-[3-(4-fluoroanilino)-1-(2,2,2-trifluoroethyl)pyrazolo[4,3-c]pyridin-6-yl]methanone |
| 42 | 1,4-oxazepan-4-yl-[3-(2-pyridylamino)-1-(2,2,2-trifluoroethyl)pyrazolo[4,3-c]pyridin-6-yl]methanone |
| 43 | 1,4-oxazepan-4-yl-[3-(4-pyridylamino)-1-(2,2,2-trifluoroethyl)pyrazolo[4,3-c]pyridin-6-yl]methanone |
| 44 | [3-[(5-fluoro-2-pyridyl)amino]-1-(2,2,2-trifluoroethyl)pyrazolo[4,3-c]pyridin-6-yl]-(1,4-oxazepan-4-yl)methanone |
| 45 | [3-[(6-methoxy-2-pyridyl)amino]-1-(2,2,2-trifluoroethyl)pyrazolo[4,3-c]pyridin-6-yl]-(1,4-oxazepan-4-yl)methanone |
| 46 | [3-[(4-fluoro-2-pyridyl)amino]-1-(2,2,2-trifluoroethyl)pyrazolo[4,3-c]pyridin-6-yl]-(1,4-oxazepan-4-yl)methanone |

| | |
|---|---|
| 47 | 8-oxa-3-azabicyclo[3.2.1]octan-3-yl-[3-(2-pyridylamino)-1-(2,2,2-trifluoroethyl)pyrazolo[4,3-c]pyridin-6-yl]methanone |
| 48 | [3-[(5-chloro-2-pyridyl)amino]-1-(2,2,2-trifluoroethyl)pyrazolo[4,3-c]pyridin-6-yl]-(1,4-oxazepan-4-yl)methanone |
| 49 | [3-[(6-fluoro-2-pyridyl)amino]-1-(2,2,2-trifluoroethyl)pyrazolo[4,3-c]pyridin-6-yl]-(1,4-oxazepan-4-yl)methanone |
| 50 | [3-[(5-methoxy-3-methyl-2-pyridyl)amino]-1-(2,2,2-trifluoroethyl)pyrazolo[4,3-c]pyridin-6-yl]-(1,4-oxazepan-4-yl)methanone |
| 51 | [3-[(6-chloro-2-pyridyl)amino]-1-(2,2,2-trifluoroethyl)pyrazolo[4,3-c]pyridin-6-yl]-(1,4-oxazepan-4-yl)methanone |
| 52 | (6-hydroxy-1,4-oxazepan-4-yl)-[3-(2-pyridylamino)-1-(2,2,2-trifluoroethyl)pyrazolo[4,3-c]pyridin-6-yl]methanone |
| 53 | (4-hydroxy-4-methyl-1-piperidyl)-[3-(2-pyridylamino)-1-(2,2,2-trifluoroethyl)pyrazolo[4,3-c]pyridin-6-yl]methanone |
| 54 | [3-[(3-fluoro-2-pyridyl)amino]-1-(2,2,2-trifluoroethyl)pyrazolo[4,3-c]pyridin-6-yl]-(1,4-oxazepan-4-yl)methanone |
| 55 | [3-[(3-chloro-2-pyridyl)amino]-1-(2,2,2-trifluoroethyl)pyrazolo[4,3-c]pyridin-6-yl]-(1,4-oxazepan-4-yl)methanone |
| 56 | [3-[(5-fluoro-3-methyl-2-pyridyl)amino]-1-(2,2,2-trifluoroethyl)pyrazolo[4,3-c]pyridin-6-yl]-(1,4-oxazepan-4-yl)methanone |
| 57 | [3-[(5-fluoro-4-methyl-2-pyridyl)amino]-1-(2,2,2-trifluoroethyl)pyrazolo[4,3-c]pyridin-6-yl]-(1,4-oxazepan-4-yl)methanone |
| 58 | [3-[(5-fluoro-6-methyl-2-pyridyl)amino]-1-(2,2,2-trifluoroethyl)pyrazolo[4,3-c]pyridin-6-yl]-(1,4-oxazepan-4-yl)methanone |
| 59 | (6,6-dideuterio-1,4-oxazepan-4-yl)-[3-(2-pyridylamino)-1-(2,2,2-trifluoroethyl)pyrazolo[4,3-c]pyridin-6-yl]methanone |
| 60 | (6,6-dideuterio-1,4-oxazepan-4-yl)-[3-[(4-fluoro-2-pyridyl)amino]-1-(2,2,2-trifluoroethyl)pyrazolo[4,3-c]pyridin-6-yl]methanone |
| 61 | 1,4-oxazepan-4-yl-[3-(pyrazin-2-ylamino)-1-(2,2,2-trifluoroethyl)pyrazolo[4,3-c]pyridin-6-yl]methanone |
| 62 | 1,4-oxazepan-4-yl-[1-(2,2,2-trifluoroethyl)-3-[[4-(trifluoromethyl)-2-pyridyl]amino]pyrazolo[4,3-c]pyridin-6-yl]methanone |
| 63 | [3-[(4-methoxy-2-pyridyl)amino]-1-(2,2,2-trifluoroethyl)pyrazolo[4,3-c]pyridin-6-yl]-(1,4-oxazepan-4-yl)methanone |
| 64 | [3-[(4-chloro-2-pyridyl)amino]-1-(2,2,2-trifluoroethyl)pyrazolo[4,3-c]pyridin-6-yl]-(1,4-oxazepan-4-yl)methanone |
| 65 | [3-[(6-chloro-5-fluoro-2-pyridyl)amino]-1-(2,2,2-trifluoroethyl)pyrazolo[4,3-c]pyridin-6-yl]-(1,4-oxazepan-4-yl)methanone |
| 66 | [3-[(4-chloro-5-fluoro-2-pyridyl)amino]-1-(2,2,2-trifluoroethyl)pyrazolo[4,3-c]pyridin-6-yl]-(1,4-oxazepan-4-yl)methanone |
| 67 | [3-[(3-chloro-5-fluoro-2-pyridyl)amino]-1-(2,2,2-trifluoroethyl)pyrazolo[4,3-c]pyridin-6-yl]-(1,4-oxazepan-4-yl)methanone |
| 68 | [3-[(4-methyl-2-pyridyl)amino]-1-(2,2,2-trifluoroethyl)pyrazolo[4,3-c]pyridin-6-yl]-(1,4-oxazepan-4-yl)methanone |
| 69 | 1,4-oxazepan-4-yl-[3-(pyridazin-3-ylamino)-1-(2,2,2-trifluoroethyl)pyrazolo[4,3-c]pyridin-6-yl]methanone |
| 70 | [3-[(4-fluoro-3-methyl-2-pyridyl)amino]-1-(2,2,2-trifluoroethyl)pyrazolo[4,3-c]pyridin-6-yl]-(1,4-oxazepan-4-yl)methanone |
| 71 | [3-[(5-chloro-4-fluoro-2-pyridyl)amino]-1-(2,2,2-trifluoroethyl)pyrazolo[4,3-c]pyridin-6-yl]-(1,4-oxazepan-4-yl)methanone |
| 72 | [3-[(3,5-difluoro-2-pyridyl)amino]-1-(2,2,2-trifluoroethyl)pyrazolo[4,3-c]pyridin-6-yl]-(1,4-oxazepan-4-yl)methanone |
| 73 | [1,4]Oxazepan-4-yl-[3-(pyrimidin-4-ylamino)-1-(2,2,2-trifluoro-ethyl)-1H-pyrazolo[4,3-c]pyridin-6-yl]-methanone |
| 74 | (4-Hydroxy-piperidin-1-yl)-[3-(pyrazin-2-ylamino)-1-(2,2,2-trifluoro-ethyl)-1H-pyrazolo[4,3-c]pyridin-6-yl]-methanone |
| 75 | [3-(5-Chloro-pyrazin-2-ylamino)-1-(2,2,2-trifluoro-ethyl)-1H-pyrazolo[4,3-c]pyridin-6-yl]-(4-hydroxy-piperidin-1-yl)-methanone |
| 76 | (4-Hydroxy-piperidin-1-yl)-[3-(pyrimidin-4-ylamino)-1-(2,2,2-trifluoro-ethyl)-1H-pyrazolo[4,3-c]pyridin-6-yl]-methanone |
| 77 | [3-(5-Fluoro-pyridin-2-ylamino)-1-methanesulfonylmethyl-1H-pyrazolo[4,3-c]pyridin-6-yl]-[1,4]oxazepan-4-yl-methanone |
| 78 | [3-(5-Chloro-pyridin-2-ylamino)-1-methanesulfonylmethyl-1H-pyrazolo[4,3-c]pyridin-6-yl]-[1,4]oxazepan-4-yl-methanone |
| 79 | [3-(4-Chloro-pyridin-2-ylamino)-1-methanesulfonylmethyl-1H-pyrazolo[4,3-c]pyridin-6-yl]-[1,4]oxazepan-4-yl-methanone |
| 80 | [3-[(5,6-difluoro-2-pyridyl)amino]-1-(2,2,2-trifluoroethyl)pyrazolo[4,3-c]pyridin-6-yl]-(1,4-oxazepan-4-yl)methanone |
| 81 | [3-[(5-fluoro-4-methoxy-2-pyridyl)amino]-1-(2,2,2-trifluoroethyl)pyrazolo[4,3-c]pyridin-6-yl]-(1,4-oxazepan-4-yl)methanone |
| 82 | [3-[(5-fluoro-6-methoxy-2-pyridyl)amino]-1-(2,2,2-trifluoroethyl)pyrazolo[4,3-c]pyridin-6-yl]-(1,4-oxazepan-4-yl)methanone |
| 83 | [3-(5-Methoxy-pyridin-2-ylamino)-1-(2,2,2-trifluoro-ethyl)-1H-pyrazolo[4,3-c]pyridin-6-yl]-[1,4]oxazepan-4-yl-methanone |
| 84 | [1,4]Oxazepan-4-yl-[3-(thiazol-5-ylamino)-1-(2,2,2-trifluoro-ethyl)-1H-pyrazolo[4,3-c]pyridin-6-yl]methanone |

| | |
|---|---|
| 85 | [1,4]Oxazepan-4-yl-[3-(thiazol-2-ylamino)-1-(2,2,2-trifluoro-ethyl)-1H-pyrazolo[4,3-c]pyridin-6-yl]methanone |
| 86 | 6-[6-([1,4]Oxazepane-4-carbonyl)-1-(2,2,2-trifluoro-ethyl)-1H-pyrazolo[4,3-c]pyridin-3-ylamino]-1H-pyridin-2-one |
| 87 | 3-[[6-(1,4-oxazepane-4-carbonyl)-1-(2,2,2-trifluoroethyl)pyrazolo[4,3-c]pyridin-3-yl]amino]-1H-pyridin-2-one |
| 88 | [3-[(5-fluoro-4-hydroxy-2-pyridyl)amino]-1-(2,2,2-trifluoroethyl)pyrazolo[4,3-c]pyridin-6-yl]-(1,4-oxazepan-4-yl)methanone |
| 89 | [3-[(5-fluoro-3-hydroxy-2-pyridyl)amino]-1-(2,2,2-trifluoroethyl)pyrazolo[4,3-c]pyridin-6-yl]-(1,4-oxazepan-4-yl)methanone |
| 90 | [3-[(4-fluoro-3-hydroxy-2-pyridyl)amino]-1-(2,2,2-trifluoroethyl)pyrazolo[4,3-c]pyridin-6-yl]-(1,4-oxazepan-4-yl)methanone |
| 91 | (6,6-dideuterio-1,4-oxazepan-4-yl)-[3-[(5-fluoro-2-pyridyl)amino]-1-(2,2,2-trifluoroethyl)pyrazolo[4,3-c]pyridin-6-yl]methanone |
| 92 | [3-[(5-fluoro-2-pyridyl)amino]-1-(2,2,2-trifluoroethyl)pyrazolo[4,3-c]pyridin-6-yl]-(6-hydroxy-1,4-oxazepan-4-yl)methanone |
| 93 | [(6S)-6-fluoro-1,4-oxazepan-4-yl]-[3-[(5-fluoro-2-pyridyl)amino]-1-(2,2,2-trifluoroethyl)pyrazolo[4,3-c]pyridin-6-yl]methanone |
| 94 | [3-[(5-fluoro-2-pyridyl)amino]-1-(2,2,2-trifluoroethyl)pyrazolo[4,3-c]pyridin-6-yl]-(4-hydroxypiperidin-1-yl)methanone |
| 95 | [3-(5-Fluoro-pyridin-2-ylamino)-1-(2,2,2-trifluoro-ethyl)-1H-pyrazolo[4,3-c]pyridin-6-yl]-(4-hydroxy-4-methyl-piperidin-1-yl)-methanone |
| 96 | (4-Fluoro-piperidin-1-yl)-[3-(5-fluoro-pyridin-2-ylamino)-1-(2,2,2-trifluoro-ethyl)-1H-pyrazolo[4,3-c]pyridin-6-yl]-methanone |
| 97 | [(3R)-3-hydroxy-piperidin-1-yl]-[3-(5-Fluoro-pyridin-2-ylamino)-1-(2,2,2-trifluoro-ethyl)-1H-pyrazolo[4,3-c]pyridin-6-yl]methanone |
| 98 | [(3S)-3-hydroxy-piperidin-1-yl]-[3-(5-Fluoro-pyridin-2-ylamino)-1-(2,2,2-trifluoro-ethyl)-1H-pyrazolo[4,3-c]pyridin-6-yl]methanone |
| 99 | [(3R)-3-fluoro-piperidin-1-yl]-[3-(5-Fluoro-pyridin-2-ylamino)-1-(2,2,2-trifluoro-ethyl)-1H-pyrazolo[4,3-c]pyridin-6-yl]methanone |
| 100 | [(3S)-3-fluoro-piperidin-1-yl]-[3-(5-Fluoro-pyridin-2-ylamino)-1-(2,2,2-trifluoro-ethyl)-1H-pyrazolo[4,3-c]pyridin-6-yl]methanone |
| 101 | [3-[(5-fluoro-2-pyridyl)amino]-1-(2,2,2-trifluoroethyl)pyrazolo[4,3-c]pyridin-6-yl]-[(3R)-3-(hydroxymethyl)-1-piperidyl]methanone |
| 102 | [3-[(5-fluoro-2-pyridyl)amino]-1-(2,2,2-trifluoroethyl)pyrazolo[4,3-c]pyridin-6-yl]-[(3S)-3-(hydroxymethyl)-1-piperidyl]methanone |
| 103 | (3,3-Difluoro-4-hydroxy-piperidin-1-yl)-[3-(5-fluoro-pyridin-2-ylamino)-1-(2,2,2-trifluoro-ethyl)-1H-pyrazolo[4,3-c]pyridin-6-yl]-methanone |
| 104 | [3-[(5-fluoro-2-pyridyl)amino]-1-(2,2,2-trifluoroethyl)pyrazolo[4,3-c]pyridin-6-yl]-(3-hydroxy-3-methyl-piperidin-1-yl)methanone |
| 105 | Cis-[3-(5-Fluoro-pyridin-2-ylamino)-1-(2,2,2-trifluoro-ethyl)-1H-pyrazolo[4,3-c]pyridin-6-yl]-(3-hydroxy-4-methyl-piperidin-1-yl)-methanone |
| 106 | Cis-(3-Fluoro-4-hydroxy-piperidin-1-yl)-[3-(5-fluoro-pyridin-2-ylamino)-1-(2,2,2-trifluoro-ethyl)-1H-pyrazolo[4,3-c]pyridin-6-yl]-methanone |
| 107 | [3-[(5-fluoro-2-pyridyl)amino]-1-(2,2,2-trifluoroethyl)pyrazolo[4,3-c]pyridin-6-yl]-(3-endo-hydroxy-8-azabicyclo[3.2.1]octan-8-yl)methanone |
| 108 | 1-[3-[(5-fluoro-2-pyridyl)amino]-1-(2,2,2-trifluoroethyl)pyrazolo[4,3-c]pyridine-6-carbonyl]pyridine-4-carboxylic acid |
| 109 | [3-[(4-fluoro-2-pyridyl)amino]-1-(2,2,2-trifluoroethyl)pyrazolo[4,3-c]pyridin-6-yl]-(6-hydroxy-1,4-oxazepan-4-yl)methanone |
| 110 | [(6S)-6-fluoro-1,4-oxazepan-4-yl]-[3-(4-fluoro-pyridin-2-ylamino)-1-(2,2,2-trifluoro-ethyl)-1H-pyrazolo[4,3-c]pyridin-6-yl]-methanone |
| 111 | [3-[(4-fluoro-2-pyridyl)amino]-1-(2,2,2-trifluoroethyl)pyrazolo[4,3-c]pyridin-6-yl]-(4-hydroxypiperidin-1-yl)methanone |
| 112 | [3-(4-Fluoro-pyridin-2-ylamino)-1-(2,2,2-trifluoro-ethyl)-1H-pyrazolo[4,3-c]pyridin-6-yl]-(4-hydroxy-4-methyl-piperidin-1-yl)-methanone |
| 113 | [3-(4-Fluoro-pyridin-2-ylamino)-1-(2,2,2-trifluoro-ethyl)-1H-pyrazolo[4,3-c]pyridin-6-yl]-(4-ethyl-4-hydroxypiperidin-1-yl)-methanone |
| 114 | [3-(4-Fluoro-pyridin-2-ylamino)-1-(2,2,2-trifluoro-ethyl)-1H-pyrazolo[4,3-c]pyridin-6-yl]-(4-isopropyl-4-hydroxypiperidin-1-yl)-methanone |
| 115 | [3-(4-Fluoro-pyridin-2-ylamino)-1-(2,2,2-trifluoro-ethyl)-1H-pyrazolo[4,3-c]pyridin-6-yl]-(4-cyclopropyl-4-hydroxypiperidin-1-yl)-methanone |
| 116 | (4-Fluoro-piperidin-1-yl)-[3-(4-fluoro-pyridin-2-ylamino)-1-(2,2,2-trifluoro-ethyl)-1H-pyrazolo[4,3-c]pyridin-6-yl]-methanone |
| 117 | [(3S)-3-hydroxy-piperidin-1-yl]-[3-(4-fluoro-pyridin-2-ylamino)-1-(2,2,2-trifluoro-ethyl)-1H-pyrazolo[4,3-c]pyridin-6-yl]methanone |
| 118 | [3-(4-Fluoro-pyridin-2-ylamino)-1-(2,2,2-trifluoro-ethyl)-1H-pyrazolo[4,3-c]pyridin-6-yl]-(4-hydroxy-2,2-dimethyl-piperidin-1-yl)-methanone |
| 119 | (3,3-Difluoro-4-hydroxy-piperidin-1-yl)-[3-(4-fluoro-pyridin-2-ylamino)-1-(2,2,2-trifluoro-ethyl)-1H-pyrazolo[4,3-c]pyridin-6-yl]-methanone |
| 120 | [3-[(4-fluoro-2-pyridyl)amino]-1-(2,2,2-trifluoroethyl)pyrazolo[4,3-c]pyridin-6-yl]-(3-endo-hydroxy-8-azabicyclo[3.2.1]octan-8-yl)methanone |
| 121 | 6,6-dideuterio-1,4-oxazepan-4-yl)-[3-(pyrazin-2ylamino)-1-(2,2,2-trifluoroethyl)pyrazolo[4,3-c]pyridin-6-yl]methanone |
| 122 | [(6S)-6-fluoro-1,4-oxazepan-4-yl]-[3-(pyrazin-2ylamino)-1-(2,2,2-trifluoro-ethyl)-1H-pyrazolo[4,3-c]pyridin-6-yl]-methanone |

-continued

| 123 | [3-(pyrazin-2ylamino)-1-(2,2,2-trifluoro-ethyl)-1H-pyrazolo[4,3-c]pyridin-6-yl]-(4-hydroxy-4-methyl-piperidin-1-yl)-methanone |
| --- | --- |
| 124 | [3-(pyrazin-2ylamino)-1-(2,2,2-trifluoro-ethyl)-1H-pyrazolo[4,3-c]pyridin-6-yl]-(4-fluoro-piperidin-1-yl)-methanone |
| 125 | [3-[(5-fluoro-2-pyridyl)amino]-1-(2,2,2-trifluoroethyl)pyrazolo[4,3-c]pyridin-6-yl]-[(2R)-2-(2-hydroxy-2-methyl-propyl)pyrrolidin-1-yl]methanone |
| 126 | [3-[(5-fluoro-2-pyridyl)amino]-1-(2,2,2-trifluoroethyl)pyrazolo[4,3-c]pyridin-6-yl]-[(2S)-2-(2-hydroxy-2-methyl-propyl)pyrrolidin-1-yl]methanone |
| 127 | (3-endo-hydroxy-8-azabicyclo[3.2.1]octan-8-yl)-[3-(2-pyridylamino)-1-(2,2,2-trifluoroethyl)pyrazolo[4,3-c]pyridin-6-yl]methanone | and pharmaceutically acceptable salts and solvates thereof.

9. A pharmaceutical composition comprising the compound of claim 1 and a pharmaceutically acceptable excipient.

10. A set or kit comprising separate packs of:
(a) the compound as defined in claim 1; and
(b) a further therapeutic agent.

11. The compound of claim 1, wherein ring A is phenyl, pyridinyl, pyrimidinyl or pyrazinyl, wherein said phenyl, said pyridinyl, said pyrimidinyl and said pyrazinyl are each optionally substituted with one or more groups $R^4$.

12. The compound of claim 1, wherein each $R^4$ is independently halogen.

13. A pharmaceutical composition comprising the compound of claim 1 and a pharmaceutically acceptable excipient and one or more further pharmaceutically active agents.

14. The compound of claim 1, or a pharmaceutically acceptable salt thereof.

15. The compound of claim 8, or a pharmaceutically acceptable salt thereof.

* * * * *